(12) United States Patent
Lee et al.

(10) Patent No.: US 8,741,312 B2
(45) Date of Patent: Jun. 3, 2014

(54) HIGH YIELD YELLOW FEVER VIRUS STRAIN WITH INCREASED PROPAGATION IN CELLS

(75) Inventors: Cynthia K. Lee, Needham, MA (US); Thomas P. Monath, Harvard, MA (US); Patrick M. Guertin, Mendon, MA (US); Edward G. Hayman, Hanover, NH (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 246 days.

(21) Appl. No.: 13/012,917

(22) Filed: Jan. 25, 2011

(65) Prior Publication Data

US 2011/0287519 A1    Nov. 24, 2011

Related U.S. Application Data

(63) Continuation-in-part of application No. PCT/US2010/043010, filed on Jul. 23, 2010.

(60) Provisional application No. 61/230,483, filed on Jul. 31, 2009.

(51) Int. Cl.
*A61K 39/12* (2006.01)
*C12N 7/00* (2006.01)

(52) U.S. Cl.
USPC ............................ 424/218.1; 435/5; 435/235.1

(58) Field of Classification Search
None
See application file for complete search history.

(56) References Cited

U.S. PATENT DOCUMENTS

| | | | | |
|---|---|---|---|---|
| 4,810,492 | A | 3/1989 | Fujita | A61K 37/02 |
| 6,432,411 | B1 | 8/2002 | Ivy | A61K 39/12 |
| 6,589,531 | B1 | 7/2003 | Andino-Pavlovsky | A61K 39/12 |
| 6,893,643 | B2 | 5/2005 | Andino-Pavlovsky | A61K 39/12 |
| 6,962,708 | B1 | 11/2005 | Chambers | C12N 7/01 |
| 7,049,428 | B1 | 5/2006 | Rice | C07H 21/00 |
| 7,060,280 | B2 | 6/2006 | Lee | A61K 39/00 |
| 7,227,011 | B2 | 6/2007 | Chang | C07H 21/04 |
| 7,417,136 | B1 | 8/2008 | Chang | C07H 21/04 |
| 7,521,177 | B2 | 4/2009 | Chang | C12Q 1/70 |
| 7,632,510 | B2 | 12/2009 | Chang | A61K 39/12 |
| 7,662,394 | B2 | 2/2010 | Chang | A61K 39/12 |
| 2005/0002968 | A1 | 1/2005 | Monath et al. | |
| 2007/0031451 | A1 | 2/2007 | Slifka | A61K 39/12 |
| 2007/0269458 | A1 | 11/2007 | Guirakhoo et al. | |
| 2008/0241186 | A1 | 10/2008 | Chang | A61K 39/00 |
| 2008/0248064 | A1 | 10/2008 | Chang | A61K 39/12 |
| 2009/0263470 | A1 | 10/2009 | Coller | A61K 9/127 |
| 2010/0003273 | A1 | 1/2010 | Chang | A61K 39/193 |
| 2010/0040643 | A1 | 2/2010 | Chang | A61K 39/12 |
| 2010/0158938 | A1 | 6/2010 | Guirakhoo | A61K 39/295 |

FOREIGN PATENT DOCUMENTS

| | | |
|---|---|---|
| EP | WO 03054174 | 7/2003 |
| EP | 1 894 998 A1 | 5/2008 |
| WO | WO 2004/009764 | 1/2004 |
| WO | WO2011/014416 | 2/2011 |

OTHER PUBLICATIONS

International Search Report and Written Opinion, dated Mar. 2, 2011, for PCT/US2010/043010 (the parent case), 12 pages (in English).
Search History by International Searching Authority mail date Mar. 2, 2011, for PCT/US2010/043010 (the parent case), 7 pages (in English).
Schlesinger, Jacob J., et al. "Replication of yellow fever virus in the mouse central nervous system: comparison of neuroadapted and non-neuroadaped virus and partial sequence analysis of the neuroadapted strain," *Journal of General Virology*, 77, 1277-1285 (1996).
Lee, Eva, et al. "E Protein Domain III Determinants of Yellow Fever Virus 17D Vaccine Strain Enhance Binding to Glycosaminoglycans, Impede Virus Spread, and Attenuate Virulence," *Journal of Virology*, 6024-6033 (Jun. 2008).
Monath, Thomas P., et al. "Single Mutation in the Flavivirus Envelope Protein Hinge Region Increases Neurovirulence for Mice and Monkeys but Decreases Viscerotropism for Monkeys: Relevance to Development and Safety Testing of Live, Attenuated Vaccines," *Journal of Virology*, 1932-1943 (Feb. 2002).
International Preliminary Report on Patentability, dated Feb. 9, 2012, for PCT/US2010/043010 (the parent case, 8 pages (in English).
Kessler, N., et al, "Suitability of MDCK Cells Grown in a Serum-Free Medium for Influenza Virus Production." Brown F. Robertson JS, Schild GC, Wood JM (eds): Inactivated Influenza Vaccines Prepared in Cell Culture, Dev Biol Stand, Basel karger, 1999, vol. 98, pp. 13-21.
Merten, O-W., et al. "Production of Influenza Virus in Serum-Free Mammalian Cell Cultures." Brown F, Robertson JS, Schild GC, Wood JM (eds): Inactivated Influenza Vaccines Prepared in Cell Culture, Dev Biol Stand, Basel, Karger, 1999, vol. 98, pp. 23-37.
Rourou, Samia, et al. "A microcarrier cell culture process for propagating rabies virus in Vero cells grown in a stirred bioreactor under fully animal component free conditions." Elsevier Ltd.—Vaccine 25 (2007) 3879-3889.
Caij, A., et al. "High titre Hog Cholera virus production on Cytodex 3® microcarrier cultures." Archives of Virology © by Springer-Verlag 1989 Arch Virol (1989) 105: 113-118.
Berry, J.M., et al. "Production of Reovirus Type-1 and Type-3 from Vero Cells Grown on Solid and Macroporous Microcarriers." Biotechnology and Bioengineering, vol. 62, No. 1, Jan. 5, 1999, pp. 12-19.
Yokomizo, A.Y., et al. "Rabies Virus Production in High Vero Cell Density Cultures on Macroporous Microcarriers." Biotechnology and Bioengineering, vol. 85, No. 5, Mar. 5, 2004, pp. 506-515.

(Continued)

*Primary Examiner* — Stacy B. Chen

(57) ABSTRACT

The invention provides a an inactive, non-replicating vaccine comprising whole virion, chemically inactivated Yellow Fever virus which is inactivated using a method that ensures preservation of critical, neutralizing epitopes. The Yellow Fever virus has been adapted to propagate in cells to higher yields than the unadapted virus. The invention also provides methods for preventing Yellow Fever viral infection.

11 Claims, 73 Drawing Sheets

(56) References Cited

OTHER PUBLICATIONS

Sheets, Rebecca, "History and Characterization of the Vero Cell Line," A report prepared by CDR Rebecca Sheets, Ph.D., USPHS CBER/OVRR/DVRPA/VVB for the Vaccines and related Biological Products Advisory Committee Meeting to be held on May 12, 2000. Time Stamped: May 8, 2000.

International Search Report and Written Opinion, dated Aug. 18, 2011, for PCT/US2011/022347 (the parent case), 13 pages (in English).

Search History by International Searching Authority mail date Aug. 18, 2011, for PCT/US2011/022347 (the parent case), 3 pages (in English).

Wang, Eryu, et al. "Comparison of the genomes of the wild-type French viscerotropic strain of yellow fever virus with its vaccine derivative French neurotropic vaccine." *Journal of General Virology*, (1995) 76, 2749-2755.

Search Report and Written Opinion from corresponding EP Application No. 10804909.9-1405 dated Feb. 11, 2013.

Chang, G. J. et al., "Nucleotide sequence variation of the envelope protein gene identifies two distinct genotypes of yellow fever virus.", Journal of Virology, vol. 69, No. 9, pp. 5773-5780, Jan. 1, 1995.

Database UniProt [Online], "SubName: Full=Envelope glycoprotein; Flags:Fragment;" Dec. 15, 2009.

Souza, M., et al., Vaccine, vol. 27, No. 46, 2009, p. 6420-6423.

Monath, T., Vaccine, vol. 28, No. 22, 2010, p. 3827-3840.

Beasley, D., et al., Virus Research, vol. 176, No. 1-2, 2013, p. 280-284.

Monath, T., et al., American Journal of Tropical Medicine and Hygiene, vol. 83, No. 5, Suppl. S, 2010, p. 16.

Extended European Search Report dated Jan. 2, 2014 issued on corresponding EP application No. 11809985.2.

FIG. 3B

```
SEQ ID NO:1) P1_cons  : AGTAAATCCTGTGTGCTAATTGAGGTGCATTGCTCTGCAGTTGCTAGCCAATCCAGTTGCTAGGCAATAAACACATTTGGATTAA :  75
SEQ ID NO:2) P11_cons : AGTAAATCCTGTGTGCTAATTGAGGTGCATTGCTCTGCAGTTGCTAGCCAATCCAGTTGCTAGGCAATAAACACATTTGGATTAA :  75
                                 *         20         *         40         *         60         *

SEQ ID NO:1) P1_cons  : TTTTAATCGTTCGTTGAGCGATTAGCAGAGAACTGACCAGAACATGTCTGGTCGTAAAGCTCAGGGAAAAACCCT : 150
SEQ ID NO:2) P11_cons : TTTTAATCGTTCGTTGAGCGATTAGCAGAGAACTGACCAGAACATGTCTGGTCGTAAAGCTCAGGGAAAAACCCT : 150
                              80         *        100         *        120         *        140

SEQ ID NO:1) P1_cons  : GGGCGTCAATATGGTACGACGAGGAGTTCGCTCCTTGTCAAACAAATAAAACAAAAACAAATTGGAAA : 225
SEQ ID NO:2) P11_cons : GGGCGTCAATATGGTACGACGAGGAGTTCGCTCCTTGTCAAACAAATAAAACAAAAACAAACAAATTGGAAA : 225
                                 *        160         *        180         *        200         *        220

SEQ ID NO:1) P1_cons  : CAGACCTGGACCTTCAAGAGGTGTTCAAGGAGGATTTATCTTTTTCTTTTTGTTCAACA-TTTGACTGGAAAAAAGAT : 300
SEQ ID NO:2) P11_cons : CAGACCTGGACCTTCAAGAGGTGTTCAAGGAGGATTTATCTTTTTCTTTTTTTGTTCAACATTTTGACTGGAAAAAAGAT : 300
                              240         *        260         *        280         *        300

SEQ ID NO:1) P1_cons  : CACAGCCCACCTAAAGAGTTGTGGAAAATGCTGGACCCAAGACAAGGCTTGGCTGTTCTTAAGGAAAGTCAAGAG : 375
SEQ ID NO:2) P11_cons : CACAGCCCACCTAAAGAGTTGTGGAAAATGCTGGACCCAAGACAAGGCTTGGCTGTTCTTAAGGAAAGTCAAGAG : 375
                                 *        320         *        340         *        360         *

SEQ ID NO:1) P1_cons  : AGTGGTGGCCAGTTTGATGAGAGAGGATTGTCCTCAAGGAAACCCGTTCCCATGATGTTCTGACTGTGCAATTCCT : 450
SEQ ID NO:2) P11_cons : AGTGGTGGCCAGTTTGATGAGAGAGGATTGTCCTCAAGGAAACCCGTTCCCATGATGTTCTGACTGTGCAATTCCT : 450
                              380         *        400         *        420         *        440

SEQ ID NO:1) P1_cons  : AATTTTGGGAATGCTGTTGATGACGGTGGAGTGACCTTGGTGTGCGGAAAAACAGATGGTTGCTCCTAAATGTGAC : 525
SEQ ID NO:2) P11_cons : AATTTTGGGAATGCTGTTGATGACGGTGGAGTGACCTTGGTGTGCGGAAAAACAGATGGTTGCTCCTAAATGTGAC : 525
                                 *        460         *        480         *        500         *        520
```

FIG. 4A

```
SEQ ID NO:1) P1_cons  : ATCTGAGGACCTCGGGAAAACATTCTCTGTGGGCAACTGCACAGGCAACTGCACAACAAACATTTTGGAAGCCAAGTACTG : 600
SEQ ID NO:2) P11_cons : ATCTGAGGACCTCGGGAAAACATTCTCTGTGGGCAACTGCACAGGCAACTGCACAACAAACATTTTGGAAGCCAAGTACTG : 600

SEQ ID NO:1) P1_cons  : GTGCCCCAGACTTCAATGGAATACAACTGTCCCAATCTCAGTCCAAGAGAGGAGCCAGATGACATTGATTGCTGGTG : 675
SEQ ID NO:2) P11_cons : GTGCCCCAGACTTCAATGGAATGCAATGTCCCAATCTCAGTCCAAGAGAGGAGCCAGATGACATTGATTGCTGGTG : 675

SEQ ID NO:1) P1_cons  : CTATGGGGTGCAAAACGTTAGAGTCGCATATGGTAAGTGTGACTCAGCAGGCAGGTCTAGGAGGTCAAGAAGGGC : 750
SEQ ID NO:2) P11_cons : CTATGGGGTGCAAAACGTTAGAGTCGCATATGGTAAGTGTGACTCAGCAGGCAGGTCTAGGAGGTCAAGAAGGGC : 750

SEQ ID NO:1) P1_cons  : CATTGACTTGCCTACGCCATGAGAGTTTGAAGACCCGGCAAGAAAAATGGATGACTGGAAGAATCCGTCA : 825
SEQ ID NO:2) P11_cons : CATTGACTTGCCTACGCCATGAGAGTTTGAAGACCCGGCAAGAAAAATGGATGACTGGAAGAATGGGTGA : 825

SEQ ID NO:1) P1_cons  : AAGGCAACTCCAAAAGATTGAGAGATGGTTCGTGAGGAACCCCTTTTTTGCAGTGACGGCTCTGACCATTGCCTA : 900
SEQ ID NO:2) P11_cons : AAGGCAACTCCAAAAGATTGAGAGATGGTTCGTGAGGAACCCCTTTTTTGCAGTGACGGCTCTGACCATTGCCTA : 900

SEQ ID NO:1) P1_cons  : CCTTGTGGGAAGCAACATGACGCAACGAGTCGTGATTGCCCTGGTCTTGGCTGTTGGTCCGGCCTACTCAGC : 975
SEQ ID NO:2) P11_cons : CCTTGTGGGAAGCAACATGACGCAACGAGTCGTGATTGCCCTGGTCTTGGCTGTTGGTCCGGCCTACTCAGC : 975

SEQ ID NO:1) P1_cons  : TCACTGCATTGGAATTACTGACAGGGATTTCATTGAGGGGTGCATGGAGGAACTTGGGTTTCAGCTACCCTGGA : 1050
SEQ ID NO:2) P11_cons : TCACTGCATTGGAATTACTGACAGGGATTTCATTGAGGGGTGCATGGAGGAACTTGGGTTTCAGCTACCCTGGA : 1050
```

FIG. 4B

```
(SEQ ID NO:1) P1_cons   : GCAAGACAAGTGTGTCACTGTTTATGGCCCCTGACAAGCCTTCATTGGACACATCTCACTAGAGACAGTAGCCATTGA : 1125
(SEQ ID NO:2) P11_cons  : GCAAGACAAGTGTGTCACTGTTTATGGCCCCTGACAAGCCTTCATTGGACACATCTCACTAGAGACAGTAGCCATTGA : 1125

(SEQ ID NO:1) P1_cons   : TAGACCTGCTGAGGTGAGGAAAGTGTGTTACAATGCAGTTCTCACTCATGTGAAGATTAATGACAAGTGCCCCAG : 1200
(SEQ ID NO:2) P11_cons  : TAGACCTGCTGAGGTGAGGAAAGTGTGTTACAATGCAGTTCTCACTCATGTGAAGATTAATGACAAGTGCCCCAG : 1200

(SEQ ID NO:1) P1_cons   : CACTGGAGAGGCCCACCTAGCTGAAGAGAACGAAGGGACAATGCGTGCAAGCGCACTTATTCTGATAGAGGCTG : 1275
(SEQ ID NO:2) P11_cons  : CACTGGAGAGGCCCACCTAGCTGAAGAGAACGAAGGGACAATGCGTGCAAGCGCACTTATTCTGATAGAGGCTG : 1275

(SEQ ID NO:1) P1_cons   : GGGCAATGGCTGTGGCCTATTTGGGAAAGGGAGCATTGTGGCATGCCCCAAATTCACTGTGCCAAATCCATGAG : 1350
(SEQ ID NO:2) P11_cons  : GGGCAATGGCTGTGGCCTATTTGGGAAAGGGAGCATTGTGGCATGCCCCAAATTCACTGTGCCAAATCCATGAG : 1350

(SEQ ID NO:1) P1_cons   : TTTGTTTGAGGTTGATCAGACCAAAATTCAGTATGTCATCAGAGCACAATTGCATGTAGGGCCAAGCAGGAAAA : 1425
(SEQ ID NO:2) P11_cons  : TTTGTTTGAGGTTGATCAGACCAAAATTCAGTATGTCATCAGAGCACAATTGCATGTAGGGCCAAGCAGGAAAA : 1425

(SEQ ID NO:1) P1_cons   : TTGGACTACCGACATTAAGACTCTCAAGTTTGATGCCCCTCCAGGCTCCCAGGAAGTCGAGTTCATTGGGTATGG : 1500
(SEQ ID NO:2) P11_cons  : TTGGACTACCGACATTAAGACTCTCAAGTTTGATGCCCCTCCAGGCTCCCAGGAAGTCGAGTTCATTGGGTATGG : 1500

(SEQ ID NO:1) P1_cons   : AAAAGCTACACTGGAATGCCAGTGCAAACTGCGGTGGACTTTGGTAACAGTTACATCGCTGAGATGGAAACAGA : 1575
(SEQ ID NO:2) P11_cons  : AAAAGCTACACTGGAATGCCAGTGCAAACTGCGGTGGACTTTGGTAACAGTTACATCGCTGAGATGGAAACAGA : 1575
```

FIG. 4C

```
(SEQIDNO:1) P1_cons  : GAGCTGGATAGTGGACAGACAGTGGGCCCAGGACTTGACCCTGCCATGGCAGAGTGGAAGTGGCGGGGTGTGGAG : 1650
(SEQIDNO:2) P11_cons : GAGCTGGATAGTGGACAGACAGTGGGCCCAGGACTTGACCCTGCCATGGCAGAGTGGAAGTGGCGGGGTGTGGAG : 1650

(SEQIDNO:1) P1_cons  : AGAGATGCATCATCTTGTCGAATTTGAACCTCCGCATGCCGCCACTATCAGAGTACTGGCCCTGGAAACCACGA : 1725
(SEQIDNO:2) P11_cons : AGAGATGCATCATCTTGTCGAATTTGAACCTCCGCATGCCGCCACTATCAGAGTACTGGCCCTGGAAACCAGGA : 1725

(SEQIDNO:1) P1_cons  : AGGCTCCTTGAAAACAGCTCTTACTGCGCAATGAGGGTTACAAAGGACACAAATGACAACAACCTTTACAAACT : 1800
(SEQIDNO:2) P11_cons : AGGCTCCTTGAAAACAGCTCTTACTGCGCAATGAGGGTTACAAAGGACACAAATGACAACAACCTTTACAAACT : 1800

(SEQIDNO:1) P1_cons  : ACATGGTGGACATGTTTCTTGCAGAGTGAAATTGTCAGCTTTGACACTCAAGGGACATCCTACAAAATATGCAC : 1875
(SEQIDNO:2) P11_cons : ACATGGTGGACATGTTTCTTGCAGAGTGAAATTGTCAGCTTTGACACTCAAGGGACATCCTACAAAATATGCAC : 1875

(SEQIDNO:1) P1_cons  : TGACAAAATGTTTTTTTGTCAAGAACCCAACTGACTGGCCATGGCACTGTTGTGATGCAGGTGAAAGTGTCAAA : 1950
(SEQIDNO:2) P11_cons : TGACAAAATGTTTTTTTGTCAAGAACCCAACTGACTGGCCATGGCACTGTTGTGATGCAGGTGAAAGTGTCAAA : 1950

(SEQIDNO:1) P1_cons  : AGGAGCCCCCTGCAGGATTCCAGTGACTGATAGTCGATGATGATCTTACAGCGGCAATCAATAAAAGGCATTTTGGTTAC : 2025
(SEQIDNO:2) P11_cons : AGGAGCCCCCTGCAGGATTCCAGTGACTGATAGTCGATGATGATCTTACAGCGGCAATCAATAAAAGGCATTTTGGTTAC : 2025

(SEQIDNO:1) P1_cons  : AGTTAACCCCATCGCCTCAACCAATGATGATGAAGTGCTGATTGAGGTGAACCCACCTTTTGGAGACAGCTACAT : 2100
(SEQIDNO:2) P11_cons : AGTTAACCCCATCGCCTCAACCAATGATGATGAAGTGCTGATTGAGGTGAACCCACCTTTTGGAGACAGCTACAT : 2100
```

FIG. 4D

```
SEQ ID NO:1) P1_cons  : TATCGTTGGGAGAGGAGATTCACGTCTCACTTACCAGTGGCACAAAGAGGAAGCTCAATAGGAAAGTTGTTCAC : 2175
SEQ ID NO:2) P11_cons : TATCGTTGGGAGAGGAGATTCACGTCTCACTTACCAGTGGCACAAAGAGGAAGCTCAATAGGAAAGTTGT-TCAC : 2175

SEQ ID NO:1) P1_cons  : TCAGACCATGAAAGGCGTGAACGCCCTGGCCGTCATGGGAGACACCGCCTGGGATTTCAGCTCCGCTGGAGGGTT : 2250
SEQ ID NO:2) P11_cons : TCAGACCATGAAAGGCGTGAACGCCCTGGCCGTCATGGGAGACACCGCCTGGGATT-CAGCTCCGCTGGAGGGTT : 2250

SEQ ID NO:1) P1_cons  : CTTCACTTCGGTTGGGAAAGGAATTCATACGGTGTTTGGCTCTGCCTTTCAGGGGCTATTTGGCGGCTTGAACTG : 2325
SEQ ID NO:2) P11_cons : CTTCACTTCGGTTGGGAAAGGAATTCATACGGTGTTTGGCTCTGCCTTTCAGGGGCTATTTGGCGGCTTGAACTG : 2325

SEQ ID NO:1) P1_cons  : GATAACAAAGTCATCATGGGGCGGTACTTATATGGGTTGGCATCAACACAAGAAACATGACAATGTCCATGAG : 2400
SEQ ID NO:2) P11_cons : GATAACAAAGTCATCATGGGGCGGTACTTATATGGGTTGGCATCAACACAAGAAACATGACAATGTCCATGAG : 2400

SEQ ID NO:1) P1_cons  : CATGATCTTGGTAGGAGTGATCATGATGTTTTTGTCTCTAGGAGTTGGGCGGATCAAGGATGCGCCATCAACTT : 2475
SEQ ID NO:2) P11_cons : CATGATCTTGGTAGGAGTGATCATGATGTTTTTGTCTCTAGGAGTTGGGCGGATCAAGGATGCGCCATCAACTT : 2475

SEQ ID NO:1) P1_cons  : TGGCAAGAGAGAGCTCAAGTGCGGAGATGGTATCTTCATATTTAGAGACTCTGATGACTGAACAAGTACTC : 2550
SEQ ID NO:2) P11_cons : TGGCAAGAGAGAGCTCAAGTGCGGAGATGGTATCTTCATATTTAGAGACTCTGATGACTGAACAAGTACTC : 2550

SEQ ID NO:1) P1_cons  : ATACTATCCAGAAGATCCTGTGAAGCTTGCATCAATAGTGAAAGCCTCTCTTTTGAAGAAGAAGCCTAAA : 2625
SEQ ID NO:2) P11_cons : ATACTATCCAGAAGATCCTGTGAAGCTTGCATCAATAGTGAAAGCCTCTCTTTTGAAGAAGAAGCCTAAA : 2625
```

FIG. 4E

```
(SEQ ID NO:1) P1_cons  : TTCAGTTGACTCCCCTTGAGCATGAGATGAGATGTGGAGAAGCAGGGCAGATGAGATGAGATCAATGCCATTTTTGAGGAAAAACGA : 2700
(SEQ ID NO:2) P11_cons : TTCAGTTGACTCCCCTTGAGCATGAGATGAGATGTGGAGAAGCAGGCAGATGAGATGAGATCAATGCCATTTTTGAGGAAAAACGA : 2700

(SEQ ID NO:1) P1_cons  : GGTGGACATTTCTGTTGTCGTGCACGATGTCAAAGAATGTTTACCAGAGAGGAACTCATCCATTTTCCAGAATTCC : 2775
(SEQ ID NO:2) P11_cons : GGTGGACATTTCTGTTGTCGTGCAGGATGTCAAAGAATGTTTACCAGAGAGGAACTCATCCATTTTCCAGAATTCG : 2775

(SEQ ID NO:1) P1_cons  : GGATGGTCTGCAGTATGGTTGGAAGACTTGGGTAAGAACCTTGTGTTCTCCCCAGGGAGGAAGAATGGAAGCTT : 2850
(SEQ ID NO:2) P11_cons : GGATGGTCTGCAGTATGGTTGGAAGACTTGGGTAAGAACCTTGTGTTCTCCCCAGGGAGGAAGAATGGAAGCTT : 2850

(SEQ ID NO:1) P1_cons  : CATCATAGATGGAAAGTCCAGGAAAGATGCCCGTTTTCAAACCGGGTCTGGAATTCTTTCCAGATAGAGGAGTT : 2925
(SEQ ID NO:2) P11_cons : CATCATAGATGGAAAGTCCAGGAAAGATGCCCGTTTTCAAACCGGGTCTGGAATTCTTTCCAGATAGAGGAGTT : 2925

(SEQ ID NO:1) P1_cons  : TGGGACGGGAGTGTTCACCACACGCGTGTACATGGACGCCAGTCTTTGAATACACCATAGACTGCGATGGATCTAT : 3000
(SEQ ID NO:2) P11_cons : TGGGACGGGAGTGTTCACCACACGCGTGTACATGGACGCCAGTCTTTGAATACACCATAGACTGCGATGGATCTAT : 3000

(SEQ ID NO:1) P1_cons  : CTTGGGTGCAGCGGTGAACGGTGAAAAAAGAGTGCCCATGGCTCTCCAACATTTTGATGGGAAGTCATGAAGTAAA : 3075
(SEQ ID NO:2) P11_cons : CTTGGGTGCAGCGGTGAACGGTGAAAAAAGAGTGCCCATGGCTCTCCAACATTTTGATGGGAAGTCATGAAGTAAA : 3075

(SEQ ID NO:1) P1_cons  : TGGGACATGGATGATCCACACCTTGGAGGCATTAGATTACAAGGAGTGTGAGTGGCCACTGACGACATACGATTGG : 3150
(SEQ ID NO:2) P11_cons : TGGGACATGGATGATCCACACCTTGGAGGCATTAGATTACAAGGAGTGTGAGTGGCCACTGACGACATACGATTGG : 3150
```

FIG. 4F

```
SEQIDNO:1) P1_cons    : AACATCAGTTGAAGAGAGTGAAATGTTCATGCCGAGATCAATCGGAGGCCCAGTTAGCTCTCACAATCATATCCC :  3225
SEQIDNO:2) P11_cons   : AACATCAGTTGAAGAGAGTGAAATGTTCATGCCGAGATCAATCGGAGGCCCAGTTAGCTCTCACAATCATATCCC :  3225
                                3160          *          3180          *          3200          *          3220

SEQIDNO:1) P1_cons    : TGGATACAAGGTTCAGACGAACGGACCTTGGATGCAGTACCACTAGAAGTGAAGAGAGAAGCTTGCCCAGGGAC  :  3300
SEQIDNO:2) P11_cons   : TGGATACAAGGTTCAGACGAACGGACCTTGGATGCAGTACCACTAGAAGTGAAGAGAGAAGCTTGCCCAGGGAC  :  3300
                                 *          3240          *          3260          *          3280          *          3300

SEQIDNO:1) P1_cons    : TAGCGTGATCATTGATGGCAACTGTGATGGACGGGAAAATCAACCAGATCCACCACGATAGCGGGAAAGTTAT  :  3375
SEQIDNO:2) P11_cons   : TAGCGTGATCATTGATGGCAACTGTGATGGACGGGAAAATCAACCAGATCCACCACGATAGCGGGAAAGTTAT  :  3375
                                 *          3320          *          3340          *          3360          *

SEQIDNO:1) P1_cons    : TCCTGAATGGTGTTGCCGCTCCTGCACAATCCGCCCTGTGAGCTTCCATGGTAGTGATGGGTGTTGGTATCCCAT :  3450
SEQIDNO:2) P11_cons   : TCCTGAATGGTGTTGCCGCTCCTGCACAATCCGCCCTGTGAGCTTCCATGGTAGTGATGGGTGTTGGTATCCCAT :  3450
                            3380          *          3400          *          3420          *          3440          *

SEQIDNO:1) P1_cons    : GGAAATTAGGCCAAGGAAAACGCATGAAAGCCATCTGGTGCGCTCCTGGGTTACAGCTGGAGAAATACATGCTGT :  3525
SEQIDNO:2) P11_cons   : GGAAATTAGGCCAAGGAAAACGCATGAAAGCCATCTGGTGCGCTCCTGGGTTACAGCTGGAGAAATACATGCTGT :  3525
                                 *          3460          *          3480          *          3500          *          3520

SEQIDNO:1) P1_cons    : CCCTTTTGGTTTGGTGAGCATGATGATGAGCAATGGAAGTGTCCTAAGGAAAAGACAGGGACCAAAGCAAATGTT :  3600
SEQIDNO:2) P11_cons   : CCCTTTTGGTTTGGTGAGCATGATGATGAGCAATGGAAGTGTCCTAAGGAAAAGACAGGGACCAAAGCAAATGTT :  3600
                                 *          3540          *          3560          *          3580          *          3600

SEQIDNO:1) P1_cons    : GGTTGGAGGAGTAGTGCTCTTGGGAGCAAGTAACCTGGTCGGCAAGTAACTCTCCTTGATTTGCTGAAACTCACAGT :  3675
SEQIDNO:2) P11_cons   : GGTTGGAGGAGTAGTGCTCTTGGGAGCAAGTAACCTGGTCGGCAAGTAACTCTCCTTGATTTGCTGAAACTCACAGT :  3675
                                 *          3620          *          3640          *          3660          *
```

FIG. 4G

```
                        3680         *        3700         *        3720         *        3740         *
SEQIDNO:1) P1_cons  : GGCTGTGTGGATTGCATTTCCATGAGATGAACAATGGAGGAGACGCCATGTATATGGCGTTGATTGCTGCCTTTC :  3750
SEQIDNO:2) P11_cons : GGCTGTGTGGATTGCATTTCCATGAGATGAACAATGGAGGAGACGCCATGTATATGGCGTTGATTGCTGCCTTTC :  3750

3760         *        3780         *        3800         *        3820
SEQIDNO:1) P1_cons  : AATCAGACCAGGGCTGCTCATCGGCTTTGGGCTCAGGACCCTATGGAGCCCTTCGGGAACGCCTTGTGCTGACCCT :  3825
SEQIDNO:2) P11_cons : AATCAGACCAGGGCTGCTCATCGGCTTTGGGCTCAGGACCCTATGGAGCCCTTCGGGAACGCCTTGTGCTGACCCT :  3825

*        3840         *        3860         *        3880         *        3900
SEQIDNO:1) P1_cons  : AGGAGCAGCCATGGTGGAGATTGCCTTGGGTGGCGTGATGGGCGGCCTGTGGAAGTATCTAAATGCAGTTTCTCT :  3900
SEQIDNO:2) P11_cons : AGGAGCAGCCATGGTGGAGATTGCCTTGGGTGGCGTGATGGGCGGCCTGTGGAAGTATCTAAATGCAGTTTCTCT :  3900

*        3920         *        3940         *        3960         *
SEQIDNO:1) P1_cons  : CTGCATCCTGACAATAAATGCTGTTGCTTCTAGGAAAGCATCAAATACCATCTTGCCCCTCATGGCTCTGTTGAC :  3975
SEQIDNO:2) P11_cons : CTGCATCCTGACAATAAATGCTGTTGCTTCTAGGAAAGCATCAAATACCATCTTGCCCCTCATGGCTCTGTTGAC :  3975

3980         *        4000         *        4020         *        4040         *
SEQIDNO:1) P1_cons  : ACCTGTCACTATGGCTGAGGTGAGACTTGCCGCAATGTTCTTTTGTGCCGTGGTTATCATAGGGGTCCTTCACCA :  4050
SEQIDNO:2) P11_cons : ACCTGTCACTATGGCTGAGGTGAGACTTGCCGCAATGTTCTTTTGTGCCGTGGTTATCATAGGGGTCCTTCACCA :  4050

*        4060         *        4080         *        4100         *        4120
SEQIDNO:1) P1_cons  : GAATTTCAAGGACACCTCCATGCAGAAGACTATACCTCTGGTGGCCCTCACACTCTTACCTGGGCTTGAC :  4125
SEQIDNO:2) P11_cons : GAATTTCAAGGACACCTCCATGCAGAAGACTATACCTCTGGTGGCCCTCACACTCTTACCTGGGCTTGAC :  4125

*        4140         *        4160         *        4180         *        4200
SEQIDNO:1) P1_cons  : ACAACCTTTTTTGGGCCTGTGTGCATTTCTGGCAACCCGCATATTTGGGCGAAGGAGTATCCCAGTGAATGAGGC :  4200
SEQIDNO:2) P11_cons : ACAACCTTTTTTGGGCCTGTGTGCATTTCTGGCAACCCGCATATTTGGGCGAAGGAGTATCCCAGTGAATGAGGC :  4200
```

FIG. 4H

```
EQIDNO:1) P1_cons  : ACTCGCAGCAGCTGGTCTAGTGGGAGTGCTGGCAGGACTGGCTTTTCAGGAGATGGAGAACTTCCTTGGTCCGAT : 4275
EQIDNO:2) P11_cons : ACTCGCAGCAGCTGGTCTAGTGGGAGTGCTGGCAGGACTGGCTTTTCAGGAGATGGAGAACTTCCTTGGTCCGAT : 4275
                                    4220          *         4240          *         4260          *
                     4280          *         4300          *         4320          *         4340
EQIDNO:1) P1_cons  : TGCAGTTGGAGGACTCCTGATGATGCTGGTTAGCGTGGCTGGATGGGCTGGATGGGCTAGAGCTCAAGAAGCTTGG : 4350
EQIDNO:2) P11_cons : TGCAGTTGGAGGACTCCTGATGATGCTGGTTAGCGTGGCTGGATGGGCTGGATGGGCTAGAGCTCAAGAAGCTTGG : 4350

EQIDNO:1) P1_cons  : TGAAGTTTCATGGGAACAGGAGGAGGCGGAGATCAGCGGGAGTTCCGCCCCGCTATGATGTGGCACTCAGTGAACAAGG : 4425
EQIDNO:2) P11_cons : TGAAGTTTCATGGGAAGAGGAGGAGGCGGAGATCAGCGGGAGTTCCGCCCCGCTATGATGTGGCACTCAGTGAACAAGG : 4425
                          *         4360          *         4380          *         4400          *         4420

4440          *         4460          *         4480          *         4500
EQIDNO:1) P1_cons  : GGAGTTCAAGCTGCTTTCTGAAGAGAAAGTGCCATGGGACCAGGTTGTGATGACCTCGCTGGCCTTGGTTGGGGC : 4500
EQIDNO:2) P11_cons : GGAGTTCAAGCTGCTTTCTGAAGAGAAAGTGCCATGGGACCAGGTTGTGATGACCTCGCTGGCCTTGGTTGGGGC : 4500

EQIDNO:1) P1_cons  : TGCCCTCCATCCATTTGCTCTTCTGCTTGCTCGTGGGCTGTGTTTCATGTCAGGGGAGCTAGGAGAAGTGG : 4575
EQIDNO:2) P11_cons : TGCCCTCCATCCATTTGCTCTTCTGCTTGCTCGTGGGCTGTGTTTCATGTCAGGGGAGCTAGGAGAAGTGG : 4575
                          *         4520          *         4540          *         4560          *

4580          *         4600          *         4620          *         4640
EQIDNO:1) P1_cons  : GGATGTCTTGTGGGATATTCCCACTCCTAAGATCATCGAGGAATGTGAACATCTGAGGATGGGATTTATGGCAT : 4650
EQIDNO:2) P11_cons : GGATGTCTTGTGGGATATTCCCACTCCTAAGATCATCGAGGAATGTGAACATCTGAGGATGGGATTTATGGCAT : 4650

EQIDNO:1) P1_cons  : ATTCCAGTCAACCTTCTTGGGGCCTCCCAGCGAGGAGTGGCACAGGAGGGGTGTTCCACACAATGTG : 4725
EQIDNO:2) P11_cons : ATTCCAGTCAACCTTCTTGGGGCCTCCCAGCGAGGAGTGGCACAGGAGGGGTGTTCCACACAATGTG : 4725
                          *         4660          *         4680          *         4700          *         4720
```

FIG. 4I

```
SEQIDNO:1) P1_cons   : GCATGTCACAAGAGAAGCTTTCCTTGTCAGGAATGGCAAGAAGTTGATTCCATCTTGGGCTTCAGTAAAGGAAGA : 4800
SEQIDNO:2) P11_cons  : GCATGTCACAAGAGAAGCTTTCCTTGTCAGGAATGGCAAGAAGTTGATTCCATCTTGGGCTTCAGTAAAGGAAGA : 4800
                                    4740               *              4760               *              4780               *             4800

SEQIDNO:1) P1_cons   : CCTTGTCGCCTATGTGGCTCATGGAAGTTGGAAGGCAGATGGGATGGAGAGGAAGAGTCCAGTTGATCGCGGC   : 4875
SEQIDNO:2) P11_cons  : CCTTGTCGCCTATGTGGCTCATGGAAGTTGGAAGGCAGATGGGATGGAGAGGAAGAGTCCAGTTGATCGCGGC   : 4875
                                    *              4820               *              4840               *              4860               *

SEQIDNO:1) P1_cons   : TGTTCCAGGAAAGAACGTGGTCAACGTCCAGACAAAACCGAGCTTGTTCAAAGTGAGGAATGGGGAGAAATCGG  : 4950
SEQIDNO:2) P11_cons  : TGTTCCAGGAAAGAACGTGGTCAACGTCCAGACAAAACCGAGCTTGTTCAAAGTGAGGAATGGGGAGAAATCGG  : 4950
                                   4880               *              4900               *              4920               *              4940

SEQIDNO:1) P1_cons   : GGCTGTCGCTCTTGACTATCCGAGTGGCACTTCAGGATCTCCTATTGTTAACAGGAACGGAGAGGTGATTGGGCT : 5025
SEQIDNO:2) P11_cons  : GGCTGTCGCTCTTGACTATCCGAGTGGCACTTCAGGATCTCCTATTGTTAACAGGAACGGAGAGGTGATTGGGCT : 5025
                                    *              4960               *              4980               *              5000               *

SEQIDNO:1) P1_cons   : GTACGGCAATGGCATCCTTGTGTCGGTGACAACTCCTTCGTGTCCGCCATATCCCAGACTGAGGTCAAGGAAGG  : 5100
SEQIDNO:2) P11_cons  : GTACGGCAATGGCATCCTTGTGTCGGTGACAACTCCTTCGTGTCCGCCATATCCCAGACTGAGGTCAAGGAAGG  : 5100
                                   5040               *              5060               *              5080               *              5100

SEQIDNO:1) P1_cons   : AAAGGAGGAGCTCCAAGAGATCCCAAGACAATGCTAAAGAAGGAATGACAACTGTCCTTCCTTGATTTTCATCCTGGAGC : 5175
SEQIDNO:2) P11_cons  : AAAGGAGGAGCTCCAAGAGATCCCAAGACAATGCTAAAGAAGGAATGACAACTGTCCTTCCTTGATTTTCATCCTGGAGC : 5175
                                    *              5120               *              5140               *              5160               *

SEQIDNO:1) P1_cons   : TGGGAAGACAAGAGCGTTTCCTCCCACAGATCTTGGCCGAGTGCGCACGGAGACGCTTGCGCACTCTTGTGTTGGC : 5250
SEQIDNO:2) P11_cons  : TGGGAAGACAAGAGCGTTTCCTCCCACAGATCTTGGCCGAGTGCGCACGGAGACGCTTGCGCACTCTTGTGTTGGC : 5250
                                   5180               *              5200               *              5220               *              5240
```

FIG. 4J

```
(SEQ ID NO:1) P1_cons  : CCCCACCAGGGTTGTTCTTTTCTGAAATGAAGGAGGCTTTTCACGGCCTGACGTGAAATTCCACACAGGCTTT : 5325
(SEQ ID NO:2) P11_cons : CCCCACCAGGGTTGTTCTTTTCTGAAATGAAGGAGGCTTTTCACGGCCTGACGTGAAATTCCACACAGGCTTT : 5325
                                 5260            *           5280            *           5300            *           5320

(SEQ ID NO:1) P1_cons  : TTCCGCTCACGGCAGCGGGAGAGAAGTCATTGATGCTATGTGCCATGCCACCCTAACTTACAGGATGTTGGAACC : 5400
(SEQ ID NO:2) P11_cons : TTCCGCTCACGGCAGCGGGAGAGAAGTCATTGATGCTATGTGCCATGCCACCCTAACTTACAGGATGTTGGAACC : 5400
                                 *           5340            *           5360            *           5380            *           5400

(SEQ ID NO:1) P1_cons  : AACTAGGGTTGTTAACTGGGAAGTGATGATCATTATGAAGCCCATTTTTGGATCCAGCTAGCATAGCCGCTAG : 5475
(SEQ ID NO:2) P11_cons : AACTAGGGTTGTTAACTGGGAAGTGATGATCATTATGAAGCCCATTTTTGGATCCAGCTAGCATAGCCGCTAG : 5475
                                         5420            *           5440            *           5460            *

(SEQ ID NO:1) P1_cons  : AGGTTGGGCAGCGCACAGAGCTAGGGCAAATGAAAGTGCAACAATCTTGATGACAGCCACACCGCCTGGGACTAG : 5550
(SEQ ID NO:2) P11_cons : AGGTTGGGCAGCGCACAGAGCTAGGGCAAATGAAAGTGCAACAATCTTGATGACAGCCACACCGCCTGGGACTAG : 5550
                                 5480            *           5500            *           5520            *           5540            *

(SEQ ID NO:1) P1_cons  : TGATGAATTTCCACATTCAAATGGTGAAATAGAAGATGTTCAAACGGACATACCCAGTGAGCCCTGAACACAGG : 5625
(SEQ ID NO:2) P11_cons : TGATGAATTTCCACATTCAAATGGTGAAATAGAAGATGTTCAAACGGACATACCCAGTGAGCCCTGAACACAGG : 5625
                                         5560            *           5580            *           5600            *           5620

(SEQ ID NO:1) P1_cons  : GCATGACTGGATCCTGGCTGACAAAAGGCCCACGGCCATGGTTCCTTCCATCCATCAGAGCTGCAAATGTCATGGC : 5700
(SEQ ID NO:2) P11_cons : GCATGACTGGATCCTGGCTGACAAAAGGCCCACGGCCATGGTTCCTTCCATCCATCAGAGCTGCAAATGTCATGGC : 5700
                                 *           5640            *           5660            *           5680            *           5700

(SEQ ID NO:1) P1_cons  : TGCCTCTTTGCGTAAGCCTGAAGCTGGAAAGAGTGTGGTGGTCCTGAACAGGAAAACCTTTGAGAGAGAATACCCCACGAT : 5775
(SEQ ID NO:2) P11_cons : TGCCTCTTTGCGTAAGCCTGAAGCTGGAAAGAGTGTGGTGGTCCTGAACAGGAAAACCTTTGAGAGAGAATACCCCACGAT : 5775
                                         5720            *           5740            *           5760            *
```

FIG. 4K

```
EQIDNO:1) P1_cons   : AAAGCAGAAGAAACCTGACTTTATATTGGCCACTGACATAGCTGAAATGGGAGCCAACCTTTGCTTGGAGCGAGT : 5850
EQIDNO:2) P11_cons  : AAAGCAGAAGAAACCTGACTTTATATTGGCCACTGACATAGCTGAAATGGGAGCCAACCTTTGCTTGGAGCGAGT : 5850

EQIDNO:1) P1_cons   : GCTGGATTGCAGGAGACGGCTTTTAAGCCTGCTTGTGGATGAAGGGAGGAAGGTGGCAATAAAAAGGGCCACTTCG : 5925
EQIDNO:2) P11_cons  : GCTGGATTGCAGGAGACGGCTTTTAAGCCTGCTTGTGGATGAAGGGAGGAAGGTGGCAATAAAAAGGGCCACTTCG : 5925

EQIDNO:1) P1_cons   : TATCTCCGCATCCTCTGCTGCTCAAAGGAGGGGGCGCATTGGGAGAAATCCCAACAGAGATGGAGACTCATACTA : 6000
EQIDNO:2) P11_cons  : TATCTCCGCATCCTCTGCTGCTCAAAGGAGGGGGCGCATTGGGAGAAATCCCAACAGAGATGGAGACTCATACTA : 6000

EQIDNO:1) P1_cons   : CTATTCTGAGCCTACAAGTGAAAATAATGCCCACCACGTCTGCTGGTTGGAGGCCTCAATGCTCTTGGACAACAT : 6075
EQIDNO:2) P11_cons  : CTATTCTGAGCCTACAAGTGAAAATAATGCCCACCACGTCTGCTGGTTGGAGGCCTCAATGCTCTTGGACAACAT : 6075

EQIDNO:1) P1_cons   : GGAGGTGAGGGGTGGAATGGTCGCCCCCACTCTCTATGCGTTGAAGGAACTAAAACACCAGTTTCCCCTGGTGAAAT : 6150
EQIDNO:2) P11_cons  : GCAGGTGAGGGGTGGAATGGTCGCCCCCACTCTCTATGCGTTGAAGGAACTAAAACACCAGTTTCCCCTGGTGAAAT : 6150

EQIDNO:1) P1_cons   : GAGACTGAGGGATGACCAGAGGAAAGTCTTCAGAGAGAACTAGTGAGAATTGTGACCTGCCCGTTTGGCTTTCGTG : 6225
EQIDNO:2) P11_cons  : GAGACTGAGGGATGACCAGAGGAAAGTCTTCAGAGAGAACTAGTGAGAATTGTGACCTGCCCGTTTGGCTTTCGTG : 6225

EQIDNO:1) P1_cons   : GCAAGTGGCCAAGGCTGGTTGAAGACGAATGATCGTAAGTGGTGTTTTGAAGGCCCTGAGGAACATGAGATCTT : 6300
EQIDNO:2) P11_cons  : GCAAGTGGCCAAGGCTGGTTGAAGACGAATGATCGTAAGTGGTGTTTTGAAGGCCCTGAGGAACATGAGATCTT : 6300
```

FIG. 4L

```
                                    *        20         *        40         *
SEQ ID NO:3) P1_transla  : MSGRKAQGKTLGVNMVRRGVRSLSNKIKQKTKQIGNRPGPSRGVQGFIFFFLFNILTGKKITAHLKRLWKMLD :  73
SEQ ID NO:4) P1l_transl  : MSGRKAQGKTLGVNMVRRGVRSLSNKIKQKTKQIGNRPGPSRGVQGFIFFFLFNILTGKKITAHLKRLWKMLD :  73
SEQ ID NO:5) B-P1_prM-E  : ------------------------------------------------------------------------ :   -
SEQ ID NO:6) B3-P1l_prM  : ------------------------------------------------------------------------ :   -

*        80         *       100         *       120         *       140
SEQ ID NO:3) P1_transla  : PRQGLAVLRKVKRVVASLMRGLSSRKRRSHDVLTVQFLILGMLLMTGGVTLVRKNRWLLLNVTSEDLGKTFSV : 146
SEQ ID NO:4) P1l_transl  : PRQGLAVLRKVKRVVASLMRGLSSRKRRSHDVLTVQFLILGMLLMTGGVTLVRKNRWLLLNVTSEDLGKTFSV : 146
SEQ ID NO:5) B-P1_prM-E  : ------------------------------ILGMLLMTGGVTLVRKNRWLLLNVTSEDLGKTFSV :  35
SEQ ID NO:6) B3-P1l_prM  : -------------------------------GMLLMTGGVTLVRKNRWLLLNVTSEDLGKTFSV :  33

*       160         *       180         *       200         *       22
SEQ ID NO:3) P1_transla  : GTGNCTTNILEAKYWCPDSMEYNCPNLSPREEPDDIDCWCYGVENVRVAYGKCDSAGRSRSRRAIDLPTHEN : 219
SEQ ID NO:4) P1l_transl  : GTGNCTTNILEAKYWCPDSMEYNCPNLSPREEPDDIDCWCYGVENVRVAYGKCDSAGRSRSRRAIDLPTHEN : 219
SEQ ID NO:5) B-P1_prM-E  : GTGNCTTNILEAKYWCPDSMEYNCPNLSPREEPDDIDCWCYGVENVRVAYGKCDSAGRSRSRRAIDLPTHEN : 108
SEQ ID NO:6) B3-P1l_prM  : GTGNCTTNILEAKYWCPDSMEYNCPNLSPREEPDDIDCWCYGVENVRVAYGKCDSAGRSRSRRAIDLPTHEN : 106

0        *       240         *       260         *       280         *
SEQ ID NO:3) P1_transla  : HGLKTRQEKWMTGRMGERQLQKIERWFVRNPFFAVTALTIAYLVGSNMTQRVVIALLVLAVGPAYSAHCIGIT : 292
SEQ ID NO:4) P1l_transl  : HGLKTRQEKWMTGRMGERQLQKIERWFVRNPFFAVTALTIAYLVGSNMTQRVVIALLVLAVGPAYSAHCIGIT : 292
SEQ ID NO:5) B-P1_prM-E  : HGLKTRQEKWMTGRMGERQLQKIERWFVRNPFFAVTALTIAYLVGSNMTQRVVIALLVLAVGPAYSAHCIGIT : 181
SEQ ID NO:6) B3-P1l_prM  : HGLKTRQEKWMTGRMGERQLQKIERWFVRNPFFAVTALT'IAYLVGSNMTQRVVIALLVLAVGPAYSAHCIGIT : 179

*       300         *       320         *       340         *       360
SEQ ID NO:3) P1_transla  : DRDFIEGVHGGTWVSATLEQDKCVTVMAPDKPSLDISLETVAIDRPAEVRKVCYNAVLTHVKINDKCPSTGEA : 365
SEQ ID NO:4) P1l_transl  : DRDFIEGVHGGTWVSATLEQDKCVTVMAPDKPSLDISLETVAIDRPAEVRKVCYNAVLTHVKINDKCPSTGEA : 365
SEQ ID NO:5) B-P1_prM-E  : DRDFIEGVHGGTWVSATLEQDKCVTVMAPDKPSLDISLETVAIDRPAEVRKVCYNAVLTHVKINDKCPSTGEA : 254
SEQ ID NO:6) B3-P1l_prM  : DRDFIEGVHGGTWVSATLEQDKCVTVMAPDKPSLDISLETVAIDRPAEVRKVCYNAVLTHVKINDKCPSTGEA : 252
```

```
SEQIDNO:3) P1_transla : FGGLNWITKVIMGAVLIWVGINTRNMTMSMSMILVGVIMMFLSLGVGADQGCAINFGKRELKCGDGIFIFRDS : 803
SEQIDNO:4) P11_transl : FGGLNWITKVIMGAVLIWVGINTRNMTMSMSMILVGVIMMFLSLGVGADQGCAINFGKRELKCGDGIFIFRDS : 803
SEQIDNO:5) B-P1_prM-E : FGGLNWITKVIMGAVLIWVGINTRNMTMSMSMILVGVIMMFLSLGVGADQGCAINFGKRELKCGD-------- : 684
SEQIDNO:6) B3-P11_prM : FGGLNWITKVIMGAVLIWVGINTRNMTMSMSMILVGVIMMFLSLGVGADQGCAINFGKREL----------- : 678

SEQIDNO:3) P1_transla : DDWLNKYSYYPEDPVKLASIVKASFEEGKCGLNSVDSLEHEMWRSRADEINAIFEENEVDISVVVQDPKNVYQ : 876
SEQIDNO:4) P11_transl : DDWLNKYSYYPEDPVKLASIVKASFEEGKCGLNSVDSLEHEMWRSRADEINAIFEENEVDISVVVQDPKNVYQ : 876
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : RGTHPFSRIRDGLQYGWKTWGKNLVFSPGRKNGSFIIDGKSRKECPFSNRVWNSFQIEEFGTGVFTTRVVMDA : 949
SEQIDNO:4) P11_transl : RGTHPFSRIRDGLQYGWKTWGKNLVFSPGRKNGSFIIDGKSRKECPFSNRVWNSFQIEEFGTGVFTTRVVMDA : 949
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : VFEYTIDCDGSILGAAVNGKKSAHGSPTFWMGSHEVNGTWMIHTLEALDYKECEWPLTHTIGTSVEESEMFMP : 1022
SEQIDNO:4) P11_transl : VFEYTIDCDGSILGAAVNGKKSAHGSPTFWMGSHEVNGTWMIHTLEALDYKECEWPLTHTIGTSVEESEMFMP : 1022
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : RSIGGPVSSHNHIPGYKVQTNGPWMQVPLEVKREACPGTSVIIDGNCDGRGKSTRSTTDSGKVIPEWCCRSCT : 1095
SEQIDNO:4) P11_transl : RSIGGPVSSHNHIPGYKVQTNGPWMQVPLEVKREACPGTSVIIDGNCDGRGKSTRSTTDSGKVIPEWCCRSCT : 1095
SEQIDNO:5) B-P1_prM-E : ------------------------------------------------------------------------ : -
SEQIDNO:6) B3-P11_prM : ------------------------------------------------------------------------ : -
```

FIG. 5C

```
SEQIDNO:3) P1_transla : MPPVSFHGSDGCWYPMEIRPRKTHESHLVRSWVTAGEIHAVPFGLVSMMIAMEVVLRKRQGPKQMLVGGVVLL : 1168
SEQIDNO:4) P11_transl : MPPVSFHGSDGCWYPMEIRPRKTHESHLVRSWVTAGEIHAVPFGLVSMMIAMEVVLRKRQGPKQMLVGGVVLL : 1168
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : GAMLVGQVTLLDLLKLTVAVGLHFHEMNNGGDAMYMALIAAFSIRPGLLIGFGLRTLWSPRERLVLTLGAAMV : 1241
SEQIDNO:4) P11_transl : GAMLVGQVTLLDLLKLTVAVGLHFHEMNNGGDAMYMALIAAFSIRPGLLIGFGLRTLWSPRERLVLTLGAAMV : 1241
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : EIALGGVMGGLWKYINAVSLCILTINAVASRKASNTILPLMALLTPVTMAEVRLAAMFFCAVVIIGVLHQNFK : 1314
SEQIDNO:4) P11_transl : EIALGGVMGGLWKYINAVSLCILTINAVASRKASNTILPLMALLTPVTMAEVRLAAMFFCAVVIIGVLHQNFK : 1314
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : DTSMQKTIPLVALTLTSYLGLTQPFLGLCAFLATRIFGRRSIPVNEALAAAGLVGVLAGLAFQEMENFLGPIA : 1387
SEQIDNO:4) P11_transl : DTSMQKTIPLVALTLTSYLGLTQPFLGLCAFLATRIFGRRSIPVNEALAAAGLVGVLAGLAFQEMENFLGPIA : 1387
SEQIDNO:5) B-P1_prM-E : ------------------------------------------------------------------------ : -
SEQIDNO:6) B3-P11_prM : ------------------------------------------------------------------------ : -

SEQIDNO:3) P1_transla : VGGLLMMLVSVAGRVDGLELKKLGEVSWEEEAEISGSSARYDVALSEQGEFKLLSEEKVPWDQVVMTSLALVG : 1460
SEQIDNO:4) P11_transl : VGGLLMMLVSVAGRVDGLELKKLGEVSWEEEAEISGSSARYDVALSEQGEFKLLSEEKVPWDQVVMTSLALVG : 1460
SEQIDNO:5) B-P1_prM-E : ------------------------------------------------------------------------ : -
SEQIDNO:6) B3-P11_prM : ------------------------------------------------------------------------ : -
```

FIG. 5D

```
                           *         1480         *         1500         *         1520         *
(SEQIDNO:3) P1_transla : AALHPFALLLVLAGWLFHVRGARRSGDVLWDIPTPKIIEECEHLEDGIYGIFQSTFLGASQRGVGVAQGGVFH : 1533
(SEQIDNO:4) P11_transl : AALHPFALLLVLAGWLFHVRGARRSGDVLWDIPTPKIIEECEHLEDGIYGIFQSTFLGASQRGVGVAQGGVFH : 1533
(SEQIDNO:5) B-P1_prM-E : ------------------------------------------------------------------------ : -
(SEQIDNO:6) B3-P11_prM : ------------------------------------------------------------------------ : -

*         1540         *         1560         *         1580         *         1600
(SEQIDNO:3) P1_transla : TMWHVTRGAFLVRNGKKLIPSWASVKEDLVAYGGSWKLEGRWDGEEEVQLIAAVPGKNVVNVQTKPSLFKVRN : 1606
(SEQIDNO:4) P11_transl : TMWHVTRGAFLVRNGKKLIPSWASVKEDLVAYGGSWKLEGRWDGEEEVQLIAAVPGKNVVNVQTKPSLFKVRN : 1606
(SEQIDNO:5) B-P1_prM-E : ------------------------------------------------------------------------ : -
(SEQIDNO:6) B3-P11_prM : ------------------------------------------------------------------------ : -

*         1620         *         1640         *         1660         *         168
(SEQIDNO:3) P1_transla : GGEIGAVALDYPSGTSGSPIVNRNGEVIGLYGNILVGDNSFVSAISQTEVKEEGKEELQEIPTMLKKGMTTV : 1679
(SEQIDNO:4) P11_transl : GGEIGAVALDYPSGTSGSPIVNRNGEVIGLYGNILVGDNSFVSAISQTEVKEEGKEELQEIPTMLKKGMTTV : 1679
(SEQIDNO:5) B-P1_prM-E : ------------------------------------------------------------------------ : -
(SEQIDNO:6) B3-P11_prM : ------------------------------------------------------------------------ : -

0         *         1700         *         1720         *         1740         *
(SEQIDNO:3) P1_transla : LDFHPGAGKTRRFLPQIIAECARRRLRTIVLAPTRVVLSEMKEAFHGLDVKFHTQAFSAHGSGREVIDAMCHA : 1752
(SEQIDNO:4) P11_transl : LDFHPGAGKTRRFLPQIIAECARRRLRTIVLAPTRVVLSEMKEAFHGLDVKFHTQAFSAHGSGREVIDAMCHA : 1752
(SEQIDNO:5) B-P1_prM-E : ------------------------------------------------------------------------ : -
(SEQIDNO:6) B3-P11_prM : ------------------------------------------------------------------------ : -

*         1760         *         1780         *         1800         *         1820
(SEQIDNO:3) P1_transla : TLTYRMLEPTRVVNWEVIIMDEAHFLDPASIAARGWAAHRARANESATILMTATPPGTSDEFPHSNGEIEDVQ : 1825
(SEQIDNO:4) P11_transl : TLTYRMLEPTRVVNWEVIIMDEAHFLDPASIAARGWAAHRARANESATILMTATPPGTSDEFPHSNGEIEDVQ : 1825
(SEQIDNO:5) B-P1_prM-E : ------------------------------------------------------------------------ : -
(SEQIDNO:6) B3-P11_prM : ------------------------------------------------------------------------ : -
```

FIG. 5E

| | | |
|---|---|---|
| SEQ ID NO:3) P1_transla | : TDIPSEPWNTGHDWILADKRPTAWFLPSIRAANVMAASLRKAGKSVVVLNRKTFEREYPTIKQKKPDFILATD | : 1898 |
| SEQ ID NO:4) P11_transl | : TDIPSEPWNTGHDWILADKRPTAWFLPSIRAANVMAASLRKAGKSVVVLNRKTFEREYPTIKQKKPDFILATD | : 1898 |
| SEQ ID NO:5) B-P1_prM-E | : ------------------------------------------------------------------------ | : -- |
| SEQ ID NO:6) B3-P11_prM | : ------------------------------------------------------------------------ | : -- |

| | | |
|---|---|---|
| SEQ ID NO:3) P1_transla | : IAEMGANLCVERVLDCRTAFKPVLVDEGRKVAIKGPLRISASSAAQRRGRIGRNPNRDGDSYYYSEPTSENNA | : 1971 |
| SEQ ID NO:4) P11_transl | : IAEMGANLCVERVLDCRTAFKPVLVDEGRKVAIKGPLRISASSAAQRRGRIGRNPNRDGDSYYYSEPTSENNA | : 1971 |
| SEQ ID NO:5) B-P1_prM-E | : ------------------------------------------------------------------------ | : -- |
| SEQ ID NO:6) B3-P11_prM | : ------------------------------------------------------------------------ | : -- |

| | | |
|---|---|---|
| SEQ ID NO:3) P1_transla | : HHVCWLEASMLLDNMEVRGGMVAPLYGVEGTKTPVSPGEMRLRDDQRKVFRELVRNCDLPVWLSWQVAKAGLK | : 2044 |
| SEQ ID NO:4) P11_transl | : HHVCWLEASMLLDNMEVRGGMVAPLYGVEGTKTPVSPGEMRLRDDQRKVFRELVRNCDLPVWLSWQVAKAGLK | : 2044 |
| SEQ ID NO:5) B-P1_prM-E | : ------------------------------------------------------------------------ | : -- |
| SEQ ID NO:6) B3-P11_prM | : ------------------------------------------------------------------------ | : -- |

| | | |
|---|---|---|
| SEQ ID NO:3) P1_transla | : TNDRKWCFEGPEEHEILNDSGETVKCRAPGGAKKPLRPRWCDERVSSDQSALSEFIKFAEGRRGAAEVLVVLS | : 2117 |
| SEQ ID NO:4) P11_transl | : TNDRKWCFEGPEEHEILNDSGETVKCRAPGGAKKPLRPRWCDERVSSDQSALSEFIKFAEGRRGAAEVLVVLS | : 2117 |
| SEQ ID NO:5) B-P1_prM-E | : ------------------------------------------------------------------------ | : -- |
| SEQ ID NO:6) B3-P11_prM | : ------------------------------------------------------------------------ | : -- |

| | | |
|---|---|---|
| SEQ ID NO:3) P1_transla | : ELPDFLAKKGGEAMDTISVFLHSEEGSRAYRNALSMMPEAMTIVMLFILAGLLTSGMVIFFMSPKGISRMSMA | : 2190 |
| SEQ ID NO:4) P11_transl | : ELPDFLAKKGGEAMDTISVFLHSEEGSRAYRNALSMMPEAMTIVMLFILAGLLTSGMVIFFMSPKGISRMSMA | : 2190 |
| SEQ ID NO:5) B-P1_prM-E | : ------------------------------------------------------------------------ | : -- |
| SEQ ID NO:6) B3-P11_prM | : ------------------------------------------------------------------------ | : -- |

FIG. 5F

```
                                 *      2200         *        2220         *        2240         *              2250
(SEQ ID NO:3) P1_transla  : MGTMAGCGYLMFLGGVKPTHISYIMLIFFVLMVVVIPEPGQQRSIQDNQVAYLIIGILTLVSAVAANELGMLE : 2263
(SEQ ID NO:4) P11_transl  : MGTMAGCGYLMFLGGVKPTHISYIMLIFFVLMVVVIPEPGQQRSIQDNQVAYLIIGILTLVSAVAANELGMLE : 2263
(SEQ ID NO:5) B-P1_prM-E  : ------------------------------------------------------------------------ :   -
(SEQ ID NO:6) B3-P11_prM  : ------------------------------------------------------------------------ :   -

*      2280         *        2300         *        2320         *
(SEQ ID NO:3) P1_transla  : KTKEDLFGKKNLIPSSASPWSPDLDLKPGAAWTVYVGIVTMLSPMLHHWIKVEYGNLSLSGIAQSASVLSFM : 2336
(SEQ ID NO:4) P11_transl  : KTKEDLFGKKNLIPSSASPWSPDLDLKPGAAWTVYVGIVTMLSPMLHHWIKVEYGNLSLSGIAQSASVLSFM : 2336
(SEQ ID NO:5) B-P1_prM-E  : ---------------------------------------------------------------------- :   -
(SEQ ID NO:6) B3-P11_prM  : ---------------------------------------------------------------------- :   -

2340         *        2360         *        2380         *       2400
(SEQ ID NO:3) P1_transla  : DKGIPFMKMNISVIMLLVSGWNSITVMPLLCGIGCAMLHWSLILPGIKAQQSKLAQRRVFHGVAKNPVVDGNP : 2409
(SEQ ID NO:4) P11_transl  : DKGIPFMKMNISVIMLLVSGWNSITVMPLLCGIGCAMLHWSLILPGIKAQQSKLAQRRVFHGVAKNPVVDGNP : 2409
(SEQ ID NO:5) B-P1_prM-E  : ------------------------------------------------------------------------ :   -
(SEQ ID NO:6) B3-P11_prM  : ------------------------------------------------------------------------ :   -

*      2420         *        2440         *        2460         *    2480
(SEQ ID NO:3) P1_transla  : TVDIEEAPEMPALYEKKLALYLLLALSLASVAMCRTPFSLAEGIVLASAALGPLIEGNTSLLWNGPMAVSMTG : 2482
(SEQ ID NO:4) P11_transl  : TVDIEEAPEMPALYEKKLALYLLLALSLASVAMCRTPFSLAEGIVLASAALGPLIEGNTSLLWNGPMAVSMTG : 2482
(SEQ ID NO:5) B-P1_prM-E  : ------------------------------------------------------------------------ :   -
(SEQ ID NO:6) B3-P11_prM  : ------------------------------------------------------------------------ :   -

*      2500         *        2520         *        2540         *
(SEQ ID NO:3) P1_transla  : VMRGNHYAFVGVMYNLWKMKTGRRGSANGKTLGEVWKRELNLLDKRQFELYKRTDIVEVDRDTARRHLAEGKV : 2555
(SEQ ID NO:4) P11_transl  : VMRGNHYAFVGVMYNLWKMKTGRRGSANGKTLGEVWKRELNLLDKRQFELYKRTDIVEVDRDTARRHLAEGKV : 2555
(SEQ ID NO:5) B-P1_prM-E  : ------------------------------------------------------------------------ :   -
(SEQ ID NO:6) B3-P11_prM  : ------------------------------------------------------------------------ :   -
```

FIG. 5G

```
SEQIDNO:3) P1_transla  : DTGVAVSRGTAKLRWFHERGYVKLEGRVIDLGCGRGGWCYYAAAQKEVSGVKGFTLGRDGHEKPMNVQSLGWN : 2628
SEQIDNO:4) P11_transl  : DTGVAVSRGTAKLRWFHERGYVKLEGRVIDLGCGRGGWCYYAAAQKEVSGVKGFTLGRDGHEKPMNVQSLGWN : 2628
SEQIDNO:5) B-P1_prM-E  : ------------------------------------------------------------------------ : -
SEQIDNO:6) B3-P11_prM  : ------------------------------------------------------------------------ : -

SEQIDNO:3) P1_transla  : IITFKDKTDIHRLEPVKCDTLLCDIGESSSSSVTEGERTVRVLDTVEKWLACGVDNFCVKVLAPYMPDVLEKL : 2701
SEQIDNO:4) P11_transl  : IITFKDKTDIHRLEPVKCDTLLCDIGESSSSSVTEGERTVRVLDTVEKWLACGVDNFCVKVLAPYMPDVLEKL : 2701
SEQIDNO:5) B-P1_prM-E  : ------------------------------------------------------------------------ : -
SEQIDNO:6) B3-P11_prM  : ------------------------------------------------------------------------ : -

SEQIDNO:3) P1_transla  : ELLQRRFGGTVIRNPLSRNSTHEMYVSGARSNVTFTVNQTSRLLMRRMRRPTGKVTLEADVILPIGTRSVET : 2774
SEQIDNO:4) P11_transl  : ELLQRRFGGTVIRNPLSRNSTHEMYVSGARSNVTFTVNQTSRLLMRRMRRPTGKVTLEADVILPIGTRSVET : 2774
SEQIDNO:5) B-P1_prM-E  : ------------------------------------------------------------------------ : -
SEQIDNO:6) B3-P11_prM  : ------------------------------------------------------------------------ : -

SEQIDNO:3) P1_transla  : DKGPLDKFATFFRVERIKSEYMTSWFYDNDNPYRTMWHYCGSYVTKTSGSAASMVNGVIKILTYPWDRIEEVTR : 2847
SEQIDNO:4) P11_transl  : DKGPLDKEAIEERVERIKSEYMTSWFYDNDNPYRTMWHYCGSYVTKTSGSAASMVNGVIKILTYPWDRIEEVTR : 2847
SEQIDNO:5) B-P1_prM-E  : ------------------------------------------------------------------------ : -
SEQIDNO:6) B3-P11_prM  : ------------------------------------------------------------------------ : -

SEQIDNO:3) P1_transla  : MAMTDTTPFGQQRVFKEKVDTRAKDPPAGTRKIMKVVNRWLFRHLAREKNPRLCTKEEFIAKVRSHAAIGAYL : 2920
SEQIDNO:4) P11_transl  : MAMTDTTPFGQQRVFKEKVDTRAKDPPAGTRKIMKVVNRWLFRHLAREKNPRLCTKEEFIAKVRSHAAIGAYL : 2920
SEQIDNO:5) B-P1_prM-E  : ------------------------------------------------------------------------ : -
SEQIDNO:6) B3-P11_prM  : ------------------------------------------------------------------------ : -
```

FIG. 5H

```
                              2940              2960              2980              *
SEQIDNO:3) P1_transla : EEQEQWKTANEAVQDPKFWELVDEERKLHQQGRCRTCVYNMMGKREKKLSEFGKAKGSRAIWYMWLGARYLEF : 2993
SEQIDNO:4) P11_transl : EEQEQWKTANEAVQDPKFWELVDEERKLHQQGRCRTCVYNMMGKREKKLSEFGKAKGSRAIWYMWLGARYLEF : 2993
SEQIDNO:5) B-P1_prM-E : ---------------------------------------------------------------------- : -
SEQIDNO:6) B3-P11_prM : ---------------------------------------------------------------------- : -

3000              *              3020              *              3040              *              3060
SEQIDNO:3) P1_transla : EALGFLNEDHWASRENSGGVEGIGLQYLGYVIRDLAAMDGGGFYADDTAGWDTRITEADLDDEQEILNYMSP : 3066
SEQIDNO:4) P11_transl : EALGFLNEDHWASRENSGGVEGIGLQYLGYVIRDLAAMDGGGFYADDTAGWDTRITEADLDDEQEILNYMSP : 3066
SEQIDNO:5) B-P1_prM-E : ---------------------------------------------------------------------- : -
SEQIDNO:6) B3-P11_prM : ---------------------------------------------------------------------- : -

*              3080              *              3100              *              3120              *              314
SEQIDNO:3) P1_transla : HHKKLAQAVMEMTYKNKVVKVLRPAPGGKAYMDVISRRDQRGSGQVVTYALNTITNLKVQLIRMAEAEMVIHH : 3139
SEQIDNO:4) P11_transl : HHKKLAQAVMEMTYKNKVVKVLRPAPGGKAYMDVISRRDQRGSGQVVTYALNTITNLKVQLIRMAEAEMVIHH : 3139
SEQIDNO:5) B-P1_prM-E : ---------------------------------------------------------------------- : -
SEQIDNO:6) B3-P11_prM : ---------------------------------------------------------------------- : -

0              *              3160              *              3180              *              3200              *
SEQIDNO:3) P1_transla : QHVQDCDESVLTRLEAWLTEHGCNRLKRMAVSGDDCVVRPIDDRFGLALSHLNAMSKVRKDISEWQPSKGWND : 3212
SEQIDNO:4) P11_transl : QHVQDCDESVLTRLEAWLTEHGCNRLKRMAVSGDDCVVRPIDDRFGLALSHLNAMSKVRKDISEWQPSKGWND : 3212
SEQIDNO:5) B-P1_prM-E : ---------------------------------------------------------------------- : -
SEQIDNO:6) B3-P11_prM : ---------------------------------------------------------------------- : -

3220              *              3240              *              3260              *              3280
SEQIDNO:3) P1_transla : WENVPFCSHHFHELQLKDGRRIVVPCREQDELIGRGRVSPGNGWMIKETACLSKAYANMWSLMYFHKRDMRLL : 3285
SEQIDNO:4) P11_transl : WENVPFCSHHFHELQLKDGRRIVVPCREQDELIGRGRVSPGNGWMIKETACLSKAYANMWSLMYFHKRDMRLL : 3285
SEQIDNO:5) B-P1_prM-E : ---------------------------------------------------------------------- : -
SEQIDNO:6) B3-P11_prM : ---------------------------------------------------------------------- : -
```

FIG. 5I

```
                                    *       3300      *      3320       *      3340       *        33
SEQIDNO:3) P1_transla : SLAVSSAVPTSWVPQGRTTWSIHGKGEWMTTEDMLEVWNRVWITNNPHMQDKTMVKKWRDVPYLTKRQDKLCG : 3358
SEQIDNO:4) P11_transl : SLAVSSAVPTSWVPQGRTTWSIHGKGEWMTTEDMLEVWNRVWITNNPHMQDKTMVKKWRDVPYLTKRQDKLCG : 3358
SEQIDNO:5) B-P1_prM-E : ------------------------------------------------------------------------ : -
SEQIDNO:6) B3-P11_prM : ------------------------------------------------------------------------ : -

60       *      3380       *      3400       *
SEQIDNO:3) P1_transla : SLIGMTNRATWASHIHLVIHRIRTLIGQEKYTDYLTVMDRYSVDADLQLGELI- : 3411
SEQIDNO:4) P11_transl : SLIGMTNRATWASHIHLVIHRIRTLIGQEKYTDYLTVMDRYSVDADLQLGELI- : 3411
SEQIDNO:5) B-P1_prM-E : ----------------------------------------------------- : -
SEQIDNO:6) B3-P11_prM : ----------------------------------------------------- : -
```

FIG. 5J

```
                            *        20         *        40         *        60         *
(SEQ ID NO: 15) P1_consens : AGTAAATCCTGTGTGCTAATTGAGTGCATTGGTCTGCAAATCGAGTTGCTAGGCAATAAACACATTTGGAT :  72
(SEQ ID NO: 9)  B-P1_conse : ------------------------------------AATCGAGTTGCTAGGCAATAAACACATTTGGAT :  33
(SEQ ID NO: 10) C-P1_genom : ------------------------------------AATCGAGTTGCTAGGCAATAAACACATTTGGAT :  33
(SEQ ID NO: 11) B3-P11_con : --------------------TGCATTGGTCTGCAAATCGAGTTGCTAGGCAATAAACACATTTGGAT :  47
(SEQ ID NO: 12) C1-P11_con : ----------------------------------TCGAGTTGCTAGGCAATAAACACATTTGGAT :  31

*        80         *       100         *       120         *       140
(SEQ ID NO: 15) P1_consens : TAATTTTAATCGTTCGTTGAGCGATTAGCAGAGAACTGACCAGAACATGTCTGGTCGTAAAGCTCAGGGAAA : 144
(SEQ ID NO: 9)  B-P1_conse : TAATTTTAATCGTTCGTTGAGCGATTAGCAGAGAACTGACCAGAACATGTCTGGTCGTAAAGCTCAGGGAAA : 105
(SEQ ID NO: 10) C-P1_genom : TAATTTTAATCGTTCGTTGAGCGATTAGCAGAGAACTGACCAGAACATGTCTGGTCGTAAAGCTCAGGGAAA : 105
(SEQ ID NO: 11) B3-P11_con : TAATTTTAATCGTTCGTTGAGCGATTAGCAGAGAACTGACCAGAACATGTCCTGGTCGTAAAGCTCAGGGAAA : 119
(SEQ ID NO: 12) C1-P11_con : TAATTTTAATCGTTCGTTGAGCGATTAGCAGAGAACTGACCAGAACATGTCTGGTCGTAAAGCTCAGGGAAA : 103

*       160         *       180         *       200         *
(SEQ ID NO: 15) P1_consens : AACCCTGGGCGTCAATATGGTACGACGAGGAGTTCGCTCCTTGTCAAACAAAATAAAACAAAAACAAAACA : 216
(SEQ ID NO: 9)  B-P1_conse : AACCCTGGGCGTCAATATGGTACGACGAGGAGTTCGCTCCTCCTTGTCAAACAAAATAAAACAAAAACAAAACA : 177
(SEQ ID NO: 10) C-P1_genom : AACCCTGGGCGTCAATATGGTACGACGAGGAGTTCGCTCCTCCTTGTCAAACAAAATAAAACAAAAACAAAACA : 177
(SEQ ID NO: 11) B3-P11_con : AACCCTGGGCGTCGTCAATATGGTACGACGAGGAGTTCGCTCCTCCTTGTCAAACAAAACAAAATAAAAACGAAACA : 191
(SEQ ID NO: 12) C1-P11_con : AACCCTGGGCGTCAATATGGTACGACGAGGAGTTCGCTCCTCCTTGTCAAACAAAACAAAATAAAACAAAAACAAAACA : 175

*       220         *       240         *       260         *       280
(SEQ ID NO: 15) P1_consens : AATTGGAAACAGACCTGACCTTCAAGAGGTGTTCAAGAGGATTATCTTTTCTTTTTGTTCAACATTTTGAC : 288
(SEQ ID NO: 9)  B-P1_conse : AATTGGAAACAGACCTGACCTTCAAGAGGTGTTCAAGAGGATTATCTTTTCTTTTTGTTCAACATTTTGAC : 249
(SEQ ID NO: 10) C-P1_genom : AATTGGAAACAGACCTGACCTTCAAGAGGTGTTCAAGAGGATTATCTTTTCTTTTTGTTCAACATTTTGAC : 249
(SEQ ID NO: 11) B3-P11_con : AATTGGAAACAGACCTGACCTTCAAGAGGTGTTCAAGAGGATTATCTTTTCTTTTTTGTTCAACATTTTGAC : 263
(SEQ ID NO: 12) C1-P11_con : AATTGGAAACAGACCTGACCTTCAAGAGGTGTTCAAGAGGATTATCTTTTCTTTTTGTTCAACATTTTGAC : 247

*       300         *       320         *       340         *       360
(SEQ ID NO: 15) P1_consens : TGGAAAAAGATCACAGCCCACCTAAAGAGGTCTGTGAAAATGCTGACCAAGAACAAGGCTTGGCTGTTCT : 360
(SEQ ID NO: 9)  B-P1_conse : TGGAAAAAGATCACAGCCCACCTAAAGAGGTTGTGAAAATGCTGACCAAGAACAAGGCTTGGCTGTTCT : 321
(SEQ ID NO: 10) C-P1_genom : TGGAAAAAGATCACAGCCCACCTAAAGAGGTTGTGAAAATGCTGACCAAGAACAAGGCTTGGCTGTTCT : 321
(SEQ ID NO: 11) B3-P11_con : TGGAAAAAAGATCACAGCCCACCTAAAGAGGTTGTGAAAATGCTGACCAAGAACAAGGCTTGGCTGTTCT : 335
(SEQ ID NO: 12) C1-P11_con : TGGAAAAAGATCACAGCCCACCTAAAGAGGTTGTGAAAATGCTGACCAAGAACAAGGCTTGGCTGTTCT : 319
```

FIG. 8A

```
                              *         380         *         400         *         420         *
(SEQ ID NO: 15)  P1_consens  : AAGGAAAGTCAAGAGAGTGGTGGCCAGTTTGATGAGAGATTGTCTCTCAAGGAAACGCCGTTCCCATGATGT  : 432
(SEQ ID NO: 9)   B-P1_conse  : AAGGAAAGTCAAGAGAGTGGTGGCCAGTTTGATGAGAGATTGTCTCTCAAGGAAACGCCGTTCCCATGATGT  : 393
(SEQ ID NO: 10)  C-P1_genom  : AAGGAAAGTCAAGAGAGTGGTGGCCAGTTTGATGAGAGATTGTCTCTCAAGGAAACGCCGTTCCCATGATGT  : 393
(SEQ ID NO: 11)  B3-P11_con  : AAGGAAAGTCAAGAGAGTGGTGGCCAGTTTGATGAGAGATTGTCTCTCAAGGAAACGCCGTTCCCATGATGT  : 407
(SEQ ID NO: 12)  C1-P11_con  : AAGGAAAGTCAAGAGAGTGGTGGCCAGTTTGATGAGAGATTGTCTCTCAAGGAAACGCCGTTCCCATGATGT  : 391

*         440         *         460         *         480         *         500
(SEQ ID NO: 15)  P1_consens  : TCTGACTGTGCAATTCCTAATTTTGGGAATGCTGTTGATGACGGGTGGAGTGACCTTGGTGCGGAAAAACAG  : 504
(SEQ ID NO: 9)   B-P1_conse  : TCTGACTGTGCAATTCCTAATTTTGGGAATGCTGTTGATGACGGGTGGAGTGACCTTGGTGCGGAAAAACAG  : 465
(SEQ ID NO: 10)  C-P1_genom  : TCTGACTGTGCAATTCCTAATTTTGGGAATGCTGTTGATGACGGGTGGAGTGACCTTGGTGCGGAAAAACAG  : 465
(SEQ ID NO: 11)  B3-P11_con  : TCTGACTGTGCAATTCCTAATTTTGGGAATGCTGTTGATGACGGGTGGAGTGACCTTGGTGCGGAAAAACAG  : 479
(SEQ ID NO: 12)  C1-P11_con  : TCTGACTGTGCAATTCCTAATTTTGGGAATGCTGTTGATGACGGGTGGAGTGACCTTGGTGCGGAAAAACAG  : 463

*         520         *         540         *         560         *
(SEQ ID NO: 15)  P1_consens  : ATGGTTGCTCCTAAATGTGACATCTGAGGACCTCGGGAAAACATTCTCTGTGGGCACAGGCAACTGCACAAC  : 576
(SEQ ID NO: 9)   B-P1_conse  : ATGGTTGCTCCTAAATGTGACATCTGAGGACCTCGGGAAAACATTCTCTGTGGGCACAGGCAACTGCACAAC  : 537
(SEQ ID NO: 10)  C-P1_genom  : ATGGTTGCTCCTAAATGTGACATCTGAGGACCTCGGGAAAACATTCTCTGTGGGCACAGGCAACTGCACAAC  : 537
(SEQ ID NO: 11)  B3-P11_con  : ATGGTTGCTCCTAAATGTGACATCTGAGGACCTCGGGAAAACATTCTCTGTGGGCACAGGCAACTGCACAAC  : 551
(SEQ ID NO: 12)  C1-P11_con  : ATGGTTGCTCCTAAATGTGACATCTGAGGAATCTCGGGAAAACATTCTCTGTGGGCACAGGCAACTGCACAAC  : 535

*         580         *         600         *         620         *         640
(SEQ ID NO: 15)  P1_consens  : AAACATTTTGGAAGCCAAGTACTGGTGCCCAGAGACTCAATGAATACAACTGTCCCAATCTCAGTCCAAGAGA  : 648
(SEQ ID NO: 9)   B-P1_conse  : AAACATTTTGGAAGCCAAGTACTGGTGCCCAGAGACTCAATGAATACAACTGTCCCAATCTCAGTCCAAGAGA  : 609
(SEQ ID NO: 10)  C-P1_genom  : AAACATTTTGGAAGCCAAGTACTGGTGCCCAGAGACTCAATGAATACAACTGTCCCAATCTCAGTCCAAGAGA  : 609
(SEQ ID NO: 11)  B3-P11_con  : AAACATTTTGGAAGCCAAGTACTGGTGCCCAGAGACTCAATGAATACAACTGTCCCAATCTCAGTCCAAGAGA  : 623
(SEQ ID NO: 12)  C1-P11_con  : AAACATTTTGGAAGCCAAGTACTGGTGCCCAGAGACTCAATGAATACAACTGTCCCAATCTCAGTCCAAGAGA  : 607

*         660         *         680         *         700         *         720
(SEQ ID NO: 15)  P1_consens  : GGAGCCAGATGACATTGATTGCTGGTGCTATGGGTGGAAAACGTTAGAGTCGCATATGGTAAGTGTGACTC  : 720
(SEQ ID NO: 9)   B-P1_conse  : GGAGCCAGATGACATTGATTGCTGGTGCTATGGGTGGAAAACGTTAGAGTCGCATATGGTAAGTGTGACTC  : 681
(SEQ ID NO: 10)  C-P1_genom  : GGAGCCAGATGACATTGATTGCTGGTGCTATGGGTGGAAAACGTTAGAGTCGCATATGGTAAGTGTGACTC  : 681
(SEQ ID NO: 11)  B3-P11_con  : GGAGCCAGATGACATTGATTGCTGGTGCTATGGGTGGAAAACGTTAGAGTCGCATATGGTAAGTGTGACTC  : 695
(SEQ ID NO: 12)  C1-P11_con  : GGAGCCAGATGACATTGATTGCTGGTGCTATGGGTGGAAAACGTTAGAGTCGCATATGGTAAGTGTGACTC  : 679
```

FIG. 8B

```
                             *         740         *         760         *         780         *
P1_consens   (SEQ ID NO:15) : AGCAGGCAGGTCTAGGAGAGTCAAGAGAAGGGCCATTGACTTGCCTACGCATGAAAACCATGGTTTGAAGACCCG :  792
B-P1_conse   (SEQ ID NO:9)  : AGCAGGCAGGTCTAGGAGAGTCAAGAGAAGGGCCATTGACTTGCCTACGCATGAAAACCATGGTTTGAAGACCCG :  753
C-P1_genom   (SEQ ID NO:10) : AGCAGGCAGGTCTAGGAGAGTCAAGAGAAGGGCCATTGACTTGCCTACGCATGAAAACCATGGTTTGAAGACCCG :  753
B3-P11_con   (SEQ ID NO:11) : AGCAGGCAGGTCTAGGAGAGTCAAGAGAAGGGCCATTGACTTGCCTACGCATGAAAACCATGGTTTGAAGACCCG :  767
C1-P11_con   (SEQ ID NO:12) : AGCAGGCAGGTCTAGGAGAGTCAAGAGAAGGGCCATTGACTTGCCTACGCATGAAAACCATGGTTTGAAGACCCG :  751

800         *         820         *         840         *         860
P1_consens   (SEQ ID NO:15) : GCAAGAAAAAATGGATGACTGGAAGAATGGGTGAAAGGCAACTCCAAAAGATTGAGAGATTCGTGAGGAA :  864
B-P1_conse   (SEQ ID NO:9)  : GCAAGAAAAAATGGATGACTGGAAGAATGGGTGAAAGGCAACTCCAAAAGATTGAGAGATTCGTGAGGAA :  825
C-P1_genom   (SEQ ID NO:10) : GCAAGAAAAAATGGATGACTGGAAGAATGGGTGAAAGGCAACTCCAAAAGATTGAGAGATTCGTGAGGAA :  825
B3-P11_con   (SEQ ID NO:11) : GCAAGAAAAAATGGATGACTGGAAGAATGGGTGAAAGGCAACTCCAAAAGATTGAGAGATTCGTGAGGAA :  839
C1-P11_con   (SEQ ID NO:12) : GCAAGAAAAAATGGATGACTGGAAGAATGGGTGAAAGGCAACTCCAAAAGATTGAGAGATTCGTGAGGAA :  823

*         880         *         900         *         920         *
P1_consens   (SEQ ID NO:15) : CCCCTTTTTGCAGTGACGGCTCTGACGAGTTGCCTACCTTGTGGGAAGCAACATGACGCAACAGTCGTGAT :  936
B-P1_conse   (SEQ ID NO:9)  : CCCCTTTTTGCAGTGACGGCTCTGACGAGTTGCCTACCTTGTGGGAAGCAACATGACGCAACAGTCGTGAT :  897
C-P1_genom   (SEQ ID NO:10) : CCCCTTTTTGCAGTGACGGCTCTGACGAGTTGCCTACCTTGTGGGAAGCAACATGACGCAACAGTCGTGAT :  897
B3-P11_con   (SEQ ID NO:11) : CCCCTTTTTGCAGTGACGGCTCTGACGAGTTGCCTACCTTGTGGGAAGCAACATGACGCAACAGTCGTGAT :  911
C1-P11_con   (SEQ ID NO:12) : CCCCTTTTTGCAGTGACGGCTCTGACGAGTTGCCTACCTTGTGGGAAGCAACATGACGCAACAGTCGTGAT :  895

940         *         960         *         980         *         1000
P1_consens   (SEQ ID NO:15) : TGCCCTACTGGTCTGGTCTTGGCTGTTGGCTGTTGGCCGGCCCTACTCAGCTCAGCTCAGCTCAGTTGGAATTACTGACAGGGATTTCAT : 1008
B-P1_conse   (SEQ ID NO:9)  : TGCCCTACTGGTCTGGTCTTGGCTGTTGGCTGTTGGCCGGCCCTACTCAGCTCAGCTCAGCTCAGTTGGAATTACTGACAGGGATTTCAT :  969
C-P1_genom   (SEQ ID NO:10) : TGCCCTACTGGTCTGGTCTTGGCTGTTGGCTGTTGGCCGGCCCTACTCAGCTCAGCTCAGCTCAGTTGGAATTACTGACAGGGATTTCAT :  969
B3-P11_con   (SEQ ID NO:11) : TGCCCTACTGGTCTGGTCTTGGCTGTTGGCTGTTGGCCGGCCCTACTCAGCTCAGCTCAGCTCAGTTGGAATTACTGACAGGGATTTCAT :  983
C1-P11_con   (SEQ ID NO:12) : TGCCCTACTGGTCTGGTCTTGGCTGTTGGCTGTTGGCCGGCCCTACTCAGCTCAGCTCAGCTCAGTTGGAATTACTGACAGGGATTTCAT :  967

*         1020         *         1040         *         1060         *         1080
P1_consens   (SEQ ID NO:15) : TGAGGGGGTGCATGGAGGAACTTGGGTTTCAGCTACCCTGGAGCAAGAACAAGTGTCTCACTGTTATGGCCCCC : 1080
B-P1_conse   (SEQ ID NO:9)  : TGAGGGGGTGCATGGAGGAACTTGGGTTTCAGCTACCCTGGAGCAAGAACAAGTGTCTCACTGTTATGGCCCCC : 1041
C-P1_genom   (SEQ ID NO:10) : TGAGGGGGTGCATGGAGGAACTTGGGTTTCAGCTACCCTGGAGCAAGAACAAGTGTCTCACTGTTATGGCCCCC : 1041
B3-P11_con   (SEQ ID NO:11) : TGAGGGGGTGCATGGAGGAACTTGGGTTTCAGCTACCCTGGAGCAAGAACAAGTGTCTCACTGTTATGGCCCCC : 1055
C1-P11_con   (SEQ ID NO:12) : TGAGGGGGTGCATGGAGGAACTTGGGTTTCAGCTACCCTGGAGCAAGAACAAGTGTCTCACTGTTATGGCCCCC : 1039
```

```
(SEQ ID NO: 15)  P1_consens  : TAAGACTTCAAGTTTGATGCCCTGTCAGGCTCCCAGGAAGTCGAGTTCATTGGGTATGGGAAAAAGCTACACT : 1512
(SEQ ID NO: 9)   B-P1_conse  : TAAGACTTCAAGTTTGATGCCCTGTCAGGCTCCCAGGAAGTCGAGTTCATTGGGTATGGGAAAAAGCTACACT : 1473
(SEQ ID NO: 10)  C-P1_genom  : TAAGACTTCAAGTTTGATGCCCTGTCAGGCTCCCAGGAAGTCGAGTTCATTGGGTATGGGAAAAAGCTACACT : 1473
(SEQ ID NO: 11)  B3-P11_con  : TAAGACTTCAAGTTTGATGCCCTGTCAGGCTCCCAGGAAGTCGAGTTCATTGGGTATGGGAAAAGCCACACT  : 1487
(SEQ ID NO: 12)  C1-P11_con  : TAAGACTTCAAGTTTGATGCCCTGTCAGGCTCCCAGGAAGTCGAGTTCATTGGGTATGGGAAAAAGCTACACT : 1471

(SEQ ID NO: 15)  P1_consens  : GGAATGCCAGGTGCAAACTGCGGTGGACTTTGGTAACAGTTACATCGCTGAGATGGAAACAGAGAGCTGGAT : 1584
(SEQ ID NO: 9)   B-P1_conse  : GGAATGCCAGGTGCAAACTGCGGTGGACTTTGGTAACAGTTACATCGCTGAGATGGAAACAGAGAGCTGGAT : 1545
(SEQ ID NO: 10)  C-P1_genom  : GGAATGCCAGGTGCAAACTGCGGTGGACTTTGGTAACAGTTACATCGCTGAGATGGAAACAGAGAGCTGGAT : 1545
(SEQ ID NO: 11)  B3-P11_con  : GGAATGCCAGGTGCAAACTGCGGTGGACTTTGGTAACAGTTACATCGCTGAGATGGAAACAGAGAGCTGGAT : 1559
(SEQ ID NO: 12)  C1-P11_con  : GGAATGCCAGGTGCAAACTGCGGTGGACTTTGGTAACAGTTACATCGCTGAGATGGAAACAGAGAGCTGGAT : 1543

(SEQ ID NO: 15)  P1_consens  : AGTGGACAGACAGTGGGCCCAGGACTTGACCCTGCCATGGCAGAGTGAAGTGGCGGGGGTGTGGAGAGAGAT : 1656
(SEQ ID NO: 9)   B-P1_conse  : AGTGGACAGACAGTGGGCCCAGGACTTGACCCTGCCATGGCAGAGTGAAGTGGCGGGGGTGTGGAGAGAGAT : 1617
(SEQ ID NO: 10)  C-P1_genom  : AGTGGACAGACAGTGGGCCCAGGACTTGACCCTGCCATGGCAGAGTGAAGTGGCGGGGGTGTGGAGAGAGAT : 1617
(SEQ ID NO: 11)  B3-P11_con  : AGTGGACAGACAGTGGGCCCAGGACTTGACCCTGCCATGGCAGAGTGAAGTGGCGGGGGTGTGGAGAGAGAT : 1631
(SEQ ID NO: 12)  C1-P11_con  : AGTGGACAGACAGTGGGCCCAGGACTTGACCCTGCCATGGCAGAGTGAAGTGGCGGGGGTGTGGAGAGAGAT : 1615

(SEQ ID NO: 15)  P1_consens  : GCATCATCTTGTCGAATTTGAACCTCCGCATGCCGCCACTATCAGAGTACTGGCCCTGGGAAACCAGGAAGG : 1728
(SEQ ID NO: 9)   B-P1_conse  : GCATCATCTTGTCGAATTTGAACCTCCGCATGCCGCCACTATCAGAGTACTGGCCCTGGGAAACCAGGAAGG : 1689
(SEQ ID NO: 10)  C-P1_genom  : GCATCATCTTGTCGAATTTGAACCTCCGCATGCCGCCACTATCAGAGTACTGGCCCTGGGAAACCAGGAAGG : 1689
(SEQ ID NO: 11)  B3-P11_con  : GCATCATCTTGTCGAATTTGAACCTCCGCATGCCGCCACTATCAGAGTACTGGCCCTGGGAAACCAGGAAGG : 1703
(SEQ ID NO: 12)  C1-P11_con  : GCATCATCTTGTCGAATTTGAACCTCCGCATGCCGCCACTATCAGAGTACTGGCCCTGGGAAACCAGGAAGG : 1687

(SEQ ID NO: 15)  P1_consens  : CTCCTTGAAAACAGCTCTTACTGGCGCAATGAGGGTTACAAAGGACACAAATGACAACAACCTTTACAAACT : 1800
(SEQ ID NO: 9)   B-P1_conse  : CTCCTTGAAAACAGCTCTTACTGGCGCAATGAGGGTTACAAAGGACACAAATGACAACAACCTTTACAAACT : 1761
(SEQ ID NO: 10)  C-P1_genom  : CTCCTTGAAAACAGCTCTTACTGGCGCAATGAGGGTTACAAAGGACACAAATGACAACAACCTTTACAAACT : 1761
(SEQ ID NO: 11)  B3-P11_con  : CTCCTTGAAAACAGCTCTTACTGGCGCAATGAGGGTTACAAAGGACACAAATGACAACAACCTTTACAAACT : 1775
(SEQ ID NO: 12)  C1-P11_con  : CTCCTTGAAAACAGCTCTTACTGGCGCAATGAGGGTTACAAAGGACACAAATGACAACAACCTTTACAAACT : 1759
```

FIG. 8E

```
                                          *         1820         *         1840         *         1860         *
(SEQ ID NO: 15)  P1_consens  : ACATGGTGGACATGTTTCTTGCAGAGTGAAATTGTCAGCTTTGACACTCAAGGGACATCCTACAAAATATG : 1872
(SEQ ID NO: 9)   B-P1_conse  : ACATGGTGGACATGTTTCTTGCAGAGTGAAATTGTCAGCTTTGACACTCAAGGGACATCCTACAAAATATG : 1833
(SEQ ID NO: 10)  C-P1_genom  : ACATGGTGGACATGTTTCTTGCAGAGTGAAATTGTCAGCTTTGACACTCAAGGGACATCCTACAAAATATG : 1833
(SEQ ID NO: 11)  B3-P11_con  : ACATGGTGGACATGTTTCTTGCAGAGTGAAATTGTCAGCTTTGACACTCAAGGGACATCCTACAAAATATG : 1847
(SEQ ID NO: 12)  C1-P11_con  : ACATGGTGGACATGTTTCTTGCAGAGTGAAATTGTCAGCTTTGACACTCAAGGGACATCCTACAAAATATG : 1831

1880         *         1900         *         1920         *         1940
(SEQ ID NO: 15)  P1_consens  : CACTGACAAAATGTTTTTTGTCAAGAACCCAACTGACACTGGCCATGGCACTGTTGTGATGCAGTGAAAGT : 1944
(SEQ ID NO: 9)   B-P1_conse  : CACTGACAAAATGTTTTTTGTCAAGAACCCAACTGACACTGGCCATGGCACTGTTGTGATGCAGTGAAAGT : 1905
(SEQ ID NO: 10)  C-P1_genom  : CACTGACAAAATGTTTTTTGTCAAGAACCCAACTGACACTGGCCATGGCACTGTTGTGATGCAGTGAAAGT : 1905
(SEQ ID NO: 11)  B3-P11_con  : CACTGACAAAATGTTTTTTGTCAAGAACCCAACTGACACTGGCCATGGCACTGTTGTGATGCAGTGAAAGT : 1919
(SEQ ID NO: 12)  C1-P11_con  : CACTGACAAAATGTTTTTTGTCAAAAACCCAACTGACACTGGCCATGGCACTGTTGTGATGCAGTGAAAGT : 1903

*         1960         *         1980         *         2000         *
(SEQ ID NO: 15)  P1_consens  : GTCAAAAGGAGCCCCCTGCAGGATTCCAGTGACAGTAGCTCGATGATCTTACAGCGGCAATCAATAAGGCAT : 2016
(SEQ ID NO: 9)   B-P1_conse  : GTCAAAAGGAGCCCCCTGCAGGATTCCAGTGACAGTAGCTCGATGATCTTACAGCGGCAATCAATAAGGCAT : 1977
(SEQ ID NO: 10)  C-P1_genom  : GTCAAAAGGAGCCCCCTGCAGGATTCCAGTGACAGTAGCTCGATGATCTTACAGCGGCAATCAATAAGGCAT : 1977
(SEQ ID NO: 11)  B3-P11_con  : GTCAAAAGGAGCCCCCTGCAGGATTCCAGTGACAGTAGCTCGATGATCTTACAGCGGCAATCAATAAGGCAT : 1991
(SEQ ID NO: 12)  C1-P11_con  : GTCAAAAGGAGCCCCCTGCAGGATTCCAGTGACAGTAGCTCGATGATCTTACAGCGGCAATCAATAAGGCAT : 1975

2020         *         2040         *         2060         *         2080
(SEQ ID NO: 15)  P1_consens  : TTTGGTTACAGTTAACCCCATGCCTCAACCAATGATGATGAAGTGCTGATTGAGGTGAACCCACCTTTTGG : 2088
(SEQ ID NO: 9)   B-P1_conse  : TTTGGTTACAGTTAACCCCATGCCTCAACCAATGATGATGAAGTGCTGATTGAGGTGAACCCACCTTTTGG : 2049
(SEQ ID NO: 10)  C-P1_genom  : TTTGGTTACAGTTAACCCCATGCCTCAACCAATGATGATGAAGTGCTGATTGAGGTGAACCCACCTTTTGG : 2049
(SEQ ID NO: 11)  B3-P11_con  : TTTGGTTACAGTTAACCCCATGCCTCAACCAATGATGATGAAGTGCTGATTGAGGTGAACCCACCTTTTGG : 2063
(SEQ ID NO: 12)  C1-P11_con  : TTTGGTTACAGTTAACCCCATGCCTCAACCAATGATGATGAAGTGCTGATTGAGGTGAACCCACCTTTTGG : 2047

*         2100         *         2120         *         2140         *         2160
(SEQ ID NO: 15)  P1_consens  : AGACAGCTACATTATCGTTGGGAGAGAGGAGATTCACGTCTCACTTACCAGTGGCACAAAGAGGAAGCTCAAT : 2160
(SEQ ID NO: 9)   B-P1_conse  : AGACAGCTACATTATCGTTGGGAGAGAGGAGATTCACGTCTCACTTACCAGTGGCACAAAGAGGAAGCTCAAT : 2121
(SEQ ID NO: 10)  C-P1_genom  : AGACAGCTACATTATCGTTGGGAGAGAGGAGATTCACGTCTCACTTACCAGTGGCACAAAGAGGAAGCTCAAT : 2121
(SEQ ID NO: 11)  B3-P11_con  : AGACAGCTACATTATCGTTGGGAGAGAGGAGATTCACGTCTCACTTACCAGTGGCACAAAGAGGAAGCTCAAT : 2135
(SEQ ID NO: 12)  C1-P11_con  : AGACAGCTACATTATCGTTGGGAGAGAGGAGATTCACGTCTCACTTACCAGTGGCACAAAGAGGAAGCTCAAT : 2119
```

```
                        *         2540         *         2560         *         2580         *
P1_consens   : AGACTCTGATGACTGGCTGCTGAACAAGTACTCATACTATCCAGAAGATCCTGTGAAGCTTGCATCAATAGTGAA : 2592
B-P1_conse   : AGACTCTGATGACTGGCTGCTGAACAAGTACTCATACTATCCAGAAGATCCTGTGAAGCTTGCATCAATAGTGAA : 2553
C-P1_genom   : AGACTCTGATGACTGGCTGCTGAACAAGTACTCATACTATCCAGAAGATCCTGTGAAGCTTGCATCAATAGTGAA : 2553
B3-P11_con   : AGACTCTGATGACTGGCTGCTGAACAAGTACTCATACTATCCAGAAGATCCTGTGAAGCTTGCATCAATAGTGAA : 2567
C1-P11_con   : AGACTCTGATGACTGGCTGCTGAACAAGTACTCATACTATCCAGAAGATCCTGTGAAGCTTGCATCAATAGTGAA : 2551

*         2600         *         2620         *         2640         *         2660
P1_consens   : AGCCTCTTTTGAAGAAGGGAAGTGTGGCCTAAATTCAGTTGACTCCCTTGAGCATGATGTGGAGAAGCAG : 2664
B-P1_conse   : AGCCTCTTTTGAAGAAGGGAAGTGTGGCCTAAATTCAGTTGACTCCCTTGAGCATGATGTGGAGAAGCAG : 2625
C-P1_genom   : AGCCTCTTTTGAAGAAGGGAAGTGTGGCCTAAATTCAGTTGACTCCCTTGAGCATGATGTGGAGAAGCAG : 2625
B3-P11_con   : AGCCTCTTTTGAAGAAGGGAAGTGTGGCCTAAATTCAGTTGACTCCCTTGAGCATGATGTGGAGAAGCAG : 2639
C1-P11_con   : AGCCTCTTTTGAAGAAGGGAAGTGTGGCCTAAATTCAGTTGACTCCCTTGAGCATGATGTGGAGAAGCAG : 2623

*         2680         *         2700         *         2720         *
P1_consens   : GGCAGAGATGAGATCAATGCCATTTTTGAGGAAAACGAGGTGGACATTTCTGTTGTCGTGCAGGATCCAAAGAA : 2736
B-P1_conse   : GGCAGAGATGAGATCAATGCCATTTTTGAGGAAAACGAGGTGGACATTTCTGTTGTCGTGCAGGATCCAAAGAA : 2697
C-P1_genom   : GGCAGAGATGAGATCAATGCCATTTTTGAGGAAAACGAGGTGGACATTTCTGTTGTCGTGCAGGATCCAAAGAA : 2697
B3-P11_con   : GGCAGAGATGAGATCAATGCCATTTTTGAGGAAAACGAGGTGGACATTTCTGTTGTCGTGCAGGATCCAAAGAA : 2711
C1-P11_con   : GGCAGAGATGAGATCAATGCCATTTTT-GAGGAAAACGAGGTGGACATTTCTGTTGTCGTGCAGGATCCAAAGAA : 2695

2740         *         2760         *         2780         *         2800         *
P1_consens   : TGTTTACCAGAGAGGAGAACTCATCATCCATTTTCCAGAATTCGGGATGGTCTGCAGTATGGTTGGAAGACTTGGGG : 2808
B-P1_conse   : TGTTTACCAGAGAGGAGAACTCATCATCCATTTTCCAGAATTCGGGATGGTCTGCAGTATGGTTGGAAGACTTGGGG : 2769
C-P1_genom   : TGTTTACCAGAGAGGAGAACTCATCATCCATTTTCCAGAATTCGGGATGGTCTGCAGTATGGTTGGAAGACTTGGGG : 2769
B3-P11_con   : TGTTTACCAGAGAGGAGAACTCATCATCCATTTTCCAGAATTCGGGATGGTCTGCAGTATGGTTGGAAGACTTGGGG : 2783
C1-P11_con   : TGTTTACCAGAGAGGAGAACTCATCATCCATTTTCCAGAATTCGGGATGGTCTGCAGTATGGTTGGAAGACTTGGGG : 2767

*         2820         *         2840         *         2860         *         2880
P1_consens   : TAAGAACCTTGTGTTCTCCCCAGGGAGGAGGAATGAAGCTTCATCATAGATGAATGGAAAGTCCAGGAAAGAGAATG : 2880
B-P1_conse   : TAAGAACCTTGTGTTCTCCCCAGGGAGGAGGAATGAAGCTTCATCATAGATGAATGGAAAGTCCAGGAAAGAGAATG : 2841
C-P1_genom   : TAAGAACCTTGTGTTCTCCCCAGGGAGGAGGAATGAAGCTTCATCATAGATGAATGGAAAGTCCAGGAAAGAGAATG : 2841
B3-P11_con   : TAAGAACCTTGTGTTCTCCCCAGGGAGGAGGAATGAAGCTTCATCATAGATGAATGGAAAGTCCAGGAAAGAGAATG : 2855
C1-P11_con   : TAAGAACCTTGTGTTCTCCCCAGGGAGGAGGAATGAAGCTTCATCATAGATGAATGGAAAGTCCAGGAAAGAGAATG : 2839
```

FIG. 8H

| | | | |
|---|---|---|---|
| (SEQ ID NO: 15) | P1_consens | : CCCGTTTTCAAACCGGTCTGGAATTCTTTCCAGATAGAGGAGTTTGGACGGGAGTGTTCACCACACGCGT : | 2952 |
| (SEQ ID NO: 9) | B-P1_conse | : CCCGTTTTCAAACCGGTCTGGAATTCTTTCCAGATAGAGGAGTTTGGACGGGAGTGTTCACCACACGCGT : | 2913 |
| (SEQ ID NO: 10) | C-P1_genom | : CCCGTTTTCAAACCGGTCTGGAATTCTTTCCAGATAGAGGAGTTTGGACGGGAGTGTTCACCACACGCGT : | 2913 |
| (SEQ ID NO: 11) | B3-P11_con | : CCCGTTTTCAAACCGGTCTGGAATTCTTTCCAGATAGAGGAGTTTGGACGGGAGTGTTCACCACACGCGT : | 2927 |
| (SEQ ID NO: 12) | C1-P11_con | : CCCGTTTTCAAACCGGTCTGGAATTCTTTCCAGATAGAGGAGTTTGGACGGGAGTGTTCACCACACGCGT : | 2911 |
| (SEQ ID NO: 15) | P1_consens | : GTACATGGACCCAGTCTTTGAATACACCATAGACTGCGATGGATCTATCTTGGGTGCAGCGGTGAACGGAAA : | 3024 |
| (SEQ ID NO: 9) | B-P1_conse | : GTACATGGACCCAGTCTTTGAATACACCATAGACTGCGATGGATCTATCTTGGGTGCAGCGGTGAACGGAAA : | 2985 |
| (SEQ ID NO: 10) | C-P1_genom | : GTACATGGACGCCAGTCTTTGAATACACCATAGACTGCGATGGATCTATCTTGGGTGCAGCGGTGAACGGAAA : | 2985 |
| (SEQ ID NO: 11) | B3-P11_con | : GTACATGGACCCAGTCTTTGAATACACCATAGACTGCGATGGATCTATCTTGGGTGCAGCGGTGAACGGAAA : | 2999 |
| (SEQ ID NO: 12) | C1-P11_con | : GTACATGGACGCCAGTCTTTGAATACACCATAGACTGCGATGGATCTATCTTGGGTGCAGCGGTGAACGGAAA : | 2983 |
| (SEQ ID NO: 15) | P1_consens | : AAAGAGTGCCCATGGCTCTCCAACATTTTGATGGAAGTCATGAAGTAAATGGACATGATGATCCACAC : | 3096 |
| (SEQ ID NO: 9) | B-P1_conse | : AAAGAGTGCCCATGGCTCTCCAACATTTTGATGGAAGTCATGAAGTAAATGGACATGATGATCCACAC : | 3057 |
| (SEQ ID NO: 10) | C-P1_genom | : AAAGAGTGCCCATGGCTCTCCAACATTTTGATGGAAGTCATGAAGTAAATGGACATGATGATCCACAC : | 3057 |
| (SEQ ID NO: 11) | B3-P11_con | : AAAGAGTGCCCATGGCTCTCCAACATTTTGATGGAAGTCATGAAGTAAATGGACATGATGATCCACAC : | 3071 |
| (SEQ ID NO: 12) | C1-P11_con | : AAAGAGTGCCCATGGCTCTCCAACATTTTGATGGAAGTCATGAAGTAAATGGACATGATGATCCACAC : | 3055 |
| (SEQ ID NO: 15) | P1_consens | : CTTGGAGGCATTAGATTACAAGGAGTGTGAGTGGCCACTGACACATACGATTGAACATCAGTTGAAGAGAG : | 3168 |
| (SEQ ID NO: 9) | B-P1_conse | : CTTGGAGGCATTAGATTACAAGGAGTGTGAGTGGCCACTGACACATACGATTGAACATCAGTTGAAGAGAG : | 3129 |
| (SEQ ID NO: 10) | C-P1_genom | : CTTGGAGGCATTAGATTACAAGGAGTGTGAGTGGCCACTGACACATACGATTGAACATCAGTTGAAGAGAG : | 3129 |
| (SEQ ID NO: 11) | B3-P11_con | : CTTGGAGGCATTAGATTACAAGGAGTGTGAGTGGCCACTGACACATACGATTGAACATCAGTTGAAGAGAG : | 3143 |
| (SEQ ID NO: 12) | C1-P11_con | : CTTGGAGGCATTAGATTACAAGGAGTGTGAGTGGCCACTGACACATACGATTGAACATCAGTTGAAGAGAG : | 3127 |
| (SEQ ID NO: 15) | P1_consens | : TGAAATGTTCATGCCGAGATCAATCGGAGGCCCAGTTAGCTCTCACAATCATATCCCTGATACAAGGTTCA : | 3240 |
| (SEQ ID NO: 9) | B-P1_conse | : TGAAATGTTCATGCCGAGATCAATCGGAGGCCCAGTTAGCTCTCACAATCATATCCCTGATACAAGGTTCA : | 3201 |
| (SEQ ID NO: 10) | C-P1_genom | : TGAAATGTTCATGCCGAGATCAATCGGAGGCCCAGTTAGCTCTCACAATCATATCCCTGATACAAGGTTCA : | 3201 |
| (SEQ ID NO: 11) | B3-P11_con | : TGAAATGTTCATGCCGAGATCAATCGGAGGCCCAGTTAGCTCTCACAATCATATCCCTGATACAAGGTTCA : | 3215 |
| (SEQ ID NO: 12) | C1-P11_con | : TGAAATGTTCATGCCGAGATCAATCGGAGGCCCAGTTAGCTCTCACAATCATATCCCTGATACAAGGTTCA : | 3199 |

FIG. 8I

| | | | |
|---|---|---|---|
| (SEQ ID NO: 15) | P1_consens | : GACGAACGGACCTTGGATGCAGGTACCAGTACCACTAGAAGTGAAGAGAGAAGCTTGCCCAGGGACTAGCGTGATCAT | 3312 |
| (SEQ ID NO: 9) | B-P1_conse | : GACGAACGGACCTTGGATGCAGGTACCAGTACCACTAGAAGTGAAGAGAGAAGCTTGCCCAGGGACTAGCGTGATCAT | 3273 |
| (SEQ ID NO: 10) | C-P1_genom | : GACGAACGGACCTTGGATGCAGGTACCAGTACCACTAGAAGTGAAGAGAGAAGCTTGCCCAGGGACTAGCGTGATCAT | 3273 |
| (SEQ ID NO: 11) | B3-P11_con | : GACGAACGGACCTTGGATGCAGGTACCAGTACCACTAGAAGTGAAGAGAGAAGCTTGCCCAGGGACTAGCGTGATCAT | 3287 |
| (SEQ ID NO: 12) | C1-P11_con | : GACGAACGGACCTTGGATGCAGGTACCAGTACCACTAGAAGTGAAGAGAGAAGCTTGCCCAGGGACTAGCGTGATCAT | 3271 |

| | | | |
|---|---|---|---|
| (SEQ ID NO: 15) | P1_consens | : TGATGGCAACTGTGATGGACGGGAAAATCAACCAGATCCACCACGATAGCGGGAAAGTTATTCCTGAATG | 3384 |
| (SEQ ID NO: 9) | B-P1_conse | : TGATGGCAACTGTGATGGACGGGAAAATCAACCAGATCCACCACGATAGCGGGAAAGTTATTCCTGAATG | 3345 |
| (SEQ ID NO: 10) | C-P1_genom | : TGATGGCAACTGTGATGGACGGGAAAATCAACCAGATCCACCACGATAGCGGGAAAGTTATTCCTGAATG | 3345 |
| (SEQ ID NO: 11) | B3-P11_con | : TGATGGCAACTGTGATGGACGGGAAAATCAACCAGATCCACCACGATAGCGGGAAAGTTATTCCTGAATG | 3359 |
| (SEQ ID NO: 12) | C1-P11_con | : TGATGGCAACTGTGATGGACGGGAAAATCAACCAGATCCACCACGATAGCGGGAAAGTTATTCCTGAATG | 3343 |

| | | | |
|---|---|---|---|
| (SEQ ID NO: 15) | P1_consens | : GTGTTGCCGCTCCTGCACAATGCCGCCGCCTGTGAGCTTCCATGGTAGTGATGGTGTTGGTATCCCATGGAAAT | 3456 |
| (SEQ ID NO: 9) | B-P1_conse | : GTGTTGCCGCTCCTGCACAATGCCGCCGCCTGTGAGCTTCCATGGTAGTGATGGTGTTGGTATCCCATGGAAAT | 3417 |
| (SEQ ID NO: 10) | C-P1_genom | : GTGTTGCCGCTCCTGCACAATGCCGCCGCCTGTGAGCTTCCATGGTAGTGATGGTGTTGGTATCCCATGGAAAT | 3417 |
| (SEQ ID NO: 11) | B3-P11_con | : GTGTTGCCGCTCCTGCATAATGCCGCCGCCTGTGAGCTTCCATGGTAGTGATGGTGTTGGTATCCCATGGAAAT | 3431 |
| (SEQ ID NO: 12) | C1-P11_con | : GTGTTGCCGCTCCTGCACAATGCCGCCGCCTGTGAGCTTCCATGGTAGTGATGGTGTTGGTATCCCATGGAAAT | 3415 |

| | | | |
|---|---|---|---|
| (SEQ ID NO: 15) | P1_consens | : TAGGCCAAGGAAAACGCATGAAAGCCATCTGGTTACAGCTGGTGCGCTCCTGGGTTGGTGCGCCATGAAATACATGCTGTCCC | 3528 |
| (SEQ ID NO: 9) | B-P1_conse | : TAGGCCAAGGAAAACGCATGAAAGCCATCTGGTTACAGCTGGTGCGCTCCTGGGTTGGTGCGCCATGAAATACATGCTGTCCC | 3489 |
| (SEQ ID NO: 10) | C-P1_genom | : TAGGCCAAGGAAAACGCATGAAAGCCATCTGGTTACAGCTGGTGCGCTCCTGGGTTGGTGCGCCATGAAATACATGCTGTCCC | 3489 |
| (SEQ ID NO: 11) | B3-P11_con | : TAGGCCAAGGAAAACGCATGAAAGCCATCTGGTTACAGCTGGTGCGCTCCTGGGTTGGTGCGCCATGAAATACATGCTGTCCC | 3503 |
| (SEQ ID NO: 12) | C1-P11_con | : TAGGCCAAGGAAAACGCATGAAAGCCATCTGGTTACAGCTGGTGCGCTCCTGGGTTGGTGCGCCATGAAATACATGCTGTCCC | 3487 |

| | | | |
|---|---|---|---|
| (SEQ ID NO: 15) | P1_consens | : TTTTGGTTTGGTGAGCATGAGCATGATAGCAATGGAAGTGGTCCTAAGGAAAAGACAGGGACCAAAGCAAATGTT | 3600 |
| (SEQ ID NO: 9) | B-P1_conse | : TTTTGGTTTGGTGAGCATGAGCATGATAGCAATGGAAGTGGTCCTAAGGAAAAGACAGGGACCAAAGCAAATGTT | 3561 |
| (SEQ ID NO: 10) | C-P1_genom | : TTTTGGTTTGGTGAGCATGAGCATGATAGCAATGGAAGTGGTCCTAAGGAAAAGACAGGGACCAAAGCAAATGTT | 3561 |
| (SEQ ID NO: 11) | B3-P11_con | : TTTTGGTTTGGTGAGCATGAGCATGATAGCAATGGAAGTGGTCCTAAGGAAAAGACAGGGACCAAAGCAAATGTT | 3575 |
| (SEQ ID NO: 12) | C1-P11_con | : TTTTGGTTTGGTGAGCATGAGCATGATAGCAATGGAAGTGGTCCTAAGGAAAAGACAGGGACCAAAGCAAATGTT | 3559 |

FIG. 8J

```
                                         *         3620         *         3640         *         3660         *
(SEQ ID NO: 15) P1_consens  : GGTTGGAGGAGTAGTGCTCTTGGAGCAATGCTGGTCGGGCAAGTAACTCTCCTTGATTTGCTGAAACTCAC : 3672
(SEQ ID NO: 9)  B-P1_conse  : GGTTGGAGGAGTAGTGCTCTTGGAGCAATGCTGGTCGGGCAAGTAACTCTCCTTGATTTGCTGAAACTCAC : 3633
(SEQ ID NO: 10) C-P1_genom  : GGTTGGAGGAGTAGTGCTCTTGGAGCAATGCTGGTCGGGCAAGTAACTCTCCTTGATTTGCTGAAACTCAC : 3633
(SEQ ID NO: 11) B3-P11_con  : GGTTGGAGGAGTAGTGCTCTTGGAGCAATGCTGGTCGGGCAAGTAACTCTCCTTGATTGCTGAAACTCAC  : 3647
(SEQ ID NO: 12) C1-P11_con  : GGTTGGAGGAGTAGTGCTCTTGGAGCAATGCTGGTCGGGCAAGTAACTCTCCTTGA-TTGCTGAAACTCAC : 3631

*         3680         *         3700         *         3720         *         3740
(SEQ ID NO: 15) P1_consens  : AGTGGCTGTGGGATTGCATTTCCATGAGATGAACAATGAGAGACGCCATGTATATGGCGTTGATTGCTGC  : 3744
(SEQ ID NO: 9)  B-P1_conse  : AGTGGCTGTGGGATTGCATTTCCATGAGATGAACAATGAGAGACGCCATGTATATGGCGTTGATTGCTGC  : 3705
(SEQ ID NO: 10) C-P1_genom  : AGTGGCTGTGGGATTGCATTTCCATGAGATGAACAATGAGAGACGCCATGTATATGGCGTTGATTGCTGC  : 3705
(SEQ ID NO: 11) B3-P11_con  : AGTGGCTGTGGGATTGCATTTCCATGAGATGAACAATGAGAGACGCCATGTATATGGCGTTGATTGCTGC  : 3719
(SEQ ID NO: 12) C1-P11_con  : AGTGGCTGTGGGATTGCATTTCCATGAGATGAACAATGAGAGACGCCATGTATATGGCGTTGATTGCTGC  : 3703

*         3760         *         3780         *         3800         *
(SEQ ID NO: 15) P1_consens  : CTTTTCAATCAGACCAGGGCTGCTCATCCGCTTGGGCTTCAGGACCCTATGGAGCCCTCGGGAACGCCTTGT : 3816
(SEQ ID NO: 9)  B-P1_conse  : CTTTTCAATCAGACCAGGGCTGCTCATCCGCTTGGGCTTCAGGACCCTATGGAGCCCTCGGGAACGCCTTGT : 3777
(SEQ ID NO: 10) C-P1_genom  : CTTTTCAATCAGACCAGGGCTGCTCATCCGCTTGGGCTTCAGGACCCTATGGAGCCCTCGGGAACGCCTTGT : 3777
(SEQ ID NO: 11) B3-P11_con  : CTTTTCAATCAGACCAGGGCTGCTCATCCGCTTGGGCTTCAGGACCCTATGGAGCCCTCGGGAACGCCTTGT : 3791
(SEQ ID NO: 12) C1-P11_con  : CTTTTCAATCAGACCAGGGCTGCTCATCCGCTTGGGCTTCAGGACCCTATGGAGCCCTCGGGAACGCCTTGT : 3775

3820         *         3840         *         3860         *         3880         *
(SEQ ID NO: 15) P1_consens  : GCTGACCCTAGGAGCAGCAGCCATGGTGGAGATTGCCTTGGGTGGCGTGATGGGCGTGTGGAAGTATCTAAA : 3888
(SEQ ID NO: 9)  B-P1_conse  : GCTGACCCTAGGAGCAGCAGCCATGGTGGAGATTGCCTTGGGTGGCGTGATGGGCGTGTGGAAGTATCTAAA : 3849
(SEQ ID NO: 10) C-P1_genom  : GCTGACCCTAGGAGCAGCAGCCATGGTGGAGATTGCCTTGGGTGGCGTGATGGGCGTGTGGAAGTATCTAAA : 3849
(SEQ ID NO: 11) B3-P11_con  : GCTGACCCTAGGAGCAGCAGCCATGGTGGAGATTGCCTTGGGTGGCGTGATGGGCGTGTGGAAGTATCTAAA : 3863
(SEQ ID NO: 12) C1-P11_con  : GCTGACCCTAGGAGCAGCAGCCATGGTGGAGATTGCCTTGGGTGGCGTGATGGGCGTGTGGAAGTATCTAAA : 3847

*         3900         *         3920         *         3940         *         3960
(SEQ ID NO: 15) P1_consens  : TGCAGTTTCTCTCTGCATCCTGACAATAAATGCTGTTGCTTCTAGGAAAGCATCAAATACCATCTTGCCCCT : 3960
(SEQ ID NO: 9)  B-P1_conse  : TGCAGTTTCTCTCTGCATCCTGACAATAAATGCTGTTGCTTCTAGGAAAGCATCAAATACCATCTTGCCCCT : 3921
(SEQ ID NO: 10) C-P1_genom  : TGCAGTTTCTCTCTGCATCCTGACAATAAATGCTGTTGCTTCTAGGAAAGCATCAAATACCATCTTGCCCCT : 3921
(SEQ ID NO: 11) B3-P11_con  : TGCAGTTTCTCTCTGCATCCTGACAATAAATGCTGTTGCTTCTAGGAAAGCATCAAATACCATCTTGCCCCT : 3935
(SEQ ID NO: 12) C1-P11_con  : TGCAGTTTCTCTCTGCATCCTGACAATAAATGCTGTTGCTTCTAGGAAAGCATCAAATACCATCTTGCCCCT : 3919
```

FIG. 8K

| | | | |
|---|---|---|---|
| (SEQ ID NO: 15) | P1_consens | : CATGGCTCTGTTGACACCTGTCACTATGGCTGAGGTGAGACTTGCCGCAATGTTCTTTTGTGCCGTGGTTAT | 4032 |
| (SEQ ID NO: 9)  | B-P1_conse | : CATGGCTCTGTTGACACCTGTCACTATGGCTGAGGTGAGACTTGCCGCAATGTTCTTTTGTGCCGTGGTTAT | 3993 |
| (SEQ ID NO: 10) | C-P1_genom | : CATGGCTCTGTTGACACCTGTCACTATGGCTGAGGTGAGACTTGCCGCAATGTTCTTTTGTGCCGTGGTTAT | 3993 |
| (SEQ ID NO: 11) | B3-P11_con | : CATGGCTCTGTTGACACCTGTCACTATGGCTGAGGTGAGACTTGCCGCAATGTTCCTTTGTGCCGTGGTTAT | 4007 |
| (SEQ ID NO: 12) | C1-P11_con | : CATGGCTCTGTTGACACCTGTCACTATGGCTGAGGTGAGACTTGCCGCAATGTTCTTTTTGTGCCGTGGTTAT | 3991 |

| (SEQ ID NO: 15) | P1_consens | : CATAGGGGTCCTTCACCAGAATTTCAAGGACACCTCGGTGGCCCTCACACT | 4104 |
| (SEQ ID NO: 9)  | B-P1_conse | : CATAGGGGTCCTTCACCAGAATTTCAAGGACACCTCAAGACTATACCTCGGTGGCCCTCACACT | 4065 |
| (SEQ ID NO: 10) | C-P1_genom | : CATAGGGGTCCTTCACCAGAATTTCAAGGACACCTCAAGACTATACCTCGGTGGCCCTCACACT | 4065 |
| (SEQ ID NO: 11) | B3-P11_con | : CATAGGGGTCCTTCACCAGAATTTCAAGGACACCTCAAGACTATACCTCGGTGGCCCTCACACT | 4079 |
| (SEQ ID NO: 12) | C1-P11_con | : CATAGGGGTCCTTCACCAGAATTTCAAGGACACCTCAAGACTATACCTCGGTGGCCCTCACACT | 4063 |

| (SEQ ID NO: 15) | P1_consens | : CACATCTTACCTGGGCTTGACACAACCTTTTTGGGCCTGTGTGCATTTCTGGCAACCCGCATATTGGGCG | 4176 |
| (SEQ ID NO: 9)  | B-P1_conse | : CACATCTTACCTGGGCTTGACACAACCTTTTTGGGCCTGTGTGCATTTCTGGCAACCCGCATATTGGGCG | 4137 |
| (SEQ ID NO: 10) | C-P1_genom | : CACATCTTACCTGGGCTTGACACAACCTTTTTGGGCCTGTGTGCATTTCTGGCAACCCGCATATTGGGCG | 4137 |
| (SEQ ID NO: 11) | B3-P11_con | : CACATCTTACCTGGGCTTGACACAACCTTTTTGGGCCTGTGTGCATTTCTGGCAACCCGCATATTGGGCG | 4151 |
| (SEQ ID NO: 12) | C1-P11_con | : CACATCTTACCTGGGCTTGACACAACCTTTTTGGGCCTGTGTGCATTTCTGGCAACCCGCATATTGGGCG | 4135 |

| (SEQ ID NO: 15) | P1_consens | : AAGGAGTATCCCAGTGAATGAGGCACTCGCAGCAGCTGGTCTAGTGGGAGTGCTGGCAGGACTGGCTTTTCA | 4248 |
| (SEQ ID NO: 9)  | B-P1_conse | : AAGGAGTATCCCAGTGAATGAGGCACTCGCAGCAGCTGGTCTAGTGGGAGTGCTGGCAGGACTGGCTTTTCA | 4209 |
| (SEQ ID NO: 10) | C-P1_genom | : AAGGAGTATCCCAGTGAATGAGGCACTCGCAGCAGCTGGTCTAGTGGGAGTGCTGGCAGGACTGGCTTTTCA | 4209 |
| (SEQ ID NO: 11) | B3-P11_con | : AAGGAGTATCCCAGTGAATGAGGCACTCGCAGCAGCTGGTCTAGTGGGAGTGCTGGCAGGACTGGCTTTTCA | 4223 |
| (SEQ ID NO: 12) | C1-P11_con | : AAGGAGTATCCCAGTGAATGAGGCACTCGCAGCAGCTGGTCTAGTGGGAGTGCTGGCAGGACTGGCTTTTCA | 4207 |

| (SEQ ID NO: 15) | P1_consens | : GGAGATGGAGAACTTCCTTGGTCCGATTGCAGTTGGAGGACTCCTGATGATGCTGGTTAGCGTGGCTGGGAG | 4320 |
| (SEQ ID NO: 9)  | B-P1_conse | : GGAGATGGAGAACTTCCTTGGTCCGATTGCAGTTGGAGGACTCCTGATGATGCTGGTTAGCGTGGCTGGGAG | 4281 |
| (SEQ ID NO: 10) | C-P1_genom | : GGAGATGGAGAACTTCCTTGGTCCGATTGCAGTTGGAGGACTCCTGATGATGCTGGTTAGCGTGGCTGGGAG | 4281 |
| (SEQ ID NO: 11) | B3-P11_con | : GGAGATGGAGAACTTCCTTGGTCCGATTGCAGTTGGAGGACTCCTGATGATGCTGGTTAGCGTGGCTGGGAG | 4295 |
| (SEQ ID NO: 12) | C1-P11_con | : GGAGATGGAGAACTTCCTTGGTCCGATTGCAGTTGGAGGACTCCTGATGATGCTGGTTAGCGTGGCTGGGAG | 4279 |

FIG. 8L

```
                          *         4340         *         4360         *         4380         *
(SEQ ID NO: 15) P1_consens  : GGTGGATGGGCTAGAGCTCAAGAAGCTTGGTGAAGTTTCATGGAAGAGAGGCGGAGATCAGCGGAGTTC  :  4392
(SEQ ID NO: 9)  B-P1_conse  : GGTGGATGGGCTAGAGCTCAAGAAGCTTGGTGAAGTTTCATGGAAGAGAGGCGGAGATCAGCGGAGTTC  :  4353
(SEQ ID NO: 10) C-P1_genom  : GGTGGATGGGCTAGAGCTCAAGAAGCTTGGTGAAGTTTCATGGAAGAGAGGCGGAGATCAGCGGAGTTC  :  4353
(SEQ ID NO: 11) B3-P11_con  : GGTGGATGGGCTAGAGCTCAAGAAGCTTGGTGAAGTTTCATGGAAGAGAGGCGGAGATCAGCGGAGTTC  :  4367
(SEQ ID NO: 12) C1-P11_con  : GGTGGATGGGCTAGAGCTCAAGAAGCTTGGTGAAGTTTCATGGAAGAGAGGCGGAGATCAGCGGAGTTC  :  4351

4400        *         4420         *         4440         *         4460
(SEQ ID NO: 15) P1_consens  : CGCCCGCTATGATGTGGCACTCAGTGAACAAGGGGAGTTCAAGCTGCTTCTGAAGAGAAAGTGCCATGGA  :  4464
(SEQ ID NO: 9)  B-P1_conse  : CGCCCGCTATGATGTGGCACTCAGTGAACAAGGGGAGTTCAAGCTGCTTCTGAAGAGAAAGTGCCATGGA  :  4425
(SEQ ID NO: 10) C-P1_genom  : CGCCCGCTATGATGTGGCACTCAGTGAACAAGGGGAGTTCAAGCTGCTTCTGAAGAGAAAGTGCCATGGA  :  4425
(SEQ ID NO: 11) B3-P11_con  : CGCCCGCTATGATGTGGCACTCAGTGAACAAGGGGAGTTCAAGCTGCTTCTGAAGAGAAAGTGCCATGGA  :  4439
(SEQ ID NO: 12) C1-P11_con  : CGCCCGCTATGATGTGGCACTCAGTGAACAAGGGGAGTTCAAGCTGCTTCTGAAGAGAAAGTGCCATGGA  :  4423

*         4480         *         4500         *         4520         *
(SEQ ID NO: 15) P1_consens  : CCAGGTTGTGATGACCTGCTGCTGCCCTGGTTGGGCTGCCCCTCCATCCATTGCTCTTCTGCTGTCCTTGC  :  4536
(SEQ ID NO: 9)  B-P1_conse  : CCAGGTTGTGATGACCTGCTGCTGCCCTGGTTGGGCTGCCCCTCCATCCATTGCTCTTCTGCTGTCCTTGC  :  4497
(SEQ ID NO: 10) C-P1_genom  : CCAGGTTGTGATGACCTGCTGCTGCCCTGGTTGGGCTGCCCCTCCATCCATTGCTCTTCTGCTGTCCTTGC  :  4497
(SEQ ID NO: 11) B3-P11_con  : CCAGGTTGTGATGACCTGCTGCTGCCCTGGTTGGGCTGCCCCTCCATCCATTGCTCTTCTGCTGTCCTTGC  :  4511
(SEQ ID NO: 12) C1-P11_con  : CCAGGTTGTGATGACCTGCTGCTGCCCTGGTTGGGCTGCCCCTCCATCCATTGCTCTTCTGCTGTCCTTGC  :  4495

4540        *         4560         *         4580         *         4600
(SEQ ID NO: 15) P1_consens  : TGGGTGGCTGTGTTCATGTCAGGGGAGCTAGGAGAAGTGGGATGTCTTGTGGGATATTCCCACTCCTAAGAT  :  4608
(SEQ ID NO: 9)  B-P1_conse  : TGGGTGGCTGTGTTCATGTCAGGGGAGCTAGGAGAAGTGGGATGTCTTGTGGGATATTCCCACTCCTAAGAT  :  4569
(SEQ ID NO: 10) C-P1_genom  : TGGGTGGCTGTGTTCATGTCAGGGGAGCTAGGAGAAGTGGGATGTCTTGTGGGATATTCCCACTCCTAAGAT  :  4569
(SEQ ID NO: 11) B3-P11_con  : TGGGTGGCTGTGTTCATGTCAGGGGAGCTAGGAGAAGTGGGATGTCTTGTGGGATATTCCCACTCCTAAGAT  :  4583
(SEQ ID NO: 12) C1-P11_con  : TGGGTGGCTGTGTTCATGTCAGGGGAGCTAGGAGAAGTGGGATGTCTTGTGGGATATTCCCACTCCTAAGAT  :  4567

*         4620         *         4640         *         4660         *         4680
(SEQ ID NO: 15) P1_consens  : CATCGAGGAATGTGAACATCTGGAGGATGGGGATTTATGCCATATTCCAGTCAACCTTCTTGGGGCCTCCCA  :  4680
(SEQ ID NO: 9)  B-P1_conse  : CATCGAGGAATGTGAACATCTGGAGGATGGGGATTTATGCCATATTCCAGTCAACCTTCTTGGGGCCTCCCA  :  4641
(SEQ ID NO: 10) C-P1_genom  : CATCGAGGAATGTGAACATCTGGAGGATGGGGATTTATGCCATATTCCAGTCAACCTTCTTGGGGCCTCCCA  :  4641
(SEQ ID NO: 11) B3-P11_con  : CATCGAGGAATGTGAACATCTGGAGGATGGGGATTTATGCCATATTCCAGTCAACCTTCTTGGGGCCTCCCA  :  4655
(SEQ ID NO: 12) C1-P11_con  : CATCGAGGAATGTGAACATCTGGAGGATGGGGATTTATGCCATATTCCAGTCAACCTTCTTGGGGCCTCCCA  :  4639
```

```
(SEQ ID NO: 15)  P1_consens : CCTTGTGTCGGTGACAACTCCTTCGTGTCCGCCATATCCCAGACTGAGGTGAAGGAAGAAGGAGGAGCT : 5112
(SEQ ID NO: 9)   B-P1_conse : CCTTGTGTCGGTGACAACTCCTTCGTGTCCGCCATATCCCAGACTGAGGTGAAGGAAGAAAGGAGGAGCT : 5073
(SEQ ID NO: 10)  C-P1_genom : CCTTGTGTCGGTGACAACTCCTTCGTGTCCGCCATATCCCAGACTGAGGTGAAGGAAGAAAGGAGGAGCT : 5073
(SEQ ID NO: 11)  B3-P11_con : CCTTGTGTCGGTGACAACTCCTTCGTGTCCGCCATATCCCAGACTGAGGTGAAGGAAGAAAGGAGGAGCT : 5087
(SEQ ID NO: 12)  C1-P11_con : CCTTGTGTCGGTGACAACTCCTTCGTGTCCGCCATATCCCAGACTGAGGTGAAGGAAGAAAGGAGGAGCT : 5071

(SEQ ID NO: 15)  P1_consens : CCAAGAGATCCGACAATGCTAAAGAAAGGAATGACAACTGTCTTGATTTTCATCCTGAGCTGGAAGAC : 5184
(SEQ ID NO: 9)   B-P1_conse : CCAAGAGATCCGACAATGCTAAAGAAAGGAATGACAACTGTCTTGATTTTCATCCTGAGCTGGAAGAC : 5145
(SEQ ID NO: 10)  C-P1_genom : CCAAGAGATCCGACAATGCTAAAGAAAGGAATGACAACTGTCTTGATTTTCATCCTGAGCTGGAAGAC : 5145
(SEQ ID NO: 11)  B3-P11_con : CCAAGAGATCCGACAATGCTAAAGAAAGGAATGACAACTGTCTTGATTTTCATCCTGAGCTGGAAGAC : 5159
(SEQ ID NO: 12)  C1-P11_con : CCAAGAGATCCGACAATGCTAAAGAAAGGAATGACAACTGTCTTGATTTTCATCCTGAGCTGGAAGAC : 5143

(SEQ ID NO: 15)  P1_consens : AAGACGTTTCCTCCCACAGATCTTGGCCGAGTGCGCACGGAGACGCTTGCGCACTCTTGTGTTGGCCCCCAC : 5256
(SEQ ID NO: 9)   B-P1_conse : AAGACGTTTCCTCCCACAGATCTTGGCCGAGTGCGCACGGAGACGCTTGCGCACTCTTGTGTTGGCCCCCAC : 5217
(SEQ ID NO: 10)  C-P1_genom : AAGACGTTTCCTCCCACAGATCTTGGCCGAGTGCGCACGGAGACGCTTGCGCACTCTTGTGTTGGCCCCCAC : 5217
(SEQ ID NO: 11)  B3-P11_con : AAGACGTTTCCTCCCACAGATCTTGGCCGAGTGCGCACGGAGACGCTTGCGCACTCTTGTGTTGGCCCCCAC : 5231
(SEQ ID NO: 12)  C1-P11_con : AAGACGTTTCCTCCCACAGATCTTGGCCGAGTGCGCACGGAGACGCTTGCGCACTCTTGTGTTGGCCCCCAC : 5215

(SEQ ID NO: 15)  P1_consens : CAGGGTTGTTCTTCTTCTGAAATGAAGGAGGCTTTCACGGCCTGGACGTGAAATTCCACACACAGGCTTTTC : 5328
(SEQ ID NO: 9)   B-P1_conse : CAGGGTTGTTCTTCTTCTGAAATGAAGGAGGCTTTCACGGCCTGGACGTGAAATTCCACACACAGGCTTTTC : 5289
(SEQ ID NO: 10)  C-P1_genom : CAGGGTTGTTCTTCTTCTGAAATGAAGGAGGCTTTCACGGCCTGGACGTGAAATTCCACACACAGGCTTTTC : 5289
(SEQ ID NO: 11)  B3-P11_con : CAGGGTTGTTCTTCTTCTGAAATGAAGGAGGCTTTCACGGCCTGGACGTGAAATTCCACACACAGGCTTTTC : 5303
(SEQ ID NO: 12)  C1-P11_con : CAGGGTTGTTCTTCTTCTGAAATGAAGGAGGCTTTCACGGCCTGGACGTGAAATTCCACACACAGGCTTTTC : 5287

(SEQ ID NO: 15)  P1_consens : CGCTCACGGCAGCGGGAGAGAAGTCATTGATGCTATCTGCCATGCCACCCTAACTTACAGGATGTTGGAACC : 5400
(SEQ ID NO: 9)   B-P1_conse : CGCTCACGGCAGCGGGAGAGAAGTCATTGATGCTATCTGCCATGCCACCCTAACTTACAGGATGTTGGAACC : 5361
(SEQ ID NO: 10)  C-P1_genom : CGCTCACGGCAGCGGGAGAGAAGTCATTGATGCTATCTGCCATGCCACCCTAACTTACAGGATGTTGGAACC : 5361
(SEQ ID NO: 11)  B3-P11_con : CGCTCACGGCAGCGGGAGAGAAGTCATTGATGCTATCTGCCATGCCACCCTAACTTACAGGATGTTGGAACC : 5375
(SEQ ID NO: 12)  C1-P11_con : CGCTCACGGCAGCGGGAGAGAAGTCATTGATGCTATCTGCCATGCCACCCTAACTTACAGGATGTTGGAACC : 5359
```

FIG. 80

```
                                        *          5420          *          5440          *          5460          *
(SEQ ID NO: 15)  P1_consens  : AACTAGGGTTGTTAACTGGGAAGTGATCATTATGATGAAGCCCATTTTTTGGATCCAGCTAGCATAGCCGC : 5472
(SEQ ID NO: 9)   B-P1_conse  : AACTAGGGTTGTTAACTGGGAAGTGATCATTATGATGAAGCCCATTTTTTGGATCCAGCTAGCATAGCCGC : 5433
(SEQ ID NO: 10)  C-P1_genom  : AACTAGGGTTGTTAACTGGGAAGTGATCATTATGATGAAGCCCATTTTTTGGATCCAGCTAGCATAGCCGC : 5433
(SEQ ID NO: 11)  B3-P11_con  : AACTAGGGTTGTTAACTGGGAAGTGATCATTATGATGAAGCCCATTTTTTGGATCCAGCTAGCATAGCCGC : 5447
(SEQ ID NO: 12)  C1-P11_con  : AACTAGGGTTGTTAACTGGGAAGTGATCATTATGATGAAGCCCATTTTTTGGATCCAGCTAGCATAGCCGC : 5431

5480         *          5500          *          5520          *          5540
(SEQ ID NO: 15)  P1_consens  : TAGAGGTTGGGCAGCGCACAGAGCTAGGGCAAATGAAAGTGCAACAATCTTGATGACAGCCACACCGCCTGG : 5544
(SEQ ID NO: 9)   B-P1_conse  : TAGAGGTTGGGCAGCGCACAGAGCTAGGGCAAATGAAAGTGCAACAATCTTGATGACAGCCACACCGCCTGG : 5505
(SEQ ID NO: 10)  C-P1_genom  : TAGAGGTTGGGCAGCGCACAGAGCTAGGGCAAATGAAAGTGCAACAATCTTGATGACAGCCACACCGCCTGG : 5505
(SEQ ID NO: 11)  B3-P11_con  : TAGAGGTTGGGCAGCGCACAGAGCTAGGGCAAATGAAAGTGCAACAATCTTGATGACAGCCACACCGCCTGG : 5519
(SEQ ID NO: 12)  C1-P11_con  : TAGAGGTTGGGCAGCGCACAGAGCTAGGGCAAATGAAAGTGCAACAATCTTGATGACAGCCACACCGCCTGG : 5503

*          5560          *          5580          *          5600          *
(SEQ ID NO: 15)  P1_consens  : GACTAGTGATGAATTTCCACATTCAAATGGTGAAAGATGTTCAAACGGACATACCCAGTGAGCCCTG : 5616
(SEQ ID NO: 9)   B-P1_conse  : GACTAGTGATGAATTTCCACATTCAAATGGTGAAAGATGTTCAAACGGACATACCCAGTGAGCCCTG : 5577
(SEQ ID NO: 10)  C-P1_genom  : GACTAGTGATGAATTTCCACATTCAAATGGTGAAAGATGTTCAAACGGACATACCCAGTGAGCCCTG : 5577
(SEQ ID NO: 11)  B3-P11_con  : GACTAGTGATGAATTTCCACATTCAAATGGTGAAAGATGTTCAAACGGACATACCCAGTGAGCCCTG : 5591
(SEQ ID NO: 12)  C1-P11_con  : GACTAGTGATGAATTTCCACATTCAAATGGTGAAAGATGTTCAAACGGACATACCCAGTGAGCCCTG : 5575

5620         *          5640          *          5660          *          5680
(SEQ ID NO: 15)  P1_consens  : GAACACAGGGCATGACTGGATCCTGGCTGACTGGATCCTGCTGACAAAAGGCCACGGCATGGTTCCTTCCATCCATCAGAGCTGC : 5688
(SEQ ID NO: 9)   B-P1_conse  : GAACACAGGGCATGACTGGATCCTGGCTGACTGGATCCTGCTGACAAAAGGCCACGGCATGGTTCCTTCCATCCATCAGAGCTGC : 5649
(SEQ ID NO: 10)  C-P1_genom  : GAACACAGGGCATGACTGGATCCTGGCTGACTGGATCCTGCTGACAAAAGGCCACGGCATGGTTCCTTCCATCCATCAGAGCTGC : 5649
(SEQ ID NO: 11)  B3-P11_con  : GAACACAGGGCATGACTGGATCCTGGCTGACTGGATCCTGCTGACAAAAGGCCACGGCATGGTTCCTTCCATCCATCAGAGCTGC : 5663
(SEQ ID NO: 12)  C1-P11_con  : GAACACAGGGCATGACTGGATCCTGGCTGACTGGATCCTGCTGACAAAAGGCCACGGCATGGTTCCTTCCATCCATCAGAGCTGC : 5647

*          5700          *          5720          *          5740          *
(SEQ ID NO: 15)  P1_consens  : AAATGTCATGGCTGCCTCTTTGCGTAAGGCTGAAAGAGTGGTCCTGAACAGGAAAACCTTTGAGAG : 5760
(SEQ ID NO: 9)   B-P1_conse  : AAATGTCATGGCTGCCTCTTTGCGTAAGGCTGAAAGAGTGGTCCTGAACAGGAAAACCTTTGAGAG : 5721
(SEQ ID NO: 10)  C-P1_genom  : AAATGTCATGGCTGCCTCTTTGCGTAAGGCTGAAAGAGTGGTCCTGAACAGGAAAACCTTTGAGAG : 5721
(SEQ ID NO: 11)  B3-P11_con  : AAATGTCATGGCTGCCTCTTTGCGTAAGGCTGAAAGAGTGGTCCTGAACAGGAAAACCTTTGAGAG : 5735
(SEQ ID NO: 12)  C1-P11_con  : AAATGTCATGGCTGCCTCTTTGCGTAAGGCTGAAAGAGTGGTCCTGAACAGGAAAACCTTTGAGAG : 5719
```

FIG. 8P

```
(SEQ ID NO: 15)  P1_consens  : AGAATACCCCACGATAAAGCAGAAGAAGAAAACCTGACTTTATATTGCCACTGACATAGCTGAAATGGGAGCCAA : 5832
(SEQ ID NO: 9)   B-P1_conse  : AGAATACCCCACGATAAAGCAGAAGAAGAAAACCTGACTTTATATTGCCACTGACATAGCTGAAATGGGAGCCAA : 5793
(SEQ ID NO: 10)  C-P1_genom  : AGAATACCCCACGATAAAGCAGAAGAAGAAAACCTGACTTTATATTGCCACTGACATAGCTGAAATGGGAGCCAA : 5793
(SEQ ID NO: 11)  B3-P11_con  : AGAATACCCCACGATAAAGCAGAAGAAGAAAACCTGACTTTATATTGCCACTGACATAGCTGAAATGGGAGCCAA : 5807
(SEQ ID NO: 12)  C1-P11_con  : AGAATACCCCACGATAAAGCAGAAGAAGAAAACCTGACTTTATATTGCCACTGACATAGCTGAAATGGGAGCCAA : 5791

(SEQ ID NO: 15)  P1_consens  : CCTTTGCGTGGAGCGAGTGCTGCAGGACGGCTTTTAAGCCTGCTTGTGCTTGTGATGAAGGAGGAGGAAGGT : 5904
(SEQ ID NO: 9)   B-P1_conse  : CCTTTGCGTGGAGCGAGTGCTGCAGGACGGCTTTTAAGCCTGCTTGTGCTTGTGATGAAGGAGGAGGAAGGT : 5865
(SEQ ID NO: 10)  C-P1_genom  : CCTTTGCGTGGAGCGAGTGCTGCAGGACGGCTTTTAAGCCTGCTTGTGCTTGTGATGAAGGAGGAGGAAGGT : 5865
(SEQ ID NO: 11)  B3-P11_con  : CCTTTGCGTGGAGCGAGTGCTGCAGGACGGCTTTTAAGCCTGCTTGTGCTTGTGATGAAGGAGGAGGAAGGT : 5879
(SEQ ID NO: 12)  C1-P11_con  : CCTTTGCGTGGAGCGAGTGCTGCAGGACGGCTTTTAAGCCTGCTTGTGCTTGTGATGAAGGAGGAGGAAGGT : 5863

(SEQ ID NO: 15)  P1_consens  : GGCAATAAAAAGGGCCACTTCGTATCTCCGCATCCTGCTCAAAGGAGGAGGCCATTGGAGAAATCC : 5976
(SEQ ID NO: 9)   B-P1_conse  : GGCAATAAAAAGGGCCACTTCGTATCTCCGCATCCTGCTCAAAGGAGGAGGCCATTGGAGAAATCC : 5937
(SEQ ID NO: 10)  C-P1_genom  : GGCAATAAAAAGGGCCACTTCGTATCTCCGCATCCTGCTCAAAGGAGGAGGCCATTGGAGAAATCC : 5937
(SEQ ID NO: 11)  B3-P11_con  : GGCAATAAAAAGGGCCACTTCGTATCTCCGCATCCTGCTCAAAGGAGGAGGCCATTGGAGAAATCC : 5951
(SEQ ID NO: 12)  C1-P11_con  : GGCAATAAAAAGGGCCACTTCGTATCTCCGCATCCTGCTCAAAGGAGGAGGCCATTGGAGAAATCC : 5935

(SEQ ID NO: 15)  P1_consens  : CAACAGAGATGGAGACTCATACTACTATTCTGAGCCTACAAGTGAAAATAATGCCCACCACGTCTGCTGGTT : 6048
(SEQ ID NO: 9)   B-P1_conse  : CAACAGAGATGGAGACTCATACTACTATTCTGAGCCTACAAGTGAAAATAATGCCCACCACGTCTGCTGGTT : 6009
(SEQ ID NO: 10)  C-P1_genom  : CAACAGAGATGGAGACTCATACTACTATTCTGAGCCTACAAGTGAAAATAATGCCCACCACGTCTGCTGGTT : 6009
(SEQ ID NO: 11)  B3-P11_con  : CAACAGAGATGGAGACTCATACTACTATTCTGAGCCTACAAGTGAAAATAATGCCCACCACGTCTGCTGGTT : 6023
(SEQ ID NO: 12)  C1-P11_con  : CAACAGAGATGGAGACTCATACTACTATTCTGAGCCTACAAGTGAAAATAATGCCCACCACGTCTGCTGGTT : 6007

(SEQ ID NO: 15)  P1_consens  : GGAGGCCTCAATGCTCTTGGACAACATGGAGGTGAGGGTGAATGTCGCCCCACTCACTCTATGCGTTGAAGG : 6120
(SEQ ID NO: 9)   B-P1_conse  : GGAGGCCTCAATGCTCTTGGACAACATGGAGGTGAGGGTGAATGTCGCCCCACTCACTCTATGCGTTGAAGG : 6081
(SEQ ID NO: 10)  C-P1_genom  : GGAGGCCTCAATGCTCTTGGACAACATGGAGGTGAGGGTGAATGTCGCCCCACTCACTCTATGCGTTGAAGG : 6081
(SEQ ID NO: 11)  B3-P11_con  : GGAGGCCTCAATGCTCTTGGACAACATGGAGGTGAGGGTGAATGTCGCCCCACTCACTCTATGCGTTGAAGG : 6095
(SEQ ID NO: 12)  C1-P11_con  : GGAGGCCTCAATGCTCTTGGACAACATGGAGGTGAGGGTGAATGTCGCCCCACTCACTCTATGCGTTGAAGG : 6079
```

FIG. 8Q

| | | |
|---|---|---|
| (SEQ ID NO: 15) P1_consens | : AACTAAAAACACCAGTTTCCCTGGTGAAATGAGACTGAGGATGACCAGAGGAAAGTCTTCAGAGAACTAGT | 6192 |
| (SEQ ID NO: 9) B-P1_conse | : AACTAAAAACACCAGTTTCCCTGGTGAAATGAGACTGAGGATGACCAGAGGAAAGTCTTCAGAGAACTAGT | 6153 |
| (SEQ ID NO: 10) C-P1_genom | : AACTAAAAACACCAGTTTCCCTGGTGAAATGAGACTGAGGATGACCAGAGGAAAGTCTTCAGAGAACTAGT | 6153 |
| (SEQ ID NO: 11) B3-P11_con | : AACTAAAAACACCAGTTTCCCTGGTGAAATGAGACTGAGGATGACCAGAGGAAAGTCTTCAGAGAACTAGT | 6167 |
| (SEQ ID NO: 12) C1-P11_con | : AACTAAAAACACCAGTTTCCCTGGTGAAATGAGACTGAGGATGACCAGAGGAAAGTCTTCAGAGAACTAGT | 6151 |
| | | |
| (SEQ ID NO: 15) P1_consens | : GAGGAATTGTGACCTGCTGCCCGTTTGGCTTTCGTGGCAAGTGGCCAAGGCTGGTTTGAAGACGAATGATCGTAA | 6264 |
| (SEQ ID NO: 9) B-P1_conse | : GAGGAATTGTGACCTGCTGCCCGTTTGGCTTTCGTGGCAAGTGGCCAAGGCTGGTTTGAAGACGAATGATCGTAA | 6225 |
| (SEQ ID NO: 10) C-P1_genom | : GAGGAATTGTGACCTGCTGCCCGTTTGGCTTTCGTGGCAAGTGGCCAAGGCTGGTTTGAAGACGAATGATCGTAA | 6225 |
| (SEQ ID NO: 11) B3-P11_con | : GAGGAATTGTGACCTGCTGCCCGTTTGGCTTTCGTGGCAAGTGGCCAAGGCTGGTTTGAAGACGAATGATCGTAA | 6239 |
| (SEQ ID NO: 12) C1-P11_con | : GAGGAATTGTGACCTGCTGCCCGTTTGGCTTTCGTGGCAAGTGGCCAAGGCTGGTTTGAAGACGAATGATCGTAA | 6223 |
| | | |
| (SEQ ID NO: 15) P1_consens | : GTGGTGTTTGAAGGCCCTGAGGAACATGAGATCTTGAATGACAGCCGTGAAACAGTGAAGTGCAGGGCTCC | 6336 |
| (SEQ ID NO: 9) B-P1_conse | : GTGGTGTTTGAAGGCCCTGAGGAACATGAGATCTTGAATGACAGCCGTGAAACAGTGAAGTGCAGGGCTCC | 6297 |
| (SEQ ID NO: 10) C-P1_genom | : GTGGTGTTTGAAGGCCCTGAGGAACATGAGATCTTGAATGACAGCCGTGAAACAGTGAAGTGCAGGGCTCC | 6297 |
| (SEQ ID NO: 11) B3-P11_con | : GTGGTGTTTGAAGGCCCTGAGGAACATGAGATCTTGAATGACAGCCGTGAAACAGTGAAGTGCAGGGCTCC | 6311 |
| (SEQ ID NO: 12) C1-P11_con | : GTGGTGTTTGAAGGCCCTGAGGAACATGAGATCTTGAATGACAGCCGTGAAACAGTGAAGTGCAGGGCTCC | 6295 |
| | | |
| (SEQ ID NO: 15) P1_consens | : TGGAGGAGCAAAGAAGAAGCCTCTGCGCCCCAAGGTGGTGTGATGAAAAGGGTGTCATCTGACCAGAGTGCGCTGTC | 6408 |
| (SEQ ID NO: 9) B-P1_conse | : TGGAGGAGCAAAGAAGAAGCCTCTGCGCCCCAAGGTGGTGTGATGAAAAGGGTGTCATCTGACCAGAGTGCGCTGTC | 6369 |
| (SEQ ID NO: 10) C-P1_genom | : TGGAGGAGCAAAGAAGAAGCCTCTGCGCCCCAAGGTGGTGTGATGAAAAGGGTGTCATCTGACCAGAGTGCGCTGTC | 6369 |
| (SEQ ID NO: 11) B3-P11_con | : TGGAGGAGCAAAGAAGAAGCCTCTGCGCCCCAAGGTGGTGTGATGAAAAGGGTGTCATCTGACCAGAGTGCGCTGTC | 6383 |
| (SEQ ID NO: 12) C1-P11_con | : TGGAGGAGCAAAGAAGAAGCCTCTGCGCCCCAAGGTGGTGTGATGAAAAGGGTGTCATCTGACCAGAGTGCGCTGTC | 6367 |
| | | |
| (SEQ ID NO: 15) P1_consens | : TGAATTTATTAAGTTTGCTGAAGGTAGGAGGGGAGCTGCTGAAGTGCTAGTGTTGTGCTGAGTGAACTCCCTGA | 6480 |
| (SEQ ID NO: 9) B-P1_conse | : TGAATTTATTAAGTTTGCTGAAGGTAGGAGGGGAGCTGCTGAAGTGCTAGTGTTGTGCTGAGTGAACTCCCTGA | 6441 |
| (SEQ ID NO: 10) C-P1_genom | : TGAATTTATTAAGTTTGCTGAAGGTAGGAGGGGAGCTGCTGAAGTGCTAGTGTTGTGCTGAGTGAACTCCCTGA | 6441 |
| (SEQ ID NO: 11) B3-P11_con | : TGAATTTATTAAGTTTGCTGAAGGTAGGAGGGGAGCTGCTGAAGTGCTAGTGTTGTGCTGAGTGAACTCCCTGA | 6455 |
| (SEQ ID NO: 12) C1-P11_con | : TGAATTTATTAAGTTTGCTGAAGGTAGGAGGGGAGCTGCTGAAGTGCTAGTGTTGTGCTGAGTGAACTCCCTGA | 6439 |

FIG. 8R

|                   |                | | |
|---|---|---|---|
| (SEQ ID NO: 15) | P1_consens  | : TTTCCTGGCTAAAAAAGGTGGAGAGGCAATGGCAATGGATACCATCAGTGTGTTTCTCCACTCTGAGGAAGGCTCTAG | : 6552 |
| (SEQ ID NO: 9)  | B-P1_conse  | : TTTCCTGGCTAAAAAAGGTGGAGAGGCAATGGCAATGGATACCATCAGTGTGTTTCTCCACTCTGAGGAAGGCTCTAG | : 6513 |
| (SEQ ID NO: 10) | C-P1_genom  | : TTTCCTGGCTAAAAAAGGTGGAGAGGCAATGGCAATGGATACCATCAGTGTGTTTCTCCACTCTGAGGAAGGCTCTAG | : 6513 |
| (SEQ ID NO: 11) | B3-P11_con  | : TTTCCTGGCTAAAAAAGGTGGAGAGGCAATGGCAATGGATACCATCAGTGTGTTTCTCCACTCTGAGGAAGGCTCTAG | : 6527 |
| (SEQ ID NO: 12) | C1-P11_con  | : TTTCCTGGCTAAAAAAGGTGGAGAGGCAATGGCAATGGATACCATCAGTGTGTTTCTCCACTCTGAGGAAGGCTCTAG | : 6511 |
| (SEQ ID NO: 15) | P1_consens  | : GGCTTACCGCAATGCACTATCAATGATGCCTGAGGCAATGACAATAGTACATGCTGTTTATACTGGCTGGACT | : 6624 |
| (SEQ ID NO: 9)  | B-P1_conse  | : GGCTTACCGCAATGCACTATCAATGATGCCTGAGGCAATGACAATAGTACATGCTGTTTATACTGGCTGGACT | : 6585 |
| (SEQ ID NO: 10) | C-P1_genom  | : GGCTTACCGCAATGCACTATCAATGATGCCTGAGGCAATGACAATAGTACATGCTGTTTATACTGGCTGGACT | : 6585 |
| (SEQ ID NO: 11) | B3-P11_con  | : GGCTTACCGCAATGCACTATCAATGATGCCTGAGGCAATGACAATAGTACATGCTGTTTATACTGGCTGGACT | : 6599 |
| (SEQ ID NO: 12) | C1-P11_con  | : GGCTTACCGCAATGCACTATCAATGATGCCTGAGGCAATGACAATAGTACATGCTGTTTATACTGGCTGGACT | : 6583 |
| (SEQ ID NO: 15) | P1_consens  | : ACTGACATCGGGAATGGTCATCTTTTTCATGTCTCCCAAAGGCATCAGTAGAATGTCTATGGCGATGGGCAC | : 6696 |
| (SEQ ID NO: 9)  | B-P1_conse  | : ACTGACATCGGGAATGGTCATCTTTTTCATGTCTCCCAAAGGCATCAGTAGAATGTCTATGGCGATGGGCAC | : 6657 |
| (SEQ ID NO: 10) | C-P1_genom  | : ACTGACATCGGGAATGGTCATCTTTTTCATGTCTCCCAAAGGCATCAGTAGAATGTCTATGGCGATGGGCAC | : 6657 |
| (SEQ ID NO: 11) | B3-P11_con  | : ACTGACATCGGGAATGGTCATCTTTTTCATGTCTCCCAAAGGCATCAGTAGAATGTCTATGGCGATGGGCAC | : 6671 |
| (SEQ ID NO: 12) | C1-P11_con  | : ACTGACATCGGGAATGGTCATCTTTTTCATGTCTCCCAAAGGCATCAGTAGAATGTCTATGGCGATGGGCAC | : 6655 |
| (SEQ ID NO: 15) | P1_consens  | : AATGGCCGGCCGGCTGTGATATCTCATGTTCCTTGGAGGCGTCAAACCCACTCACATCTCCTATATCATGCTCAT | : 6768 |
| (SEQ ID NO: 9)  | B-P1_conse  | : AATGGCCGGCCGGCTGTGATATCTCATGTTCCTTGGAGGCGTCAAACCCACTCACATCTCCTATATCATGCTCAT | : 6729 |
| (SEQ ID NO: 10) | C-P1_genom  | : AATGGCCGGCCGGCTGTGATATCTCATGTTCCTTGGAGGCGTCAAACCCACTCACATCTCCTATATCATGCTCAT | : 6729 |
| (SEQ ID NO: 11) | B3-P11_con  | : AATGGCCGGCCGGCTGTGATATCTCATGTTCCTTGGAGGCGTCAAACCCACTCACATCTCCTATATCATGCTCAT | : 6743 |
| (SEQ ID NO: 12) | C1-P11_con  | : AATGGCCGGCCGGCTGTGATATCTCATGTTCCTTGGAGGCGTCAAACCCACTCACATCTCCTATATCATGCTCAT | : 6727 |
| (SEQ ID NO: 15) | P1_consens  | : ATTCTTTGTCCTGATGGTGGTTGTGATCCCGAGCCAGGCAACAAAGGTCCATCCAAGACAACCAAGTGGC | : 6840 |
| (SEQ ID NO: 9)  | B-P1_conse  | : ATTCTTTGTCCTGATGGTGGTTGTGATCCCGAGCCAGGCAACAAAGGTCCATCCAAGACAACCAAGTGGC | : 6801 |
| (SEQ ID NO: 10) | C-P1_genom  | : ATTCTTTGTCCTGATGGTGGTTGTGATCCCGAGCCAGGCAACAAAGGTCCATCCAAGACAACCAAGTGGC | : 6801 |
| (SEQ ID NO: 11) | B3-P11_con  | : ATTCTTTGTCCTGATGGTGGTTGTGATCCCGAGCCAGGCAACAAAGGTCCATCCAAGACAACCAAGTGGC | : 6815 |
| (SEQ ID NO: 12) | C1-P11_con  | : ATTCTTTGTCCTGATGGTGGTTGTGATCCCGAGCCAGGCAACAAAGGTCCATCCAAGACAACCAAGTGGC | : 6799 |

FIG. 8S

```
                              *         6860         *         6880         *         6900         *
(SEQ ID NO: 15) P1_consens  : ATACCTCATTATTGGCATCCTGACGCTGTTTCAGCGGTGGCAGCCAACGAGCTAGGCATGCTGGAGAAAC : 6912
(SEQ ID NO: 9)  B-P1_conse  : ATACCTCATTATTGGCATCCTGACGCTGTTTCAGCGGTGGCAGCCAACGAGCTAGGCATGCTGGAGAAAC : 6873
(SEQ ID NO: 10) C-P1_genom  : ATACCTCATTATTGGCATCCTGACGCTGTTTCAGCGGTGGCAGCCAACGAGCTAGGCATGCTGGAGAAAC : 6873
(SEQ ID NO: 11) B3-P11_con  : ATACCTCATTATTGGCATCCTGACGCTGTTTCAGCGGTGGCAGCCAACGAGCTAGGCATGCTGGAGAAAC : 6887
(SEQ ID NO: 12) C1-P11_con  : ATACCTCATTATTGGCATCCTGACGCTGTTTCAGCGGTGGCAGCCAACGAGCTAGGCATGCTGGAGAAAC : 6871

*         6920         *         6940         *         6960         *         6980
(SEQ ID NO: 15) P1_consens  : CAAAGAGGACCTCTTTGGGAAGAAGAACTTAATTCCATCTAGTGCTTCACCCTGGAGTTGGCCGGATCTTGA : 6984
(SEQ ID NO: 9)  B-P1_conse  : CAAAGAGGACCTCTTTGGGAAGAAGAACTTAATTCCATCTAGTGCTTCACCCTGGAGTTGGCCGGATCTTGA : 6945
(SEQ ID NO: 10) C-P1_genom  : CAAAGAGGACCTCTTTGGGAAGAAGAACTTAATTCCATCTAGTGCTTCACCCTGGAGTTGGCCGGATCTTGA : 6945
(SEQ ID NO: 11) B3-P11_con  : CAAAGAGGACCTCTTTGGGAAGAAGAACTTAATTCCATCTAGTGCTTCACCCTGGAGTTGGCCGGATCTTGA : 6959
(SEQ ID NO: 12) C1-P11_con  : CAAAGAGGACCTCTTTGGGAAGAAGAACTTAATTCCATCTAGTGCTTCACCCTGGAGTTGGCCGGATCTTGA : 6943

*         7000         *         7020         *         7040         *
(SEQ ID NO: 15) P1_consens  : CCTGAAGCCAGGAGCTGCCTGGACAGTGTACGTTGGCATTGTTACAATGCTCTCCAATGTTGCACCACTG : 7056
(SEQ ID NO: 9)  B-P1_conse  : CCTGAAGCCAGGAGCTGCCTGGACAGTGTACGTTGGCATTGTTACAATGCTCTCCAATGTTGCACCACTG : 7017
(SEQ ID NO: 10) C-P1_genom  : CCTGAAGCCAGGAGCTGCCTGGACAGTGTACGTTGGCATTGTTACAATGCTCTCCAATGTTGCACCACTG : 7017
(SEQ ID NO: 11) B3-P11_con  : CCTGAAGCCAGGAGCTGCCTGGACAGTGTACGTTGGCATTGTTACAATGCTCTCCAATGTTGCACCACTG : 7031
(SEQ ID NO: 12) C1-P11_con  : CCTGAAGCCAGGAGCTGCCTGGACAGTGTACGTTGGCATTGTTACAATGCTCTCCAATGTTGCACCACTG : 7015

7060        *         7080         *         7100         *         7120        *
(SEQ ID NO: 15) P1_consens  : GATCAAAGTCGAATATGGCAACCTGTCTCTGTCTCTGGAATAGCCCAGTCCAGCCTCAGTCCTTCTTTCATGGA : 7128
(SEQ ID NO: 9)  B-P1_conse  : GATCAAAGTCGAATATGGCAACCTGTCTCTGTCTCTGGAATAGCCCAGTCCAGCCTCAGTCCTTCTTTCATGGA : 7089
(SEQ ID NO: 10) C-P1_genom  : GATCAAAGTCGAATATGGCAACCTGTCTCTGTCTCTGGAATAGCCCAGTCCAGCCTCAGTCCTTCTTTCATGGA : 7089
(SEQ ID NO: 11) B3-P11_con  : GATCAAAGTCGAATATGGCAACCTGTCTCTGTCTCTGGAATAGCCCAGTCCAGCCTCAGTCCTTCTTTCATGGA : 7103
(SEQ ID NO: 12) C1-P11_con  : GATCAAAGTCGAATATGGCAACCTGTCTCTGTCTCTGGAATAGCCCAGTCCAGCCTCAGTCCTTCTTTCATGGA : 7087

*         7140         *         7160         *         7180         *         7200
(SEQ ID NO: 15) P1_consens  : CAAGGGGATACCATTCATGAAGATGAATATCTCGGTCATAATGCTGGTCAGTGGCTGGAATTCAATAAC : 7200
(SEQ ID NO: 9)  B-P1_conse  : CAAGGGGATACCATTCATGAAGATGAATATCTCGGTCATAATGCTGGTCAGTGGCTGGAATTCAATAAC : 7161
(SEQ ID NO: 10) C-P1_genom  : CAAGGGGATACCATTCATGAAGATGAATATCTCGGTCATAATGCTGGTCAGTGGCTGGAATTCAATAAC : 7161
(SEQ ID NO: 11) B3-P11_con  : CAAGGGGATACCATTCATGAAGATGAATATCTCGGTCATAATGCTGGTCAGTGGCTGGAATTCAATAAC : 7175
(SEQ ID NO: 12) C1-P11_con  : CAAGGGGATACCATTCATGAAGATGAATATCTCGGTCATAATGCTGGTCAGTGGCTCCAATTCAATAAC : 7159
```

| | | | |
|---|---|---|---|
| (SEQ ID NO: 15) | P1_consens | : AGGAGTCATGAGGGGGAATCACTATGCTTTTGTGGAGTCATGTGGAGATGAAGATGAAAACTGGACG | : 7632 |
| (SEQ ID NO: 9) | B-P1_conse | : AGGAGTCATGAGGGGGAATCACTATGCTTTTGTGGAGTCATGTGAAGATGAAGATGAAAACTGGACG | : 7593 |
| (SEQ ID NO: 10) | C-P1_genom | : AGGAGTCATGAGGGGGAATCACTATGCTTTTGTGGAGTCATGTGAAGATGAAGATGAAAACTGGACG | : 7593 |
| (SEQ ID NO: 11) | B3-P1_con | : AGGAGTCATGAGGGGGAATCACTATGCTTTTGTGGAGTCATGTGAAGATGAAGATGAAAACTGGACG | : 7607 |
| (SEQ ID NO: 12) | C1-P11_con | : AGGAGTCATGAGGGGGAATCACTATGCTTTTGTGGAGTCATGTGAAGATGAAGATGAAAACTGGACG | : 7591 |
| | | | |
| (SEQ ID NO: 15) | P1_consens | : CCGGGGAGCGCGCAATGGAAAAACTTTGGTGAAGTCTGAAGAGGGAACTGAATCTGTTGACAAGCGACA | : 7704 |
| (SEQ ID NO: 9) | B-P1_conse | : CCGGGGAGCGCGCAATGGAAAAACTTTGGTGAAGTCTGAAGAGGGAACTGAATCTGTTGACAAGCGACA | : 7665 |
| (SEQ ID NO: 10) | C-P1_genom | : CCGGGGAGCGCGCAATGGAAAAACTTTGGTGAAGTCTGAAGAGGGAACTGAATCTGTTGACAAGCGACA | : 7665 |
| (SEQ ID NO: 11) | B3-P1_con | : CCGGGGAGCGCGCAATGGAAAAACTTTGGTGAAGTCTGAAGAGGGAACTGAATCTGTTGACAAGCGACA | : 7679 |
| (SEQ ID NO: 12) | C1-P11_con | : CCGGGGAGCGCGCAATGGAAAAACTTTGGTGAAGTCTGAAGAGGGAACTGAATCTGTTGACAAGCGACA | : 7663 |
| | | | |
| (SEQ ID NO: 15) | P1_consens | : GTTTGAGTTGTATAAAAGGACCGACATTGTGGAGGTGATCGTGATACGGCACGCAGGCATTTGCCGAAGG | : 7776 |
| (SEQ ID NO: 9) | B-P1_conse | : GTTTGAGTTGTATAAAAGGACCGACATTGTGGAGGTGATCGTGATACGGCACGCAGGCATTTGCCGAAGG | : 7737 |
| (SEQ ID NO: 10) | C-P1_genom | : GTTTGAGTTGTATAAAAGGACCGACATTGTGGAGGTGATCGTGATACGGCACGCAGGCATTTGCCGAAGG | : 7737 |
| (SEQ ID NO: 11) | B3-P1_con | : GTTTGAGTTGTATAAAAGGACCGACATTGTGGAGGTGATCGTGATACGGCACGCAGGCATTTGCCGAAGG | : 7751 |
| (SEQ ID NO: 12) | C1-P11_con | : GTTTGAGTTGTATAAAAGGACCGACATTGTGGAGGTGATCGTGATACGGCACGCAGGCATTTGCCGAAGG | : 7735 |
| | | | |
| (SEQ ID NO: 15) | P1_consens | : GAAGGTGGACACCGGGGTGGCGGTTCTCCAGGGGGACCGCAAAGTTAAGGTGGTTCCATGAGCGTGGCTATGT | : 7848 |
| (SEQ ID NO: 9) | B-P1_conse | : GAAGGTGGACACCGGGGTGGCGGTTCTCCAGGGGGACCGCAAAGTTAAGGTGGTTCCATGAGCGTGGCTATGT | : 7809 |
| (SEQ ID NO: 10) | C-P1_genom | : GAAGGTGGACACCGGGGTGGCGGTTCTCCAGGGGGACCGCAAAGTTAAGGTGGTTCCATGAGCGTGGCTATGT | : 7809 |
| (SEQ ID NO: 11) | B3-P1_con | : GAAGGTGGACACCGGGGTGGCGGTTCTCCAGGGGGACCGCAAAGTTAAGGTGGTTCCATGAGCGTGGCTATGT | : 7823 |
| (SEQ ID NO: 12) | C1-P11_con | : GAAGGTGGACACCGGGGTGGCGGTTCTCCAGGGGGACCGCAAAGTTAAGGTGGTTCCATGAGCGTGGCTATGT | : 7807 |
| | | | |
| (SEQ ID NO: 15) | P1_consens | : CAAGCTGGAAGGTAGGGTGATTGACCTGGGTGGCCGGAGGCTGCTGTTACTACGCTGCTGCGCAAAA | : 7920 |
| (SEQ ID NO: 9) | B-P1_conse | : CAAGCTGGAAGGTAGGGTGATTGACCTGGGTGGCCGGAGGCTGCTGTTACTACGCTGCTGCGCAAAA | : 7881 |
| (SEQ ID NO: 10) | C-P1_genom | : CAAGCTGGAAGGTAGGGTGATTGACCTGGGTGGCCGGAGGCTGCTGTTACTACGCTGCTGCGCAAAA | : 7881 |
| (SEQ ID NO: 11) | B3-P1_con | : CAAGCTGGAAGGTAGGGTGATTGACCTGGGTGGCCGGAGGCTGCTGTTACTACGCTGCTGCGCAAAA | : 7895 |
| (SEQ ID NO: 12) | C1-P11_con | : CAAGCTGGAAGGTAGGGTGATTGACCTGGGTGGCCGGAGGCTGCTGTTACTACGCTGCTGCCCCAAAA | : 7879 |

FIG. 8V

```
                           *         7940         *         7960         *         7980         *
(SEQ ID NO: 15) P1_consens  : GGAAGTGAGTGGGGTCAAAGGATTTACTCTTGGAAGAGACGGCCATGAGAAACCCATGAATGTGCAAAGTCT : 7992
(SEQ ID NO: 9)  B-P1_conse  : GGAAGTGAGTGGGGTCAAAGGATTTACTCTTGGAAGAGACGGCCATGAGAAACCCATGAATGTGCAAAGTCT : 7953
(SEQ ID NO: 10) C-P1_genom  : GGAAGTGAGTGGGGTCAAAGGATTTACTCTTGGAAGAGACGGCCATGAGAAACCCATGAATGTGCAAAGTCT : 7953
(SEQ ID NO: 11) B3-P11_con  : GGAAGTGAGTGGGGTCAAAGGATTTACTCTTGGAAGAGACGGCCATGAGAAACCCATGAATGTGCAAAGTCT : 7967
(SEQ ID NO: 12) C1-P11_con  : GGAAGTGAGTGGGGTCAAAGGATTTACTCTTGGAAGAGACGGCCATGAGAAACCCATGAATGTGCAAAGTCT : 7951

8000         *         8020         *         8040         *         8060
(SEQ ID NO: 15) P1_consens  : GGGATGGAACATCATCACCTTCAAGGACAAAACTGATATCCACCGCCTAGAACCAGTGAAATGTGACACCCT : 8064
(SEQ ID NO: 9)  B-P1_conse  : GGGATGGAACATCATCACCTTCAAGGACAAAACTGATATCCACCGCCTAGAACCAGTGAAATGTGACACCCT : 8025
(SEQ ID NO: 10) C-P1_genom  : GGGATGGAACATCATCACCTTCAAGGACAAAACTGATATCCACCGCCTAGAACCAGTGAAATGTGACACCCT : 8025
(SEQ ID NO: 11) B3-P11_con  : GGGATGGAACATCATCACCTTCAAGGACAAAACTGATATCCACCGCCTAGAACCAGTGAAATGTGACACCCT : 8039
(SEQ ID NO: 12) C1-P11_con  : GGGATGGAACATCATCACCTTCAAGGACAAAACTGATATCCACCGCCTAGAACCAGTGAAATGTGACACCCT : 8023

*         8080         *         8100         *         8120         *
(SEQ ID NO: 15) P1_consens  : TTTGTGTGACATTGGAGAGTCATCATCGTCATCGTCACAGAGGGGAAAGACCGTGAGAGTTCTTGATAC : 8136
(SEQ ID NO: 9)  B-P1_conse  : TTTGTGTGACATTGGAGAGTCATCATCGTCATCGTCACAGAGAGGGAAAGACCGTGAGAGTTCTTGATAC : 8097
(SEQ ID NO: 10) C-P1_genom  : TTTGTGTGACATTGGAGAGTCATCATCGTCATCGTCACAGAGAGGGAAAGACCGTGAGAGTTCTTGATAC : 8097
(SEQ ID NO: 11) B3-P11_con  : TTTGTGTGACATTGGAGAGTCATCATCGTCATCGTCACAGAGAGGGAAAGACCGTGAGAGTTCTTGATAC : 8111
(SEQ ID NO: 12) C1-P11_con  : TTTGTGTGACATTGGAGAGTCATCATCGTCATCGTCACAGAGAGGGAAAGACCGTGAGAGTTCTTGATAC : 8095

8140         *         8160         *         8180         *         8200
(SEQ ID NO: 15) P1_consens  : TGTAGAAAAATGGCTGGCTTGTGGGCTTGTGACAACTTCTGTGTGTCTCAAGGTGTTAGCTCCATACATGCCAGATGT : 8208
(SEQ ID NO: 9)  B-P1_conse  : TGTAGAAAAATGGCTGGCTTGTGGGCTTGTGACAACTTCTGTGTGTCTCAAGGTGTTAGCTCCATACATGCCAGATGT : 8169
(SEQ ID NO: 10) C-P1_genom  : TGTAGAAAAATGGCTGGCTTGTGGGCTTGTGACAACTTCTGTGTGTCTCAAGGTGTTAGCTCCATACATGCCAGATGT : 8169
(SEQ ID NO: 11) B3-P11_con  : TGTAGAAAAATGGCTGGCTTGTGGGCTTGTGACAACTTCTGTGTGTCTCAAGGTGTTAGCTCCATACATGCCAGATGT : 8183
(SEQ ID NO: 12) C1-P11_con  : TGTAGAAAAATGGCTGGCTTGTGGGCTTGTGACAACTTCTGTGTGTCTCAAGGTGTTAGCTCCATACATGCCAGATGT : 8167

*         8220         *         8240         *         8260         *         8280
(SEQ ID NO: 15) P1_consens  : TCTCGAGAAACTGAATTGCTCCAAAGGAGGAGTTTGGCGGAACAGTGATCAGGAACCCTCTCTCCAGGAATTC : 8280
(SEQ ID NO: 9)  B-P1_conse  : TCTCGAGAAACTGAATTGCTCCAAAGGAGGAGTTTGGCGGAACAGTGATCAGGAACCCTCTCTCCAGGAATTC : 8241
(SEQ ID NO: 10) C-P1_genom  : TCTCGAGAAACTGAATTGCTCCAAAGGAGGAGTTTGGCGGAACAGTGATCAGGAACCCTCTCTCCAGGAATTC : 8241
(SEQ ID NO: 11) B3-P11_con  : TCTCGAGAAACTGAATTGCTCCAAAGGAGGAGTTTGGCGGAACAGTGATCAGGAACCCTCTCTCCAGGAATTC : 8255
(SEQ ID NO: 12) C1-P11_con  : TCTCGAGAAACTGAATTGCTCCAAAGGAGGAGTTTGGCGGAACAGTGATCAGGAACCCTCTCTCCAGGAATTC : 8239
```

FIG. 8W

|                  |              |                                                                                                    |        |
|------------------|--------------|----------------------------------------------------------------------------------------------------|--------|
|                  |              | *           8300           *           8320           *           8340           *                 |        |
| (SEQ ID NO: 15)  | P1_consens   | : CACTCATGAAATGTACTACGTGTCTGGAGCCCGCAGCAATGTCACATTTACTGTGAACCAAACATCCCGCCT                          | : 8352 |
| (SEQ ID NO: 9)   | B-P1_conse   | : CACTCATGAAATGTACTACGTGTCTGGAGCCCGCAGCAATGTCACATTTACTGTGAACCAAACATCCCGCCT                          | : 8313 |
| (SEQ ID NO: 10)  | C-P1_genom   | : CACTCATGAAATGTACTACGTGTCTGGAGCCCGCAGCAATGTCACATTTACTGTGAACCAAACATCCCGCCT                          | : 8313 |
| (SEQ ID NO: 11)  | B3-P11_con   | : CACTCATGAAATGTACTACGTGTCTGGAGCCCGCAGCAATGTCACATTTACTGTGAACCAAACATCCCGCCT                          | : 8327 |
| (SEQ ID NO: 12)  | C1-P11_con   | : CACTCATGAAATGTACTACGTGTCTGGAGCCCGCAGCAATGTCACATTTACTGTGAACCAAACATCCCGCCT                          | : 8311 |

|                  |              |                                                                                                     |        |
|------------------|--------------|-----------------------------------------------------------------------------------------------------|--------|
|                  |              | 8360           *           8380           *           8400           *           8420               |        |
| (SEQ ID NO: 15)  | P1_consens   | : CCTGATGAGGAGGAGAATGAGGCGTCCAACTGGAAAAGTGACCCTGACGTCATCCTCCCAATTGGGAC                               | : 8424 |
| (SEQ ID NO: 9)   | B-P1_conse   | : CCTGATGAGGAGGAGAATGAGGCGTCCAACTGGAAAAGTGACCCTGACGTCATCCTCCCAATTGGGAC                               | : 8385 |
| (SEQ ID NO: 10)  | C-P1_genom   | : CCTGATGAGGAGGAGAATGAGGCGTCCAACTGGAAAAGTGACCCTGACGTCATCCTCCCAATTGGGAC                               | : 8385 |
| (SEQ ID NO: 11)  | B3-P11_con   | : CCTGATGAGGAGGAGAATGAGGCGTCCAACTGGAAAAGTGACCCTGACGTCATCCTCCCAATTGGGAC                               | : 8399 |
| (SEQ ID NO: 12)  | C1-P11_con   | : CCTGATGAGGAGGAGAATGAGGCGTCCAACTGGAAAAGTGACCCTGACGTCATCCTCCCAATTGGGAC                               | : 8383 |

|                  |              |                                                                                                     |        |
|------------------|--------------|-----------------------------------------------------------------------------------------------------|--------|
|                  |              | *           8440           *           8460           *           8480           *                  |        |
| (SEQ ID NO: 15)  | P1_consens   | : ACGCAGTGTTGAGACAGACAAGGGACCCCTGACAAAGAGGCCATAGAAGAAAGGGTTGAGAGGATAAAATC                            | : 8496 |
| (SEQ ID NO: 9)   | B-P1_conse   | : ACGCAGTGTTGAGACAGACAAGGGACCCCTGACAAAGAGGCCATAGAAGAAAGGGTTGAGAGGATAAAATC                            | : 8457 |
| (SEQ ID NO: 10)  | C-P1_genom   | : ACGCAGTGTTGAGACAGACAAGGGACCCCTGACAAAGAGGCCATAGAAGAAAGGGTTGAGAGGATAAAATC                            | : 8457 |
| (SEQ ID NO: 11)  | B3-P11_con   | : ACGCAGTGTTGAGACAGACAAGGGACCCCTGACAAAGAGGCCATAGAAGAAAGGGTTGAGAGGATAAAATC                            | : 8471 |
| (SEQ ID NO: 12)  | C1-P11_con   | : ACGCAGTGTTGAGACAGACAAGGGACCCCTGACAAAGAGGCCATAGAAGAAAGGGTTGAGAGGATAAAATC                            | : 8455 |

|                  |              |                                                                                                     |        |
|------------------|--------------|-----------------------------------------------------------------------------------------------------|--------|
|                  |              | 8500           *           8520           *           8540           *           8560               |        |
| (SEQ ID NO: 15)  | P1_consens   | : TGAGTACATGACCTCTTGGTTTATGACAATGACAACCCCTACAGGACCTGGCCACTACTGTGGCTCCTATGT                           | : 8568 |
| (SEQ ID NO: 9)   | B-P1_conse   | : TGAGTACATGACCTCTTGGTTTATGACAATGACAACCCCTACAGGACCTGGCCACTACTGTGGCTCCTATGT                           | : 8529 |
| (SEQ ID NO: 10)  | C-P1_genom   | : TGAGTACATGACCTCTTGGTTTATGACAATGACAACCCCTACAGGACCTGGCCACTACTGTGGCTCCTATGT                           | : 8529 |
| (SEQ ID NO: 11)  | B3-P11_con   | : TGAGTACATGACCTCTTGGTTTATGACAATGACAACCCCTACAGGACCTGGCCACTACTGTGGCTCCTATGT                           | : 8543 |
| (SEQ ID NO: 12)  | C1-P11_con   | : TGAGTACATGACCTCTTGGTTTATGACAATGACAACCCCTACAGGACCTGGCCACTACTGTGGCTCCTATGT                           | : 8527 |

|                  |              |                                                                                                     |        |
|------------------|--------------|-----------------------------------------------------------------------------------------------------|--------|
|                  |              | *           8580           *           8600           *           8620           *           8640   |        |
| (SEQ ID NO: 15)  | P1_consens   | : CACAAAAACCTCAGGAAGTGCGGCGAGCATGTAAATGGTGTTATTAAAATTCTGACATATCCATGGGACAG                            | : 8640 |
| (SEQ ID NO: 9)   | B-P1_conse   | : CACAAAAACCTCAGGAAGTGCGGCGAGCATGTAAATGGTGTTATTAAAATTCTGACATATCCATGGGACAG                            | : 8601 |
| (SEQ ID NO: 10)  | C-P1_genom   | : CACAAAAACCTCAGGAAGTGCGGCGAGCATGTAAATGGTGTTATTAAAATTCTGACATATCCATGGGACAG                            | : 8601 |
| (SEQ ID NO: 11)  | B3-P11_con   | : CACAAAAACCTCAGGAAGTGCGGCGAGCATGTAAATGGTGTTATTAAAATTCTGACATATCCATGGGACAG                            | : 8615 |
| (SEQ ID NO: 12)  | C1-P11_con   | : CACAAAAACCTCAGGAAGTGCGGCGAGCATGTAAATGGTGTTATTAAAATTCTGACATATCCATGGGACAG                            | : 8599 |

```
                                                          *      9020      *      9040      *      9050      *
(SEQ ID NO: 15)  P1_consens  : GATGGGGAAAAGAGAGAGAAGAAGCTGTCAGAGTTTGGGAAGCAAAAGGGAAGCCGTGCCATATGGTATATGTG :  9072
(SEQ ID NO: 9)   B-P1_conse  : GATGGGGAAAAGAGAGAGAAGAAGCTGTCAGAGTTTGGGAAGCAAAAGGGAAGCCGTGCCATATGGTATATGTG :  9033
(SEQ ID NO: 10)  C-P1_genom  : GATGGGGAAAAGAGAGAGAAGAAGCTGTCAGAGTTTGGGAAAGCAAAAGGGAAGCCGTGCCATATGGTATATGTG :  9033
(SEQ ID NO: 11)  B3-P11_con  : GATGGGGAAAAGAGAGAGAAGAAGCTGTCAGAGTTTGGGAAGCAAAAGGGAAGCCGTGCCATATGGTATATGTG :  9047
(SEQ ID NO: 12)  C1-P11_con  : GATGGGGAAAAGAGAGAGAAGAAGCTGTCAGAGTTTGGGAAGCAAAAGGGAAGCCGTGCCATATGGTATATGTG :  9031

*      9080      *      9100      *      9120      *      9140
(SEQ ID NO: 15)  P1_consens  : GCTGGGAGCGCGGTATCTTGAGTTTGAGGCCCTGGGATTCCTGAATGAGAACCATTGGGCTTCCAGGGAAAA :  9144
(SEQ ID NO: 9)   B-P1_conse  : GCTGGGAGCGCGGTATCTTGAGTTTGAGGCCCTGGGATTCCTGAATGAGAACCATTGGGCTTCCAGGGAAAA :  9105
(SEQ ID NO: 10)  C-P1_genom  : GCTGGGAGCACCCCGTATCTTGAGTTTGAGGCCCTGGGATTCCTGAATGAGAACCATTGGGCTTCCAGGGAAAA :  9105
(SEQ ID NO: 11)  B3-P11_con  : GCTGGGAGCGCGGTATCTTGAGTTTGAGGCCCTGGGATTCCTGAATGAGAACCATTGGGCTTCCAGGGAAAA :  9119
(SEQ ID NO: 12)  C1-P11_con  : GCTGGGAGCGCGGTATCTTGAGTTTGAGGCCCTGGGATTCCTGAATGAGAACCATTGGGCTTCCAGGGAAAA :  9103

*      9160      *      9180      *      9200      *
(SEQ ID NO: 15)  P1_consens  : CTCAGGAGGAGGAGTGGAAGGCATTGGCTTACAATACCTAGGATATGTGATCAGAGACCTGGCTGCAATGGA :  9216
(SEQ ID NO: 9)   B-P1_conse  : CTCAGGAGGAGGAGTGGAAGGCATTGGCTTACAATACCTAGGATATGTGATCAGAGACCTGGCTGCAATGGA :  9177
(SEQ ID NO: 10)  C-P1_genom  : CTCAGGAGGAGGAGTGGAAGGCATTGGCTTACAATACCTAGGATATGTGATCAGAGACCTGGCTGCAATGGA :  9177
(SEQ ID NO: 11)  B3-P11_con  : CTCAGGAGGAGGAGTGGAAGGCATTGGCTTACAATACCTAGGATATGTGATCAGAGACCTGGCTGCAATGGA :  9191
(SEQ ID NO: 12)  C1-P11_con  : CTCAGGAGGAGGAGTGGAAGGCATTGGCTTACAATACCTAGGATATGTGATCAGAGACCTGGCTGCAATGGA :  9175

9220      *      9240      *      9260      *      9280      *
(SEQ ID NO: 15)  P1_consens  : TGGTGGTGGATTCTACGCGGATGACACGCTGCATCACAGAGGCAGACCTTGATGATGA :  9288
(SEQ ID NO: 9)   B-P1_conse  : TGGTGGTGGATTCTACGCGGATGACACGCTGCATCACAGAGGCAGACCTTGATGATGA :  9249
(SEQ ID NO: 10)  C-P1_genom  : TGGTGGTGGATTCTACGCGGATGACACGCTGCATCACAGAGGCAGACCTTGATGATGA :  9249
(SEQ ID NO: 11)  B3-P11_con  : TGGTGGTGGATTCTACGCGGATGACACGCTGCATCACAGAGGCAGACCTTGATGATGA :  9263
(SEQ ID NO: 12)  C1-P11_con  : TGGTGGTGGATTCTACGCGGATGACACGCTGCATCACAGAGGCAGACCTTGATGATGA :  9247

*      9300      *      9320      *      9340      *      9360
(SEQ ID NO: 15)  P1_consens  : ACAGGAGGATCTTGAACTACATGAGCCCACATCACAAAAAACTGGCACAAGCAGTGAAATGACATACAA :  9360
(SEQ ID NO: 9)   B-P1_conse  : ACAGGAGGATCTTGAACTACATGAGCCCACATCACAAAAAACTGGCACAAGCAGTGAAATGACATACAA :  9321
(SEQ ID NO: 10)  C-P1_genom  : ACAGGAGGATCTTGAACTACATGAGCCCACATCACAAAAAACTGGCACAAGCAGTGAAATGACATACAA :  9321
(SEQ ID NO: 11)  B3-P11_con  : ACAGGAGGATCTTGAACTACATGAGCCCACATCACAAAAAACTGGCACAAGCAGTGATGGAAATGACATACAA :  9335
(SEQ ID NO: 12)  C1-P11_con  : ACAGGAGGATCTTGAACTACATGAGCCCACATCACAAAAAACTGGCACAAGCAGTGATGGAAATGACATACAA :  9319
```

FIG. 8Z

|                | | |
|---|---|---|
| P1_consens (SEQ ID NO: 15) | : GAACAAAGTGGTGAAAGTGTTGAGACCAGCAGCCCCAGGAGGAGGGAAAGCCTACATGATGTCATAAGTCGACGAGA : | 9432 |
| B-P1_conse (SEQ ID NO: 9) | : GAACAAAGTGGTGAAAGTGTTGAGACCAGCAGCCCCAGGAGGAGGGAAAGCCTACATGATGTCATAAGTCGACGAGA : | 9393 |
| C-P1_genom (SEQ ID NO: 10) | : GAACAAAGTGGTGAAAGTGTTGAGACCAGCAGCCCCAGGAGGAGGGAAAGCCTACATGATGTCATAAGTCGACGAGA : | 9393 |
| B3-P11_con (SEQ ID NO: 11) | : GAACAAAGTGGTGAAAGTGTTGAGACCAGCAGCCCCAGGAGGAGGGAAAGCCTACATGATGTCATAAGTCGACGAGA : | 9407 |
| C1-P11_con (SEQ ID NO: 12) | : GAACAAAGTGGTGAAAGTGTTGAGACCAGCAGCCCCAGGAGGAGGGAAAGCCTACATGATGTCATAAGTCGACGAGA : | 9391 |

|                | | |
|---|---|---|
| P1_consens (SEQ ID NO: 15) | : CCAGAGAGGATCCGGGCCAGGTAGTGACTTATGCTCTGAACACCATCACCAACTTGAAAGTCCAATTGATCAG : | 9504 |
| B-P1_conse (SEQ ID NO: 9) | : CCAGAGAGGATCCGGGCCAGGTAGTGACTTATGCTCTGAACACCATCACCAACTTGAAAGTCCAATTGATCAG : | 9465 |
| C-P1_genom (SEQ ID NO: 10) | : CCAGAGAGGATCCGGGCCAGGTAGTGACTTATGCTCTGAACACCATCACCAACTTGAAAGTCCAATTGATCAG : | 9465 |
| B3-P11_con (SEQ ID NO: 11) | : CCAGAGAGGATCCGGGCCAGGTAGTGACTTATGCTCTGAACACCATCACCAACTTGAAAGTCCAATTGATCAG : | 9479 |
| C1-P11_con (SEQ ID NO: 12) | : CCAGAGAGGATCCGGGCCAGGTAGTGACTTATGCTCTGAACACCATCACCAACTTGAAAGTCCAATTGATCAG : | 9463 |

|                | | |
|---|---|---|
| P1_consens (SEQ ID NO: 15) | : AATGGCAGAAGCAGAGATGGTGATACATCACCAACATGTTCAAGATTGTGATGAATCAGTTCTGACCAGGCT : | 9576 |
| B-P1_conse (SEQ ID NO: 9) | : AATGGCAGAAGCAGAGATGGTGATACATCACCAACATGTTCAAGATTGTGATGAATCAGTTCTGACCAGGCT : | 9537 |
| C-P1_genom (SEQ ID NO: 10) | : AATGGCAGAAGCAGAGATGGTGATACATCACCAACATGTTCAAGATTGTGATGAATCAGTTCTGACCAGGCT : | 9537 |
| B3-P11_con (SEQ ID NO: 11) | : AATGGCAGAAGCAGAGATGGTGATACATCACCAACATGTTCAAGATTGTGATGAATCAGTTCTGACCAGGCT : | 9551 |
| C1-P11_con (SEQ ID NO: 12) | : AATGGCAGAAGCAGAGATGGTGATACATCACCAACATGTTCAAGATTGTGATGAATCAGTTCTGACCAGGCT : | 9535 |

|                | | |
|---|---|---|
| P1_consens (SEQ ID NO: 15) | : GGAGGCATGGCTCACTGAGCTGAGCACGATGTAACAGACTGAAGAGGATGGCGGTGAGTGGAGACGACTGTGTGGT : | 9648 |
| B-P1_conse (SEQ ID NO: 9) | : GGAGGCATGGCTCACTGAGCTGAGCACGATGTAACAGACTGAAGAGGATGGCGGTGAGTGGAGACGACTGTGTGGT : | 9609 |
| C-P1_genom (SEQ ID NO: 10) | : GGAGGCATGGCTCACTGAGCTGAGCACGATGTAACAGACTGAAGAGGATGGCGGTGAGTGGAGACGACTGTGTGGT : | 9609 |
| B3-P11_con (SEQ ID NO: 11) | : GGAGGCATGGCTCACTGAGCTGAGCACGATGTAACAGACTGAAGAGGATGGCGGTGAGTGGAGACGACTGTGTGGT : | 9623 |
| C1-P11_con (SEQ ID NO: 12) | : GGAGGCATGGCTCACTGAGCTGAGCACGATGTAACAGACTGAAGAGGATGGCGGTGAGTGGAGACGACTGTGTGGT : | 9607 |

|                | | |
|---|---|---|
| P1_consens (SEQ ID NO: 15) | : CCGGCCCATCGATGACAGGTTCGGCCTGGCCCTGTCCCATCTCAACGCCATGTCCAAGTTAGAAGGACAT : | 9720 |
| B-P1_conse (SEQ ID NO: 9) | : CCGGCCCATCGATGACAGGTTCGGCCTGGCCCTGTCCCATCTCAACGCCATGTCCAAGTTAGAAGGACAT : | 9681 |
| C-P1_genom (SEQ ID NO: 10) | : CCGGCCCATCGATGACAGGTTCGGCCTGGCCCTGTCCCATCTCAACGCCATGTCCAAGTTAGAAGGACAT : | 9681 |
| B3-P11_con (SEQ ID NO: 11) | : CCGGCCCATCGATGACAGGTTCGGCCTGGCCCTGTCCCATCTCAACGCCATGTCCAAGTTAGAAGGACAT : | 9695 |
| C1-P11_con (SEQ ID NO: 12) | : CCGGCCCATCGATGACAGGTTCGGCCTGGCCCTGTCCCATCTCAACGCCATGTCCAAGTTAGAAGGACAT : | 9679 |

FIG. 8AA

| | | | | |
|---|---|---|---|---|
| (SEQ ID NO: 15) | P1_consens | : | ATCTGAATGGCAGCCATCAAAAGGTGGAATGATTGGGAGAATGTGCCCTTCTGTTCCCACCACTTCCATGA | : 9792 |
| (SEQ ID NO: 9) | B-P1_conse | : | ATCTGAATGGCAGCCATCAAAAGGTGGAATGATTGGGAGAATGTGCCCTTCTGTTCCCACCACTTCCATGA | : 9753 |
| (SEQ ID NO: 10) | C-P1_genom | : | ATCTGAATGGCAGCCATCAAAAGGTGGAATGATTGGGAGAATGTGCCCTTCTGTTCCCACCACTTCCATGA | : 9753 |
| (SEQ ID NO: 11) | B3-P11_con | : | ATCTGAATGGCAGCCATCAAAAGGTGGAATGATTGGGAGAATGTGCCCTTCTGTTCCCACCACTTCCATGA | : 9767 |
| (SEQ ID NO: 12) | C1-P11_con | : | ATCTGAATGGCAGCCATCAAAAGGTGGAATGATTGGGAGAATGTGCCCTTCTGTTCCCACCACTTCCATGA | : 9751 |
| (SEQ ID NO: 15) | P1_consens | : | ACTACAGCTGAAGGATGGCAGGAGGATTGTGGTGCCTTGCCGAGAACAGGACAGAGCTCATTGGGAGAGGAAG | : 9864 |
| (SEQ ID NO: 9) | B-P1_conse | : | ACTACAGCTGAAGGATGGCAGGAGGATTGTGGTGCCTTGCCGAGAACAGGACAGAGCTCATTGGGAGAGGAAG | : 9825 |
| (SEQ ID NO: 10) | C-P1_genom | : | ACTACAGCTGAAGGATGGCAGGAGGATTGTGGTGCCTTGCCGAGAACAGGACAGAGCTCATTGGGAGAGGAAG | : 9825 |
| (SEQ ID NO: 11) | B3-P11_con | : | ACTACAGCTGAAGGATGGCAGGAGGATTGTGGTGCCTTGCCGAGAACAGGACAGAGCTCATTGGGAGAGGAAG | : 9839 |
| (SEQ ID NO: 12) | C1-P11_con | : | ACTACAGCTGAAGGATGGCAGGAGGATTGTGGTGCCTTGCCGAGAACAGGACAGAGCTCATTGGGAGAGGAAG | : 9823 |
| (SEQ ID NO: 15) | P1_consens | : | GGTGTCTCCAGGAAACGGCTGGATGATCAAGGAAACAGCTTGCCTCCTCAGCAAAGCCTATGCCAACATGTGGTC | : 9936 |
| (SEQ ID NO: 9) | B-P1_conse | : | GGTGTCTCCAGGAAACGGCTGGATGATCAAGGAAACAGCTTGCCTCCTCAGCAAAGCCTATGCCAACATGTGGTC | : 9897 |
| (SEQ ID NO: 10) | C-P1_genom | : | GGTGTCTCCAGGAAACGGCTGGATGATCAAGGAAACAGCTTGCCTCCTCAGCAAAGCCTATGCCAACATGTGGTC | : 9897 |
| (SEQ ID NO: 11) | B3-P11_con | : | GGTGTCTCCAGGAAACGGCTGGATGATCAAGGAAACAGCTTGCCTCCTCAGCAAAGCCTATGCCAACATGTGGTC | : 9911 |
| (SEQ ID NO: 12) | C1-P11_con | : | GGTGTCTCCAGGAAACGGCTGGATGATCAAGGAAACAGCTTGCCTCCTCAGCAAAGCCTATGCCAACATGTGGTC | : 9895 |
| (SEQ ID NO: 15) | P1_consens | : | ACTGATGTATTTTCACAAAAGGACACATGGCTACTGTCATTGGCTGTGTTCCTCCAGCTGTTCCCACCTCATG | : 10008 |
| (SEQ ID NO: 9) | B-P1_conse | : | ACTGATGTATTTTCACAAAAGGACACATGGCTACTGTCATTGGCTGTGTTCCTCCAGCTGTTCCCACCTCATG | : 9969 |
| (SEQ ID NO: 10) | C-P1_genom | : | ACTGATGTATTTTCACAAAAGGACACATGGCTACTGTCATTGGCTGTGTTCCTCCAGCTGTTCCCACCTCATG | : 9969 |
| (SEQ ID NO: 11) | B3-P11_con | : | ACTGATGTATTTTCACAAAAGGACACATGGCTACTGTCATTGGCTGTGTTCCTCCAGCTGTTCCCACCTCATG | : 9983 |
| (SEQ ID NO: 12) | C1-P11_con | : | ACTGATGTATTTTCACAAAAGGACACATGGCTACTGTCATTGGCTGTGTTCCTCCAGCTGTTCCCACCTCATG | : 9967 |
| (SEQ ID NO: 15) | P1_consens | : | GGTTCCACAAGGACGCACAACATGTGGATCAGCGCGAGTGATGACCACGGAAGACATGCTTGA | : 10080 |
| (SEQ ID NO: 9) | B-P1_conse | : | GGTTCCACAAGGACGCACAACATGTGGATCAGCGCGAGTGATGACCACGGAAGACATGCTTGA | : 10041 |
| (SEQ ID NO: 10) | C-P1_genom | : | GGTTCCACAAGGACGCACAACATGTGGATCAGCGCGAGTGATGACCACGGAAGACATGCTTGA | : 10041 |
| (SEQ ID NO: 11) | B3-P11_con | : | GGTTCCACAAGGACGCACAACATGTGGATCAGCGCGAGTGATGACCACGGAAGACATGCTTGA | : 10055 |
| (SEQ ID NO: 12) | C1-P11_con | : | GGTTCCACAAGGACGCACAACATGTGGATCAGCGCGAGTGATGACCACGGAAGACATGCTTGA | : 10039 |

| | | | |
|---|---|---|---|
| P1_consens (SEQ ID NO: 15) | GCTGGAGAACCGGACTCCGCACTTAAAATGAAACAGAAACCGGATAAAACTACGATGGAGAACCGGACT | : | 10512 |
| B-P1_conse (SEQ ID NO: 9) | GCTGGAGAACCGGACTCCGCACTTAAAATGAAACAGAAACCGGATAAAACTACGATGGAGAACCGGACT | : | 10473 |
| C-P1_genom (SEQ ID NO: 10) | GCTGGAGAACCGGACTCCGCACTTAAAATGAAACAGAAACCGGATAAAACTACGATGAGAACCGGACT | : | 10473 |
| B3-P11_con (SEQ ID NO: 11) | GCTGGAGAACCGGACTCCGCACTTAAAATGAAACAGAAACCGGATAAAACTACGATGAGAACCGGACT | : | 10487 |
| C1-P11_con (SEQ ID NO: 12) | GCTGGAGAACCGGACTCCGCACTTAAAATGAAACAGAAACCGGATAAAACTACGATGAGAACCGGACT | : | 10471 |

| | | | |
|---|---|---|---|
| P1_consens (SEQ ID NO: 15) | CCACACATTGAGACAGAAGAAGTTGTCAGCCCAGAACCCCACACGAGTTTTGCCACTGCTAAGCTGTGAGGC | : | 10584 |
| B-P1_conse (SEQ ID NO: 9) | CCACACATTGAGACAGAAGAAGTTGTCAGCCCAGAACCCCACACGAGTTTTGCCACTGCTAAGCTGTGAGGC | : | 10545 |
| C-P1_genom (SEQ ID NO: 10) | CCACACATTGAGACAGAAGAAGTTGTCAGCCCAGAACCCCACACGAGTTTTGCCACTGCTAAGCTGTGAGGC | : | 10545 |
| B3-P11_con (SEQ ID NO: 11) | CCACACATTGAGACAGAAGAAGTTGTCAGCCCAGAACCCCACACGAGTTTTGCCACTGCTAAGCTGTGAGGC | : | 10559 |
| C1-P11_con (SEQ ID NO: 12) | CCACACATTGAGACAGAAGAAGTTGTCAGCCCAGAACCCCACACGAGTTTTGCCACTGCTAAGCTGTGAGGC | : | 10543 |

| | | | |
|---|---|---|---|
| P1_consens (SEQ ID NO: 15) | AGTGCAGGCTGGGACAGCCGACCTCCAGGTTGCGAAAAACCTGGTTTCTTCGGACCTCCCACCCCAGAGTAAA | : | 10656 |
| B-P1_conse (SEQ ID NO: 9) | AGTGCAGGCTGGGACAGCCGACCTCCAGGTTGCGAAAAACCTGGTTTCTTCGGACCTCCCACCCCAGAGTAAA | : | 10617 |
| C-P1_genom (SEQ ID NO: 10) | AGTGCAGGCTGGGACAGCCGACCTCCAGGTTGCGAAAAACCTGGTTTCTTCGGACCTCCCACCCCAGAGTAAA | : | 10617 |
| B3-P11_con (SEQ ID NO: 11) | AGTGCAGGCTGGGACAGCCGACCTCCAGGTTGCGAAAAACCTGGTTTCTTCGGACCTCCCACCCCAGAGTAAA | : | 10631 |
| C1-P11_con (SEQ ID NO: 12) | AGTGCAGGCTGGGACAGCCGACCTCCAGGTTGCGAAAAACCTGGTTTCTTCGGACCTCCCACCCCAGAGTAAA | : | 10615 |

| | | | |
|---|---|---|---|
| P1_consens (SEQ ID NO: 15) | AAGAACGGAGCCTCCGCTACCACCTCCCACGTGGTGTAGAAAGACGGGGTCTAGAGGTTAGAGGAGACCC | : | 10728 |
| B-P1_conse (SEQ ID NO: 9) | AAGAACGGAGCCTCCGCTACCACCTCCCACGTGGTGTAGAAAGACGGGGTCTAGAGGTTAGAGAGACCC | : | 10689 |
| C-P1_genom (SEQ ID NO: 10) | AAGAACGGAGCCTCCGCTACCACCTCCCACGTGGTGTAGAAAGACCGGGTCTAGAGGTTAGAGAGACCC | : | 10689 |
| B3-P11_con (SEQ ID NO: 11) | AAGAACGGAGCCTCCGCTACCACCTCCCACGTGGTGTAGAAAGACGGGGTCTAGAGGTTAGAGGAGACCC | : | 10703 |
| C1-P11_con (SEQ ID NO: 12) | AAGAACGGAGCCTCCGCTACCACCTCCCACGTGGTGTAGAAAGACGGGGTCTAGAGGTTAGAGGAGACCC | : | 10687 |

| | | | |
|---|---|---|---|
| P1_consens (SEQ ID NO: 15) | TCCAGGGAACAAATAGTGGGACCATATTGACGCCAGGGAAAGACCGAGTGGTTCTCTGCTTTTCCTCCAGA | : | 10800 |
| B-P1_conse (SEQ ID NO: 9) | TCCAGGGAACAAATAGTGCCACCATATTGACGCCAGGGAAAGACCGAGTGGTTCTCTGCTTTTCCTCCAGA | : | 10761 |
| C-P1_genom (SEQ ID NO: 10) | TCCAGGGAACAAATAGTGGGACCATATTGACGCCAGGGAAAGACCGAGTGGTTCTCTGCTTTTCCTCCAGA | : | 10761 |
| B3-P11_con (SEQ ID NO: 11) | TCCAGGGAACAAATAGTGGGACCATATTGACGCCAGGGAAAGACCGAGTGGTTCTCTGCTTTTCCTCCAGA | : | 10775 |
| C1-P11_con (SEQ ID NO: 12) | TCCAGGGAACAAATAGTGGGACCATATTGACGCCAGGGAAAGACCGAGTGGTTCTCTGCTTTTCCTCCAGA | : | 10759 |

FIG. 8DD

```
                                         *         10820         *         10840         *         10860
(SEQ ID NO:15) P1_consens  : GGTCTGTGAGCACAGTTTGCTCAAGAATAAGCAGACCTTTGGATGACAAACACAAAACCACT : 10862
(SEQ ID NO:9)  B-P1_conse  : GGTCTGTGAGCACAG--------------------------------------------- : 10776
(SEQ ID NO:10) C-P1_genom  : GGTCTGTGAGCACAGTTTGCTCAAGAA--------------------------------- : 10788
(SEQ ID NO:11) B3-P11_con  : GGTCTGTGAGCACAGTTTGCTCAAGAATAAGCAGAC------------------------ : 10811
(SEQ ID NO:12) C1-P11_con  : GGTCTGTGAGCACAGTTTGCTCAAGA---------------------------------- : 10785

FIG. 8EE
```

```
(SEQ ID NO: 13)  B-P1_polyp : MSGRKAQGKTLGVNMVRRGVRSLSNKIKQKTKQIGNRPGPSRGVQGFIFFFLFNILTGKKITAHLKRLWKMLD :  73
(SEQ ID NO: 7)   B3-P11_pol : MSGRKAQGKTLGVNMVRRGVRSLSNKIKQKTKQIGNRPGPSRGVQGFIFFFLFNILTGKKITAHLKRLWKMLD :  73

(SEQ ID NO: 13)  B-P1_polyp : PRQGLAVLRKVKRVASLMRGLSSRKRRSHDVLTVQFLILGMLLMTGGVTLVRKNRWLLLNVTSEDLGKTFSV  : 146
(SEQ ID NO: 7)   B3-P11_pol : PRQGLAVLRKVKRVASLMRGLSSRKRRSHDVLTVQFLILGMLLMTGGVTLVRKNRWLLLNVTSEDLGKTFSV  : 146

(SEQ ID NO: 13)  B-P1_polyp : GTGNCTTNILEAKYWCPDSMEYNCPNLSPREEPDDIDCWCYGVENVRVAYGKCDSAGRSRSRRAIDLPTHEN  : 219
(SEQ ID NO: 7)   B3-P11_pol : GTGNCTTNILEAKYWCPDSMEYNCPNLSPREEPDDIDCWCYGVENVRVAYGKCDSAGRSRSRRAIDLPTHEN  : 219

(SEQ ID NO: 13)  B-P1_polyp : HGLKTRQEKWMTGRMGERQLQKIERWFVRNPFFAVTALTIAYLVGSNMTQRVVIALLVLAVGPAYSAHCIGIT : 292
(SEQ ID NO: 7)   B3-P11_pol : HGLKTRQEKWMTGRMGERQLQKIERWFVRNPFFAVTALTIAYLVGSNMTQRVVIALLVLAVGPAYSAHCIGIT : 292

(SEQ ID NO: 13)  B-P1_polyp : DRDFIEGVHGGTWVSATLEQDKCVTVMAPDKPSLDISLETVAIDRPAEVRKVCYNAVLTHVKINDKCPSTGEA : 365
(SEQ ID NO: 7)   B3-P11_pol : DRDFIEGVHGGTWVSATLEQDKCVTVMAPDKPSLDISLETVAIDRPAEVRKVCYNAVLTHVKINDKCPSTGEA : 365

(SEQ ID NO: 13)  B-P1_polyp : HLAEENEGDNACKRTYSDRGWGNGCGLFGKGSIVACAKFTCAKSMSLFEVDQTKIQYVIRAQLHVGAKQENWT : 438
(SEQ ID NO: 7)   B3-P11_pol : HLAEENEGDNACKRTYSDRGWGNGCGLFGKGSIVACAKFTCAKSMSLFEVDQTKIQYVIRAQLHVGAKQENWT : 438

(SEQ ID NO: 13)  B-P1_polyp : TDIKTLKFDALSGSQEVEFIGYGKATLECQVQTAVDFGNSYIAEMETESWIVDRQWAQDLITLPWQSGSGGVWR : 511
(SEQ ID NO: 7)   B3-P11_pol : TDIKTLRFDALSGSQEVEFIGYGKATLECQVQTAVDFGNSYIAEMETESWIVDRQWAQDLITLPWQSGSGGVWR : 511

(SEQ ID NO: 13)  B-P1_polyp : EMHHLVEFEPPHAATIRVLALGNQEGSLKTALTGAMRVTKDTNDNNLYKLHGGHVSCRVKLSALITLKGTSYKI : 584
(SEQ ID NO: 7)   B3-P11_pol : EMHHLVEFEPPHAATIRVLALGNQEGSLKTALTGAMRVTKDTNDNNLYKLHGGHVSCRVKLSALITLKGTSYKI : 584
```

FIG. 9A

| | | | |
|---|---|---|---|
| (SEQ ID NO: 13) | B-P1_polyp | : CTDKMFFVKNPTDTGHGTVMQVKVSKGAPCRIPVIVADDLTAAINKGILVTVNPIASTNDDEVLIEVNPPFG | 657 |
| (SEQ ID NO: 7) | B3-P11_pol | : CTDKMFFVKNPTDTGHGTVMQVKVSKGAPCRIPVIVADDLTAAINKGILVTVNPIASTNDDEVLIEVNPPFG | 657 |
| (SEQ ID NO: 13) | B-P1_polyp | : DSYIIVGRGDSRLTYQWHKEGSSIGKLFTQTMKGVERLAVMGDTAWDFSSAGGFFTSVGKGIHTVFGSAFQGL | 730 |
| (SEQ ID NO: 7) | B3-P11_pol | : DSYIIVGRGDSRLTYQWHKEGSSIGKLFTQTMKGVERLAVMGDTAWDFSSAGGFFTSVGKGIHTVFGSAFQGL | 730 |
| (SEQ ID NO: 13) | B-P1_polyp | : FGGLNWITKVIMGAVLIWVGINTRNMTMSMSMILVGVIMMFLSLGVGADQGCAINFGKKRELKCGDGIFIFRDS | 803 |
| (SEQ ID NO: 7) | B3-P11_pol | : FGGLNWITKVIMGAVLIWVGINTRNMTMSMSMILVGVIMMFLSLGVGADQGCAINFGKKRELKCGDGIFIFRDS | 803 |
| (SEQ ID NO: 13) | B-P1_polyp | : DDWLNKYSYYPEDPVKLASIVKASFEEGKCGLNSVDSLEHEMWRSRADEINAIFEENEVDISVVVQDPKNVYQ | 876 |
| (SEQ ID NO: 7) | B3-P11_pol | : DDWLNKYSYYPEDPVKLASIVKASFEEGKCGLNSVDSLEHEMWRSRADEINAIFEENEVDISVVVQDPKNVYQ | 876 |
| (SEQ ID NO: 13) | B-P1_polyp | : RGTHPFSRIRDGLQYGWKTWGKNLVFSPGRKNGSFIIDGKSRKECPFSNRVWNSFQIEEFGTGVFTTRVYMDA | 949 |
| (SEQ ID NO: 7) | B3-P11_pol | : RGTHPFSRIRDGLQYGWKTWGKNLVFSPGRKNGSFIIDGKSRKECPFSNRVWNSFQIEEFGTGVFTTRVYMDA | 949 |
| (SEQ ID NO: 13) | B-P1_polyp | : VFEYTIDCDGSILGAAVNGKKSAHGSPTFWMGSHEVNGTWMIHTLEALDYKECEWPLTHTIGTSVBESEMFMP | 1022 |
| (SEQ ID NO: 7) | B3-P11_pol | : VFEYTIDCDGSILGAAVNGKKSAHGSPTFWMGSHEVNGTWMIHTLEALDYKECEWPLTHTIGTSVBESEMFMP | 1022 |
| (SEQ ID NO: 13) | B-P1_polyp | : RSIGGPVSSHNHIPGYKVQTNGPWMQVPLEVKREACPGTSVIIDGNCDGRGKSTRSTTDSGKVIPEWCCRSCT | 1095 |
| (SEQ ID NO: 7) | B3-P11_pol | : RSIGGPVSSHNHIPGYKVQTNGPWMQVPLEVKREACPGTSVIIDGNCDGRGKSTRSTTDSGKVIPEWCCRSCI | 1095 |
| (SEQ ID NO: 13) | B-P1_polyp | : MPPVSFHGSDGCWYPMEIRPRKTHESHLVRSWVTAGEIHAVPFGLVSMMIAMEVVLRKRQGPKQMLVGGVVLL | 1168 |
| (SEQ ID NO: 7) | B3-P11_pol | : MPPVSFHGSDGCWYPMEIRPRKTHESHLVRSWVTAGEIHAVPFGLVSMMIAMEVVLRKRQGPKQMLVGGVVLL | 1168 |

FIG. 9B

```
                              1180            *          1200            *          1220            *          1240
(SEQ ID NO: 13) B-P1_polyp : GAMLVGQVTLLLLKLTVAVGLHFHEMNNGGDAMYMALIAAFSIRPGLLIGFGLRTLWSPRERLVLTLGAAMV : 1241
(SEQ ID NO: 7)  B3-P11_pol : GAMLVGQVTLLLLKLTVAVGLHFHEMNNGGDAMYMALIAAFSIRPGLLIGFGLRTLWSPRERLVLTLGAAMV : 1241

*          1260            *          1280            *          1300            *
(SEQ ID NO: 13) B-P1_polyp : EIALGGVMGGLWKYLNAVSLCILTINAVASRKASNTILPLMALLTPVTMAEVRLAAMFFCAVVIIGVLHQNFK : 1314
(SEQ ID NO: 7)  B3-P11_pol : EIALGGVMGGLWKYLNAVSLCILTINAVASRKASNTILPLMALLTPVTMAEVRLAAMFLCAVVIIGVLHQNFK : 1314

1320            *          1340            *          1360            *          1380
(SEQ ID NO: 13) B-P1_polyp : DTSMQKTIPLVALTLTSYIGLTQPFLGLCAFLATRIFGRRSIPVNEALAAAGLVGVLAGLAFQEMENFLGPIA : 1387
(SEQ ID NO: 7)  B3-P11_pol : DTSMQKTIPLVALTLTSYIGLTQPFLGLCAFLATRIFGRRSIPVNEALAAAGLVGVLAGLAFQEMENFLGPIA : 1387

*          1400            *          1420            *          1440            *          1460
(SEQ ID NO: 13) B-P1_polyp : VGGLLMMLVSVAGRVDGLELKKLGEVSWEEEAEISGSSARYDVALSEQGRFKLLSEEKVPWDQVVMTSLALVG : 1460
(SEQ ID NO: 7)  B3-P11_pol : VGGLLMMLVSVAGRVDGLELKKLGEVSWEEEAEISGSSARYDVALSEQGRFKLLSEEKVPWDQVVMTSLALVG : 1460

*          1480            *          1500            *          1520            *
(SEQ ID NO: 13) B-P1_polyp : AALHPFALLIVLAGMLFHVRGARRSGDVLWDIPTPKIIEECEHLEDGIYGIFQSTFLGASQRGVGVAQGGVFH : 1533
(SEQ ID NO: 7)  B3-P11_pol : AALHPFALLIVLAGMLFHVRGARRSGDVLWDIPTPKIIEECEHLEDGIYGIFQSTFLGASQRGVGVAQGGVFH : 1533

1540            *          1560            *          1580            *          1600
(SEQ ID NO: 13) B-P1_polyp : TMWHVTRGAFLVRNGKKLIPSWASVKEDLVAYGGSWKLEGRWDGEEEVQLIAAVPGKNVNVQTKPSLFKVRN : 1606
(SEQ ID NO: 7)  B3-P11_pol : TMWHVTRGAFLVRNGKKLIPSWASVKEDLVAYCGSWKLEGRWDGEEEVQLIAAVPCKNVNVQTKPSLFKVRN : 1606

*          1620            *          1640            *          1660            *          168
(SEQ ID NO: 13) B-P1_polyp : GGEIGAVALDYPSGTSGSPIVNRNGEVIGLYGNGILVGDNSFVSAISQTEVKEEGKEELQEIPTMLKKGMTTV : 1679
(SEQ ID NO: 7)  B3-P11_pol : GGEIGAVALDYPSGTSGSPIVNRNGEVIGLYGNGILVGDNSFVSAISQTEVKEEGKEELQEIPTMLKKGMTTV : 1679

0           *          1700            *          1720            *          1740            *
(SEQ ID NO: 13) B-P1_polyp : LDFHPGAGKTRRFLPQIIAECARRRLRTLVLAPTRVVLSEMKEAFHGLDVKFHTQAFSAHGSGREVIDAMCHA : 1752
(SEQ ID NO: 7)  B3-P11_pol : LDFHPGAGKTRRFLPQIIAECARRRLRTLVLAPTRVVLSEMKEAFHGLDVKFHTQAFSAHGSGREVIDAMCHA : 1752
```

FIG. 9C

```
(SEQ ID NO: 13) B-P1_polyp :  TLTYRMLEPTRVVNWEVIIMDEAHFLDPASIAARGWAAHRARANESATILMTATPPGTSDEFPHSNGEIEDVQ : 1825
(SEQ ID NO: 7)  B3-P11_pol :  TLTYRMLEPTRVVNWEVIIMDEAHFLDPASIAARGWAAHRARANESATILMTATPPGTSDEFPHSNGEIEDVQ : 1825
                                       1760         *        1780         *        1800         *        1820

(SEQ ID NO: 13) B-P1_polyp :  TDIPSEPWNTGHDWILADKRPTAWFLPSIRAANVMAASLRKAGKSVVVLNRKTFEREYPTIKQKKPDFILATD : 1898
(SEQ ID NO: 7)  B3-P11_pol :  TDIPSEPWNTGHDWILADKRPTAWFLPSIRAANVMAASLRKAGKSVVVLNRKTFEREYPTIKQKKPDFILATD : 1898
                                  *        1840         *        1860         *        1880         *    19

(SEQ ID NO: 13) B-P1_polyp :  IAEMGANLCVERVLDCRTAFKPVLVDEGRKVAIKGPLRISASSAAQRRGRIGRNPNRDGDSYYYSEPTSENNA : 1971
(SEQ ID NO: 7)  B3-P11_pol :  IAEMGANLCVERVLDCRTAFKPVLVDEGRKVAIKGPLRISASSAAQRRGRIGRNPNRDGDSYYYSEPTSENNA : 1971
                              00       *        1920         *        1940         *        1960         *

(SEQ ID NO: 13) B-P1_polyp :  HHVCWLEASMLLDNMEVRGGMVAPLYGVEGTKTPVSPGEMRLRDDQRKVFRELVRNCDLPWLSWQVAKAGLK : 2044
(SEQ ID NO: 7)  B3-P11_pol :  HHVCWLEASMLLDNMEVRGGMVAPLYGVEGTKTPVSPGEMRLRDDQRKVFRELVRNCDLPWLSWQVAKAGLK : 2044
                                      1980         *        2000         *        2020         *        2040

(SEQ ID NO: 13) B-P1_polyp :  TNDRKWCFEGPBEHEILNDSGETVKCRAPGGAKKPLRPRWCDERVSSDQSALSEFIKFAEGRRGAAEVLVVLS : 2117
(SEQ ID NO: 7)  B3-P11_pol :  TNDRKWCFEGPBEHEILNDSGETVKCRAPGGAKKPLRPRWCDERVSSDQSALSEFIKFAEGRRGAAEVLVVLS : 2117
                                  *        2060         *        2080         *        2100         *     2

(SEQ ID NO: 13) B-P1_polyp :  ELPDFLAKKGGEAMDTISVFLHSEEGSRAYRNALSMMPEAMTIVMLFIIAGLLTSGMVIFFMSPKGISRMSMA : 2190
(SEQ ID NO: 7)  B3-P11_pol :  ELPDFLAKKGGEAMDTISVFLHSEEGSRAYRNALSMMPEAMTIVMLFIIAGLLTSGMVIFFMSPKGISRMSMA : 2190
                              120      *        2140         *        2160         *        2180         *

(SEQ ID NO: 13) B-P1_polyp :  MGTMAGCGYLMFLGGVKPTHISYIMLIFFVLMVVIPEPGQQRSIQDNQVAYLIIGILTLVSAVAANELGMLE : 2263
(SEQ ID NO: 7)  B3-P11_pol :  MGTMAGCGYLMFLGGVKPTHISYIMLIFFVLMVVIPEPGQQRSIQDNQVAYLIIGILTLVSAVAANELGMLE : 2263
                                      2200         *        2220         *        2240         *        2260

(SEQ ID NO: 13) B-P1_polyp :  KTKEDLFGKKNLIPSSASPWSWPDLDLKPGAAWTVYVGIVTMLSPMLHHWIKVEYGNLSLSGIAQSASVLSFM : 2336
(SEQ ID NO: 7)  B3-P11_pol :  KTKEDLFGKKNLIPSSASPWSWPDLDLKPGAAWTVYVGIVTMLSPMLHHWIKVEYGNLSLSGIAQSASVLSFM : 2336
                                  *        2280         *        2300         *        2320         *
```

FIG. 9D

```
(SEQ ID NO: 13)  B-P1_polyp  :  DKGIPFMKMNISVIMLLVSGWNSITVMPLLCGIGCAMLHWSLILPGIKAQQSKLAQRRVFHGVAKNPVVDGNP  : 2409
(SEQ ID NO: 7)   B3-P11_pol  :  DKGIPFMKMNISVIMLLVSGWNSITVMPLLCGIGCAMLHWSLILPGIKAQQSKLAQRRVFHGVAKNPVVDGNP  : 2409

(SEQ ID NO: 13)  B-P1_polyp  :  TVDIEEAPEMPALYEKKLALYLLLALSLASVAMCRTPFSLAEGIVLASAALGPLIEGNTSLLWNGPMAVSMTG  : 2482
(SEQ ID NO: 7)   B3-P11_pol  :  TVDIEEAPEMPALYEKKLALYLLLALSLASVAMCRTPFSLAEGIVLASAALGPLIEGNTSLLWNGPMAVSMTG  : 2482

(SEQ ID NO: 13)  B-P1_polyp  :  VMRGNHYAFVGVMNLMKMKTGRRGSANGKTLGEVWKRELNLLDKRQFELYKRTDIVEVDRDTARRHLAEGKV  : 2555
(SEQ ID NO: 7)   B3-P11_pol  :  VMRGNHYAFVGVMNLMKMKTGRRGSANGKTLGEVWKRELNLLDKRQFELYKRTDIVEVDRDTARRHLAEGKV  : 2555

(SEQ ID NO: 13)  B-P1_polyp  :  DTGVAVSRGTAKLRWFHERGYVKLEGRVIDLGCGRGGWCYYAAAQKEVSCVKGFTLGRDGHEKPMNVQSLGWN  : 2628
(SEQ ID NO: 7)   B3-P11_pol  :  DTGVAVSRGTAKLRWFHERGYVKLEGRVIDLGCGRGGWCYYAAAQKEVSCVKGFTLGRDGHEKPMNVQSLGWN  : 2628

(SEQ ID NO: 13)  B-P1_polyp  :  IITFKDKTDIHRLEPVKCDTLLCDIGESSSSSVTEGERTVRVLDTVEKWLACGVDNFCVKVLAPYMPDVLEKL  : 2701
(SEQ ID NO: 7)   B3-P11_pol  :  IITFKDKTDIHRLEPVKCDTLLCDIGESSSSSVTEGERTVRVLDTVEKWLACGVDNFCVKVLAPYMPDVLEKL  : 2701

(SEQ ID NO: 13)  B-P1_polyp  :  ELLQRRFGGTVIRNPLSRNSTHEMYYVSGARSNVTFTVNQTSRLLMRRMRRPTGKVTLEADVILPIGTRSVET  : 2774
(SEQ ID NO: 7)   B3-P11_pol  :  ELLQRRFGGTVIRNPLSRNSTHEMYYVSGARSNVTFTVNQTSRLLMRRMRRPTGKVTLEADVILPIGTRSVET  : 2774

(SEQ ID NO: 13)  B-P1_polyp  :  DKGPLDKEAIEERVERIKSEYMTSWFYDNDNPYRTWHYCGSYVTKTSGSAASMVNGVIKILTYPWDRIEEVTR  : 2847
(SEQ ID NO: 7)   B3-P11_pol  :  DKGPLDKEAIEERVERIKSEYMTSWFYDNDNPYRTWHYCGSYVTKTSGSAASMVNGVIKILTYPWDRIEEVTR  : 2847

(SEQ ID NO: 13)  B-P1_polyp  :  MAMTDTTPFGQQRVFKEKVDTRAKDPPAGTRKIMKVVNRWLFRHLAREKNPRLCTKEEFIAKVRSHAAIGAYL  : 2920
(SEQ ID NO: 7)   B3-P11_pol  :  MAMTDTTPFGQQRVFKEKVDTRAKDPPAGTRKIMKVVNRWLFRHLAREKNPRLCTKEEFIAKVRSHAAIGAYL  : 2920
```

FIG. 9E

```
                                   *      2940       *      2960       *      2980       *
(SEQ ID NO: 13) B-P1_polyp  : EEQEQWKTANEAVQDPKFWELVDEERKLHQQGRCRTCVYNMGKREKKLSEFGKAKGSRAIWYMWLGARYLEF : 2993
(SEQ ID NO: 7)  B3-P11_pol  : EEQEQWKTANEAVQDPKFWELVDEERKLHQQGRCRTCVYNMGKREKKLSEFGKAKGSRAIWYMWLGARYLEF : 2993

3000       *      3020       *      3040       *      3060
(SEQ ID NO: 13) B-P1_polyp  : EALGFLNEDHWASRENSGGGVEGIGLQYLGYVIRDLAAMDGGGFYADDTAGWDTRITEADLDDEQEILNYMSP : 3066
(SEQ ID NO: 7)  B3-P11_pol  : EALGFLNEDHWASRENSGGGVEGIGLQYLGYVIRDLAAMDGGGFYADDTAGWDTRITEADLDDEQEILNYMSP : 3066

*      3080       *      3100       *      3120       *     314
(SEQ ID NO: 13) B-P1_polyp  : HHKKLAQAVMEMTYKNKVVKVLRPAPGGKAYMDVISRRDQRGSGQVVTYALNTITNLKVQLIRMAEAEMVIHH : 3139
(SEQ ID NO: 7)  B3-P11_pol  : HHKKLAQAVMEMTYKNKVVKVLRPAPGGKAYMDVISRRDQRGSGQVVTYALNTITNLKVQLIRMAEAEMVIHH : 3139

0       *      3160       *      3180       *      3200       *
(SEQ ID NO: 13) B-P1_polyp  : QHVQDCDESVLTRLEAWLTEHGCNRLKRMAVSGDDCVVRPIDDRFGLALSHLNAMSKVRKDISEWQPSKGWND : 3212
(SEQ ID NO: 7)  B3-P11_pol  : QHVQDCDESVLTRLEAWLTEHGCNRLKRMAVSGDDCVVRPIDDRFGLALSHLNAMSKVRKDISEWQPSKGWND : 3212

3220       *      3240       *      3260       *      3280
(SEQ ID NO: 13) B-P1_polyp  : WENVPFCSHHFHELQLKDGRRIVVPCREQDELIGRGRVSPGNGWMIKETACLSKAYANMWSLMYFHKRDMRLL : 3285
(SEQ ID NO: 7)  B3-P11_pol  : WENVPFCSHHFHELQLKDGRRIVVPCREQDELIGRGRVSPGNGWMIKETACLSKAYANMWSLMYFHKRDMRLL : 3285

*      3300       *      3320       *      3340       *      33
(SEQ ID NO: 13) B-P1_polyp  : SLAVSSAVPTSWVPQGRTTWSIHGKGEWMTTEDMLEVWNRVWITNNPHMQDKTMVKKWRDVPYLTKRQDKLCG : 3358
(SEQ ID NO: 7)  B3-P11_pol  : SLAVSSAVPTSWVPQGRTTWSIHGKGEWMTTEDMLEVWNRVWITNNPHMQDKTMVKKWRDVFYLTKRQDKLCG : 3358

60       *      3380       *      3400       *
(SEQ ID NO: 13) B-P1_polyp  : SLIGMTNRATWASHIHLVIHRIRTLIGQEKYTDYLTVMDRYSVDADLQLGELI : 3411
(SEQ ID NO: 7)  B3-P11_pol  : SLIGMTNRATWASHIHLVIHRIRTLIGQEKYTDYLTVMDRYSVDADLQLGELI : 3411
```

FIG. 9F

```
(SEQ ID NO: 14)  C-P1_polyp  : MSGRKAQGKTLGVNMVRRGVRSLSNKIKQKTKQIGNRPGPSRGVQGFIFFFLFNILTGKKITAHLKRLWKMLD :  73
(SEQ ID NO: 8)   C1-P11_pol  : MSGRKAQGKTLGVNMVRRGVRSLSNKIKQKTKQIGNRPGPSRGVQGFIFFFLFNILTGKKITAHLKRLWKMLD :  73

(SEQ ID NO: 14)  C-P1_polyp  : PRQGLAVLRKVKRVVASLMRGLSSRKRRSHDVLTVQFLILGMLLMTGGVTLVRKNRWLLLNVTSEDLGKTFSV : 146
(SEQ ID NO: 8)   C1-P11_pol  : PRQGLAVLRKVKRVVASLMRGLSSRKRRSHDVLTVQFLILGMLLMTGGVTLVRKNRWLLLNVTSEDLGKTFSV : 146

(SEQ ID NO: 14)  C-P1_polyp  : GTGNCTTNILEAKYWCPDSMEYNCPNLSPREEPDDIDCWCYGVENVRVAYGKCDSAGRSRSRRRAIDLPTHEN : 219
(SEQ ID NO: 8)   C1-P11_pol  : GTGNCTTNILEAKYWCPDSMEYNCPNLSPREEPDDIDCWCYGVENVRVAYGKCDSAGRSRSRRRAIDLPTHEN : 219

(SEQ ID NO: 14)  C-P1_polyp  : HGLKTRQEKWMTGRMGERQLQKIERWFVRNPFFAVTALTIAYLVGSNMTQRVVIALLVLAVGPAYSAHCIGIT : 292
(SEQ ID NO: 8)   C1-P11_pol  : HGLKTRQEKWMTGRMGERQLQKIERWFVRNPFFAVTALTIAYLVGSNMTQRVVIALLVLAVGPAYSAHCIGIT : 292

(SEQ ID NO: 14)  C-P1_polyp  : DRDFIEGVHGGTWVSATLEQDKCVTVMAPDKPSLDISLETVAIDRPAEVRKVCYNAVLTHVKINDKCPSTGEA : 365
(SEQ ID NO: 8)   C1-P11_pol  : DRDFIEGVHGGTWVSATLEQDKCVTVMAPDKPSLDISLETVAIDRPAEVRKVCYNAVLTHVKINDKCPSTGEA : 365

(SEQ ID NO: 14)  C-P1_polyp  : HLAEENEGDNACKRTYSDRGWGNGCGLFGKGSIVACAKFTCAKSMSLFEVDQTKIQYVIRAQLHVGAKQENWT : 438
(SEQ ID NO: 8)   C1-P11_pol  : HLAEENEGDNACKRTYSDRGWGNGCGLFGKGSIVACAKFTCAKSMSLFEVDQTKIQYVIRAQLHVGAKQENWT : 438

(SEQ ID NO: 14)  C-P1_polyp  : TDIKTLKFDALSGSQEVEFIGYGKATLECQVQTAVDFGNSYIAEMETESWIVDRQWAQDLTLPWQSGSGGVWR : 511
(SEQ ID NO: 8)   C1-P11_pol  : TDIKTLKFDALSGSQEVEFIGYGKATLECQVQTAVDFGNSYIAEMETESWIVDRQWAQDLTLPWQSGSGGVWR : 511

(SEQ ID NO: 14)  C-P1_polyp  : EMHHLVEFEPPHAATIRVLALGNQEGSLKTALTGAMRVTKDTNDNNLYKLHGGHVSCRVKLSALTLKGTSYKI : 584
(SEQ ID NO: 8)   C1-P11_pol  : EMHHLVEFEPPHAATIRVLALGNQEGSLKTALTGAMRVTKDTNDNNLYKLHGGHVSCRVKLSALTLKGTSYKI : 584
```

FIG. 10A

| | | |
|---|---|---|
| (SEQ ID NO: 14) | C-P1_polyp : | CTDKMFFVKNPTDTGHGTVVMQVKSKGAPCRIPVIVADDLTAAINKGILVTVNPIASTNDDEVLIEVNPPFG : 657 |
| (SEQ ID NO: 8) | C1-P11_pol : | CTDKMFFVKNPTDTGHGTVVMQVKSKGAPCRIPVIVADDLTAAINKGILVTVNPIASTNDDEVLIEVNPPFG : 657 |
| (SEQ ID NO: 14) | C-P1_polyp : | DSYIIVGRGDSRLTYQWHKEGSSIGKLFTQTMKGVERLAVMGDTAWDFSSAGGFFTSVGKIHTVFGSAFQGL : 730 |
| (SEQ ID NO: 8) | C1-P11_pol : | DSYIIVGRGDSRLTYQWHKEGSSIGKLFTQTMKGVERLAVMGDTAWDFSSAGGFFTSVGKIHTVFGSAFQGL : 730 |
| (SEQ ID NO: 14) | C-P1_polyp : | FGGLNWITKVIMGAVLIWVGINTRNMTMSMSMILVGVIMMFLSLGVGADQGCAINFGKRELKCGDGIFIFRDS : 803 |
| (SEQ ID NO: 8) | C1-P11_pol : | FGGLNWITKVIMGAVLIWVGINTRNMTMSMSMILVGVIMMFLSLGVGADQGCAINFGKRELKCGDGIFIFRDS : 803 |
| (SEQ ID NO: 14) | C-P1_polyp : | DDWLNKYSYPEDPVKLASIVKASFEEGKCGLNSVDSLEHEMWRSRADEINAIFEENEVDISVVVQDPKNVYQ : 876 |
| (SEQ ID NO: 8) | C1-P11_pol : | DDWLNKYSYPEDPVKLASIVKASFEEGKCGLNSVDSLEHEMWRSRADEINAIFEENEVDISVVVQDPKNVYQ : 876 |
| (SEQ ID NO: 14) | C-P1_polyp : | RGTHPFSRIRDGLQYGWKTWGKNLVFSPGRKNGSFIIDGKSRKECPFSNRVWNSFQIEEFGTGVFTTRVYMDA : 949 |
| (SEQ ID NO: 8) | C1-P11_pol : | RGTHPFSRIRDGLQYGWKTWGKNLVFSPGRKNGSFIIDGKSRKECPFSNRVWNSFQIEEFGTGVFTTRVYMDA : 949 |
| (SEQ ID NO: 14) | C-P1_polyp : | VFEYTIDCDGSILGAAVNGKKSAHGSPTFWMGSHEVNGTWMIHTLEALDYKECEWPLTHTIGTSVEESEMFMP : 1022 |
| (SEQ ID NO: 8) | C1-P11_pol : | VFEYTIDCDGSILGAAVNGKKSAHGSPTFWMGSHEVNGTWMIHTLEALDYKECEWPLTHTIGTSVEESEMFMP : 1022 |
| (SEQ ID NO: 14) | C-P1_polyp : | RSIGGPVSSHNHIPGYKVQTNGPWMQVPLEVKREACPGTSVIIDGNCDGRGKSTRSTTDSGKVIPEWCCRSCT : 1095 |
| (SEQ ID NO: 8) | C1-P11_pol : | RSIGGPVSSHNHIPGYKVQTNGPWMQVPLEVKREACPGTSVIIDGNCDGRGKSTRSTTDSGKVIPEWCCRSCT : 1095 |
| (SEQ ID NO: 14) | C-P1_polyp : | MPPVSFHGSDGCWYPMEIRPRKTHESHLVRSWVTAGEIHAVPFGLVSMMIAMEVVLRKRQGPKQMLVGGVVLL : 1168 |
| (SEQ ID NO: 8) | C1-P11_pol : | MPPVSFHGSDGCWYPMEIRPRKTHESHLVRSWVTAGEIHAVPFGLVSMMIAMEVVLRKRQGPKQMLVGGVVLL : 1168 |

FIG. 10B

```
(SEQ ID NO: 14) C-P1_polyp : GAMLVGQVTLLDLLKLTVAVGLHFHEMNNGGDAMYMALIAAFSIR2GLLIGFGLRTLWSPRERLVLTLGAAMV : 1241
(SEQ ID NO: 8)  C1-P11_pol : GAMLVGQVTLLDLLKLTVAVGLHFHEMNNGGDAMYMALIAAFSIRPGLLIGFGLRTLWSPRERLVLTLGAAMV : 1241

(SEQ ID NO: 14) C-P1_polyp : EIALGGVMGGLWKYLNAVSLCILTINAVASRKASNTILPLMALLTPVTMAEVRLAAMFFCAVVIIGVLHQNFK : 1314
(SEQ ID NO: 8)  C1-P11_pol : EIALGGVMGGLWKYLNAVSLCILTINAVASRKASNTILPLMALLTPVTMAEVRLAAMFFCAVVIIGVLHQNFK : 1314

(SEQ ID NO: 14) C-P1_polyp : DTSMQKTIPLVALTLTSYLGLTQPFLGLCAFLATRIFGRRSIPVNEALAAAGLVGVLAGLAFQEMENFLGPIA : 1387
(SEQ ID NO: 8)  C1-P11_pol : DTSMQKTIPLVALTLTSYLGLTQPFLGLCAFLATRIFGRRSIPVNEALAAAGLVGVLAGLAFQEMENFLGPIA : 1387

(SEQ ID NO: 14) C-P1_polyp : VGGLLMMLVSVAGRVDGLELKKLGEVSWEEEAEISGSSARYDVALSEQGBFKLLSEEKVPWDQVVMTSLALVG : 1460
(SEQ ID NO: 8)  C1-P11_pol : VGGLLMMLVSVAGRVDGLELKKLGEVSWEEEAEISGSSARYDVALSEQGBFKLLSEEKVPWDQVVMTSLALVG : 1460

(SEQ ID NO: 14) C-P1_polyp : AALHPFALLLVLAGWLFHVRGARRSGDVLWDIPTPKIIEECEHLEDGIYGIFQSTFLGASQRGVGVAQGGVFH : 1533
(SEQ ID NO: 8)  C1-P11_pol : AALHPFALLLVLAGWLFHVRGARRSGDVLWDIPTPKIIEECEHLEDGIYGIFQSTFLGASQRGVGVAQGGVFH : 1533

(SEQ ID NO: 14) C-P1_polyp : TMWHVTRGAFLVRNGKKLIPSWASVKEDLVAYGGSWKLEGRMDGEEEVQLIAAVPGKNVVNVQTKPSLFKVRN : 1606
(SEQ ID NO: 8)  C1-P11_pol : TMWHVTRGAFLVRNGKKLIPSWASVKEDLVAYGGSWKLEGRMDGEEEVQLIAAVPGKNVVNVQTKPSLFKVRN : 1606

(SEQ ID NO: 14) C-P1_polyp : GGEIGAVALDYPSGTSGSPIVNRNGEVIGLYGNGILVGDNSFVSAISQTEVKEEGKEELQEIPTMLKKGMTTV : 1679
(SEQ ID NO: 8)  C1-P11_pol : GGEIGAVALDYPSGTSGSPIVNRNGEVIGLYGNGILVGDNSFVSAISQTEVKEEGKEELQEIPTMLKKGMTTV : 1679

(SEQ ID NO: 14) C-P1_polyp : LDFHPGAGKTRRFLPQIIAECARRRLRTLVLAPTRVVLSEMKEAFHGLDVKFHTQAFSAHGSREVIDAMCHA : 1752
(SEQ ID NO: 8)  C1-P11_pol : LDFHPGAGKTRRFLPQIIAECARRRLRTLVLAPTRVVLSEMKEAFHGLDVKFHTQAFSAHCSREVIDAMCHA : 1752
```

FIG. 10C

```
                                            1760         *          1780         *          1800         *          1820
(SEQ ID NO: 14)  C-P1_polyp  : TLTYRMLEPTRVVNWEVIIMDEAHFLDPASIAARGWAAHRARANESATILMTATPPGTSDEFPHSNGEIEDVQ : 1825
(SEQ ID NO: 8)   C1-P11_pol  : TLTYRMLEPTRVVNWEVIIMDEAHFLDPASIAARGWAAHRARANESATILMTATPPGTSDEFPHSNGEIEDVQ : 1825

*          1840         *          1860         *          1880         *      19
(SEQ ID NO: 14)  C-P1_polyp  : TDIPSEPWNTGHDWILADKRPTAWFLPSIRAANVMAASLRKAGKSVVVLNRKTFEREYPTIKQKKPDFILATD : 1898
(SEQ ID NO: 8)   C1-P11_pol  : TDIPSEPWNTGHDWILADKRPTAWFLPSIRAANVMAASLRKAGKSVVVLNRKTFEREYPTIKQKKPDFILATD : 1898

00         *          1920         *          1940         *          1960         *
(SEQ ID NO: 14)  C-P1_polyp  : IAEMGANLCVERVLDCRTAFKPVLVDEGRKVAIKGPLRISASSAAQRRGRIGRNPNRDGDSYYYSEPTSENNA : 1971
(SEQ ID NO: 8)   C1-P11_pol  : IAEMGANLCVERVLDCRTAFKPVLVDEGRKVAIKGPLRISASSAAQRRGRIGRNPNRDGDSYYYSEPTSENNA : 1971

*          1980         *          2000         *          2020         *     2040
(SEQ ID NO: 14)  C-P1_polyp  : HHVCWLEASMLLDNMEVRGGMVAPLYGVEGTKTPVSPGEMRLRDDQRKVFRELVRNCDLPVWLSWQVAKAGLK : 2044
(SEQ ID NO: 8)   C1-P11_pol  : HHVCWLEASMLLDNMEVRGGMVAPLYGVEGTKTPVSPGEMRLRDDQRKVFRELVRNCDLPVWLSWQVAKAGLK : 2044

*          2060         *          2080         *          2100         *       2
(SEQ ID NO: 14)  C-P1_polyp  : TNDRKWCFEGPEEHEILNDSGETVKCRAPGGAKKPLRPRWCDERVSSDQSALSEFIKFAEGRRGAAEVLVVLS : 2117
(SEQ ID NO: 8)   C1-P11_pol  : TNDRKWCFEGPEEHEILNDSGETVKCRAPGGAKKPLRPRWCDERVSSDQSALSEFIKFAEGRRGAAEVLVVLS : 2117

120         *          2140         *          2160         *          2180         *
(SEQ ID NO: 14)  C-P1_polyp  : ELPDFLAKKGGEAMDTISVFLHSEEGSRAYRNALSMMPEAMTIVMLFILAGLLTSGMVIFFMSPKGISRMSMA : 2190
(SEQ ID NO: 8)   C1-P11_pol  : ELPDFLAKKGGEAMDTISVFLHSEEGSRAYRNALSMMPEAMTIVMLFILAGLLTSGMVIFFMSPKGISRMSMA : 2190

*          2200         *          2220         *          2240         *     2260
(SEQ ID NO: 14)  C-P1_polyp  : MGTMAGCGYLMFLGGVKPTHISYIMLIFFVLMVVVIPEPGQQRSIQDNQVAYLLIGILTLVSAVAANELGMLE : 2263
(SEQ ID NO: 8)   C1-P11_pol  : MGTMAGCGYLMFLGGVKPTHISYIMLIFFVLMVVVIPEPGQQRSIQDNQVAYLLIGILTLVSAVAANELGMLE : 2263

*          2280         *          2300         *          2320         *
(SEQ ID NO: 14)  C-P1_polyp  : KTKEDLFGKKNLIPSSASPWSWPDLDLKPGAAWTVYYGIVTMLSPMLHHWIKVEYGNLSLSGIAQSASVLSFM : 2336
(SEQ ID NO: 8)   C1-P11_pol  : KTKEDLFGKKNLIPSSASPWSWPDLDLKPGAAWTVYYGIVTMLSPMLHHWIKVEYGNLSLSGIAQSASVLSFM : 2336
```

FIG. 10D

```
                            2340         *         2360         *         2380         *         2400         *
(SEQ ID NO:14)  C-P1_polyp : DKGIPFMKMNISVIMLLVSGWNSITVMPLLCGIGCAMLHWSLILPGIKAQQSKLAQRRVFHGVAKNPVVDGNP : 2409
(SEQ ID NO:8)   C1-P11_pol : DKGIPFMKMNISVIMLLVSGWNSITVMPLLCGMGCAMLHWSLILPGIKAQQSKLAQRRVFHGVAKNPVVDGNP : 2409

*         2420         *         2440         *         2460         *         2480
(SEQ ID NO:14)  C-P1_polyp : TVDIEEAPEMPALYEKKLALYLLLALSLASVAMCRTPFSLAEGIVLASAALGPLIEGNTSLLWNGPMAVSMTG : 2482
(SEQ ID NO:8)   C1-P11_pol : TVDIEEAPEMPALYEKKLALYLLLALSLASVAMCRTPFSLAEGIVLASAALGPLIEGNTSLLWNGPMAVSMTG : 2482

*         2500         *         2520         *         2540         *
(SEQ ID NO:14)  C-P1_polyp : VMRGNHYAFVGVMYNLMKMKTGRRGSANGKTLGEVWKRELNLLDKRQFELYKRTDIVEVDRDTARRHLAEGKV : 2555
(SEQ ID NO:8)   C1-P11_pol : VMRGNHYAFVGVMYNLMKMKTGRRGSANGKTLGEVWKRELNLLDKRQFELYKRTDIVEVDRDTARRHLAEGKV : 2555

2560         *         2580         *         2600         *         2620         *
(SEQ ID NO:14)  C-P1_polyp : DTGVAVSRGTAKLRWFHERGYVKLEGRVIDLGCGRGGWCYYAAAQKEVSGVKGFTLGRDGHEKPMNVQSLGWN : 2628
(SEQ ID NO:8)   C1-P11_pol : DTGVAVSRGTAKLRWFHERGYVKLEGRVIDLGCGRGGWCYYAAAQKEVSGVKGFTLGRDGHEKPMNVQSLGWN : 2628

*         2640         *         2660         *         2680         *         2700
(SEQ ID NO:14)  C-P1_polyp : IITFKDKTDIHRLEPVKCDTLLCDIGESSSSVTEGERTVRVLDTVEKWLACGVDNFCVKVLAPYMPDVLEKL : 2701
(SEQ ID NO:8)   C1-P11_pol : IITFKDKTDIHRLEPVKCDTLLCDIGESSSSVTEGERTVRVLDTVEKWLACGVDNFCVKVLAPYMPDVLEKL : 2701

*         2720         *         2740         *         2760         *
(SEQ ID NO:14)  C-P1_polyp : ELLQRRFGGTVIRNPLSRNSTHEMYVVSGARSNVTFTVNQTSRLLMRRMRRPTGKVTLEADVILPIGTRSVET : 2774
(SEQ ID NO:8)   C1-P11_pol : ELLQRRFGGTVIRNPLSRNSTHEMYVVSGARSNVTFTVNQTSRLLMRRMRRPTGKVTLEADVILPIGTRSVET : 2774

2780         *         2800         *         2820         *         2840         *
(SEQ ID NO:14)  C-P1_polyp : DKGPLDKEAIEERVERIKSEYMTSWFYDNDNPYRTWHYCGSYVTKTSGSAASMVNGVIKILTYPWDRIEEVTR : 2847
(SEQ ID NO:8)   C1-P11_pol : DKGPLDKEAIEERVERIKSEYMTSWFYDNDNPYRTWHYCGSYVTKTSGSAASMVNGVIKILTYPWDRIEEVTR : 2847

*         2860         *         2880         *         2900         *         2920
(SEQ ID NO:14)  C-P1_polyp : MAMTDTTPFGQQRVFKEKVDTRAKDPPAGTRKIMKVVNRWLFRHLAREKNPRLCTKEEFIAKVRSHAAIGAYL : 2920
(SEQ ID NO:8)   C1-P11_pol : MAMTDTTPFGQQRVFKEKVDTRAKDPPAGTRKIMKVVNRWLFRHLAREKNPRLCTKEEFIAKVRSHAAIGAYL : 2920
```

FIG. 10E

```
                              *        2940         *        2960         *        2980         *
(SEQ ID NO: 14)  C-P1_polyp  : EEQEQWKTANEAVQDPKFWELVDEERKLHQQGRCRTCVYNMMGKREKKLSEFGKAKGSRAIWYMLGARYLEF : 2993
(SEQ ID NO: 8)   C1-P11_pol  : EEQEQWKTANEAVQDPKFWELVDEERKLHQQGRCRTCVYNMMGKREKKLSEFGKAKGSRAIWYMLGARYLEF : 2993

3000        *        3020         *        3040         *        3060
(SEQ ID NO: 14)  C-P1_polyp  : EALGFLNEDHWASRENSGGGVEGIGLQYLGYVIRDLAAMDGGGFYADDTAGWDTRITEADLDDEQEILNYMSP : 3066
(SEQ ID NO: 8)   C1-P11_pol  : EALGFLNEDHWASRENSGGGVEGIGLQYLGYVIRDLAAMDGGGFYADDTAGWDTRITEADLDDEQEILNYMSP : 3066

*        3080         *        3100         *        3120         *        314
(SEQ ID NO: 14)  C-P1_polyp  : HHKKLAQAVMEMTYKNKVVKVLRPAPGGKAYMDVISRRDQRGSGQVVTYALNTITNLKVQLIRMAEAEMVIHH : 3139
(SEQ ID NO: 8)   C1-P11_pol  : HHKKLAQAVMEMTYKNKVVKVLRPAPGGKAYMDVISRRDQRGSGQVVTYALNTITNLKVQLIRMAEAEMVIHH : 3139

0        *        3160         *        3180         *        3200         *
(SEQ ID NO: 14)  C-P1_polyp  : QHVQDCDESVLTRLEAWLTEHGCNRLKRMAVSGDDCVVRPIDDRFGLALSHLNAMSKVRKDISEWQPSKGWND : 3212
(SEQ ID NO: 8)   C1-P11_pol  : QHVQDCDESVLTRLEAWLTEHGCNRLKRMAVSGDDCVVRPIDDRFGLALSHLNAMSKVRKDISEWQPSKGWND : 3212

3220        *        3240         *        3260         *        3280
(SEQ ID NO: 14)  C-P1_polyp  : WENVPFCSHHFHELQLKDGRRIVPCREQDELIGRGRVSPGNGWMIKETACLSKAYANMWSLMYFHKRDMRLL : 3285
(SEQ ID NO: 8)   C1-P11_pol  : WENVPFCSHHFHELQLKDGRRIVPCREQDELIGRGRVSPGNGWMIKETACLSKAYANMWSLMYFHKRDMRLL : 3285

*        3300         *        3320         *        3340         *        33
(SEQ ID NO: 14)  C-P1_polyp  : SLAVSSAVPTSWVPQGRTTWSIHGKGEWMTTEDMLEVWNRVWITNNPHMQDKTMVKKWRDVPYLTKRQDKLCG : 3358
(SEQ ID NO: 8)   C1-P11_pol  : SLAVSSAVPTSWVPQGRTTWSIHGKGEWMTTEDMLEVWNRVWITNNPHMQDKTMVKKWRDVPYLTKRQDKLCG : 3358

60        *        3380         *        3400         *
(SEQ ID NO: 14)  C-P1_polyp  : SLIGMTNRATWASHIHLVIHRIRTLIGQEKYTDYLTVMDRYSVDADLQLGELI : 3411
(SEQ ID NO: 8)   C1-P11_pol  : SLIGMTNRATWASHIHLVIHRIRTLIGQEKYTDYLTVMDRYSVDADLQLGELI : 3411
```

FIG. 10F

```
                      SEQUENCE LISTING

<160> NUMBER OF SEQ ID NOS: 15

<210> SEQ ID NO 1
<211> LENGTH: 6300
<212> TYPE: DNA
<213> ORGANISM: Flaviviridae Flavivirus Yellow Fever Virus

<400> SEQUENCE: 1
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaaccccct ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg aggggtgca    1020 tggaggaact tgggtttcag ctaccctgga gcaagacaag tgtgtcactg ttatggcccc    1080
tgacaagcct tcattggaca tctcactaga gacagtagcc attgatagac ctgctgaggt    1140
gaggaaagtg tgttacaatg cagttctcac tcatgtgaag attaatgaca gtgccccag    1200 cactggagag gcccacctag ctgaagagaa cgaagggac aatgcgtgca agcgcactta    1260
ttctgataga ggctggggca atggctgtgg cctatttggg aaagggagca ttgtggcatg    1320
```

```
cgccaaattc acttgtgcca aatccatgag tttgtttgag gttgatcaga ccaaaattca    1380
gtatgtcatc agagcacaat tgcatgtagg ggccaagcag gaaaattgga ctaccgacat    1440
taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca aagatcctg tgaagcttgc    2580 atcaatagtg aaagcctctt ttgaagaagg gaagtgtggc ctaaattcag ttgactccct    2640
tgagcatgag atgtggagaa gcagggcaga tgagatcaat gccattttg aggaaaacga    2700 ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880 cccgtttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catgatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acgggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaagaaaa cgcatgaaag    3480 ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
gctgaaactc acagtggctg tgggattgca tttccatgag atgaacaatg gaggagacgc    3720
```

```
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcataggggg tccttcacca gaatttcaag gacacctcca tgcagaagac    4080
tatacctctg gtggccctca cactcacatc ttacctgggc ttgacacaac ctttttttggg   4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gcttttttccg ctcacggcag    5340
cgggagagaa gtcattgatg ctatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
ggctgacaaa aggcccacgg catggttcct tccatccatc agagctgcaa atgtcatggc    5700
tgcctctttg cgtaaggctg aaagagtgt ggtggtcctg aacagaaaaa cctttgagag    5760
agaatacccc acgataaagc agaagaaacc tgactttata ttggccactg acatagctga    5820
aatgggagcc aaccttttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggaggggc gcattggag aaatcccaac agagatggag actcatacta    6000
ctattctgag cctacaagtg aaaataatgc ccaccacgtc tgctggttgg aggcctcaat    6060
gctcttggac aacatggagg tgagggggtgg aatggtcgcc ccactctatg gcgttgaagg    6120
```

```
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300

<210> SEQ ID NO 2
<211> LENGTH: 6300
<212> TYPE: DNA
<213> ORGANISM: Flaviviridae Flavivirus Yellow Fever Virus

<400> SEQUENCE: 2
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa acaaaaaaac gaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaaccccctt ttttgcagtg acggctctga ccattgccta     900
ccttgtggga agcaacatga cgcaacgagt cgtgattgcc ctactggtct ggctgttgg     960 tccggcctac tcagctcact gcattggaat tactgacagg gatttcattg aggggggtgca    1020 tggaggaact tgggttcag ctaccctgga gcaagacaag tgtgtcactg ttatggcccc    1080
tgacaagcct tcattggaca tctcactaga gacagtagcc attgatagac ctgctgaggt    1140
gaggaaagtg tgttacaatg cagttctcac tcatgtgaag attaatgaca gtgccccag    1200 cactggagag gcccacctag ctgaagagaa cgaagggac aatgcgtgca agcgcactta    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ctaccgacat    1440
taagactctc aggtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
```

```
agctgatgat cttacagcgg caatcaataa aggcattttg gttacagtta accccatcgc    2040
ctcaaccaat gatgatgaag tgctgattga ggtgaaccca cctttggag acagctacat     2100 tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatcctg tgaagcttgc    2580
atcaatagtg aaagcctctt ttgaagaagg gaagtgtggc ctaaattcag ttgactccct    2640
tgagcatgag atgtggagaa gcagggcaga tgagatcaat gccattttg aggaaaacga     2700 ggtggacatt tctgttgtcg tgcaggatcc aaagaatgtt taccagagag gaactcatcc    2760
attttccaga attcgggatg gtctgcagta tggttggaag acttgggta agaaccttgt      2820 gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct gggagcaat gctggtcggg caagtaactc tccttgattt     3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcataggg tccttcacca gaatttcaag gacacctcca tgcagaagac    4080 tataccctctg gtggccctca cactcacatc ttacctgggc ttgacacaac ctttttggg    4140 cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
```

```
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg caagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa accgagctt    4920 gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gcttttttccg ctcacggcag    5340 cgggagagaa gtcattgatg ctatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc tgggactag tgatgaattt ccacattcaa atggtgaaat    5580
agaagatgtt caaacggaca tacccagtga gccctggaac acagggcatg actggatcct    5640
ggctgacaaa aggcccacgg catggttcct tccatccatc agagctgcaa atgtcatggc    5700
tgcctctttg cgtaaggctg aaagagtgt ggtggtcctg aacaggaaaa cctttgagag    5760
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggagggggc gcattgggag aaatcccaac agagatggag actcatacta    6000
ctattctgag cctacaagtg aaaataatgc ccaccacgtc tgctggtgg aggcctcaat    6060 gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
```

<210> SEQ ID NO 3
<211> LENGTH: 3411
<212> TYPE: PRT
<213> ORGANISM: Flaviviridae Flavivirus Yellow Fever Virus

<400> SEQUENCE: 3

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile

```
                     35                  40                  45
Phe Phe Phe Leu Phe Asn Ile Leu Thr Gly Lys Lys Ile Thr Ala His
                 50                  55                  60

Leu Lys Arg Leu Trp Lys Met Leu Asp Pro Arg Gln Gly Leu Ala Val
 65                  70                  75                  80

Leu Arg Lys Val Lys Arg Val Ala Ser Leu Met Arg Gly Leu Ser
                     85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Val Arg Lys Asn
                115                 120                 125

Arg Trp Leu Leu Leu Asn Val Thr Ser Glu Asp Leu Gly Lys Thr Phe
                130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
                180                 185                 190

Arg Val Ala Tyr Gly Lys Cys Asp Ser Ala Gly Arg Ser Arg Arg Ser
                195                 200                 205

Arg Arg Ala Ile Asp Leu Pro Thr His Glu Asn His Gly Leu Lys Thr
210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
                260                 265                 270

Ile Ala Leu Leu Val Leu Ala Val Gly Pro Ala Tyr Ser Ala His Cys
                275                 280                 285

Ile Gly Ile Thr Asp Arg Asp Phe Ile Glu Gly Val His Gly Gly Thr
290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Val Arg Lys Val Cys Tyr Asn Ala Val Leu Thr His
                340                 345                 350

Val Lys Ile Asn Asp Lys Cys Pro Ser Thr Gly Glu Ala His Leu Ala
                355                 360                 365

Glu Glu Asn Glu Gly Asp Asn Ala Cys Lys Arg Thr Tyr Ser Asp Arg
                370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415

Gln Thr Lys Ile Gln Tyr Val Ile Arg Ala Gln Leu His Val Gly Ala
                420                 425                 430

Lys Gln Glu Asn Trp Thr Thr Asp Ile Lys Thr Leu Lys Phe Asp Ala
                435                 440                 445

Leu Ser Gly Ser Gln Glu Val Glu Phe Ile Gly Tyr Gly Lys Ala Thr
                450                 455                 460
```

```
Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
            485                 490                 495

Asp Leu Thr Leu Pro Trp Gln Ser Gly Ser Gly Gly Val Trp Arg Glu
                500                 505                 510

Met His His Leu Val Glu Phe Glu Pro Pro His Ala Ala Thr Ile Arg
                515                 520                 525

Val Leu Ala Leu Gly Asn Gln Glu Gly Ser Leu Lys Thr Ala Leu Thr
530                 535                 540

Gly Ala Met Arg Val Thr Lys Asp Thr Asn Asp Asn Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
                595                 600                 605

Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
                675                 680                 685

Met Lys Gly Val Glu Arg Leu Ala Val Met Gly Asp Thr Ala Trp Asp
                690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
                770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
                805                 810                 815

Pro Val Lys Leu Ala Ser Ile Val Lys Ala Ser Phe Glu Glu Gly Lys
                820                 825                 830

Cys Gly Leu Asn Ser Val Asp Ser Leu Glu His Glu Met Trp Arg Ser
                835                 840                 845

Arg Ala Asp Glu Ile Asn Ala Ile Phe Glu Glu Asn Glu Val Asp Ile
850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895
```

-continued

```
Gly Lys Asn Leu Val Phe Ser Pro Gly Arg Lys Asn Gly Ser Phe Ile
            900                 905                 910
Ile Asp Gly Lys Ser Arg Lys Glu Cys Pro Phe Ser Asn Arg Val Trp
        915                 920                 925
Asn Ser Phe Gln Ile Glu Glu Phe Gly Thr Gly Val Phe Thr Thr Arg
930                 935                 940
Val Tyr Met Asp Ala Val Phe Glu Tyr Thr Ile Asp Cys Asp Gly Ser
945                 950                 955                 960
Ile Leu Gly Ala Ala Val Asn Gly Lys Lys Ser Ala His Gly Ser Pro
                965                 970                 975
Thr Phe Trp Met Gly Ser His Glu Val Asn Gly Thr Trp Met Ile His
            980                 985                 990
Thr Leu Glu Ala Leu Asp Tyr Lys Glu Cys Glu Trp Pro Leu Thr His
        995                 1000                1005
Thr Ile Gly Thr Ser Val Glu Glu Ser Glu Met Phe Met Pro Arg Ser
    1010                1015                1020
Ile Gly Gly Pro Val Ser Ser His Asn His Ile Pro Gly Tyr Lys Val
1025                1030                1035                1040
Gln Thr Asn Gly Pro Trp Met Gln Val Pro Leu Glu Val Lys Arg Glu
                1045                1050                1055
Ala Cys Pro Gly Thr Ser Val Ile Ile Asp Gly Asn Cys Asp Gly Arg
            1060                1065                1070
Gly Lys Ser Thr Arg Ser Thr Thr Asp Ser Gly Lys Val Ile Pro Glu
        1075                1080                1085
Trp Cys Cys Arg Ser Cys Thr Met Pro Pro Val Ser Phe His Gly Ser
    1090                1095                1100
Asp Gly Cys Trp Tyr Pro Met Glu Ile Arg Pro Arg Lys Thr His Glu
1105                1110                1115                1120
Ser His Leu Val Arg Ser Trp Val Thr Ala Gly Glu Ile His Ala Val
                1125                1130                1135
Pro Phe Gly Leu Val Ser Met Met Ile Ala Met Glu Val Val Leu Arg
            1140                1145                1150
Lys Arg Gln Gly Pro Lys Gln Met Leu Val Gly Gly Val Val Leu Leu
        1155                1160                1165
Gly Ala Met Leu Val Gly Gln Val Thr Leu Leu Asp Leu Leu Lys Leu
    1170                1175                1180
Thr Val Ala Val Gly Leu His Phe His Glu Met Asn Asn Gly Gly Asp
1185                1190                1195                1200
Ala Met Tyr Met Ala Leu Ile Ala Ala Phe Ser Ile Arg Pro Gly Leu
                1205                1210                1215
Leu Ile Gly Phe Gly Leu Arg Thr Leu Trp Ser Pro Arg Glu Arg Leu
            1220                1225                1230
Val Leu Thr Leu Gly Ala Ala Met Val Glu Ile Ala Leu Gly Gly Val
        1235                1240                1245
Met Gly Gly Leu Trp Lys Tyr Leu Asn Ala Val Ser Leu Cys Ile Leu
    1250                1255                1260
Thr Ile Asn Ala Val Ala Ser Arg Lys Ala Ser Asn Thr Ile Leu Pro
1265                1270                1275                1280
Leu Met Ala Leu Leu Thr Pro Val Thr Met Ala Glu Val Arg Leu Ala
                1285                1290                1295
Ala Met Phe Phe Cys Ala Val Val Ile Ile Gly Val Leu His Gln Asn
            1300                1305                1310
Phe Lys Asp Thr Ser Met Gln Lys Thr Ile Pro Leu Val Ala Leu Thr
```

```
                    1315                1320                 1325
Leu Thr Ser Tyr Leu Gly Leu Thr Gln Pro Phe Leu Gly Leu Cys Ala
1330                1335                 1340
Phe Leu Ala Thr Arg Ile Phe Gly Arg Arg Ser Ile Pro Val Asn Glu
1345                1350                 1355                 1360
Ala Leu Ala Ala Ala Gly Leu Gly Val Leu Ala Gly Leu Ala Phe
1365                1370                 1375
Gln Glu Met Glu Asn Phe Leu Gly Pro Ile Ala Val Gly Gly Leu Leu
            1380                1385                 1390
Met Met Leu Val Ser Val Ala Gly Arg Val Asp Gly Leu Glu Leu Lys
            1395                1400                 1405
Lys Leu Gly Glu Val Ser Trp Glu Glu Ala Glu Ile Ser Gly Ser
1410                1415                 1420
Ser Ala Arg Tyr Asp Val Ala Leu Ser Glu Gln Gly Glu Phe Lys Leu
1425                1430                 1435                 1440
Leu Ser Glu Glu Lys Val Pro Trp Asp Gln Val Val Met Thr Ser Leu
            1445                1450                 1455
Ala Leu Val Gly Ala Ala Leu His Pro Phe Ala Leu Leu Val Leu
1460                1465                 1470
Ala Gly Trp Leu Phe His Val Arg Gly Ala Arg Arg Ser Gly Asp Val
            1475                1480                 1485
Leu Trp Asp Ile Pro Thr Pro Lys Ile Ile Glu Glu Cys Glu His Leu
            1490                1495                 1500
Glu Asp Gly Ile Tyr Gly Ile Phe Gln Ser Thr Phe Leu Gly Ala Ser
1505                1510                 1515                 1520
Gln Arg Gly Val Gly Val Ala Gln Gly Gly Val Phe His Thr Met Trp
            1525                1530                 1535
His Val Thr Arg Gly Ala Phe Leu Val Arg Asn Gly Lys Lys Leu Ile
            1540                1545                 1550
Pro Ser Trp Ala Ser Val Lys Glu Asp Leu Val Ala Tyr Gly Gly Ser
            1555                1560                 1565
Trp Lys Leu Glu Gly Arg Trp Asp Gly Glu Glu Val Gln Leu Ile
1570                1575                 1580
Ala Ala Val Pro Gly Lys Asn Val Val Asn Val Gln Thr Lys Pro Ser
1585                1590                 1595                 1600
Leu Phe Lys Val Arg Asn Gly Gly Glu Ile Gly Ala Val Ala Leu Asp
            1605                1610                 1615
Tyr Pro Ser Gly Thr Ser Gly Ser Pro Ile Val Asn Arg Asn Gly Glu
            1620                1625                 1630
Val Ile Gly Leu Tyr Gly Asn Gly Ile Leu Val Gly Asp Asn Ser Phe
            1635                1640                 1645
Val Ser Ala Ile Ser Gln Thr Glu Val Lys Glu Glu Gly Lys Glu Glu
            1650                1655                 1660
Leu Gln Glu Ile Pro Thr Met Leu Lys Lys Gly Met Thr Thr Val Leu
1665                1670                 1675                 1680
Asp Phe His Pro Gly Ala Gly Lys Thr Arg Arg Phe Leu Pro Gln Ile
            1685                1690                 1695
Leu Ala Glu Cys Ala Arg Arg Arg Leu Arg Thr Leu Val Leu Ala Pro
            1700                1705                 1710
Thr Arg Val Val Leu Ser Glu Met Lys Glu Ala Phe His Gly Leu Asp
            1715                1720                 1725
Val Lys Phe His Thr Gln Ala Phe Ser Ala His Gly Ser Gly Arg Glu
            1730                1735                 1740
```

-continued

```
Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
            1765                1770                1775

Phe Leu Asp Pro Ala Ser Ile Ala Ala Arg Gly Trp Ala Ala His Arg
        1780                1785                1790

Ala Arg Ala Asn Glu Ser Ala Thr Ile Leu Met Thr Ala Thr Pro Pro
    1795                1800                1805

Gly Thr Ser Asp Glu Phe Pro His Ser Asn Gly Glu Ile Glu Asp Val
1810                1815                1820

Gln Thr Asp Ile Pro Ser Glu Pro Trp Asn Thr Gly His Asp Trp Ile
1825                1830                1835                1840

Leu Ala Asp Lys Arg Pro Thr Ala Trp Phe Leu Pro Ser Ile Arg Ala
            1845                1850                1855

Ala Asn Val Met Ala Ala Ser Leu Arg Lys Ala Gly Lys Ser Val Val
        1860                1865                1870

Val Leu Asn Arg Lys Thr Phe Glu Arg Glu Tyr Pro Thr Ile Lys Gln
    1875                1880                1885

Lys Lys Pro Asp Phe Ile Leu Ala Thr Asp Ile Ala Glu Met Gly Ala
1890                1895                1900

Asn Leu Cys Val Glu Arg Val Leu Asp Cys Arg Thr Ala Phe Lys Pro
1905                1910                1915                1920

Val Leu Val Asp Glu Gly Arg Lys Val Ala Ile Lys Gly Pro Leu Arg
            1925                1930                1935

Ile Ser Ala Ser Ser Ala Ala Gln Arg Arg Gly Arg Ile Gly Arg Asn
        1940                1945                1950

Pro Asn Arg Asp Gly Asp Ser Tyr Tyr Tyr Ser Glu Pro Thr Ser Glu
    1955                1960                1965

Asn Asn Ala His His Val Cys Trp Leu Glu Ala Ser Met Leu Leu Asp
1970                1975                1980

Asn Met Glu Val Arg Gly Gly Met Val Ala Pro Leu Tyr Gly Val Glu
1985                1990                1995                2000

Gly Thr Lys Thr Pro Val Ser Pro Gly Glu Met Arg Leu Arg Asp Asp
            2005                2010                2015

Gln Arg Lys Val Phe Arg Glu Leu Val Arg Asn Cys Asp Leu Pro Val
        2020                2025                2030

Trp Leu Ser Trp Gln Val Ala Lys Ala Gly Leu Lys Thr Asn Asp Arg
    2035                2040                2045

Lys Trp Cys Phe Glu Gly Pro Glu Glu His Glu Ile Leu Asn Asp Ser
2050                2055                2060

Gly Glu Thr Val Lys Cys Arg Ala Pro Gly Gly Ala Lys Lys Pro Leu
2065                2070                2075                2080

Arg Pro Arg Trp Cys Asp Glu Arg Val Ser Ser Asp Gln Ser Ala Leu
            2085                2090                2095

Ser Glu Phe Ile Lys Phe Ala Glu Gly Arg Arg Gly Ala Ala Glu Val
        2100                2105                2110

Leu Val Val Leu Ser Glu Leu Pro Asp Phe Leu Ala Lys Lys Gly Gly
    2115                2120                2125

Glu Ala Met Asp Thr Ile Ser Val Phe Leu His Ser Glu Glu Gly Ser
2130                2135                2140

Arg Ala Tyr Arg Asn Ala Leu Ser Met Met Pro Glu Ala Met Thr Ile
2145                2150                2155                2160

Val Met Leu Phe Ile Leu Ala Gly Leu Leu Thr Ser Gly Met Val Ile
            2165                2170                2175
```

```
Phe Phe Met Ser Pro Lys Gly Ile Ser Arg Met Ser Met Ala Met Gly
            2180                2185                2190

Thr Met Ala Gly Cys Gly Tyr Leu Met Phe Leu Gly Gly Val Lys Pro
            2195                2200                2205

Thr His Ile Ser Tyr Ile Met Leu Ile Phe Phe Val Leu Met Val Val
            2210                2215                2220

Val Ile Pro Glu Pro Gly Gln Gln Arg Ser Ile Gln Asp Asn Gln Val
2225                2230                2235                2240

Ala Tyr Leu Ile Ile Gly Ile Leu Thr Leu Val Ser Ala Val Ala Ala
            2245                2250                2255

Asn Glu Leu Gly Met Leu Glu Lys Thr Lys Glu Asp Leu Phe Gly Lys
            2260                2265                2270

Lys Asn Leu Ile Pro Ser Ser Ala Ser Pro Trp Ser Trp Pro Asp Leu
            2275                2280                2285

Asp Leu Lys Pro Gly Ala Ala Trp Thr Val Tyr Val Gly Ile Val Thr
            2290                2295                2300

Met Leu Ser Pro Met Leu His His Trp Ile Lys Val Glu Tyr Gly Asn
2305                2310                2315                2320

Leu Ser Leu Ser Gly Ile Ala Gln Ser Ala Ser Val Leu Ser Phe Met
            2325                2330                2335

Asp Lys Gly Ile Pro Phe Met Lys Met Asn Ile Ser Val Ile Met Leu
            2340                2345                2350

Leu Val Ser Gly Trp Asn Ser Ile Thr Val Met Pro Leu Leu Cys Gly
            2355                2360                2365

Ile Gly Cys Ala Met Leu His Trp Ser Leu Ile Leu Pro Gly Ile Lys
            2370                2375                2380

Ala Gln Gln Ser Lys Leu Ala Gln Arg Arg Val Phe His Gly Val Ala
2385                2390                2395                2400

Lys Asn Pro Val Val Asp Gly Asn Pro Thr Val Asp Ile Glu Glu Ala
            2405                2410                2415

Pro Glu Met Pro Ala Leu Tyr Glu Lys Lys Leu Ala Leu Tyr Leu Leu
            2420                2425                2430

Leu Ala Leu Ser Leu Ala Ser Val Ala Met Cys Arg Thr Pro Phe Ser
            2435                2440                2445

Leu Ala Glu Gly Ile Val Leu Ala Ser Ala Ala Leu Gly Pro Leu Ile
            2450                2455                2460

Glu Gly Asn Thr Ser Leu Leu Trp Asn Gly Pro Met Ala Val Ser Met
2465                2470                2475                2480

Thr Gly Val Met Arg Gly Asn His Tyr Ala Phe Val Gly Val Met Tyr
            2485                2490                2495

Asn Leu Trp Lys Met Lys Thr Gly Arg Arg Gly Ser Ala Asn Gly Lys
            2500                2505                2510

Thr Leu Gly Glu Val Trp Lys Arg Glu Leu Asn Leu Leu Asp Lys Arg
            2515                2520                2525

Gln Phe Glu Leu Tyr Lys Arg Thr Asp Ile Val Glu Val Asp Arg Asp
            2530                2535                2540

Thr Ala Arg Arg His Leu Ala Glu Gly Lys Val Asp Thr Gly Val Ala
2545                2550                2555                2560

Val Ser Arg Gly Thr Ala Lys Leu Arg Trp Phe His Glu Arg Gly Tyr
            2565                2570                2575

Val Lys Leu Glu Gly Arg Val Ile Asp Leu Gly Cys Gly Arg Gly Gly
            2580                2585                2590

Trp Cys Tyr Tyr Ala Ala Ala Gln Lys Glu Val Ser Gly Val Lys Gly
```

```
                    2595                2600                2605
Phe Thr Leu Gly Arg Asp Gly His Glu Lys Pro Met Asn Val Gln Ser
    2610                2615                2620
Leu Gly Trp Asn Ile Ile Thr Phe Lys Asp Lys Thr Asp Ile His Arg
2625                2630                2635                2640
Leu Glu Pro Val Lys Cys Asp Thr Leu Leu Cys Asp Ile Gly Glu Ser
            2645                2650                2655
Ser Ser Ser Ser Val Thr Glu Gly Glu Arg Thr Val Arg Val Leu Asp
        2660                2665                2670
Thr Val Glu Lys Trp Leu Ala Cys Gly Val Asp Asn Phe Cys Val Lys
        2675                2680                2685
Val Leu Ala Pro Tyr Met Pro Asp Val Leu Glu Lys Leu Glu Leu Leu
    2690                2695                2700
Gln Arg Arg Phe Gly Gly Thr Val Ile Arg Asn Pro Leu Ser Arg Asn
2705                2710                2715                2720
Ser Thr His Glu Met Tyr Tyr Val Ser Gly Ala Arg Ser Asn Val Thr
            2725                2730                2735
Phe Thr Val Asn Gln Thr Ser Arg Leu Leu Met Arg Arg Met Arg Arg
    2740                2745                2750
Pro Thr Gly Lys Val Thr Leu Glu Ala Asp Val Ile Leu Pro Ile Gly
        2755                2760                2765
Thr Arg Ser Val Glu Thr Asp Lys Gly Pro Leu Asp Lys Glu Ala Ile
    2770                2775                2780
Glu Glu Arg Val Glu Arg Ile Lys Ser Glu Tyr Met Thr Ser Trp Phe
2785                2790                2795                2800
Tyr Asp Asn Asp Asn Pro Tyr Arg Thr Trp His Tyr Cys Gly Ser Tyr
                2805                2810                2815
Val Thr Lys Thr Ser Gly Ser Ala Ala Ser Met Val Asn Gly Val Ile
            2820                2825                2830
Lys Ile Leu Thr Tyr Pro Trp Asp Arg Ile Glu Glu Val Thr Arg Met
        2835                2840                2845
Ala Met Thr Asp Thr Thr Pro Phe Gly Gln Gln Arg Val Phe Lys Glu
    2850                2855                2860
Lys Val Asp Thr Arg Ala Lys Asp Pro Pro Ala Gly Thr Arg Lys Ile
2865                2870                2875                2880
Met Lys Val Val Asn Arg Trp Leu Phe Arg His Leu Ala Arg Glu Lys
                2885                2890                2895
Asn Pro Arg Leu Cys Thr Lys Glu Glu Phe Ile Ala Lys Val Arg Ser
        2900                2905                2910
His Ala Ala Ile Gly Ala Tyr Leu Glu Glu Gln Glu Gln Trp Lys Thr
    2915                2920                2925
Ala Asn Glu Ala Val Gln Asp Pro Lys Phe Trp Glu Leu Val Asp Glu
    2930                2935                2940
Glu Arg Lys Leu His Gln Gln Gly Arg Cys Arg Thr Cys Val Tyr Asn
2945                2950                2955                2960
Met Met Gly Lys Arg Glu Lys Lys Leu Ser Glu Phe Gly Lys Ala Lys
            2965                2970                2975
Gly Ser Arg Ala Ile Trp Tyr Met Trp Leu Gly Ala Arg Tyr Leu Glu
        2980                2985                2990
Phe Glu Ala Leu Gly Phe Leu Asn Glu Asp His Trp Ala Ser Arg Glu
    2995                3000                3005
Asn Ser Gly Gly Gly Val Glu Gly Ile Gly Leu Gln Tyr Leu Gly Tyr
    3010                3015                3020
```

```
Val Ile Arg Asp Leu Ala Ala Met Asp Gly Gly Phe Tyr Ala Asp
3025                3030                3035                3040

Asp Thr Ala Gly Trp Asp Thr Arg Ile Thr Glu Ala Asp Leu Asp Asp
            3045                3050                3055

Glu Gln Glu Ile Leu Asn Tyr Met Ser Pro His His Lys Lys Leu Ala
    3060                3065                3070

Gln Ala Val Met Glu Met Thr Tyr Lys Asn Lys Val Lys Val Leu
    3075                3080                3085

Arg Pro Ala Pro Gly Gly Lys Ala Tyr Met Asp Val Ile Ser Arg Arg
    3090                3095                3100

Asp Gln Arg Gly Ser Gly Gln Val Val Thr Tyr Ala Leu Asn Thr Ile
3105                3110                3115                3120

Thr Asn Leu Lys Val Gln Leu Ile Arg Met Ala Glu Ala Glu Met Val
                3125                3130                3135

Ile His His Gln His Val Gln Asp Cys Asp Glu Ser Val Leu Thr Arg
                3140                3145                3150

Leu Glu Ala Trp Leu Thr Glu His Gly Cys Asn Arg Leu Lys Arg Met
                3155                3160                3165

Ala Val Ser Gly Asp Asp Cys Val Val Arg Pro Ile Asp Asp Arg Phe
    3170                3175                3180

Gly Leu Ala Leu Ser His Leu Asn Ala Met Ser Lys Val Arg Lys Asp
3185                3190                3195                3200

Ile Ser Glu Trp Gln Pro Ser Lys Gly Trp Asn Asp Trp Glu Asn Val
            3205                3210                3215

Pro Phe Cys Ser His His Phe His Glu Leu Gln Leu Lys Asp Gly Arg
                3220                3225                3230

Arg Ile Val Val Pro Cys Arg Glu Gln Asp Glu Leu Ile Gly Arg Gly
            3235                3240                3245

Arg Val Ser Pro Gly Asn Gly Trp Met Ile Lys Glu Thr Ala Cys Leu
    3250                3255                3260

Ser Lys Ala Tyr Ala Asn Met Trp Ser Leu Met Tyr Phe His Lys Arg
3265                3270                3275                3280

Asp Met Arg Leu Leu Ser Leu Ala Val Ser Ser Ala Val Pro Thr Ser
                3285                3290                3295

Trp Val Pro Gln Gly Arg Thr Thr Trp Ser Ile His Gly Lys Gly Glu
            3300                3305                3310

Trp Met Thr Thr Glu Asp Met Leu Glu Val Trp Asn Arg Val Trp Ile
            3315                3320                3325

Thr Asn Asn Pro His Met Gln Asp Lys Thr Met Val Lys Lys Trp Arg
            3330                3335                3340

Asp Val Pro Tyr Leu Thr Lys Arg Gln Asp Lys Leu Cys Gly Ser Leu
3345                3350                3355                3360

Ile Gly Met Thr Asn Arg Ala Thr Trp Ala Ser His Ile His Leu Val
                3365                3370                3375

Ile His Arg Ile Arg Thr Leu Ile Gly Gln Glu Lys Tyr Thr Asp Tyr
            3380                3385                3390

Leu Thr Val Met Asp Arg Tyr Ser Val Asp Ala Asp Leu Gln Leu Gly
                3395                3400                3405

Glu Leu Ile
    3410

<210> SEQ ID NO 4
<211> LENGTH: 3411
<212> TYPE: PRT
<213> ORGANISM: Flaviviridae Flavivirus Yellow Fever Virus
```

```
<400> SEQUENCE: 4

Met Ser Gly Arg Lys Ala Gln Gly Lys Thr Leu Gly Val Asn Met Val
 1               5                  10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
 50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Val Arg Lys Val Cys Tyr Asn Ala Val Leu Thr His
            340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
    370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415
```

```
Gln Thr Lys Ile Gln Tyr Val Ile Arg Ala Gln Leu His Val Gly Ala
            420                 425                 430
Lys Gln Glu Asn Trp Thr Thr Asp Ile Lys Thr Leu Arg Phe Asp Ala
            435                 440                 445
Leu Ser Gly Ser Gln Glu Val Glu Phe Ile Gly Tyr Gly Lys Ala Thr
450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
            485                 490                 495
Asp Leu Thr Leu Pro Trp Gln Ser Gly Ser Gly Val Trp Arg Glu
            500                 505                 510
Met His His Leu Val Glu Phe Glu Pro Pro His Ala Ala Thr Ile Arg
            515                 520                 525
Val Leu Ala Leu Gly Asn Gln Glu Gly Ser Leu Lys Thr Ala Leu Thr
            530                 535                 540
Gly Ala Met Arg Val Thr Lys Asp Thr Asn Asp Asn Asn Leu Tyr Lys
545                 550                 555                 560
Leu His Gly Gly His Val Ser Cys Arg Val Lys Leu Ser Ala Leu Thr
            565                 570                 575
Leu Lys Gly Thr Ser Tyr Lys Ile Cys Thr Asp Lys Met Phe Phe Val
            580                 585                 590
Lys Asn Pro Thr Asp Thr Gly His Gly Thr Val Val Met Gln Val Lys
            595                 600                 605
Val Ser Lys Gly Ala Pro Cys Arg Ile Pro Val Ile Val Ala Asp Asp
            610                 615                 620
Leu Thr Ala Ala Ile Asn Lys Gly Ile Leu Val Thr Val Asn Pro Ile
625                 630                 635                 640
Ala Ser Thr Asn Asp Asp Glu Val Leu Ile Glu Val Asn Pro Pro Phe
            645                 650                 655
Gly Asp Ser Tyr Ile Ile Val Gly Arg Gly Asp Ser Arg Leu Thr Tyr
            660                 665                 670
Gln Trp His Lys Glu Gly Ser Ser Ile Gly Lys Leu Phe Thr Gln Thr
            675                 680                 685
Met Lys Gly Val Glu Arg Leu Ala Val Met Gly Asp Thr Ala Trp Asp
            690                 695                 700
Phe Ser Ser Ala Gly Gly Phe Phe Thr Ser Val Gly Lys Gly Ile His
705                 710                 715                 720
Thr Val Phe Gly Ser Ala Phe Gln Gly Leu Phe Gly Gly Leu Asn Trp
            725                 730                 735
Ile Thr Lys Val Ile Met Gly Ala Val Leu Ile Trp Val Gly Ile Asn
            740                 745                 750
Thr Arg Asn Met Thr Met Ser Met Ser Met Ile Leu Val Gly Val Ile
            755                 760                 765
Met Met Phe Leu Ser Leu Gly Val Gly Ala Asp Gln Gly Cys Ala Ile
            770                 775                 780
Asn Phe Gly Lys Arg Glu Leu Lys Cys Gly Asp Gly Ile Phe Ile Phe
785                 790                 795                 800
Arg Asp Ser Asp Asp Trp Leu Asn Lys Tyr Ser Tyr Tyr Pro Glu Asp
            805                 810                 815
Pro Val Lys Leu Ala Ser Ile Val Lys Ala Ser Phe Glu Glu Gly Lys
            820                 825                 830
Cys Gly Leu Asn Ser Val Asp Ser Leu Glu His Glu Met Trp Arg Ser
```

```
                835                 840                 845
Arg Ala Asp Glu Ile Asn Ala Ile Phe Glu Glu Asn Glu Val Asp Ile
850                 855                 860

Ser Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
            900                 905                 910

Ile Asp Gly Lys Ser Arg Lys Glu Cys Pro Phe Ser Asn Arg Val Trp
            915                 920                 925

Asn Ser Phe Gln Ile Glu Glu Phe Gly Thr Gly Val Phe Thr Thr Arg
            930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
                965                 970                 975

Thr Phe Trp Met Gly Ser His Glu Val Asn Gly Thr Trp Met Ile His
                980                 985                 990

Thr Leu Glu Ala Leu Asp Tyr Lys Glu Cys Glu Trp Pro Leu Thr His
            995                 1000                1005

Thr Ile Gly Thr Ser Val Glu Glu Ser Glu Met Phe Met Pro Arg Ser
        1010                1015                1020

Ile Gly Gly Pro Val Ser Ser His Asn His Ile Pro Gly Tyr Lys Val
1025                1030                1035                1040

Gln Thr Asn Gly Pro Trp Met Gln Val Pro Leu Glu Val Lys Arg Glu
                1045                1050                1055

Ala Cys Pro Gly Thr Ser Val Ile Ile Asp Gly Asn Cys Asp Gly Arg
            1060                1065                1070

Gly Lys Ser Thr Arg Ser Thr Thr Asp Ser Gly Lys Val Ile Pro Glu
            1075                1080                1085

Trp Cys Cys Arg Ser Cys Thr Met Pro Pro Val Ser Phe His Gly Ser
        1090                1095                1100

Asp Gly Cys Trp Tyr Pro Met Glu Ile Arg Pro Arg Lys Thr His Glu
1105                1110                1115                1120

Ser His Leu Val Arg Ser Trp Val Thr Ala Gly Glu Ile His Ala Val
                1125                1130                1135

Pro Phe Gly Leu Val Ser Met Met Ile Ala Met Glu Val Val Leu Arg
            1140                1145                1150

Lys Arg Gln Gly Pro Lys Gln Met Leu Val Gly Gly Val Val Leu Leu
            1155                1160                1165

Gly Ala Met Leu Val Gly Gln Val Thr Leu Leu Asp Leu Leu Lys Leu
        1170                1175                1180

Thr Val Ala Val Gly Leu His Phe His Glu Met Asn Asn Gly Gly Asp
1185                1190                1195                1200

Ala Met Tyr Met Ala Leu Ile Ala Ala Phe Ser Ile Arg Pro Gly Leu
                1205                1210                1215

Leu Ile Gly Phe Gly Leu Arg Thr Leu Trp Ser Pro Arg Glu Arg Leu
            1220                1225                1230

Val Leu Thr Leu Gly Ala Ala Met Val Glu Ile Ala Leu Gly Gly Val
        1235                1240                1245

Met Gly Gly Leu Trp Lys Tyr Leu Asn Ala Val Ser Leu Cys Ile Leu
        1250                1255                1260
```

-continued

```
Thr Ile Asn Ala Val Ala Ser Arg Lys Ala Ser Asn Thr Ile Leu Pro
1265                1270                1275                1280

Leu Met Ala Leu Leu Thr Pro Val Thr Met Ala Glu Val Arg Leu Ala
            1285                1290                1295

Ala Met Phe Phe Cys Ala Val Val Ile Ile Gly Val Leu His Gln Asn
        1300                1305                1310

Phe Lys Asp Thr Ser Met Gln Lys Thr Ile Pro Leu Val Ala Leu Thr
    1315                1320                1325

Leu Thr Ser Tyr Leu Gly Leu Thr Gln Pro Phe Leu Gly Leu Cys Ala
1330                1335                1340

Phe Leu Ala Thr Arg Ile Phe Gly Arg Ser Ile Pro Val Asn Glu
1345                1350                1355                1360

Ala Leu Ala Ala Ala Gly Leu Val Gly Val Leu Ala Gly Leu Ala Phe
            1365                1370                1375

Gln Glu Met Glu Asn Phe Leu Gly Pro Ile Ala Val Gly Gly Leu Leu
        1380                1385                1390

Met Met Leu Val Ser Val Ala Gly Arg Val Asp Gly Leu Glu Leu Lys
    1395                1400                1405

Lys Leu Gly Glu Val Ser Trp Glu Glu Ala Glu Ile Ser Gly Ser
1410                1415                1420

Ser Ala Arg Tyr Asp Val Ala Leu Ser Glu Gln Gly Glu Phe Lys Leu
1425                1430                1435                1440

Leu Ser Glu Glu Lys Val Pro Trp Asp Gln Val Val Met Thr Ser Leu
            1445                1450                1455

Ala Leu Val Gly Ala Ala Leu His Pro Phe Ala Leu Leu Val Leu
        1460                1465                1470

Ala Gly Trp Leu Phe His Val Arg Gly Ala Arg Arg Ser Gly Asp Val
    1475                1480                1485

Leu Trp Asp Ile Pro Thr Pro Lys Ile Ile Glu Glu Cys Glu His Leu
1490                1495                1500

Glu Asp Gly Ile Tyr Gly Ile Phe Gln Ser Thr Phe Leu Gly Ala Ser
1505                1510                1515                1520

Gln Arg Gly Val Gly Val Ala Gln Gly Gly Val Phe His Thr Met Trp
            1525                1530                1535

His Val Thr Arg Gly Ala Phe Leu Val Arg Asn Gly Lys Lys Leu Ile
        1540                1545                1550

Pro Ser Trp Ala Ser Val Lys Glu Asp Leu Val Ala Tyr Gly Gly Ser
    1555                1560                1565

Trp Lys Leu Glu Gly Arg Trp Asp Gly Glu Glu Val Gln Leu Ile
1570                1575                1580

Ala Ala Val Pro Gly Lys Asn Val Val Asn Val Gln Thr Lys Pro Ser
1585                1590                1595                1600

Leu Phe Lys Val Arg Asn Gly Gly Glu Ile Gly Ala Val Ala Leu Asp
            1605                1610                1615

Tyr Pro Ser Gly Thr Ser Gly Ser Pro Ile Val Asn Arg Asn Gly Glu
        1620                1625                1630

Val Ile Gly Leu Tyr Gly Asn Gly Ile Leu Val Gly Asp Asn Ser Phe
    1635                1640                1645

Val Ser Ala Ile Ser Gln Thr Glu Val Lys Glu Glu Gly Lys Glu Glu
1650                1655                1660

Leu Gln Glu Ile Pro Thr Met Leu Lys Lys Gly Met Thr Thr Val Leu
1665                1670                1675                1680

Asp Phe His Pro Gly Ala Gly Lys Thr Arg Arg Phe Leu Pro Gln Ile
            1685                1690                1695
```

```
Leu Ala Glu Cys Ala Arg Arg Leu Arg Thr Leu Val Leu Ala Pro
            1700                1705                1710

Thr Arg Val Val Leu Ser Glu Met Lys Glu Ala Phe His Gly Leu Asp
        1715                1720                1725

Val Lys Phe His Thr Gln Ala Phe Ser Ala His Gly Ser Gly Arg Glu
    1730                1735                1740

Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
            1765                1770                1775

Phe Leu Asp Pro Ala Ser Ile Ala Ala Arg Gly Trp Ala Ala His Arg
        1780                1785                1790

Ala Arg Ala Asn Glu Ser Ala Thr Ile Leu Met Thr Ala Thr Pro Pro
    1795                1800                1805

Gly Thr Ser Asp Glu Phe Pro His Ser Asn Gly Glu Ile Glu Asp Val
    1810                1815                1820

Gln Thr Asp Ile Pro Ser Glu Pro Trp Asn Thr Gly His Asp Trp Ile
1825                1830                1835                1840

Leu Ala Asp Lys Arg Pro Thr Ala Trp Phe Leu Pro Ser Ile Arg Ala
            1845                1850                1855

Ala Asn Val Met Ala Ala Ser Leu Arg Lys Ala Gly Lys Ser Val Val
        1860                1865                1870

Val Leu Asn Arg Lys Thr Phe Glu Arg Glu Tyr Pro Thr Ile Lys Gln
    1875                1880                1885

Lys Lys Pro Asp Phe Ile Leu Ala Thr Asp Ile Ala Glu Met Gly Ala
    1890                1895                1900

Asn Leu Cys Val Glu Arg Val Leu Asp Cys Arg Thr Ala Phe Lys Pro
1905                1910                1915                1920

Val Leu Val Asp Glu Gly Arg Lys Val Ala Ile Lys Gly Pro Leu Arg
            1925                1930                1935

Ile Ser Ala Ser Ser Ala Ala Gln Arg Arg Gly Arg Ile Gly Arg Asn
        1940                1945                1950

Pro Asn Arg Asp Gly Asp Ser Tyr Tyr Tyr Ser Glu Pro Thr Ser Glu
    1955                1960                1965

Asn Asn Ala His His Val Cys Trp Leu Glu Ala Ser Met Leu Leu Asp
    1970                1975                1980

Asn Met Glu Val Arg Gly Gly Met Val Ala Pro Leu Tyr Gly Val Glu
1985                1990                1995                2000

Gly Thr Lys Thr Pro Val Ser Pro Gly Glu Met Arg Leu Arg Asp Asp
            2005                2010                2015

Gln Arg Lys Val Phe Arg Glu Leu Val Arg Asn Cys Asp Leu Pro Val
        2020                2025                2030

Trp Leu Ser Trp Gln Val Ala Lys Ala Gly Leu Lys Thr Asn Asp Arg
    2035                2040                2045

Lys Trp Cys Phe Glu Gly Pro Glu Glu His Glu Ile Leu Asn Asp Ser
    2050                2055                2060

Gly Glu Thr Val Lys Cys Arg Ala Pro Gly Gly Ala Lys Lys Pro Leu
2065                2070                2075                2080

Arg Pro Arg Trp Cys Asp Glu Arg Val Ser Ser Asp Gln Ser Ala Leu
            2085                2090                2095

Ser Glu Phe Ile Lys Phe Ala Glu Gly Arg Arg Gly Ala Ala Glu Val
        2100                2105                2110

Leu Val Val Leu Ser Glu Leu Pro Asp Phe Leu Ala Lys Lys Gly Gly
```

```
                    2115                2120                 2125
Glu Ala Met Asp Thr Ile Ser Val Phe Leu His Ser Glu Glu Gly Ser
            2130                2135                2140

Arg Ala Tyr Arg Asn Ala Leu Ser Met Met Pro Glu Ala Met Thr Ile
2145                2150                2155                2160

Val Met Leu Phe Ile Leu Ala Gly Leu Leu Thr Ser Gly Met Val Ile
            2165                2170                2175

Phe Phe Met Ser Pro Lys Gly Ile Ser Arg Met Ser Met Ala Met Gly
            2180                2185                2190

Thr Met Ala Gly Cys Gly Tyr Leu Met Phe Leu Gly Gly Val Lys Pro
            2195                2200                2205

Thr His Ile Ser Tyr Ile Met Leu Ile Phe Phe Val Leu Met Val Val
            2210                2215                2220

Val Ile Pro Glu Pro Gly Gln Gln Arg Ser Ile Gln Asp Asn Gln Val
2225                2230                2235                2240

Ala Tyr Leu Ile Ile Gly Ile Leu Thr Leu Val Ser Ala Val Ala Ala
            2245                2250                2255

Asn Glu Leu Gly Met Leu Glu Lys Thr Lys Glu Asp Leu Phe Gly Lys
            2260                2265                2270

Lys Asn Leu Ile Pro Ser Ser Ala Ser Pro Trp Ser Trp Pro Asp Leu
            2275                2280                2285

Asp Leu Lys Pro Gly Ala Ala Trp Thr Val Tyr Val Gly Ile Val Thr
            2290                2295                2300

Met Leu Ser Pro Met Leu His His Trp Ile Lys Val Glu Tyr Gly Asn
2305                2310                2315                2320

Leu Ser Leu Ser Gly Ile Ala Gln Ser Ala Ser Val Leu Ser Phe Met
            2325                2330                2335

Asp Lys Gly Ile Pro Phe Met Lys Met Asn Ile Ser Val Ile Met Leu
            2340                2345                2350

Leu Val Ser Gly Trp Asn Ser Ile Thr Val Met Pro Leu Leu Cys Gly
            2355                2360                2365

Ile Gly Cys Ala Met Leu His Trp Ser Leu Ile Leu Pro Gly Ile Lys
            2370                2375                2380

Ala Gln Gln Ser Lys Leu Ala Gln Arg Arg Val Phe His Gly Val Ala
2385                2390                2395                2400

Lys Asn Pro Val Val Asp Gly Asn Pro Thr Val Asp Ile Glu Glu Ala
            2405                2410                2415

Pro Glu Met Pro Ala Leu Tyr Glu Lys Lys Leu Ala Leu Tyr Leu Leu
            2420                2425                2430

Leu Ala Leu Ser Leu Ala Ser Val Ala Met Cys Arg Thr Pro Phe Ser
            2435                2440                2445

Leu Ala Glu Gly Ile Val Leu Ala Ser Ala Ala Leu Gly Pro Leu Ile
            2450                2455                2460

Glu Gly Asn Thr Ser Leu Leu Trp Asn Gly Pro Met Ala Val Ser Met
2465                2470                2475                2480

Thr Gly Val Met Arg Gly Asn His Tyr Ala Phe Val Gly Val Met Tyr
            2485                2490                2495

Asn Leu Trp Lys Met Lys Thr Gly Arg Arg Gly Ser Ala Asn Gly Lys
            2500                2505                2510

Thr Leu Gly Glu Val Trp Lys Arg Glu Leu Asn Leu Leu Asp Lys Arg
            2515                2520                2525

Gln Phe Glu Leu Tyr Lys Arg Thr Asp Ile Val Glu Val Asp Arg Asp
            2530                2535                2540
```

-continued

```
Thr Ala Arg Arg His Leu Ala Glu Gly Lys Val Asp Thr Gly Val Ala
2545                2550                2555                2560

Val Ser Arg Gly Thr Ala Lys Leu Arg Trp Phe His Glu Arg Gly Tyr
            2565                2570                2575

Val Lys Leu Glu Gly Arg Val Ile Asp Leu Gly Cys Gly Arg Gly Gly
        2580                2585                2590

Trp Cys Tyr Tyr Ala Ala Gln Lys Glu Val Ser Gly Val Lys Gly
    2595                2600                2605

Phe Thr Leu Gly Arg Asp Gly His Glu Lys Pro Met Asn Val Gln Ser
2610                2615                2620

Leu Gly Trp Asn Ile Ile Thr Phe Lys Asp Lys Thr Asp Ile His Arg
2625                2630                2635                2640

Leu Glu Pro Val Lys Cys Asp Thr Leu Leu Cys Asp Ile Gly Glu Ser
            2645                2650                2655

Ser Ser Ser Ser Val Thr Glu Gly Glu Arg Thr Val Arg Val Leu Asp
            2660                2665                2670

Thr Val Glu Lys Trp Leu Ala Cys Gly Val Asp Asn Phe Cys Val Lys
        2675                2680                2685

Val Leu Ala Pro Tyr Met Pro Asp Val Leu Glu Lys Leu Glu Leu Leu
    2690                2695                2700

Gln Arg Arg Phe Gly Gly Thr Val Ile Arg Asn Pro Leu Ser Arg Asn
2705                2710                2715                2720

Ser Thr His Glu Met Tyr Tyr Val Ser Gly Ala Arg Ser Asn Val Thr
            2725                2730                2735

Phe Thr Val Asn Gln Thr Ser Arg Leu Leu Met Arg Arg Met Arg Arg
        2740                2745                2750

Pro Thr Gly Lys Val Thr Leu Glu Ala Asp Val Ile Leu Pro Ile Gly
    2755                2760                2765

Thr Arg Ser Val Glu Thr Asp Lys Gly Pro Leu Asp Lys Glu Ala Ile
        2770                2775                2780

Glu Glu Arg Val Glu Arg Ile Lys Ser Glu Tyr Met Thr Ser Trp Phe
2785                2790                2795                2800

Tyr Asp Asn Asp Asn Pro Tyr Arg Thr Trp His Tyr Cys Gly Ser Tyr
            2805                2810                2815

Val Thr Lys Thr Ser Gly Ser Ala Ala Ser Met Val Asn Gly Val Ile
        2820                2825                2830

Lys Ile Leu Thr Tyr Pro Trp Asp Arg Ile Glu Glu Val Thr Arg Met
        2835                2840                2845

Ala Met Thr Asp Thr Thr Pro Phe Gly Gln Gln Arg Val Phe Lys Glu
    2850                2855                2860

Lys Val Asp Thr Arg Ala Lys Asp Pro Pro Ala Gly Thr Arg Lys Ile
2865                2870                2875                2880

Met Lys Val Val Asn Arg Trp Leu Phe Arg His Leu Ala Arg Glu Lys
            2885                2890                2895

Asn Pro Arg Leu Cys Thr Lys Glu Glu Phe Ile Ala Lys Val Arg Ser
        2900                2905                2910

His Ala Ala Ile Gly Ala Tyr Leu Glu Glu Gln Glu Gln Trp Lys Thr
        2915                2920                2925

Ala Asn Glu Ala Val Gln Asp Pro Lys Phe Trp Glu Leu Val Asp Glu
    2930                2935                2940

Glu Arg Lys Leu His Gln Gln Gly Arg Cys Arg Thr Cys Val Tyr Asn
2945                2950                2955                2960

Met Met Gly Lys Arg Glu Lys Lys Leu Ser Glu Phe Gly Lys Ala Lys
            2965                2970                2975
```

```
Gly Ser Arg Ala Ile Trp Tyr Met Trp Leu Gly Ala Arg Tyr Leu Glu
            2980                2985                2990

Phe Glu Ala Leu Gly Phe Leu Asn Glu Asp His Trp Ala Ser Arg Glu
            2995                3000                3005

Asn Ser Gly Gly Gly Val Glu Gly Ile Gly Leu Gln Tyr Leu Gly Tyr
            3010                3015                3020

Val Ile Arg Asp Leu Ala Ala Met Asp Gly Gly Phe Tyr Ala Asp
3025            3030                3035                3040

Asp Thr Ala Gly Trp Asp Thr Arg Ile Thr Glu Ala Asp Leu Asp Asp
            3045                3050                3055

Glu Gln Glu Ile Leu Asn Tyr Met Ser Pro His His Lys Lys Leu Ala
            3060                3065                3070

Gln Ala Val Met Glu Met Thr Tyr Lys Asn Lys Val Val Lys Val Leu
            3075                3080                3085

Arg Pro Ala Pro Gly Gly Lys Ala Tyr Met Asp Val Ile Ser Arg Arg
            3090                3095                3100

Asp Gln Arg Gly Ser Gly Gln Val Val Thr Tyr Ala Leu Asn Thr Ile
3105            3110                3115                3120

Thr Asn Leu Lys Val Gln Leu Ile Arg Met Ala Glu Ala Glu Met Val
            3125                3130                3135

Ile His His Gln His Val Gln Asp Cys Asp Glu Ser Val Leu Thr Arg
            3140                3145                3150

Leu Glu Ala Trp Leu Thr Glu His Gly Cys Asn Arg Leu Lys Arg Met
            3155                3160                3165

Ala Val Ser Gly Asp Asp Cys Val Val Arg Pro Ile Asp Asp Arg Phe
            3170                3175                3180

Gly Leu Ala Leu Ser His Leu Asn Ala Met Ser Lys Val Arg Lys Asp
3185            3190                3195                3200

Ile Ser Glu Trp Gln Pro Ser Lys Gly Trp Asn Asp Trp Glu Asn Val
            3205                3210                3215

Pro Phe Cys Ser His His Phe His Glu Leu Gln Leu Lys Asp Gly Arg
            3220                3225                3230

Arg Ile Val Val Pro Cys Arg Glu Gln Asp Glu Leu Ile Gly Arg Gly
            3235                3240                3245

Arg Val Ser Pro Gly Asn Gly Trp Met Ile Lys Glu Thr Ala Cys Leu
            3250                3255                3260

Ser Lys Ala Tyr Ala Asn Met Trp Ser Leu Met Tyr Phe His Lys Arg
3265            3270                3275                3280

Asp Met Arg Leu Leu Ser Leu Ala Val Ser Ser Ala Val Pro Thr Ser
            3285                3290                3295

Trp Val Pro Gln Gly Arg Thr Thr Trp Ser Ile His Gly Lys Gly Glu
            3300                3305                3310

Trp Met Thr Thr Glu Asp Met Leu Glu Val Trp Asn Arg Val Trp Ile
            3315                3320                3325

Thr Asn Asn Pro His Met Gln Asp Lys Thr Met Val Lys Lys Trp Arg
            3330                3335                3340

Asp Val Pro Tyr Leu Thr Lys Arg Gln Asp Lys Leu Cys Gly Ser Leu
3345            3350                3355                3360

Ile Gly Met Thr Asn Arg Ala Thr Trp Ala Ser His Ile His Leu Val
            3365                3370                3375

Ile His Arg Ile Arg Thr Leu Ile Gly Gln Glu Lys Tyr Thr Asp Tyr
            3380                3385                3390

Leu Thr Val Met Asp Arg Tyr Ser Val Asp Ala Asp Leu Gln Leu Gly
```

```
                3395            3400            3405
Glu Leu Ile
    3410

<210> SEQ ID NO 5
<211> LENGTH: 684
<212> TYPE: PRT
<213> ORGANISM: Flaviviridae Flavivirus Yellow Fever Virus

<400> SEQUENCE: 5

Ile Leu Gly Met Leu Leu Met Thr Gly Gly Val Thr Leu Val Arg Lys
 1               5                  10                  15

Asn Arg Trp Leu Leu Asn Val Thr Ser Glu Asp Leu Gly Lys Thr
             20                  25                  30

Phe Ser Val Gly Thr Gly Asn Cys Thr Thr Asn Ile Leu Glu Ala Lys
         35                  40                  45

Tyr Trp Cys Pro Asp Ser Met Glu Tyr Asn Cys Pro Asn Leu Ser Pro
     50                  55                  60

Arg Glu Glu Pro Asp Asp Ile Asp Cys Trp Cys Tyr Gly Val Glu Asn
 65                  70                  75                  80

Val Arg Val Ala Tyr Gly Lys Cys Asp Ser Ala Gly Arg Ser Arg Arg
                 85                  90                  95

Ser Arg Arg Ala Ile Asp Leu Pro Thr His Glu Asn His Gly Leu Lys
            100                 105                 110

Thr Arg Gln Glu Lys Trp Met Thr Gly Arg Met Gly Glu Arg Gln Leu
        115                 120                 125

Gln Lys Ile Glu Arg Trp Phe Val Arg Asn Pro Phe Phe Ala Val Thr
    130                 135                 140

Ala Leu Thr Ile Ala Tyr Leu Val Gly Ser Asn Met Thr Gln Arg Val
145                 150                 155                 160

Val Ile Ala Leu Leu Val Leu Ala Val Gly Pro Ala Tyr Ser Ala His
                165                 170                 175

Cys Ile Gly Ile Thr Asp Arg Asp Phe Ile Glu Gly Val His Gly Gly
            180                 185                 190

Thr Trp Val Ser Ala Thr Leu Glu Gln Asp Lys Cys Val Thr Val Met
        195                 200                 205

Ala Pro Asp Lys Pro Ser Leu Asp Ile Ser Leu Glu Thr Val Ala Ile
    210                 215                 220

Asp Arg Pro Ala Glu Val Arg Lys Val Cys Tyr Asn Ala Val Leu Thr
225                 230                 235                 240

His Val Lys Ile Asn Asp Lys Cys Pro Ser Thr Gly Glu Ala His Leu
                245                 250                 255

Ala Glu Glu Asn Glu Gly Asp Asn Ala Cys Lys Arg Thr Tyr Ser Asp
            260                 265                 270

Arg Gly Trp Gly Asn Gly Cys Gly Leu Phe Gly Lys Gly Ser Ile Val
        275                 280                 285

Ala Cys Ala Lys Phe Thr Cys Ala Lys Ser Met Ser Leu Phe Glu Val
    290                 295                 300

Asp Gln Thr Lys Ile Gln Tyr Val Ile Arg Ala Gln Leu His Val Gly
305                 310                 315                 320

Ala Lys Gln Glu Asn Trp Thr Asp Ile Lys Thr Leu Lys Phe Asp
                325                 330                 335

Ala Leu Ser Gly Ser Gln Glu Val Glu Phe Ile Gly Tyr Gly Lys Ala
            340                 345                 350

Thr Leu Glu Cys Gln Val Gln Thr Ala Val Asp Phe Gly Asn Ser Tyr
```

```
              355                 360                 365
Ile Ala Glu Met Glu Thr Glu Ser Trp Ile Val Asp Arg Gln Trp Ala
370                 375                 380

Gln Asp Leu Thr Leu Pro Trp Gln Ser Gly Ser Gly Gly Val Trp Arg
385                 390                 395                 400

Glu Met His His Leu Val Glu Phe Glu Pro Pro His Ala Ala Thr Ile
                405                 410                 415

Arg Val Leu Ala Leu Gly Asn Gln Glu Gly Ser Leu Lys Thr Ala Leu
            420                 425                 430

Thr Gly Ala Met Arg Val Thr Lys Asp Thr Asn Asp Asn Asn Leu Tyr
        435                 440                 445

Lys Leu His Gly Gly His Val Ser Cys Arg Val Lys Leu Ser Ala Leu
    450                 455                 460

Thr Leu Lys Gly Thr Ser Tyr Lys Ile Cys Thr Asp Lys Met Phe Phe
465                 470                 475                 480

Val Lys Asn Pro Thr Asp Thr Gly His Gly Thr Val Val Met Gln Val
                485                 490                 495

Lys Val Ser Lys Gly Ala Pro Cys Arg Ile Pro Val Ile Val Ala Asp
            500                 505                 510

Asp Leu Thr Ala Ala Ile Asn Lys Gly Ile Leu Val Thr Val Asn Pro
        515                 520                 525

Ile Ala Ser Thr Asn Asp Asp Glu Val Leu Ile Glu Val Asn Pro Pro
    530                 535                 540

Phe Gly Asp Ser Tyr Ile Ile Val Gly Arg Gly Asp Ser Arg Leu Thr
545                 550                 555                 560

Tyr Gln Trp His Lys Glu Gly Ser Ser Ile Gly Lys Leu Phe Thr Gln
                565                 570                 575

Thr Met Lys Gly Val Glu Arg Leu Ala Val Met Gly Asp Thr Ala Trp
            580                 585                 590

Asp Phe Ser Ser Ala Gly Gly Phe Phe Thr Ser Val Gly Lys Gly Ile
        595                 600                 605

His Thr Val Phe Gly Ser Ala Phe Gln Gly Leu Phe Gly Gly Leu Asn
    610                 615                 620

Trp Ile Thr Lys Val Ile Met Gly Ala Val Leu Ile Trp Val Gly Ile
625                 630                 635                 640

Asn Thr Arg Asn Met Thr Met Ser Met Ser Met Ile Leu Val Gly Val
                645                 650                 655

Ile Met Met Phe Leu Ser Leu Gly Val Gly Ala Asp Gln Gly Cys Ala
            660                 665                 670

Ile Asn Phe Gly Lys Arg Glu Leu Lys Cys Gly Asp
        675                 680

<210> SEQ ID NO 6
<211> LENGTH: 678
<212> TYPE: PRT
<213> ORGANISM: Flaviviridae Flavivirus Yellow Fever Virus

<400> SEQUENCE: 6

Gly Met Leu Leu Met Thr Gly Gly Val Thr Leu Val Arg Lys Asn Arg
1               5                   10                  15

Trp Leu Leu Leu Asn Val Thr Ser Glu Asp Leu Gly Lys Thr Phe Ser
            20                  25                  30

Val Gly Thr Gly Asn Cys Thr Thr Asn Ile Leu Glu Ala Lys Tyr Trp
        35                  40                  45

Cys Pro Asp Ser Met Glu Tyr Asn Cys Pro Asn Leu Ser Pro Arg Glu
```

```
                50                      55                      60
Glu Pro Asp Asp Ile Asp Cys Trp Cys Tyr Gly Val Glu Asn Val Arg
 65                  70                  75                  80

Val Ala Tyr Gly Lys Cys Asp Ser Ala Gly Arg Ser Arg Arg Ser Arg
                 85                  90                  95

Arg Ala Ile Asp Leu Pro Thr His Glu Asn His Gly Leu Lys Thr Arg
                100                 105                 110

Gln Glu Lys Trp Met Thr Gly Arg Met Gly Glu Arg Gln Leu Gln Lys
                115                 120                 125

Ile Glu Arg Trp Phe Val Arg Asn Pro Phe Phe Ala Val Thr Ala Leu
130                 135                 140

Thr Ile Ala Tyr Leu Val Gly Ser Asn Met Thr Gln Arg Val Val Ile
145                 150                 155                 160

Ala Leu Leu Val Leu Ala Val Gly Pro Ala Tyr Ser Ala His Cys Ile
                165                 170                 175

Gly Ile Thr Asp Arg Asp Phe Ile Glu Gly Val His Gly Gly Thr Trp
                180                 185                 190

Val Ser Ala Thr Leu Glu Gln Asp Lys Cys Val Thr Val Met Ala Pro
                195                 200                 205

Asp Lys Pro Ser Leu Asp Ile Ser Leu Glu Thr Val Ala Ile Asp Arg
210                 215                 220

Pro Ala Glu Val Arg Lys Val Cys Tyr Asn Ala Val Leu Thr His Val
225                 230                 235                 240

Lys Ile Asn Asp Lys Cys Pro Ser Thr Gly Glu Ala His Leu Ala Glu
                245                 250                 255

Glu Asn Glu Gly Asp Asn Ala Cys Lys Arg Thr Tyr Ser Asp Arg Gly
                260                 265                 270

Trp Gly Asn Gly Cys Gly Leu Phe Gly Lys Gly Ser Ile Val Ala Cys
                275                 280                 285

Ala Lys Phe Thr Cys Ala Lys Ser Met Ser Leu Phe Glu Val Asp Gln
290                 295                 300

Thr Lys Ile Gln Tyr Val Ile Arg Ala Gln Leu His Val Gly Ala Lys
305                 310                 315                 320

Gln Glu Asn Trp Thr Thr Asp Ile Lys Thr Leu Arg Phe Asp Ala Leu
                325                 330                 335

Ser Gly Ser Gln Glu Val Glu Phe Ile Gly Tyr Gly Lys Ala Thr Leu
                340                 345                 350

Glu Cys Gln Val Gln Thr Ala Val Asp Phe Gly Asn Ser Tyr Ile Ala
                355                 360                 365

Glu Met Glu Thr Glu Ser Trp Ile Val Asp Arg Gln Trp Ala Gln Asp
370                 375                 380

Leu Thr Leu Pro Trp Gln Ser Gly Ser Gly Gly Val Trp Arg Glu Met
385                 390                 395                 400

His His Leu Val Glu Phe Glu Pro Pro His Ala Ala Thr Ile Arg Val
                405                 410                 415

Leu Ala Leu Gly Asn Gln Glu Gly Ser Leu Lys Thr Ala Leu Thr Gly
                420                 425                 430

Ala Met Arg Val Thr Lys Asp Thr Asn Asp Asn Asn Leu Tyr Lys Leu
435                 440                 445

His Gly Gly His Val Ser Cys Arg Val Lys Leu Ser Ala Leu Thr Leu
                450                 455                 460

Lys Gly Thr Ser Tyr Lys Ile Cys Thr Asp Lys Met Phe Phe Val Lys
465                 470                 475                 480
```

-continued

Asn Pro Thr Asp Thr Gly His Gly Thr Val Met Gln Val Lys Val
                    485                 490                 495

Ser Lys Gly Ala Pro Cys Arg Ile Pro Val Ile Val Ala Asp Leu
            500                 505                 510

Thr Ala Ala Ile Asn Lys Gly Ile Leu Val Thr Val Asn Pro Ile Ala
            515                 520                 525

Ser Thr Asn Asp Asp Glu Val Leu Ile Glu Val Asn Pro Pro Phe Gly
        530                 535                 540

Asp Ser Tyr Ile Ile Val Gly Arg Gly Asp Ser Arg Leu Thr Tyr Gln
545                 550                 555                 560

Trp His Lys Glu Gly Ser Ser Ile Gly Lys Leu Phe Thr Gln Thr Met
                565                 570                 575

Lys Gly Val Glu Arg Leu Ala Val Met Gly Asp Thr Ala Trp Asp Phe
            580                 585                 590

Ser Ser Ala Gly Gly Phe Phe Thr Ser Val Gly Lys Gly Ile His Thr
        595                 600                 605

Val Phe Gly Ser Ala Phe Gln Gly Leu Phe Gly Gly Leu Asn Trp Ile
    610                 615                 620

Thr Lys Val Ile Met Gly Ala Val Leu Ile Trp Val Gly Ile Asn Thr
625                 630                 635                 640

Arg Asn Met Thr Met Ser Met Ser Met Ile Leu Val Gly Val Ile Met
                645                 650                 655

Met Phe Leu Ser Leu Gly Val Gly Ala Asp Gln Gly Cys Ala Ile Asn
            660                 665                 670

Phe Gly Lys Arg Glu Leu
            675

<210> SEQ ID NO 7
<211> LENGTH: 3411
<212> TYPE: PRT
<213> ORGANISM: Flaviviridae Flavivirus Yellow Fever Virus

<400> SEQUENCE: 7

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

-continued

```
Glu Glu Pro Asp Asp Ile Asp Cys Trp Cys Tyr Gly Val Glu Asn Val
            180                 185                 190
Arg Val Ala Tyr Gly Lys Cys Asp Ser Ala Gly Arg Ser Arg Arg Ser
        195                 200                 205
Arg Arg Ala Ile Asp Leu Pro Thr His Glu Asn His Gly Leu Lys Thr
    210                 215                 220
Arg Gln Glu Lys Trp Met Thr Gly Arg Met Gly Glu Arg Gln Leu Gln
225                 230                 235                 240
Lys Ile Glu Arg Trp Phe Val Arg Asn Pro Phe Phe Ala Val Thr Ala
                245                 250                 255
Leu Thr Ile Ala Tyr Leu Val Gly Ser Asn Met Thr Gln Arg Val Val
            260                 265                 270
Ile Ala Leu Leu Val Leu Ala Val Gly Pro Ala Tyr Ser Ala His Cys
        275                 280                 285
Ile Gly Ile Thr Asp Arg Asp Phe Ile Glu Gly Val His Gly Gly Thr
    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                325                 330                 335
Arg Pro Ala Glu Val Arg Lys Val Cys Tyr Asn Ala Val Leu Thr His
            340                 345                 350
Val Lys Ile Asn Asp Lys Cys Pro Ser Thr Gly Glu Ala His Leu Ala
        355                 360                 365
Glu Glu Asn Glu Gly Asp Asn Ala Cys Lys Arg Thr Tyr Ser Asp Arg
    370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
            420                 425                 430
Lys Gln Glu Asn Trp Thr Thr Asp Ile Lys Thr Leu Arg Phe Asp Ala
        435                 440                 445
Leu Ser Gly Ser Gln Glu Val Glu Phe Ile Gly Tyr Gly Lys Ala Thr
    450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                485                 490                 495
Asp Leu Thr Leu Pro Trp Gln Ser Gly Ser Gly Gly Val Trp Arg Glu
            500                 505                 510
Met His His Leu Val Glu Phe Glu Pro Pro His Ala Ala Thr Ile Arg
        515                 520                 525
Val Leu Ala Leu Gly Asn Gln Glu Gly Ser Leu Lys Thr Ala Leu Thr
    530                 535                 540
Gly Ala Met Arg Val Thr Lys Asp Thr Asn Asp Asn Leu Tyr Lys
545                 550                 555                 560
Leu His Gly Gly His Val Ser Cys Arg Val Lys Leu Ser Ala Leu Thr
                565                 570                 575
Leu Lys Gly Thr Ser Tyr Lys Ile Cys Thr Asp Lys Met Phe Phe Val
            580                 585                 590
Lys Asn Pro Thr Asp Thr Gly His Gly Thr Val Val Met Gln Val Lys
        595                 600                 605
```

-continued

Val Ser Lys Gly Ala Pro Cys Arg Ile Pro Val Ile Val Ala Asp Asp
    610                 615                 620
Leu Thr Ala Ala Ile Asn Lys Gly Ile Leu Val Thr Val Asn Pro Ile
625                 630                 635                 640
Ala Ser Thr Asn Asp Asp Glu Val Leu Ile Glu Val Asn Pro Pro Phe
                645                 650                 655
Gly Asp Ser Tyr Ile Ile Val Gly Arg Gly Asp Ser Arg Leu Thr Tyr
                660                 665                 670
Gln Trp His Lys Glu Gly Ser Ser Ile Gly Lys Leu Phe Thr Gln Thr
        675                 680                 685
Met Lys Gly Val Glu Arg Leu Ala Val Met Gly Asp Thr Ala Trp Asp
    690                 695                 700
Phe Ser Ser Ala Gly Gly Phe Phe Thr Ser Val Gly Lys Gly Ile His
705                 710                 715                 720
Thr Val Phe Gly Ser Ala Phe Gln Gly Leu Phe Gly Gly Leu Asn Trp
                725                 730                 735
Ile Thr Lys Val Ile Met Gly Ala Val Leu Ile Trp Val Gly Ile Asn
                740                 745                 750
Thr Arg Asn Met Thr Met Ser Met Ser Met Ile Leu Val Gly Val Ile
        755                 760                 765
Met Met Phe Leu Ser Leu Gly Val Gly Ala Asp Gln Gly Cys Ala Ile
    770                 775                 780
Asn Phe Gly Lys Arg Glu Leu Lys Cys Gly Asp Gly Ile Phe Ile Phe
785                 790                 795                 800
Arg Asp Ser Asp Asp Trp Leu Asn Lys Tyr Ser Tyr Pro Glu Asp
                805                 810                 815
Pro Val Lys Leu Ala Ser Ile Val Lys Ala Ser Phe Glu Glu Gly Lys
                820                 825                 830
Cys Gly Leu Asn Ser Val Asp Ser Leu Glu His Glu Met Trp Arg Ser
        835                 840                 845
Arg Ala Asp Glu Ile Asn Ala Ile Phe Glu Glu Asn Glu Val Asp Ile
    850                 855                 860
Ser Val Val Gln Asp Pro Lys Asn Val Tyr Gln Arg Gly Thr His
865                 870                 875                 880
Pro Phe Ser Arg Ile Arg Asp Gly Leu Gln Tyr Gly Trp Lys Thr Trp
                885                 890                 895
Gly Lys Asn Leu Val Phe Ser Pro Gly Arg Lys Asn Gly Ser Phe Ile
                900                 905                 910
Ile Asp Gly Lys Ser Arg Lys Glu Cys Pro Phe Ser Asn Arg Val Trp
        915                 920                 925
Asn Ser Phe Gln Ile Glu Glu Phe Gly Thr Gly Val Phe Thr Thr Arg
    930                 935                 940
Val Tyr Met Asp Ala Val Phe Glu Tyr Thr Ile Asp Cys Asp Gly Ser
945                 950                 955                 960
Ile Leu Gly Ala Ala Val Asn Gly Lys Lys Ser Ala His Gly Ser Pro
                965                 970                 975
Thr Phe Trp Met Gly Ser His Glu Val Asn Gly Thr Trp Met Ile His
                980                 985                 990
Thr Leu Glu Ala Leu Asp Tyr Lys Glu Cys Glu Trp Pro Leu Thr His
        995                 1000                1005
Thr Ile Gly Thr Ser Val Glu Glu Ser Glu Met Phe Met Pro Arg Ser
    1010                1015                1020
Ile Gly Gly Pro Val Ser Ser His Asn His Ile Pro Gly Tyr Lys Val

-continued

```
             1025                1030                1035                1040
Gln Thr Asn Gly Pro Trp Met Gln Val Pro Leu Glu Val Lys Arg Glu
                    1045                1050                1055
Ala Cys Pro Gly Thr Ser Val Ile Ile Asp Gly Asn Cys Asp Gly Arg
                    1060                1065                1070
Gly Lys Ser Thr Arg Ser Thr Thr Asp Ser Gly Lys Val Ile Pro Glu
                    1075                1080                1085
Trp Cys Cys Arg Ser Cys Ile Met Pro Pro Val Ser Phe His Gly Ser
                    1090                1095                1100
Asp Gly Cys Trp Tyr Pro Met Glu Ile Arg Pro Arg Lys Thr His Glu
1105                1110                1115                1120
Ser His Leu Val Arg Ser Trp Val Thr Ala Gly Glu Ile His Ala Val
                    1125                1130                1135
Pro Phe Gly Leu Val Ser Met Met Ile Ala Met Glu Val Val Leu Arg
                    1140                1145                1150
Lys Arg Gln Gly Pro Lys Gln Met Leu Val Gly Gly Val Val Leu Leu
                    1155                1160                1165
Gly Ala Met Leu Val Gly Gln Val Thr Leu Leu Asp Leu Leu Lys Leu
                    1170                1175                1180
Thr Val Ala Val Gly Leu His Phe His Glu Met Asn Asn Gly Gly Asp
1185                1190                1195                1200
Ala Met Tyr Met Ala Leu Ile Ala Ala Phe Ser Ile Arg Pro Gly Leu
                    1205                1210                1215
Leu Ile Gly Phe Gly Leu Arg Thr Leu Trp Ser Pro Arg Glu Arg Leu
                    1220                1225                1230
Val Leu Thr Leu Gly Ala Ala Met Val Glu Ile Ala Leu Gly Gly Val
                    1235                1240                1245
Met Gly Gly Leu Trp Lys Tyr Leu Asn Ala Val Ser Leu Cys Ile Leu
                    1250                1255                1260
Thr Ile Asn Ala Val Ala Ser Arg Lys Ala Ser Asn Thr Ile Leu Pro
1265                1270                1275                1280
Leu Met Ala Leu Leu Thr Pro Val Thr Met Ala Glu Val Arg Leu Ala
                    1285                1290                1295
Ala Met Phe Leu Cys Ala Val Val Ile Ile Gly Val Leu His Gln Asn
                    1300                1305                1310
Phe Lys Asp Thr Ser Met Gln Lys Thr Ile Pro Leu Val Ala Leu Thr
                    1315                1320                1325
Leu Thr Ser Tyr Leu Gly Leu Thr Gln Pro Phe Leu Gly Leu Cys Ala
                    1330                1335                1340
Phe Leu Ala Thr Arg Ile Phe Gly Arg Arg Ser Ile Pro Val Asn Glu
1345                1350                1355                1360
Ala Leu Ala Ala Ala Gly Leu Val Gly Val Leu Ala Gly Leu Ala Phe
                    1365                1370                1375
Gln Glu Met Glu Asn Phe Leu Gly Pro Ile Ala Val Gly Gly Leu Leu
                    1380                1385                1390
Met Met Leu Val Ser Val Ala Gly Arg Val Asp Gly Leu Glu Leu Lys
                    1395                1400                1405
Lys Leu Gly Glu Val Ser Trp Glu Glu Glu Ala Glu Ile Ser Gly Ser
                    1410                1415                1420
Ser Ala Arg Tyr Asp Val Ala Leu Ser Glu Gln Gly Glu Phe Lys Leu
1425                1430                1435                1440
Leu Ser Glu Glu Lys Val Pro Trp Asp Gln Val Val Met Thr Ser Leu
                    1445                1450                1455
```

-continued

Ala Leu Val Gly Ala Ala Leu His Pro Phe Ala Leu Leu Val Leu
        1460                1465                1470

Ala Gly Trp Leu Phe His Val Arg Gly Ala Arg Arg Ser Gly Asp Val
    1475                1480                1485

Leu Trp Asp Ile Pro Thr Pro Lys Ile Ile Glu Glu Cys Glu His Leu
    1490                1495                1500

Glu Asp Gly Ile Tyr Gly Ile Phe Gln Ser Thr Phe Leu Gly Ala Ser
1505                1510                1515                1520

Gln Arg Gly Val Gly Val Ala Gln Gly Gly Val Phe His Thr Met Trp
            1525                1530                1535

His Val Thr Arg Gly Ala Phe Leu Val Arg Asn Gly Lys Lys Leu Ile
        1540                1545                1550

Pro Ser Trp Ala Ser Val Lys Glu Asp Leu Val Ala Tyr Gly Gly Ser
    1555                1560                1565

Trp Lys Leu Glu Gly Arg Trp Asp Gly Glu Glu Val Gln Leu Ile
    1570                1575                1580

Ala Ala Val Pro Gly Lys Asn Val Val Asn Val Gln Thr Lys Pro Ser
1585                1590                1595                1600

Leu Phe Lys Val Arg Asn Gly Gly Glu Ile Gly Ala Val Ala Leu Asp
        1605                1610                1615

Tyr Pro Ser Gly Thr Ser Gly Ser Pro Ile Val Asn Arg Asn Gly Glu
    1620                1625                1630

Val Ile Gly Leu Tyr Gly Asn Gly Ile Leu Val Gly Asp Asn Ser Phe
    1635                1640                1645

Val Ser Ala Ile Ser Gln Thr Glu Val Lys Glu Gly Lys Glu Glu
    1650                1655                1660

Leu Gln Glu Ile Pro Thr Met Leu Lys Lys Gly Met Thr Thr Val Leu
1665                1670                1675                1680

Asp Phe His Pro Gly Ala Gly Lys Thr Arg Arg Phe Leu Pro Gln Ile
        1685                1690                1695

Leu Ala Glu Cys Ala Arg Arg Arg Leu Arg Thr Leu Val Leu Ala Pro
        1700                1705                1710

Thr Arg Val Val Leu Ser Glu Met Lys Glu Ala Phe His Gly Leu Asp
        1715                1720                1725

Val Lys Phe His Thr Gln Ala Phe Ser Ala His Gly Ser Gly Arg Glu
    1730                1735                1740

Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
        1765                1770                1775

Phe Leu Asp Pro Ala Ser Ile Ala Ala Arg Gly Trp Ala Ala His Arg
    1780                1785                1790

Ala Arg Ala Asn Glu Ser Ala Thr Ile Leu Met Thr Ala Thr Pro Pro
        1795                1800                1805

Gly Thr Ser Asp Glu Phe Pro His Ser Asn Gly Glu Ile Glu Asp Val
    1810                1815                1820

Gln Thr Asp Ile Pro Ser Glu Pro Trp Asn Thr Gly His Asp Trp Ile
1825                1830                1835                1840

Leu Ala Asp Lys Arg Pro Thr Ala Trp Phe Leu Pro Ser Ile Arg Ala
            1845                1850                1855

Ala Asn Val Met Ala Ala Ser Leu Arg Lys Ala Gly Lys Ser Val Val
        1860                1865                1870

Val Leu Asn Arg Lys Thr Phe Glu Arg Glu Tyr Pro Thr Ile Lys Gln
        1875                1880                1885

```
Lys Lys Pro Asp Phe Ile Leu Ala Thr Asp Ile Ala Glu Met Gly Ala
    1890                1895                1900
Asn Leu Cys Val Glu Arg Val Leu Asp Cys Arg Thr Ala Phe Lys Pro
1905                1910                1915                1920
Val Leu Val Asp Glu Gly Arg Lys Val Ala Ile Lys Gly Pro Leu Arg
                1925                1930                1935
Ile Ser Ala Ser Ser Ala Ala Gln Arg Arg Gly Arg Ile Gly Arg Asn
            1940                1945                1950
Pro Asn Arg Asp Gly Asp Ser Tyr Tyr Tyr Ser Glu Pro Thr Ser Glu
            1955                1960                1965
Asn Asn Ala His His Val Cys Trp Leu Glu Ala Ser Met Leu Leu Asp
            1970                1975                1980
Asn Met Glu Val Arg Gly Gly Met Val Ala Pro Leu Tyr Gly Val Glu
1985                1990                1995                2000
Gly Thr Lys Thr Pro Val Ser Pro Gly Glu Met Arg Leu Arg Asp Asp
                2005                2010                2015
Gln Arg Lys Val Phe Arg Glu Leu Val Arg Asn Cys Asp Leu Pro Val
            2020                2025                2030
Trp Leu Ser Trp Gln Val Ala Lys Ala Gly Leu Lys Thr Asn Asp Arg
            2035                2040                2045
Lys Trp Cys Phe Glu Gly Pro Glu His Glu Ile Leu Asn Asp Ser
            2050                2055                2060
Gly Glu Thr Val Lys Cys Arg Ala Pro Gly Gly Ala Lys Lys Pro Leu
2065                2070                2075                2080
Arg Pro Arg Trp Cys Asp Glu Arg Val Ser Ser Asp Gln Ser Ala Leu
                2085                2090                2095
Ser Glu Phe Ile Lys Phe Ala Glu Gly Arg Arg Gly Ala Ala Glu Val
            2100                2105                2110
Leu Val Val Leu Ser Glu Leu Pro Asp Phe Leu Ala Lys Lys Gly Gly
            2115                2120                2125
Glu Ala Met Asp Thr Ile Ser Val Phe Leu His Ser Glu Glu Gly Ser
            2130                2135                2140
Arg Ala Tyr Arg Asn Ala Leu Ser Met Met Pro Glu Ala Met Thr Ile
2145                2150                2155                2160
Val Met Leu Phe Ile Leu Ala Gly Leu Leu Thr Ser Gly Met Val Ile
                2165                2170                2175
Phe Phe Met Ser Pro Lys Gly Ile Ser Arg Met Ser Met Ala Met Gly
                2180                2185                2190
Thr Met Ala Gly Cys Gly Tyr Leu Met Phe Leu Gly Gly Val Lys Pro
            2195                2200                2205
Thr His Ile Ser Tyr Ile Met Leu Ile Phe Phe Val Leu Met Val Val
            2210                2215                2220
Val Ile Pro Glu Pro Gly Gln Gln Arg Ser Ile Gln Asp Asn Gln Val
2225                2230                2235                2240
Ala Tyr Leu Ile Ile Gly Ile Leu Thr Leu Val Ser Ala Val Ala Ala
                2245                2250                2255
Asn Glu Leu Gly Met Leu Glu Lys Thr Lys Glu Asp Leu Phe Gly Lys
            2260                2265                2270
Lys Asn Leu Ile Pro Ser Ser Ala Ser Pro Trp Ser Trp Pro Asp Leu
            2275                2280                2285
Asp Leu Lys Pro Gly Ala Ala Trp Thr Val Tyr Val Gly Ile Val Thr
            2290                2295                2300
Met Leu Ser Pro Met Leu His His Trp Ile Lys Val Glu Tyr Gly Asn
```

-continued

```
            2305                2310                2315                2320
        Leu Ser Leu Ser Gly Ile Ala Gln Ser Ala Val Leu Ser Phe Met
                        2325                2330                2335
        Asp Lys Gly Ile Pro Phe Met Lys Met Asn Ile Ser Val Ile Met Leu
                    2340                2345                2350
        Leu Val Ser Gly Trp Asn Ser Ile Thr Val Met Pro Leu Leu Cys Gly
                2355                2360                2365
        Ile Gly Cys Ala Met Leu His Trp Ser Leu Ile Leu Pro Gly Ile Lys
            2370                2375                2380
        Ala Gln Gln Ser Lys Leu Ala Gln Arg Arg Val Phe His Gly Val Ala
        2385                2390                2395                2400
        Lys Asn Pro Val Val Asp Gly Asn Pro Thr Val Asp Ile Glu Glu Ala
                    2405                2410                2415
        Pro Glu Met Pro Ala Leu Tyr Glu Lys Lys Leu Ala Leu Tyr Leu Leu
                    2420                2425                2430
        Leu Ala Leu Ser Leu Ala Ser Val Ala Met Cys Arg Thr Pro Phe Ser
                    2435                2440                2445
        Leu Ala Glu Gly Ile Val Leu Ala Ser Ala Leu Gly Pro Leu Ile
            2450                2455                2460
        Glu Gly Asn Thr Ser Leu Leu Trp Asn Gly Pro Met Ala Val Ser Met
        2465                2470                2475                2480
        Thr Gly Val Met Arg Gly Asn His Tyr Ala Phe Val Gly Val Met Tyr
                        2485                2490                2495
        Asn Leu Trp Lys Met Lys Thr Gly Arg Arg Gly Ser Ala Asn Gly Lys
                        2500                2505                2510
        Thr Leu Gly Glu Val Trp Lys Arg Glu Leu Asn Leu Leu Asp Lys Arg
                    2515                2520                2525
        Gln Phe Glu Leu Tyr Lys Arg Thr Asp Ile Val Glu Val Asp Arg Asp
            2530                2535                2540
        Thr Ala Arg Arg His Leu Ala Glu Gly Lys Val Asp Thr Gly Val Ala
        2545                2550                2555                2560
        Val Ser Arg Gly Thr Ala Lys Leu Arg Trp Phe His Glu Arg Gly Tyr
                        2565                2570                2575
        Val Lys Leu Glu Gly Arg Val Ile Asp Leu Gly Cys Gly Arg Gly Gly
                    2580                2585                2590
        Trp Cys Tyr Tyr Ala Ala Ala Gln Lys Glu Val Ser Gly Val Lys Gly
                        2595                2600                2605
        Phe Thr Leu Gly Arg Asp Gly His Glu Lys Pro Met Asn Val Gln Ser
                    2610                2615                2620
        Leu Gly Trp Asn Ile Ile Thr Phe Lys Asp Lys Thr Asp Ile His Arg
        2625                2630                2635                2640
        Leu Glu Pro Val Lys Cys Asp Thr Leu Leu Cys Asp Ile Gly Glu Ser
                        2645                2650                2655
        Ser Ser Ser Ser Val Thr Glu Gly Glu Arg Thr Val Arg Val Leu Asp
                    2660                2665                2670
        Thr Val Glu Lys Trp Leu Ala Cys Gly Val Asp Asn Phe Cys Val Lys
                    2675                2680                2685
        Val Leu Ala Pro Tyr Met Pro Asp Val Leu Glu Lys Leu Glu Leu Leu
                    2690                2695                2700
        Gln Arg Arg Phe Gly Gly Thr Val Ile Arg Asn Pro Leu Ser Arg Asn
        2705                2710                2715                2720
        Ser Thr His Glu Met Tyr Tyr Val Ser Gly Ala Arg Ser Asn Val Thr
                        2725                2730                2735
```

```
Phe Thr Val Asn Gln Thr Ser Arg Leu Leu Met Arg Arg Met Arg Arg
                2740                2745                2750

Pro Thr Gly Lys Val Thr Leu Glu Ala Asp Val Ile Leu Pro Ile Gly
                2755                2760            2765

Thr Arg Ser Val Glu Thr Asp Lys Gly Pro Leu Asp Lys Glu Ala Ile
            2770                2775                2780

Glu Glu Arg Val Glu Arg Ile Lys Ser Glu Tyr Met Thr Ser Trp Phe
2785                2790                2795                2800

Tyr Asp Asn Asp Asn Pro Tyr Arg Thr Trp His Tyr Cys Gly Ser Tyr
                2805                2810                2815

Val Thr Lys Thr Ser Gly Ser Ala Ala Ser Met Val Asn Gly Val Ile
                2820                2825                2830

Lys Ile Leu Thr Tyr Pro Trp Asp Arg Ile Glu Glu Val Thr Arg Met
                2835                2840                2845

Ala Met Thr Asp Thr Thr Pro Phe Gly Gln Gln Arg Val Phe Lys Glu
                2850                2855                2860

Lys Val Asp Thr Arg Ala Lys Asp Pro Pro Ala Gly Thr Arg Lys Ile
2865                2870                2875                2880

Met Lys Val Val Asn Arg Trp Leu Phe Arg His Leu Ala Arg Glu Lys
                2885                2890                2895

Asn Pro Arg Leu Cys Thr Lys Glu Glu Phe Ile Ala Lys Val Arg Ser
                2900                2905                2910

His Ala Ala Ile Gly Ala Tyr Leu Glu Glu Gln Glu Gln Trp Lys Thr
                2915                2920                2925

Ala Asn Glu Ala Val Gln Asp Pro Lys Phe Trp Glu Leu Val Asp Glu
                2930                2935                2940

Glu Arg Lys Leu His Gln Gln Gly Arg Cys Arg Thr Cys Val Tyr Asn
2945                2950                2955                2960

Met Met Gly Lys Arg Glu Lys Lys Leu Ser Glu Phe Gly Lys Ala Lys
                2965                2970                2975

Gly Ser Arg Ala Ile Trp Tyr Met Trp Leu Gly Ala Arg Tyr Leu Glu
                2980                2985                2990

Phe Glu Ala Leu Gly Phe Leu Asn Glu Asp His Trp Ala Ser Arg Glu
                2995                3000                3005

Asn Ser Gly Gly Gly Val Glu Gly Ile Gly Leu Gln Tyr Leu Gly Tyr
                3010                3015                3020

Val Ile Arg Asp Leu Ala Ala Met Asp Gly Gly Gly Phe Tyr Ala Asp
3025                3030                3035                3040

Asp Thr Ala Gly Trp Asp Thr Arg Ile Thr Glu Ala Asp Leu Asp Asp
                3045                3050                3055

Glu Gln Glu Ile Leu Asn Tyr Met Ser Pro His His Lys Lys Leu Ala
                3060                3065                3070

Gln Ala Val Met Glu Met Thr Tyr Lys Asn Lys Val Val Lys Val Leu
                3075                3080                3085

Arg Pro Ala Pro Gly Gly Lys Ala Tyr Met Asp Val Ile Ser Arg Arg
                3090                3095                3100

Asp Gln Arg Gly Ser Gly Gln Val Val Thr Tyr Ala Leu Asn Thr Ile
3105                3110                3115                3120

Thr Asn Leu Lys Val Gln Leu Ile Arg Met Ala Glu Ala Glu Met Val
                3125                3130                3135

Ile His His Gln His Val Gln Asp Cys Asp Glu Ser Val Leu Thr Arg
                3140                3145                3150

Leu Glu Ala Trp Leu Thr Glu His Gly Cys Asn Arg Leu Lys Arg Met
                3155                3160                3165
```

Ala Val Ser Gly Asp Asp Cys Val Val Arg Pro Ile Asp Asp Arg Phe
              3170                3175                3180

Gly Leu Ala Leu Ser His Leu Asn Ala Met Ser Lys Val Arg Lys Asp
3185                3190                3195                3200

Ile Ser Glu Trp Gln Pro Ser Lys Gly Trp Asn Asp Trp Glu Asn Val
              3205                3210                3215

Pro Phe Cys Ser His His Phe His Glu Leu Gln Leu Lys Asp Gly Arg
              3220                3225                3230

Arg Ile Val Val Pro Cys Arg Glu Gln Asp Glu Leu Ile Gly Arg Gly
              3235                3240                3245

Arg Val Ser Pro Gly Asn Gly Trp Met Ile Lys Glu Thr Ala Cys Leu
              3250                3255                3260

Ser Lys Ala Tyr Ala Asn Met Trp Ser Leu Met Tyr Phe His Lys Arg
3265                3270                3275                3280

Asp Met Arg Leu Leu Ser Leu Ala Val Ser Ser Ala Val Pro Thr Ser
              3285                3290                3295

Trp Val Pro Gln Gly Arg Thr Thr Trp Ser Ile His Gly Lys Gly Glu
              3300                3305                3310

Trp Met Thr Thr Glu Asp Met Leu Glu Val Trp Asn Arg Val Trp Ile
              3315                3320                3325

Thr Asn Asn Pro His Met Gln Asp Lys Thr Met Val Lys Lys Trp Arg
              3330                3335                3340

Asp Val Pro Tyr Leu Thr Lys Arg Gln Asp Lys Leu Cys Gly Ser Leu
3345                3350                3355                3360

Ile Gly Met Thr Asn Arg Ala Thr Trp Ala Ser His Ile His Leu Val
              3365                3370                3375

Ile His Arg Ile Arg Thr Leu Ile Gly Gln Glu Lys Tyr Thr Asp Tyr
              3380                3385                3390

Leu Thr Val Met Asp Arg Tyr Ser Val Asp Ala Asp Leu Gln Leu Gly
              3395                3400                3405

Glu Leu Ile
     3410

<210> SEQ ID NO 8
<211> LENGTH: 3411
<212> TYPE: PRT
<213> ORGANISM: Flaviviridae Flavivirus Yellow Fever Virus

<400> SEQUENCE: 8

Met Ser Gly Arg Lys Ala Gln Gly Lys Thr Leu Gly Val Asn Met Val
 1               5                  10                  15

Arg Arg Gly Val Arg Ser Leu Ser Asn Lys Ile Lys Gln Lys Thr Lys
              20                  25                  30

Gln Ile Gly Asn Arg Pro Gly Pro Ser Arg Gly Val Gln Gly Phe Ile
              35                  40                  45

Phe Phe Phe Leu Phe Asn Ile Leu Thr Gly Lys Lys Ile Thr Ala His
         50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                 85                  90                  95

Ser Arg Lys Arg Arg Ser His Asp Val Leu Thr Val Gln Phe Leu Ile
             100                 105                 110

Leu Gly Met Leu Leu Met Thr Gly Gly Val Thr Leu Val Arg Lys Asn
             115                 120                 125

-continued

```
Arg Trp Leu Leu Leu Asn Val Thr Ser Glu Asp Leu Gly Lys Thr Phe
    130                 135                 140
Ser Val Gly Thr Gly Asn Cys Thr Thr Asn Ile Leu Glu Ala Lys Tyr
145                 150                 155                 160
Trp Cys Pro Asp Ser Met Glu Tyr Asn Cys Pro Asn Leu Ser Pro Arg
                165                 170                 175
Glu Glu Pro Asp Asp Ile Asp Cys Trp Cys Tyr Gly Val Glu Asn Val
            180                 185                 190
Arg Val Ala Tyr Gly Lys Cys Asp Ser Ala Gly Arg Ser Arg Arg Ser
        195                 200                 205
Arg Arg Ala Ile Asp Leu Pro Thr His Glu Asn His Gly Leu Lys Thr
    210                 215                 220
Arg Gln Glu Lys Trp Met Thr Gly Arg Met Gly Glu Arg Gln Leu Gln
225                 230                 235                 240
Lys Ile Glu Arg Trp Phe Val Arg Asn Pro Phe Phe Ala Val Thr Ala
                245                 250                 255
Leu Thr Ile Ala Tyr Leu Val Gly Ser Asn Met Thr Gln Arg Val Val
            260                 265                 270
Ile Ala Leu Leu Val Leu Ala Val Gly Pro Ala Tyr Ser Ala His Cys
        275                 280                 285
Ile Gly Ile Thr Asp Arg Asp Phe Ile Glu Gly Val His Gly Gly Thr
    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                325                 330                 335
Arg Pro Ala Glu Val Arg Lys Val Cys Tyr Asn Ala Val Leu Thr His
            340                 345                 350
Val Lys Ile Asn Asp Lys Cys Pro Ser Thr Gly Glu Ala His Leu Ala
        355                 360                 365
Glu Glu Asn Glu Gly Asp Asn Ala Cys Lys Arg Thr Tyr Ser Asp Arg
    370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
            420                 425                 430
Lys Gln Glu Asn Trp Thr Thr Asp Ile Lys Thr Leu Lys Phe Asp Ala
        435                 440                 445
Leu Ser Gly Ser Gln Glu Val Glu Phe Ile Gly Tyr Gly Lys Ala Thr
    450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                485                 490                 495
Asp Leu Thr Leu Pro Trp Gln Ser Gly Ser Gly Val Trp Arg Glu
            500                 505                 510
Met His His Leu Val Glu Phe Glu Pro Pro His Ala Ala Thr Ile Arg
        515                 520                 525
Val Leu Ala Leu Gly Asn Gln Glu Gly Ser Leu Lys Thr Ala Leu Thr
    530                 535                 540
Gly Ala Met Arg Val Thr Lys Asp Thr Asn Asp Asn Asn Leu Tyr Lys
```

```
           545                 550                 555                 560
Leu His Gly Gly His Val Ser Cys Arg Val Lys Leu Ser Ala Leu Thr
                    565                 570                 575

Leu Lys Gly Thr Ser Tyr Lys Ile Cys Thr Asp Lys Met Phe Phe Val
                    580                 585                 590

Lys Asn Pro Thr Asp Thr Gly His Gly Thr Val Val Met Gln Val Lys
                    595                 600                 605

Val Ser Lys Gly Ala Pro Cys Arg Ile Pro Val Ile Val Ala Asp Asp
                    610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                    645                 650                 655

Gly Asp Ser Tyr Ile Ile Val Gly Arg Gly Asp Ser Arg Leu Thr Tyr
                    660                 665                 670

Gln Trp His Lys Glu Gly Ser Ser Ile Gly Lys Leu Phe Thr Gln Thr
                    675                 680                 685

Met Lys Gly Val Glu Arg Leu Ala Val Met Gly Asp Thr Ala Trp Asp
                    690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                    725                 730                 735

Ile Thr Lys Val Ile Met Gly Ala Val Leu Ile Trp Val Gly Ile Asn
                    740                 745                 750

Thr Arg Asn Met Thr Met Ser Met Ser Met Ile Leu Val Gly Val Ile
                    755                 760                 765

Met Met Phe Leu Ser Leu Gly Val Gly Ala Asp Gln Gly Cys Ala Ile
                    770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
                    805                 810                 815

Pro Val Lys Leu Ala Ser Ile Val Lys Ala Ser Phe Glu Glu Gly Lys
                    820                 825                 830

Cys Gly Leu Asn Ser Val Asp Ser Leu Glu His Glu Met Trp Arg Ser
                    835                 840                 845

Arg Ala Asp Glu Ile Asn Ala Ile Phe Glu Glu Asn Glu Val Asp Ile
                    850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                    885                 890                 895

Gly Lys Asn Leu Val Phe Ser Pro Gly Arg Lys Asn Gly Ser Phe Ile
                    900                 905                 910

Ile Asp Gly Lys Ser Arg Lys Glu Cys Pro Phe Ser Asn Arg Val Trp
                    915                 920                 925

Asn Ser Phe Gln Ile Glu Glu Phe Gly Thr Gly Val Phe Thr Thr Arg
                    930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
                    965                 970                 975
```

-continued

```
Thr Phe Trp Met Gly Ser His Glu Val Asn Gly Thr Trp Met Ile His
            980                 985                 990

Thr Leu Glu Ala Leu Asp Tyr Lys Glu Cys Glu Trp Pro Leu Thr His
            995                 1000                1005

Thr Ile Gly Thr Ser Val Glu Glu Ser Glu Met Phe Met Pro Arg Ser
    1010                1015                1020

Ile Gly Gly Pro Val Ser Ser His Asn His Ile Pro Gly Tyr Lys Val
1025                1030                1035                1040

Gln Thr Asn Gly Pro Trp Met Gln Val Pro Leu Glu Val Lys Arg Glu
            1045                1050                1055

Ala Cys Pro Gly Thr Ser Val Ile Ile Asp Gly Asn Cys Asp Gly Arg
            1060                1065                1070

Gly Lys Ser Thr Arg Ser Thr Thr Asp Ser Gly Lys Val Ile Pro Glu
    1075                1080                1085

Trp Cys Cys Arg Ser Cys Thr Met Pro Pro Val Ser Phe His Gly Ser
    1090                1095                1100

Asp Gly Cys Trp Tyr Pro Met Glu Ile Arg Pro Arg Lys Thr His Glu
1105                1110                1115                1120

Ser His Leu Val Arg Ser Trp Val Thr Ala Gly Glu Ile His Ala Val
            1125                1130                1135

Pro Phe Gly Leu Val Ser Met Met Ile Ala Met Glu Val Val Leu Arg
            1140                1145                1150

Lys Arg Gln Gly Pro Lys Gln Met Leu Val Gly Gly Val Val Leu Leu
    1155                1160                1165

Gly Ala Met Leu Val Gly Gln Val Thr Leu Leu Asp Leu Leu Lys Leu
    1170                1175                1180

Thr Val Ala Val Gly Leu His Phe His Glu Met Asn Asn Gly Gly Asp
1185                1190                1195                1200

Ala Met Tyr Met Ala Leu Ile Ala Ala Phe Ser Ile Arg Pro Gly Leu
            1205                1210                1215

Leu Ile Gly Phe Gly Leu Arg Thr Leu Trp Ser Pro Arg Glu Arg Leu
            1220                1225                1230

Val Leu Thr Leu Gly Ala Ala Met Val Glu Ile Ala Leu Gly Gly Val
    1235                1240                1245

Met Gly Gly Leu Trp Lys Tyr Leu Asn Ala Val Ser Leu Cys Ile Leu
    1250                1255                1260

Thr Ile Asn Ala Val Ala Ser Arg Lys Ala Ser Asn Thr Ile Leu Pro
1265                1270                1275                1280

Leu Met Ala Leu Leu Thr Pro Val Thr Met Ala Glu Val Arg Leu Ala
            1285                1290                1295

Ala Met Phe Phe Cys Ala Val Val Ile Ile Gly Val Leu His Gln Asn
            1300                1305                1310

Phe Lys Asp Thr Ser Met Gln Lys Thr Ile Pro Leu Val Ala Leu Thr
    1315                1320                1325

Leu Thr Ser Tyr Leu Gly Leu Thr Gln Pro Phe Leu Gly Leu Cys Ala
    1330                1335                1340

Phe Leu Ala Thr Arg Ile Phe Gly Arg Arg Ser Ile Pro Val Asn Glu
1345                1350                1355                1360

Ala Leu Ala Ala Ala Gly Leu Val Gly Val Leu Ala Gly Leu Ala Phe
            1365                1370                1375

Gln Glu Met Glu Asn Phe Leu Gly Pro Ile Ala Val Gly Gly Leu Leu
            1380                1385                1390

Met Met Leu Val Ser Val Ala Gly Arg Val Asp Gly Leu Glu Leu Lys
    1395                1400                1405
```

```
Lys Leu Gly Glu Val Ser Trp Glu Glu Ala Glu Ile Ser Gly Ser
    1410                1415                1420

Ser Ala Arg Tyr Asp Val Ala Leu Ser Glu Gln Gly Glu Phe Lys Leu
1425                1430                1435                1440

Leu Ser Glu Glu Lys Val Pro Trp Asp Gln Val Val Met Thr Ser Leu
            1445                1450                1455

Ala Leu Val Gly Ala Ala Leu His Pro Phe Ala Leu Leu Val Leu
        1460                1465                1470

Ala Gly Trp Leu Phe His Val Arg Gly Ala Arg Arg Ser Gly Asp Val
            1475                1480                1485

Leu Trp Asp Ile Pro Thr Pro Lys Ile Ile Glu Glu Cys Glu His Leu
    1490                1495                1500

Glu Asp Gly Ile Tyr Gly Ile Phe Gln Ser Thr Phe Leu Gly Ala Ser
1505                1510                1515                1520

Gln Arg Gly Val Gly Val Ala Gln Gly Gly Val Phe His Thr Met Trp
            1525                1530                1535

His Val Thr Arg Gly Ala Phe Leu Val Arg Asn Gly Lys Lys Leu Ile
        1540                1545                1550

Pro Ser Trp Ala Ser Val Lys Glu Asp Leu Val Ala Tyr Gly Gly Ser
    1555                1560                1565

Trp Lys Leu Glu Gly Arg Trp Asp Gly Glu Glu Val Gln Leu Ile
        1570                1575                1580

Ala Ala Val Pro Gly Lys Asn Val Val Asn Val Gln Thr Lys Pro Ser
1585                1590                1595                1600

Leu Phe Lys Val Arg Asn Gly Gly Glu Ile Gly Ala Val Ala Leu Asp
            1605                1610                1615

Tyr Pro Ser Gly Thr Ser Gly Ser Pro Ile Val Asn Arg Asn Gly Glu
        1620                1625                1630

Val Ile Gly Leu Tyr Gly Asn Gly Ile Leu Val Gly Asp Asn Ser Phe
        1635                1640                1645

Val Ser Ala Ile Ser Gln Thr Glu Val Lys Glu Glu Gly Lys Glu Glu
    1650                1655                1660

Leu Gln Glu Ile Pro Thr Met Leu Lys Lys Gly Met Thr Thr Val Leu
1665                1670                1675                1680

Asp Phe His Pro Gly Ala Gly Lys Thr Arg Arg Phe Leu Pro Gln Ile
            1685                1690                1695

Leu Ala Glu Cys Ala Arg Arg Arg Leu Arg Thr Leu Val Leu Ala Pro
        1700                1705                1710

Thr Arg Val Val Leu Ser Glu Met Lys Glu Ala Phe His Gly Leu Asp
        1715                1720                1725

Val Lys Phe His Thr Gln Ala Phe Ser Ala His Gly Ser Gly Arg Glu
    1730                1735                1740

Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
            1765                1770                1775

Phe Leu Asp Pro Ala Ser Ile Ala Ala Arg Gly Trp Ala Ala His Arg
        1780                1785                1790

Ala Arg Ala Asn Glu Ser Ala Thr Ile Leu Met Thr Ala Thr Pro Pro
    1795                1800                1805

Gly Thr Ser Asp Glu Phe Pro His Ser Asn Gly Glu Ile Glu Asp Val
    1810                1815                1820

Gln Thr Asp Ile Pro Ser Glu Pro Trp Asn Thr Gly His Asp Trp Ile
```

```
           1825                1830                1835                1840
Leu Ala Asp Lys Arg Pro Thr Ala Trp Phe Leu Pro Ser Ile Arg Ala
            1845                1850                1855

Ala Asn Val Met Ala Ala Ser Leu Arg Lys Ala Gly Lys Ser Val Val
            1860                1865                1870

Val Leu Asn Arg Lys Thr Phe Glu Arg Glu Tyr Pro Thr Ile Lys Gln
            1875                1880                1885

Lys Lys Pro Asp Phe Ile Leu Ala Thr Asp Ile Ala Glu Met Gly Ala
            1890                1895                1900

Asn Leu Cys Val Glu Arg Val Leu Asp Cys Arg Thr Ala Phe Lys Pro
1905                1910                1915                1920

Val Leu Val Asp Glu Gly Arg Lys Val Ala Ile Lys Gly Pro Leu Arg
            1925                1930                1935

Ile Ser Ala Ser Ser Ala Ala Gln Arg Arg Gly Arg Ile Gly Arg Asn
            1940                1945                1950

Pro Asn Arg Asp Gly Asp Ser Tyr Tyr Tyr Ser Glu Pro Thr Ser Glu
            1955                1960                1965

Asn Asn Ala His His Val Cys Trp Leu Glu Ala Ser Met Leu Leu Asp
            1970                1975                1980

Asn Met Glu Val Arg Gly Gly Met Val Ala Pro Leu Tyr Gly Val Glu
1985                1990                1995                2000

Gly Thr Lys Thr Pro Val Ser Pro Gly Glu Met Arg Leu Arg Asp Asp
            2005                2010                2015

Gln Arg Lys Val Phe Arg Glu Leu Val Arg Asn Cys Asp Leu Pro Val
            2020                2025                2030

Trp Leu Ser Trp Gln Val Ala Lys Ala Gly Leu Lys Thr Asn Asp Arg
            2035                2040                2045

Lys Trp Cys Phe Glu Gly Pro Glu Glu His Glu Ile Leu Asn Asp Ser
            2050                2055                2060

Gly Glu Thr Val Lys Cys Arg Ala Pro Gly Gly Ala Lys Lys Pro Leu
2065                2070                2075                2080

Arg Pro Arg Trp Cys Asp Glu Arg Val Ser Ser Asp Gln Ser Ala Leu
            2085                2090                2095

Ser Glu Phe Ile Lys Phe Ala Glu Gly Arg Arg Gly Ala Ala Glu Val
            2100                2105                2110

Leu Val Val Leu Ser Glu Leu Pro Asp Phe Leu Ala Lys Lys Gly Gly
            2115                2120                2125

Glu Ala Met Asp Thr Ile Ser Val Phe Leu His Ser Glu Glu Gly Ser
            2130                2135                2140

Arg Ala Tyr Arg Asn Ala Leu Ser Met Met Pro Glu Ala Met Thr Ile
2145                2150                2155                2160

Val Met Leu Phe Ile Leu Ala Gly Leu Leu Thr Ser Gly Met Val Ile
            2165                2170                2175

Phe Phe Met Ser Pro Lys Gly Ile Ser Arg Met Ser Met Ala Met Gly
            2180                2185                2190

Thr Met Ala Gly Cys Gly Tyr Leu Met Phe Leu Gly Gly Val Lys Pro
            2195                2200                2205

Thr His Ile Ser Tyr Ile Met Leu Ile Phe Phe Val Leu Met Val Val
            2210                2215                2220

Val Ile Pro Glu Pro Gly Gln Gln Arg Ser Ile Gln Asp Asn Gln Val
2225                2230                2235                2240

Ala Tyr Leu Ile Ile Gly Ile Leu Thr Leu Val Ser Ala Val Ala Ala
            2245                2250                2255
```

-continued

Asn Glu Leu Gly Met Leu Glu Lys Thr Lys Glu Asp Leu Phe Gly Lys
            2260                2265                2270

Lys Asn Leu Ile Pro Ser Ser Ala Ser Pro Trp Ser Trp Pro Asp Leu
            2275                2280                2285

Asp Leu Lys Pro Gly Ala Ala Trp Thr Val Tyr Val Gly Ile Val Thr
            2290                2295                2300

Met Leu Ser Pro Met Leu His His Trp Ile Lys Val Glu Tyr Gly Asn
2305                2310                2315                2320

Leu Ser Leu Ser Gly Ile Ala Gln Ser Ala Ser Val Leu Ser Phe Met
            2325                2330                2335

Asp Lys Gly Ile Pro Phe Met Lys Met Asn Ile Ser Val Ile Met Leu
            2340                2345                2350

Leu Val Ser Gly Trp Asn Ser Ile Thr Val Met Pro Leu Leu Cys Gly
            2355                2360                2365

Met Gly Cys Ala Met Leu His Trp Ser Leu Ile Leu Pro Gly Ile Lys
            2370                2375                2380

Ala Gln Gln Ser Lys Leu Ala Gln Arg Arg Val Phe His Gly Val Ala
2385                2390                2395                2400

Lys Asn Pro Val Val Asp Gly Asn Pro Thr Val Asp Ile Glu Glu Ala
            2405                2410                2415

Pro Glu Met Pro Ala Leu Tyr Glu Lys Lys Leu Ala Leu Tyr Leu Leu
            2420                2425                2430

Leu Ala Leu Ser Leu Ala Ser Val Ala Met Cys Arg Thr Pro Phe Ser
            2435                2440                2445

Leu Ala Glu Gly Ile Val Leu Ala Ser Ala Ala Leu Gly Pro Leu Ile
            2450                2455                2460

Glu Gly Asn Thr Ser Leu Leu Trp Asn Gly Pro Met Ala Val Ser Met
2465                2470                2475                2480

Thr Gly Val Met Arg Gly Asn His Tyr Ala Phe Val Gly Val Met Tyr
            2485                2490                2495

Asn Leu Trp Lys Met Lys Thr Gly Arg Arg Gly Ser Ala Asn Gly Lys
            2500                2505                2510

Thr Leu Gly Glu Val Trp Lys Arg Glu Leu Asn Leu Leu Asp Lys Arg
            2515                2520                2525

Gln Phe Glu Leu Tyr Lys Arg Thr Asp Ile Val Glu Val Asp Arg Asp
            2530                2535                2540

Thr Ala Arg Arg His Leu Ala Glu Gly Lys Val Asp Thr Gly Val Ala
2545                2550                2555                2560

Val Ser Arg Gly Thr Ala Lys Leu Arg Trp Phe His Glu Arg Gly Tyr
            2565                2570                2575

Val Lys Leu Glu Gly Arg Val Ile Asp Leu Gly Cys Gly Arg Gly Gly
            2580                2585                2590

Trp Cys Tyr Tyr Ala Ala Ala Gln Lys Glu Val Ser Gly Val Lys Gly
            2595                2600                2605

Phe Thr Leu Gly Arg Asp Gly His Glu Lys Pro Met Asn Val Gln Ser
            2610                2615                2620

Leu Gly Trp Asn Ile Ile Thr Phe Lys Asp Lys Thr Asp Ile His Arg
2625                2630                2635                2640

Leu Glu Pro Val Lys Cys Asp Thr Leu Leu Cys Asp Ile Gly Glu Ser
            2645                2650                2655

Ser Ser Ser Ser Val Thr Glu Gly Glu Arg Thr Val Arg Val Leu Asp
            2660                2665                2670

Thr Val Glu Lys Trp Leu Ala Cys Gly Val Asp Asn Phe Cys Val Lys
            2675                2680                2685

```
Val Leu Ala Pro Tyr Met Pro Asp Val Leu Glu Lys Leu Glu Leu Leu
    2690                2695                2700

Gln Arg Arg Phe Gly Gly Thr Val Ile Arg Asn Pro Leu Ser Arg Asn
2705                2710                2715                2720

Ser Thr His Glu Met Tyr Tyr Val Ser Gly Ala Arg Ser Asn Val Thr
        2725                2730                2735

Phe Thr Val Asn Gln Thr Ser Arg Leu Leu Met Arg Arg Met Arg Arg
            2740                2745                2750

Pro Thr Gly Lys Val Thr Leu Glu Ala Asp Val Ile Leu Pro Ile Gly
        2755                2760                2765

Thr Arg Ser Val Glu Thr Asp Lys Gly Pro Leu Asp Lys Glu Ala Ile
        2770                2775                2780

Glu Glu Arg Val Glu Arg Ile Lys Ser Glu Tyr Met Thr Ser Trp Phe
2785                2790                2795                2800

Tyr Asp Asn Asp Asn Pro Tyr Arg Thr Trp His Tyr Cys Gly Ser Tyr
                2805                2810                2815

Val Thr Lys Thr Ser Gly Ser Ala Ala Ser Met Val Asn Gly Val Ile
            2820                2825                2830

Lys Ile Leu Thr Tyr Pro Trp Asp Arg Ile Glu Glu Val Thr Arg Met
        2835                2840                2845

Ala Met Thr Asp Thr Thr Pro Phe Gly Gln Gln Arg Val Phe Lys Glu
        2850                2855                2860

Lys Val Asp Thr Arg Ala Lys Asp Pro Pro Ala Gly Thr Arg Lys Ile
2865                2870                2875                2880

Met Lys Val Val Asn Arg Trp Leu Phe Arg His Leu Ala Arg Glu Lys
            2885                2890                2895

Asn Pro Arg Leu Cys Thr Lys Glu Glu Phe Ile Ala Lys Val Arg Ser
            2900                2905                2910

His Ala Ala Ile Gly Ala Tyr Leu Glu Glu Gln Glu Gln Trp Lys Thr
        2915                2920                2925

Ala Asn Glu Ala Val Gln Asp Pro Lys Phe Trp Glu Leu Val Asp Glu
        2930                2935                2940

Glu Arg Lys Leu His Gln Gln Gly Arg Cys Arg Thr Cys Val Tyr Asn
2945                2950                2955                2960

Met Met Gly Lys Arg Glu Lys Lys Leu Ser Glu Phe Gly Lys Ala Lys
            2965                2970                2975

Gly Ser Arg Ala Ile Trp Tyr Met Trp Leu Gly Ala Arg Tyr Leu Glu
            2980                2985                2990

Phe Glu Ala Leu Gly Phe Leu Asn Glu Asp His Trp Ala Ser Arg Glu
        2995                3000                3005

Asn Ser Gly Gly Gly Val Glu Gly Ile Gly Leu Gln Tyr Leu Gly Tyr
        3010                3015                3020

Val Ile Arg Asp Leu Ala Ala Met Asp Gly Gly Gly Phe Tyr Ala Asp
3025                3030                3035                3040

Asp Thr Ala Gly Trp Asp Thr Arg Ile Thr Glu Ala Asp Leu Asp Asp
                3045                3050                3055

Glu Gln Glu Ile Leu Asn Tyr Met Ser Pro His His Lys Lys Leu Ala
            3060                3065                3070

Gln Ala Val Met Glu Met Thr Tyr Lys Asn Lys Val Val Lys Val Leu
        3075                3080                3085

Arg Pro Ala Pro Gly Gly Lys Ala Tyr Met Asp Val Ile Ser Arg Arg
        3090                3095                3100

Asp Gln Arg Gly Ser Gly Gln Val Val Thr Tyr Ala Leu Asn Thr Ile
```

```
                  3105                3110                3115                3120
       Thr Asn Leu Lys Val Gln Leu Ile Arg Met Ala Glu Ala Glu Met Val
                        3125                3130                3135
       Ile His His Gln His Val Gln Asp Cys Asp Glu Ser Val Leu Thr Arg
                        3140                3145                3150
       Leu Glu Ala Trp Leu Thr Glu His Gly Cys Asn Arg Leu Lys Arg Met
                    3155                3160                3165
       Ala Val Ser Gly Asp Asp Cys Val Val Arg Pro Ile Asp Asp Arg Phe
                3170                3175                3180
       Gly Leu Ala Leu Ser His Leu Asn Ala Met Ser Lys Val Arg Lys Asp
       3185                3190                3195                3200
       Ile Ser Glu Trp Gln Pro Ser Lys Gly Trp Asn Asp Trp Glu Asn Val
                        3205                3210                3215
       Pro Phe Cys Ser His His Phe His Glu Leu Gln Leu Lys Asp Gly Arg
                    3220                3225                3230
       Arg Ile Val Val Pro Cys Arg Glu Gln Asp Glu Leu Ile Gly Arg Gly
                3235                3240                3245
       Arg Val Ser Pro Gly Asn Gly Trp Met Ile Lys Glu Thr Ala Cys Leu
            3250                3255                3260
       Ser Lys Ala Tyr Ala Asn Met Trp Ser Leu Met Tyr Phe His Lys Arg
       3265                3270                3275                3280
       Asp Met Arg Leu Leu Ser Leu Ala Val Ser Ser Ala Val Pro Thr Ser
                        3285                3290                3295
       Trp Val Pro Gln Gly Arg Thr Thr Trp Ser Ile His Gly Lys Gly Glu
                    3300                3305                3310
       Trp Met Thr Thr Glu Asp Met Leu Glu Val Trp Asn Arg Val Trp Ile
                3315                3320                3325
       Thr Asn Asn Pro His Met Gln Asp Lys Thr Met Val Lys Lys Trp Arg
            3330                3335                3340
       Asp Val Pro Tyr Leu Thr Lys Arg Gln Asp Lys Leu Cys Gly Ser Leu
       3345                3350                3355                3360
       Ile Gly Met Thr Asn Arg Ala Thr Trp Ala Ser His Ile His Leu Val
                        3365                3370                3375
       Ile His Arg Ile Arg Thr Leu Ile Gly Gln Glu Lys Tyr Thr Asp Tyr
                    3380                3385                3390
       Leu Thr Val Met Asp Arg Tyr Ser Val Asp Ala Asp Leu Gln Leu Gly
                3395                3400                3405
       Glu Leu Ile
            3410

<210> SEQ ID NO 9
<211> LENGTH: 10776
<212> TYPE: DNA
<213> ORGANISM: Flaviviridae Flavivirus Yellow Fever Virus

<400> SEQUENCE: 9
aatcgagttg ctaggcaata aaacacatttg gattaattt aatcgttcgt tgagcgatta       60
gcagagaact gaccagaaca tgtctggtcg taaagctcag ggaaaaaccc tgggcgtcaa      120
tatggtacga cgaggagttc gctccttgtc aaacaaaata aaacaaaaaa caaacaaat      180 tggaaacaga cctggacctt caagaggtgt tcaaggattt atcttttct ttttgttcaa      240 cattttgact ggaaaaaaga tcacagccca cctaagaggg ttgtggaaaa tgctggaccc      300
aagacaaggc ttggctgttc taaggaaagt caagagagtg tggccagtt tgatgagagg      360 attgtcctca aggaaacgcc gttcccatga tgttctgact gtgcaattcc taattttggg      420
```

```
aatgctgttg atgacgggtg gagtgacctt ggtgcggaaa aacagatggt tgctcctaaa    480
tgtgacatct gaggacctcg ggaaaacatt ctctgtgggc acaggcaact gcacaacaaa    540
cattttggaa gccaagtact ggtgcccaga ctcaatggaa tacaactgtc ccaatctcag    600
tccaagagag gagccagatg acattgattg ctggtgctat ggggtggaaa acgttagagt    660
cgcatatggt aagtgtgact cagcaggcag gtctaggagg tcaagaaggg ccattgactt    720
gcctacgcat gaaaaccatg gtttgaagac ccggcaagaa aaatggatga ctggaagaat    780
gggtgaaagg caactccaaa agattgagag atggttcgtg aggaacccct ttttttgcagt    840 gacggctctg accattgcct accttgtggg aagcaacatg acgcaacgag tcgtgattgc    900
cctactggtc ttggctgttg gtccggccta ctcagctcac tgcattggaa ttactgacag    960
ggatttcatt gaggggggtgc atggaggaac ttgggtttca gctaccctgg agcaagacaa   1020
gtgtgtcact gttatggccc ctgacaagcc ttcattggac atctcactag agacagtagc   1080
cattgataga cctgctgagg tgaggaaagt gtgttacaat gcagttctca ctcatgtgaa   1140
gattaatgac aagtgcccca gcactggaga ggcccaccta gctgaagaga acgaagggga   1200
caatgcgtgc aagcgcactt attctgatag aggctggggc aatggctgtg gcctattgg    1260 gaaagggagc attgtggcat gcgccaaatt cacttgtgcc aaatccatga gtttgtttga   1320
ggttgatcag accaaaattc agtatgtcat cagagcacaa ttgcatgtag ggccaagca    1380 ggaaaattgg actaccgaca ttaagactct caagtttgat gccctgtcag gctcccagga   1440
agtcgagttc attgggtatg aaaagctac actggaatgc caggtgcaaa ctgcggtgga    1500
ctttggtaac agttacatcg ctgagatgga aacagagagc tggatagtgg acagacagtg   1560
ggcccaggac ttgaccctgc catggcagag tggaagtggc ggggtgtgga gagagatgca   1620
tcatcttgtc gaatttgaac ctccgcatgc cgccactatc agagtactgg ccctgggaaa   1680
ccaggaaggc tccttgaaaa cagctcttac ggcgcaatg agggttacaa aggacacaaa   1740
tgacaacaac ctttacaaac tacatggtgg acatgttttct tgcagagtga aattgtcagc   1800
tttgacactc aaggggacat cctacaaaat atgcactgac aaaatgtttt ttgtcaagaa   1860
cccaactgac actggccatg gcactgttgt gatgcaggtg aaagtgtcaa aaggagcccc   1920
ctgcaggatt ccagtgatag tagctgatga tcttacagcg gcaatcaata aaggcatttt   1980
ggttacagtt aaccccatcg cctcaaccaa tgatgatgaa gtgctgattg aggtgaaccc   2040
accttttgga gacagctaca ttatcgttgg gagaggagat tcacgtctca cttaccagtg   2100
gcacaaagag ggaagctcaa taggaaagtt gttcactcag accatgaaag gcgtggaacg   2160
cctggccgtc atgggagaca ccgcctggga tttcagctcc gctggagggt tcttcacttc   2220
ggttgggaaa ggaattcata cggtgtttgg ctctgccttt cagggggctat ttggcggctt   2280 gaactgata caaaggtca tcatgggggc ggtacttata tggttggca tcaacacaag   2340 aaacatgaca atgtccatga gcatgatctt ggtaggagtg atcatgatgt ttttgtctct   2400
aggagttggg gcggatcaag gatgcgccat caactttggc aagagagagc tcaagtgcgg   2460
agatggtatc ttcatattta gagactctga tgactggctg aacaagtact catactatcc   2520
agaagatcct gtgaagcttg catcaatagt gaaagcctct tttgaagaag ggaagtgtgg   2580
cctaaattca gttgactccc ttgagcatga gatgtggaga gcagggcag atgagatcaa   2640 tgccattttt gaggaaaacg aggtggacat ttctgttgtc gtgcaggatc aaagaatgt   2700 ttaccagaga ggaactcatc cattttccag aattcgggat ggtctgcagt atggttggaa   2760 gacttgggggt aagaaccttg tgttctcccc agggaggaag aatggaagct tcatcataga   2820
```

```
tggaaagtcc aggaaagaat gcccgttttc aaaccgggtc tggaattctt tccagataga   2880
ggagtttggg acgggagtgt tcaccacacg cgtgtacatg gacgcagtct ttgaatacac   2940
catagactgc gatggatcta tcttgggtgc agcggtgaac ggaaaaaaga gtgcccatgg   3000
ctctccaaca ttttggatgg gaagtcatga agtaaatggg acatggatga tccacacctt   3060
ggaggcatta gattacaagg agtgtgagtg gccactgaca catacgattg gaacatcagt   3120
tgaagagagt gaaatgttca tgccgagatc aatcggaggc ccagttagct ctcacaatca   3180
tatccctgga tacaaggttc agacgaacgg accttgatgt caggtaccac tagaagtgaa   3240
gagagaagct tgcccaggga ctagcgtgat cattgatggc aactgtgatg gacggggaaa   3300
atcaaccaga tccaccacgg atagcgggaa agttattcct gaatggtgtt gccgctcctg   3360
cacaatgccg cctgtgagct tccatggtag tgatgggtgt tggtatccca tggaaattag   3420
gccaaggaaa acgcatgaaa gccatctggt gcgctcctgg gttacagctg gagaaataca   3480
tgctgtccct tttggtttgg tgagcatgat gatagcaatg gaagtggtcc taaggaaaag   3540
acagggacca aagcaaatgt tggttggagg agtagtgctc ttgggagcaa tgctggtcgg   3600
gcaagtaact ctccttgatt tgctgaaact cacagtggct gtgggattgc atttccatga   3660
gatgaacaat ggaggagacg ccatgtatat ggcgttgatt gctgcctttt caatcagacc   3720
agggctgctc atcggctttg ggctcaggac cctatgagc cctcgggaac gccttgtgct   3780
gaccctagga gcagccatgg tggagattgc cttgggtggc gtgatgggcg gcctgtggaa   3840
gtatctaaat gcagtttctc tctgcatcct gacaataaat gctgttgctt ctaggaaagc   3900
atcaaatacc atcttgcccc tcatggctct gttgacacct gtcactatgg ctgaggtgag   3960
acttgccgca atgttctttt gtgccgtggt tatcatagg gtccttcacc agaatttcaa   4020
ggacacctcc atgcagaaga ctataccict ggtggccctc acactcacat cttacctggg   4080
cttgacacaa ccttttttgg gcctgtgtgc atttctggca acccgcatat ttgggcgaag   4140
gagtatccca gtgaatgagg cactcgcagc agctggtcta gtgggagtgc tggcaggact   4200
ggcttttcag gagatggaga acttccttgg tccgattgca gttggaggac tcctgatgat   4260
gctggttagc gtggctggga gggtggatgg gctagagctc aagaagcttg gtgaagtttc   4320
atgggaagag gaggcggaga tcagcggag ttccgcccgc tatgatgtgg cactcagtga   4380
acaaggggag ttcaagctgc tttctgaaga gaaagtgcca tgggaccagg ttgtgatgac   4440
ctcgctggcc ttggttgggg ctgccctcca tccatttgct cttctgctgg tccttgctgg   4500
gtggctgttt catgtcaggg gagctaggag aagtggggat gtcttgtggg atattcccac   4560
tcctaagatc atcgaggaat gtgaacatct ggaggatggg atttatggca tattccagtc   4620
aaccttcttg ggggcctccc agcgaggagt gggagtggca cagggagggg tgttccacac   4680
aatgtggcat gtcacaagag gagctttcct tgtcaggaat ggcaagaagt tgattccatc   4740
ttgggcttca gtaaaggaag accttgtcgc ctatggtggc tcatggaagt tggaaggcag   4800
atgggatgga gaggaagagg tccagttgat cgcggctgtt ccaggaaaga acgtggtcaa   4860
cgtccagaca aaaccgagct tgttcaaagt gaggaatggg ggagaaatcg gggctgtcgc   4920
tcttgactat ccgagtggca cttcaggatc tcctattgtt aacaggaacg gagaggtgat   4980
tgggctgtac ggcaatggca tccttgtcgg tgacaactcc ttcgtgtccg ccatatccca   5040
gactgaggtg aaggaagaag gaaaggagga gctccaagag atccccgacaa tgctaaagaa   5100 aggaatgaca actgtccttg attttcatcc tggagctggg aagacaagac gtttcctccc   5160
acagatcttg gccgagtgcg cacggagacg cttgcgcact cttgtgttgg cccccaccag   5220
```

```
ggttgttctt tctgaaatga aggaggcttt tcacggcctg gacgtgaaat tccacacaca    5280 ggcttttttcc gctcacggca gcgggagaga agtcattgat gctatgtgcc atgccaccct    5340
aacttacagg atgttggaac caactagggt tgttaactgg gaagtgatca ttatggatga    5400
agcccatttt ttggatccag ctagcatagc cgctagaggt tgggcagcgc acagagctag    5460
ggcaaatgaa agtgcaacaa tcttgatgac agccacaccg cctgggacta gtgatgaatt    5520
tccacattca aatggtgaaa tagaagatgt tcaaacggac atacccagtg agccctggaa    5580
cacagggcat gactggatcc tggctgacaa aaggcccacg gcatggttcc ttccatccat    5640
cagagctgca aatgtcatgg ctgcctcttt gcgtaaggct ggaaagagtg tggtggtcct    5700
gaacaggaaa acctttgaga gagaataccc cacgataaag cagaagaaac ctgactttat    5760
attggccact gacatagctg aaatgggagc caacctttgc gtggagcgag tgctggattg    5820
caggacggct tttaagcctg tgcttgtgga tgaagggagg aaggtggcaa taaaagggcc    5880
acttcgtatc tccgcatcct ctgctgctca aggaggggg cgcattggga gaaatcccaa    5940
cagagatgga gactcatact actattctga gcctacaagt gaaaataatg cccaccacgt    6000
ctgctggttg gaggcctcaa tgctcttgga caacatggag gtgaggggtg aatggtcgc    6060 cccactctat ggcgttgaag gaactaaaac accagtttcc cctggtgaaa tgagactgag    6120
ggatgaccag aggaaagtct tcagagaact agtgaggaat tgtgacctgc ccgtttggct    6180
ttcgtggcaa gtggccaagg ctggtttgaa gacgaatgat cgtaagtggt gttttgaagg    6240
ccctgaggaa catgagatct tgaatgacag cggtgaaaca gtgaagtgca gggctcctgg    6300
aggagcaaag aagcctctgc gcccaaggtg gtgtgatgaa agggtgtcat ctgaccagag    6360
tgcgctgtct gaatttatta agtttgctga aggtaggagg ggagctgctg aagtgctagt    6420
tgtgctgagt gaactccctg atttcctggc taaaaaaggt ggagaggcaa tggataccat    6480
cagtgtgttt ctccactctg aggaaggctc tagggcttac cgcaatgcac tatcaatgat    6540
gcctgaggca atgacaatag tcatgctgtt tatactggct ggactactga catcgggaat    6600
ggtcatcttt tcatgtctc ccaaaggcat cagtagaatg tctatggcga tgggcacaat    6660
ggccggctgt ggatatctca tgttccttgg aggcgtcaaa cccactcaca tctcctatat    6720
catgctcata ttcttttgtcc tgatggtggt tgtgatcccc gagccagggc aacaaaggtc    6780
catccaagac aaccaagtgg catacctcat tattggcatc ctgacgctgg tttcagcggt    6840
ggcagccaac gagctaggca tgctggagaa aaccaaagag gacctctttg gaagaagaa    6900 cttaattcca tctagtgctt caccctggag ttggccggat cttgacctga agccaggagc    6960
tgcctggaca gtgtacgttg gcattgttac aatgctctct ccaatgttgc accactggat    7020
caaagtcgaa tatggcaacc tgtctctgtc tggaatagcc cagtcagcct cagtcctttc    7080
tttcatggac aagggatac cattcatgaa gatgaatatc tcggtcataa tgctgctggt    7140
cagtggctgg aattcaataa cagtgatgcc tctgctctgt ggcataggt gcgccatgct    7200 ccactggtct ctcattttac ctggaatcaa agcgcagcag tcaaagcttg cacagagaag    7260
ggtgttccat ggcgttgcca agaaccctgt ggttgatggg aatccaacag ttgacattga    7320
ggaagctcct gaaatgcctg ccctttatga agaaactg gctctatatc tccttcttgc    7380
tctcagccta gcttctgttg ccatgtgcag aacgcccttt tcattggctg aaggcattgt    7440
cctagcatca gctgccctag ggccgctcat agagggaaac accagccttc tttggaatgg    7500
acccatggct gtctccatga caggagtcat gagggggaat cactatgctt ttgtgggagt    7560
catgtacaat ctatggaaga tgaaaactgg acgccggggg agcgcgaatg gaaaaacttt    7620
```

```
gggtgaagtc tggaagaggg aactgaatct gttggacaag cgacagtttg agttgtataa   7680
aaggaccgac attgtggagg tggatcgtga tacggcacgc aggcatttgg ccgaagggaa   7740
ggtggacacc ggggtggcgg tctccagggg gaccgcaaaa ttaaggtggt tccatgagcg   7800
tggctatgtc aagctggaag gtagggtgat tgacctgggg tgtggccgcg gaggctggtg   7860
ttactacgct gctgcgcaaa aggaagtgag tggggtcaaa ggatttactc ttggaagaga   7920
cggccatgag aaacccatga atgtgcaaag tctgggatgg aacatcatca ccttcaagga   7980
caaaactgat atccaccgcc tagaaccagt gaaatgtgac acccttttgt gtgacattgg   8040
agagtcatca tcgtcatcgg tcacagaggg ggaaaggacc gtgagagttc ttgatactgt   8100
agaaaaatgg ctggcttgtg gggttgacaa cttctgtgtg aaggtgttag ctccatacat   8160
gccagatgtt ctcgagaaac tggaattgct ccaaggagg tttggcggaa cagtgatcag   8220
gaaccctctc tccaggaatt ccactcatga aatgtactac gtgtctggag cccgcagcaa   8280
tgtcacattt actgtgaacc aaacatcccg cctcctgatg aggagaatga ggcgtccaac   8340
tggaaaagtg accctggagg ctgacgtcat cctcccaatt gggacacgca gtgttgagac   8400
agacaaggga ccccctggaca agaggccat agaagaaagg gttgagagga taaaatctga   8460
gtacatgacc tcttggtttt atgacaatga caccccctac aggacctggc actactgtgg   8520
ctcctatgtc acaaaaacct caggaagtgc ggcgagcatg gtaaatggtg ttattaaaat   8580
tctgacatat ccatgggaca ggatagagga ggtcacaaga atggcaatga ctgacacaac   8640 ccctttgga cagcaaagag tgtttaaga aaaagttgac accagagcaa aggatccacc   8700
agcgggaact aggaagatca tgaaagttgt caacaggtgg ctgttccgcc acctggccag   8760
agaaaagaac cccagactgt gcacaaagga agaatttatt gcaaaagtcc gaagtcatgc   8820
agccattgga gcttacctgg aagaacaaga acagtggaag actgccaatg aggctgtcca   8880
agacccaaag ttctgggaac tggtggatga agaaaggaag ctgcaccaac aaggcaggtg   8940
tcggacttgt gtgtacaaca tgatggggaa aagagagaag aagctgtcag agtttgggaa   9000
agcaaaggga agccgtgcca tatggtatat gtggctggga gcgcgggtatc ttgagtttga   9060 ggccctggga ttcctgaatg aggaccattg ggcttccagg gaaaactcag gaggaggagt   9120
ggaaggcatt ggcttacaat acctaggata tgtgatcaga gacctggctg caatggatgg   9180
tggtggattc tacgcggatg acaccgctgg atgggacacg cgcatcacag aggcagacct   9240
tgatgatgaa caggagatct tgaactacat gagcccacat cacaaaaaac tggcacaagc   9300
agtgatggaa atgacataca gaacaaagt ggtgaaagtg ttgagaccag ccccaggagg   9360
gaaagcctac atggatgtca taagtcgacg agaccagaga ggatccgggc aggtagtgac   9420
ttatgctctg aacaccatca ccaacttgaa agtccaattg atcagaatgg cagaagcaga   9480
gatggtgata catcaccaac atgttcaaga ttgtgatgaa tcagttctga ccaggctgga   9540
ggcatggctc actgagcacg gatgtaacag actgaagagg atggcggtga gtggagacga   9600
ctgtgtggtc cggcccatcg atgacaggtt cggcctggcc ctgtcccatc tcaacgccat   9660
gtccaaggtt agaaaggaca tatctgaatg gcagccatca aaagggtgga atgattggga   9720
gaatgtgccc ttctgttccc accacttcca tgaactacag ctgaaggatg gcaggaggat   9780
tgtggtgcct tgccgagaac aggacgagct cattgggaga ggaagggtgt ctccaggaaa   9840
cggctggatg atcaaggaaa cagcttgcct cagcaaagcc tatgccaaca tgtggtcact   9900
gatgtatttt cacaaaaggg acatgaggct actgtcattg gctgtttcct cagctgttcc   9960
cacctcatgg gttccacaag gacgcacaac atggtcgatt catgggaaag gggagtggat   10020
```

| | |
|---|---|
| gaccacggaa gacatgcttg aggtgtggaa cagagtatgg ataaccaaca acccacacat | 10080 |
| gcaggacaag acaatggtga aaaaatggag agatgtccct tatctaacca agagacaaga | 10140 |
| caagctgtgc ggatcactga ttggaatgac aatagggcc acctgggcct cccacatcca | 10200 |
| tttggtcatc catcgtatcc gaacgctgat tggacaggag aaatacactg actacctaac | 10260 |
| agtcatggac aggtattctg tggatgctga cctgcaactg ggtgagctta tctgaaacac | 10320 |
| catctaacag gaataaccgg gatacaaacc acgggtggag aaccggactc cccacaacct | 10380 |
| gaaaccggga tataaaccac ggctggagaa ccggactccg cacttaaaat gaaacagaaa | 10440 |
| ccgggataaa aactacggat ggagaaccgg actccacaca ttgagacaga agaagttgtc | 10500 |
| agcccagaac cccacacgag ttttgccact gctaagctgt gaggcagtgc aggctgggac | 10560 |
| agccgacctc caggttgcga aaacctggt ttctgggacc tcccacccca gagtaaaaag | 10620 |
| aacggagcct ccgctaccac cctcccacgt ggtggtagaa agacggggtc tagaggttag | 10680 |
| aggagaccct ccagggaaca atagtgggga ccatattgac gccagggaaa gaccggagtg | 10740 |
| gttctctgct tttcctccag aggtctgtga gcacag | 10776 |

<210> SEQ ID NO 10
<211> LENGTH: 10788
<212> TYPE: DNA
<213> ORGANISM: Flaviviridae Flavivirus Yellow Fever Virus

<400> SEQUENCE: 10

| | |
|---|---|
| aatcgagttg ctaggcaata acacatttg gattaattttt aatcgttcgt tgagcgatta | 60 |
| gcagagaact gaccagaaca tgtctggtcg taaagctcag ggaaaaaccc tgggcgtcaa | 120 |
| tatggtacga cgaggagttc gctccttgtc aaacaaaata aaacaaaaaa caaacaaat | 180 |
| tggaaacaga cctggaccttt caagaggtgt tcaaggattt atcttttttct ttttgttcaa | 240 |
| cattttgact ggaaaaaaga tcacagccca cctaaagagg ttgtggaaaa tgctggaccc | 300 |
| aagacaaggc ttggctgttc taaggaaagt caagagagtg gtggccagtt tgatgagagg | 360 |
| attgtcctca aggaaacgcc gttcccatga tgttctgact gtgcaattcc taattttggg | 420 |
| aatgctgttg atgacgggtg gagtgacctt ggtgcggaaa acagatggt tgctcctaaa | 480 |
| tgtgacatct gaggacctcg ggaaaacatt ctctgtgggc acaggcaact gcacaacaaa | 540 |
| cattttggaa gccaagtact ggtgcccaga ctcaatggaa tacaactgtc ccaatctcag | 600 |
| tccaagagag gagccagatg acattgattg ctggtgctat ggggtggaaa acgttagagt | 660 |
| cgcatatggt aagtgtgact cagcaggcag gtctaggagg tcaagaaggg ccattgactt | 720 |
| gcctacgcat gaaaaccatg gtttgaagac ccggcaagaa aaatggatga ctggaagaat | 780 |
| gggtgaaagg caactccaaa agattgagag atggttcgtg aggaacccct tttttgcagt | 840 |
| gacggctctg accattgcct accttgtggg aagcaacatg acgcaacgag tcgtgattgc | 900 |
| cctactggtc ttgctgttg gtccggccta ctcagctcac tgcattggaa ttactgacag | 960 |
| ggatttcatt gagggggtgc atggaggaac ttgggtttca gctaccctgg agcaagacaa | 1020 |
| gtgtgtcact gttatggccc ctgacaagcc ttcattggac atctcactag agacagtagc | 1080 |
| cattgataga cctgctgagg tgaggaaagt gtgttacaat gcagttctca ctcatgtgaa | 1140 |
| gattaatgac aagtgcccca gcactggaga ggcccaccta gctgaagaga cgaagggga | 1200 |
| caatgcgtgc aagcgcactt attctgatag aggctgggc aatggctgtg gcctatttgg | 1260 |
| gaaagggagc attgtggcat gcgccaaatt cacttgtgcc aaatccatga gtttgtttga | 1320 |
| ggttgatcag accaaaattc agtatgtcat cagagcacaa ttgcatgtag ggccaagca | 1380 |

```
ggaaaattgg actaccgaca ttaagactct caagtttgat gccctgtcag gctcccagga    1440
agtcgagttc attgggtatg gaaaagctac actggaatgc caggtgcaaa ctgcggtgga    1500 cttggtaac agttacatcg ctgagatgga acagagagc tggatagtgg acagacagtg     1560
ggcccaggac ttgaccctgc catggcagag tggaagtggc ggggtgtgga gagagatgca    1620
tcatcttgtc gaatttgaac ctccgcatgc cgccactatc agagtactgg ccctgggaaa    1680
ccaggaaggc tccttgaaaa cagctcttac tggcgcaatg agggttacaa aggacacaaa    1740
tgacaacaac ctttacaaac tacatggtgg acatgtttct gcagagtga aattgtcagc     1800 tttgacactc aagggacat cctacaaaat atgcactgac aaaatgtttt ttgtcaagaa      1860
cccaactgac actggccatg gcactgttgt gatgcaggtg aaagtgtcaa aaggagcccc    1920
ctgcaggatt ccagtgatag tagctgatga tcttacagcg gcaatcaata aaggcatttt    1980
ggttacagtt aacccatcg cctcaaccaa tgatgatgaa gtgctgattg aggtgaaccc     2040 acctttgga gacagctaca ttatcgttgg gagaggagt tcacgtctca cttaccagtg      2100
gcacaaagag ggaagctcaa taggaaagtt gttcactcag accatgaaag gcgtggaacg    2160
cctggccgtc atgggagaca ccgcctggga tttcagctcc gctggaggt tcttcacttc     2220 ggttgggaaa ggaattcata cggtgtttgg ctctgccttt caggggctat tggcggctt     2280 gaactggata caaaggtca tcatgggggc ggtacttata tggttggca tcaacacaag     2340 aaacatgaca atgtccatga gcatgatctt ggtaggagtg atcatgatgt ttttgtctct    2400
aggagttggg gcggatcaag gatgcgccat caactttggc aagagagagc tcaagtgcgg    2460
agatggtatc ttcatatttta gagactctga tgactggctg aacaagtact catactatcc    2520
agaagatcct gtgaagcttg catcaatagt gaaagcctct tttgaagaag ggaagtgtgg    2580
cctaaattca gttgactccc ttgagcatga gatgtggaga agcagggcag atgagatcaa    2640
tgccattttt gaggaaaacg aggtggacat ttctgttgtc gtgcaggatc caagaatgt     2700 ttaccagaga ggaactcatc cattttccag aattcgggat ggtctgcagt atggttggaa    2760
gacttggggt aagaaccttg tgttctcccc agggaggaag aatggaagct tcatcataga    2820
tggaaagtcc aggaaagaat gcccgttttc aaaccgggtc tggaattctt tccagataga    2880
ggagtttggg acgggagtgt tcaccacacg cgtgtacatg gacgcagtct ttgaatacac    2940
catagactgc gatggatcta tcttgggtgc agcggtgaac ggaaaaaaga gtgcccatgg    3000
ctctccaaca ttttggatgg gaagtcatga agtaaatggg acatggatga tccacacctt    3060
ggaggcatta gattacaagg agtgtgagtg gccactgaca catacgattg aacatcagt     3120 tgaagagagt gaaatgttca tgccgagatc aatcggaggc ccagttagct ctcacaatca    3180
tatccctgga tacaaggttc agacgaacgg accttggatg caggtaccac tagaagtgaa    3240
gagagaagct tgcccaggga ctagcgtgat cattgatggc aactgtgatg gacgggaaa    3300 atcaaccaga tccaccacgg atagcgggaa agttattcct gaatggtgtt gccgctcctg    3360
cacaatgccg cctgtgagct tccatggtag tgatgggtgt tggtatccca tggaaattag    3420
gccaaggaaa acgcatgaaa gccatctggt gcgctcctgg gttacagctg gagaaataca    3480
tgctgtccct tttggttttgg tgagcatgat gatagcaatg gaagtggtcc taaggaaaag    3540
acagggacca aagcaaatgt tggttggagg agtagtgctc ttgggagcaa tgctggtcgg    3600
gcaagtaact ctccttgatt tgctgaaact cacagtggct gtgggattgc atttccatga    3660
gatgaacaat ggaggagacg ccatgtatat ggcgttgatt gctgccttt caatcagacc     3720 agggctgctc atcggctttg gctcaggac cctatggagc cctcgggaac gccttgtgct    3780
```

```
gaccctagga gcagccatgg tggagattgc cttgggtggc gtgatgggcg gcctgtggaa    3840
gtatctaaat gcagtttctc tctgcatcct gacaataaat gctgttgctt ctaggaaagc    3900
atcaaatacc atcttgcccc tcatggctct gttgacacct gtcactatgg ctgaggtgag    3960
acttgccgca atgttctttt gtgccgtggt tatcataggg gtccttcacc agaatttcaa    4020
ggacacctcc atgcagaaga ctatacctct ggtggccctc acactcacat cttacctggg    4080
cttgacacaa cctttttttgg gcctgtgtgc atttctggca acccgcatat ttgggcgaag    4140
gagtatccca gtgaatgagg cactcgcagc agctggtcta gtgggagtgc tggcaggact    4200
ggcttttcag gagatggaga acttccttgg tccgattgca gttggaggac tcctgatgat    4260
gctggttagc gtggctggga gggtggatgg gctagagctc aagaagcttg gtgaagtttc    4320
atgggaagag gaggcggaga tcagcgggag ttccgcccgc tatgatgtgg cactcagtga    4380
acaaggggag ttcaagctgc tttctgaaga gaaagtgcca tgggaccagg ttgtgatgac    4440
ctcgctggcc ttggttgggg ctgccctcca tccatttgct cttctgctgg tccttgctgg    4500
gtggctgttt catgtcaggg gagctaggag aagtggggat gtcttgtggg atattcccac    4560
tcctaagatc atcgaggaat gtgaacatct ggaggatggg atttatggca tattccagtc    4620
aaccttcttg ggggcctccc agcgaggagt gggagtggca cagggagggg tgttccacac    4680 aatgtgcat gtcacaagag gagctttcct tgtcaggaat ggcaagaagt tgattccatc    4740
ttgggcttca gtaaaggaag accttgtcgc ctatggtggc tcatggaagt tggaaggcag    4800
atgggatgga gaggaagagg tccagttgat cgcggctgtt ccaggaaaga acgtggtcaa    4860
cgtccagaca aaaccgagct tgttcaaagt gaggaatggg ggagaaatcg gggctgtcgc    4920
tcttgactat ccgagtggca cttcaggatc tcctattgtt aacaggaacg gagaggtgat    4980
tgggctgtac ggcaatggca tccttgtcgg tgacaactcc ttcgtgtccg ccatatccca    5040
gactgaggtg aaggaagaag gaaaggagga gctccaagag atcccgacaa tgctaaagaa    5100
aggaatgaca actgtccttg attttcatcc tggagctggg aagacaagac gtttcctccc    5160
acagatcttg gccgagtgcg cacggagacg cttgcgcact cttgtgttgg ccccaccag    5220 ggttgttctt tctgaaatga aggaggcttt tcacggcctg gacgtgaaat ccacacaca    5280 ggctttttcc gctcacggca gcgggagaga agtcattgat gctatgtgcc atgccaccct    5340
aacttacagg atgttggaac caactagggt tgttaactgg gaagtgatca ttatggatga    5400
agcccatttt ttggatccag ctagcatagc cgctagaggt tgggcagcgc acagagctag    5460
ggcaaatgaa agtgcaacaa tcttgatgac agccacaccg cctgggacta gtgatgaatt    5520
tccacattca aatggtgaaa tagaagatgt tcaaacggac ataccagtg agccctggaa    5580 cacagggcat gactggatcc tggctgacaa aaggcccacg gcatggttcc ttccatccat    5640
cagagctgca aatgtcatgg ctgcctcttt gcgtaaggct ggaaagagtg tggtggtcct    5700
gaacaggaaa acctttgaga gagaatacccc acgataaag cagaagaaac ctgactttat    5760
attggccact gacatagctg aaatgggagc caacctttgc gtggagcgag tgctggattg    5820
caggacggct tttaagcctg tgcttgtgga tgaagggagg aaggtggcaa taaaagggcc    5880
acttcgtatc tccgcatcct ctgctgctca aggaggggg cgcattggga gaaatcccaa    5940
cagagatgga gactcatact actattctga gcctacaagt gaaataatg cccaccacgt    6000 ctgctggttg gaggcctcaa tgctcttgga caacatggag gtgagggtg aatggtcgc    6060 cccactctat ggcgttgaag gaactaaaac accagtttcc cctggtgaaa tgagactgag    6120
ggatgaccag aggaaagtct tcagagaact agtgaggaat tgtgacctgc ccgtttggct    6180
```

```
ttcgtggcaa gtggccaagg ctggtttgaa gacgaatgat cgtaagtggt gttttgaagg   6240
ccctgaggaa catgagatct tgaatgacag cggtgaaaca gtgaagtgca gggctcctgg   6300
aggagcaaag aagcctctgc gcccaaggtg gtgtgatgaa agggtgtcat ctgaccagag   6360
tgcgctgtct gaatttatta agtttgctga aggtaggagg ggagctgctg aagtgctagt   6420
tgtgctgagt gaactccctg atttcctggc taaaaaaggt ggagaggcaa tggataccat   6480
cagtgtgttt ctccactctg aggaaggctc tagggcttac cgcaatgcac tatcaatgat   6540
gcctgaggca atgacaatag tcatgctgtt tatactggct ggactactga catcgggaat   6600
ggtcatcttt ttcatgtctc ccaaaggcat cagtagaatg tctatggcga tgggcacaat   6660
ggccggctgt ggatatctca tgttccttgg aggcgtcaaa cccactcaca tctcctatat   6720
catgctcata ttctttgtcc tgatggtggt tgtgatcccc gagccagggc aacaaaggtc   6780
catccaagac aaccaagtgg catacctcat tattggcatc ctgacgctgg tttcagcggt   6840
ggcagccaac gagctaggca tgctggagaa aaccaaagag gacctctttg gaagaagaa   6900 cttaattcca tctagtgctt caccctggag ttggccggat cttgacctga agccaggagc   6960
tgcctggaca gtgtacgttg gcattgttac aatgctctct ccaatgttgc accactggat   7020
caaagtcgaa tatggcaacc tgtctctgtc tggaatagcc cagtcagcct cagtcctttc   7080
tttcatggac aaggggatac cattcatgaa gatgaatatc tcggtcataa tgctgctggt   7140
cagtggctgg aattcaataa cagtgatgcc tctgctctgt ggcatagggt gcgccatgct   7200
ccactggtct ctcattttac ctggaatcaa agcgcagcag tcaaagcttg cacagagaag   7260
ggtgttccat ggcgttgcca agaaccctgt ggttgatggg aatccaacag ttgacattga   7320
ggaagctcct gaaatgcctg ccctttatga gaagaaactg gctctatatc tccttccttgc   7380 tctcagccta gcttctgttg ccatgtgcag aacgccccttt tcattggctg aaggcattgt   7440
cctagcatca gctgccctag gccgctcat agagggaaac accagccttc tttggaatgg   7500
acccatggct gtctccatga caggagtcat gagggggaat cactatgctt ttgtgggagt   7560
catgtacaat ctatggaaga tgaaaactgg acgccggggg agcgcgaatg gaaaaacttt   7620
gggtgaagtc tggaagaggg aactgaatct gttggacaag cgacagtttg agttgtataa   7680
aaggaccgac attgtggagg tggatcgtga tacggcacgc aggcatttgg ccgaagggaa   7740
ggtggacacc ggggtggcgg tctccagggg gaccgcaaag ttaaggtggt tccatgagcg   7800
tggctatgtc aagctggaag gtagggtgat tgacctgggg tgtggccgcg gaggctggtg   7860
ttactacgct gctgcgcaaa aggaagtgag tggggtcaaa ggatttactc ttggaagaga   7920
cggccatgag aaacccatga atgtgcaaag tctgggatgg aacatcatca ccttcaagga   7980
caaaactgat atccaccgcc tagaaccagt gaaatgtgac accctttgt gtgacattgg   8040 agagtcatca tcgtcatcgg tcacagaggg ggaaaggacc gtgagagttc ttgatactgt   8100
agaaaaatgg ctgcttgtg gggttgacaa cttctgtgtg aaggtgttag ctccatacat   8160
gccagatgtt ctcgagaaac tggaattgct ccaaaggagg tttggcggaa cagtgatcag   8220
gaaccctctc tccaggaatt ccactcatga aatgtactac gtgtctggag cccgcagcaa   8280
tgtcacattt actgtgaacc aaacatcccg cctcctgatg aggagaatga ggcgtccaac   8340
tggaaaagtg acccctggagg ctgacgtcat cctcccaatt gggacacgca gtgttgagac   8400
agacaaggga ccctggaca aagaggccat agaagaaagg gttgagagga taaaatctga   8460
gtacatgacc tcttggtttt atgacaatga caacccctac aggacctggc actactgtgg   8520 ctccctatgtc acaaaaaacct caggaagtgc ggcgagcatg gtaaatggtg ttattaaaat   8580
```

```
tctgacatat ccatgggaca ggatagagga ggtcacaaga atggcaatga ctgacacaac    8640 ccctttttgga cagcaaagag tgtttaaaga aaaagttgac accagagcaa aggatccacc   8700
agcgggaact aggaagatca tgaaagttgt caacaggtgg ctgttccgcc acctggccag    8760
agaaaagaac cccagactgt gcacaaagga agaatttatt gcaaaagtcc gaagtcatgc   8820
agccattgga gcttacctgg aagaacaaga acagtggaag actgccaatg aggctgtcca   8880
agacccaaag ttctgggaac tggtggatga agaaaggaag ctgcaccaac aaggcaggtg   8940
tcggacttgt gtgtacaaca tgatggggaa aagagagaag aagctgtcag agtttgggaa   9000
agcaaaggga agccgtgcca tatggtatat gtggctggga gcgcggtatc ttgagtttga   9060
ggccctggga ttcctgaatg aggaccattg ggcttccagg gaaaactcag gaggaggagt   9120
ggaaggcatt ggcttacaat acctaggata tgtgatcaga gacctggctg caatggatgg   9180
tggtggattc tacgcggatg acaccgctgg atgggacacg cgcatcacag aggcagacct   9240
tgatgatgaa caggagatct tgaactacat gagcccacat cacaaaaaac tggcacaagc   9300
agtgatggaa atgacataca agaacaaagt ggtgaaagtg ttgagaccag ccccaggagg   9360
gaaagcctac atggatgtca taagtcgacg agaccagaga ggatccgggc aggtagtgac   9420
ttatgctctg aacaccatca ccaacttgaa agtccaattg atcagaatgg cagaagcaga   9480
gatggtgata catcaccaac atgttcaaga ttgtgatgaa tcagttctga ccaggctgga   9540
ggcatggctc actgagcacg gatgtaacag actgaagagg atggcggtga gtggagacga   9600
ctgtgtggtc cggcccatcg atgacaggtt cggcctggcc ctgtcccatc tcaacgccat   9660
gtccaaggtt agaaaggaca tatctgaatg gcagccatca aaagggtgga atgattggga   9720
gaatgtgccc ttctgttccc accacttcca tgaactacag ctgaaggatg gcaggaggat   9780
tgtggtgcct tgccgagaac aggacgagct cattgggaga ggaagggtgt ctccaggaaa   9840
cggctggatg atcaaggaaa cagcttgcct cagcaaagcc tatgccaaca tgtggtcact   9900
gatgtatttt cacaaaaggg acatgaggct actgtcattg ctgtttcct cagctgttcc    9960 cacctcatgg gttccacaag gacgcacaac atggtcgatt catgggaaag gggagtggat   10020
gaccacggaa gacatgcttg aggtgtggaa cagagtatgg ataaccaaca cccacacat    10080 gcaggacaag acaatggtga aaaaatggag agatgtccct tatctaacca agagacaaga   10140
caagctgtgc ggatcactga ttggaatgac caatagggcc acctgggcct cccacatcca   10200
tttggtcatc catcgtatcc gaacgctgat tggacaggag aaatacactg actacctaac   10260
agtcatggac aggtattctg tggatgctga cctgcaactg ggtgagctta tctgaaacac   10320
catctaacag gaataaccgg gatacaaacc acgggtggag aaccggactc cccacaacct   10380
gaaaccggga tataaaccac ggctggagaa ccggactccg cacttaaaat gaaacagaaa   10440
ccgggataaa aactacggat ggagaaccgg actccacaca ttgagacaga agaagttgtc   10500
agcccagaac cccacacgag ttttgccact gctaagctgt gaggcagtgc aggctgggac   10560
agccgacctc caggttgcga aaacctggt ttctgggacc tcccacccca gagtaaaaag     10620 aacgagcct ccgctaccac cctcccacgt ggtggtagaa agacgggtc tagaggttag      10680 aggagaccct ccagggaaca aatagtggga ccatattgac gccagggaaa gaccggagtg   10740
gttctctgct tttcctccag aggtctgtga gcacagtttg ctcaagaa                10788

<210> SEQ ID NO 11
<211> LENGTH: 10811
<212> TYPE: DNA
<213> ORGANISM: Flaviviridae Flavivirus Yellow Fever Virus
```

<400> SEQUENCE: 11

```
tgcattggtc tgcaaatcga gttgctaggc aataaacaca tttggattaa tttttaatcgt      60
tcgttgagcg attagcagag aactgaccag aacatgtctg gtcgtaaagc tcagggaaaa     120
accctgggcg tcaatatggt acgacgagga gttcgctcct tgtcaaacaa aataaaacaa     180
aaaacgaaac aaattggaaa cagacctgga ccttcaagag gtgttcaagg atttatcttt     240
ttctttttgt tcaacatttt gactggaaaa aagatcacag cccacctaaa gaggttgtgg     300
aaaatgctgg acccaagaca aggcttggct gttctaagga aagtcaagag agtggtggcc     360
agtttgatga gaggattgtc ctcaaggaaa cgccgttccc atgatgttct gactgtgcaa     420
ttcctaattt tgggaatgct gttgatgacg ggtggagtga ccttggtgcg aaaaacaga      480
tggttgctcc taaatgtgac atctgaggac ctcgggaaaa cattctctgt gggcacaggc     540
aactgcacaa caaacatttt ggaagccaag tactggtgcc cagactcaat ggaatacaac     600
tgtcccaatc tcagtccaag agaggagcca gatgacattg attgctggtg ctatggggtg     660
gaaaacgtta gagtcgcata tggtaagtgt gactcagcag gcaggtctag gaggtcaaga     720
agggccattg acttgcctac gcatgaaaac catggtttga agacccggca agaaaaatgg     780
atgactggaa gaatgggtga aaggcaactc caaaagattg agagatggtt cgtgaggaac     840
ccctttttttg cagtgacggc tctgaccatt gcctacttg tgggaagcaa catgacgcaa     900
cgagtcgtga ttgccctact ggtcttggct gttggtccgg cctactcagc tcactgcatt     960
ggaattactg acagggattt cattgagggg gtgcatggag aacttgggt ttcagctacc    1020
ctggagcaag acaagtgtgt cactgttatg gcccctgaca agccttcatt ggacatctca    1080
ctagagacag tagccattga tagacctgct gaggtgagga agtgtgtta caatgcagtt    1140
ctcactcatg tgaagattaa tgacaagtgc cccagcactg gagaggccca cctagctgaa    1200
gagaacgaag gggacaatgc gtgcaagcgc acttattctg atagaggctg gggcaatggc    1260
tgtggcctat ttgggaaagg gagcattgtg gcatgcgcca aattcacttg tgccaaatcc    1320
atgagtttgt ttgaggttga tcagaccaaa attcagtatg tcatcagagc acaattgcat    1380
gtaggggcca agcaggaaaa ttggactacc gacattaaga ctctcaggtt tgatgccctg    1440
tcaggctccc aggaagtcga gttcattggg tatggaaaag ccacactgga atgccaggtg    1500
caaactgcgg tggactttgg taacagttac atcgctgaga tggaaacaga gagctggata    1560
gtggacagac agtgggccca ggacttgacc ctgccatggc agagtggaag tggcggggtg    1620
tggagagaga tgcatcatct tgtcgaattt gaacctcgc atgccgccac tatcagagta    1680
ctggcctgg gaaaccagga aggctccttg aaaacagctc ttactggcgc aatgagggtt    1740
acaaaggaca caaatgacaa caacctttac aaactacatg gtggacatgt tcttgcaga      1800
gtgaaattgt cagctttgac actcaagggg acatcctaca aaatatgcac tgacaaaatg    1860
ttttttgtca agaacccaac tgacactggc catggcactg ttgtgatgca ggtgaaagtg    1920
tcaaaaggag cccctgcag gattccagtg atagtagctg atgatcttac agcggcaatc    1980
aataaaggca ttttggttac agttaacccc atcgcctcaa ccaatgatga tgaagtgctg    2040
attgaggtga acccacctt tggagacagc tacattatcg ttgggagagg agattcacgt    2100
ctcacttacc agtggcacaa agaggaagc tcaataggaa agttgttcac tcagaccatg    2160
aaaggcgtgg aacgcctggc cgtcatggga gacaccgcct gggatttcag ctccgctgga    2220
gggttcttca cttcggttgg gaaaggaatt catacggtgt ttggctctgc ctttcagggg    2280
ctatttggcg gcttgaactg gataacaaag gtcatcatgg gggcggtact tatatgggtt    2340
```

```
ggcatcaaca caagaaacat gacaatgtcc atgagcatga tcttggtagg agtgatcatg   2400
atgttttgt ctctaggagt tggggcggat caaggatgcg ccatcaactt tggcaagaga    2460
gagctcaagt gcggagatgg tatcttcata tttagagact ctgatgactg gctgaacaag   2520
tactcatact atccagaaga tcctgtgaag cttgcatcaa tagtgaaagc ctcttttgaa   2580
gaagggaagt gtggcctaaa ttcagttgac tcccttgagc atgagatgtg gagaagcagg   2640
gcagatgaga tcaatgccat ttttgaggaa aacgaggtgg acatttctgt tgtcgtgcag   2700
gatccaaaga atgttttacca gagaggaact catccatttt ccagaattcg ggatggtctg   2760
cagtatggtt ggaagacttg gggtaagaac cttgtgttct ccccagggag aagaatgga    2820
agcttcatca tagatggaaa gtccaggaaa gaatgcccgt tttcaaaccg ggtctggaat   2880
tctttccaga tagaggagtt tgggacggga gtgttcacca cacgcgtgta catgacgca    2940
gtctttgaat acaccataga ctgcgatgga tctatcttgg gtgcagcggt aacggaaaa    3000
aagagtgccc atggctctcc aacattttgg atgggaagtc atgaagtaaa tgggacatgg   3060
atgatccaca ccttggaggc attagattac aaggagtgtg agtggccact gacacatacg   3120
attggaacat cagttgaaga gagtgaaatg ttcatgccga atcaatcgg aggcccagtt    3180
agctctcaca atcatatccc tggatacaag gttcagacga acggaccttg gatgcaggta   3240
ccactagaag tgaagagaga agcttgccca gggactagcg tgatcattga tggcaactgt   3300
gatggacggg aaaatcaac cagatccacc acggatagcg ggaaagttat tcctgaatgg   3360
tgttgccgct cctgcataat gccgcctgtg agcttccatg gtagtgatgg gtgttggtat   3420
cccatggaaa ttaggccaag gaaaacgcat gaaagccatc tggtgcgctc ctgggttaca   3480
gctgagaaa tacatgctgt cccttttggt ttggtgagca tgatgatagc aatgaaagtg    3540
gtcctaagga aaagacaggg accaaagcaa atgttggttg gaggagtagt gctcttggga   3600
gcaatgctgg tcgggcaagt aactctcctt gatttgctga aactcacagt ggctgtggga   3660
ttgcatttcc atgagatgaa caatggagga gacgccatgt atatggcgtt gattgctgcc   3720
ttttcaatca gaccagggct gctcatcggc tttgggctca ggaccctatg gagccctcgg   3780
gaacgccttg tgctgacccct aggagcagcc atggtggaga ttgccttggg tggcgtgatg   3840
ggcggcctgt ggaagtatct aaatgcagtt ctctctgca tcctgacaat aaatgctgtt   3900
gcttctagga aagcatcaaa taccatcttg ccctcatgg ctctgttgac acctgtcact   3960
atggctgagg tgagacttgc cgcaatgttc ctttgtgccg tggttatcat aggggtcctt   4020
caccagaatt tcaaggacac ctccatgcag aagactatac ctctggtggc cctcacactc   4080
acatcttacc tgggcttgac acaacctttt ttgggcctgt gtgcatttct ggcaacccgc   4140
atatttgggc gaaggagtat cccagtgaat gaggcactcg cagcagctgg tctagtggga   4200
gtgctggcag gactggcttt tcaggagatg gagaacttcc ttggtccgat tgcagttgga   4260
ggactcctga tgatgctggt tagcgtggct gggagggtgg atgggctaga gctcaagaag   4320
cttggtgaag tttcatggga agaggaggcg agatcagcg ggagttccgc ccgctatgat   4380
gtggcactca gtgaacaagg ggagttcaag ctgctttctg aagagaaagt gccatgggac   4440
caggttgtga tgacctcgct ggccttggtt ggggctgccc tccatccatt tgctcttctg   4500
ctggtccttg ctgggtggct gtttcatgtc agggagcta ggagaagtgg ggatgtcttg    4560
tgggatattc ccactcctaa gatcatcgag gaatgtgaac atctggagga tgggatttat   4620
ggcatattcc agtcaacctt cttggggcc tcccagcgag gagtgggagt ggcacaggga   4680
ggggtgttcc acacaatgtg gcatgtcaca agaggagctt tccttgtcag gaatggcaag   4740
```

```
aagttgattc catcttgggc ttcagtaaag gaagaccttg tcgcctatgg tggctcatgg    4800
aagttggaag gcagatggga tggagaggaa gaggtccagt tgatcgcggc tgttccagga    4860
aagaacgtgg tcaacgtcca gacaaaaccg agcttgttca aagtgaggaa tgggggagaa    4920
atcggggctg tcgctcttga ctatccgagt ggcacttcag gatctcctat tgttaacagg    4980
aacggagagg tgattgggct gtacggcaat ggcatccttg tcggtgacaa ctccttcgtg    5040
tccgccatat cccagactga ggtgaaggaa aaggaaagg aggagctcca agagatcccg     5100
acaatgctaa agaaaggaat gacaactgtc cttgattttc atcctggagc tgggaagaca    5160
agacgtttcc tcccacagat cttggccgag tgcgcacgga gacgcttgcg cactcttgtg    5220
ttggccccca ccagggttgt tctttctgaa atgaaggagg cttttcacgg cctggacgtg    5280
aaattccaca cacaggcttt ttccgctcac ggcagcggga gagaagtcat tgatgctatg    5340
tgccatgcca ccctaactta caggatgttg gaaccaacta gggttgttaa ctgggaagtg    5400
atcattatgg atgaagccca tttttggat ccagctagca tagccgctag aggttgggca    5460
gcgcacagag ctagggcaaa tgaaagtgca acaatcttga tgacagccac accgcctggg    5520
actagtgatg aatttccaca ttcaaatggt gaaatagaag atgttcaaac ggacataccc    5580
agtgagccct ggaacacagg gcatgactgg atcctggctg acaaaaggcc cacggcatgg    5640
ttccttccat ccatcagagc tgcaaatgtc atggctgcct ctttgcgtaa ggctggaaag    5700
agtgtggtgg tcctgaacag gaaaaccttt gagagagaat accccacgat aaagcagaag    5760
aaacctgact ttatattggc cactgacata gctgaaatgg gagccaacct ttgcgtggag    5820
cgagtgctgg attgcaggac ggcttttaag cctgtgcttg tggatgaagg gaggaaggtg    5880
gcaataaaag ggccacttcg tatctccgca tcctctgctg ctcaaaggag ggggcgcatt    5940
gggagaaatc ccaacagaga tggagactca tactactatt ctgagcctac aagtgaaaat    6000 aatgccacc acgtctgctg gttggaggcc tcaatgctct tggacaacat ggaggtgagg     6060
ggtggaatgg tcgccccact ctatggcgtt gaaggaacta aaacaccagt tcccctggt     6120 gaaatgagac tgagggatga ccagaggaaa gtcttcagag aactagtgag gaattgtgac    6180
ctgcccgttt ggctttcgtg gcaagtggcc aaggctggtt tgaagacgaa tgatcgtaag    6240
tggtgttttg aaggccctga ggaacatgag atcttgaatg acagcggtga acagtgaag    6300 tgcagggctc ctggaggagc aaagaagcct ctgcgcccaa ggtggtgtga tgaaagggtg    6360
tcatctgacc agagtgcgct gtctgaattt attaagtttg ctgaaggtag gaggggagct    6420
gctgaagtgc tagttgtgct gagtgaactc cctgatttcc tggctaaaaa aggtggagag    6480
gcaatggata ccatcagtgt gtttctccac tctgaggaag gctctagggc ttaccgcaat    6540
gcactatcaa tgatgcctga ggcaatgaca atagtcatgc tgtttatact ggctggacta    6600
ctgacatcgg gaatggtcat cttttcatg tctcccaaag gcatcagtag aatgtctatg    6660
gcgatgggca caatggccgg ctgtggatat ctcatgttcc ttggaggcgt caaacccact    6720
cacatctcct atatcatgct catattcttt gtcctgatgg tggttgtgat ccccgagcca    6780
gggcaacaaa ggtccatcca agacaaccaa gtggcatacc tcattattgg catcctgacg    6840
ctggtttcag cggtggcagc caacgagcta ggcatgctgg agaaaaccaa agaggacctc    6900
tttgggaaga agaacttaat tccatctagt gcttcaccct ggagttggcc ggatcttgac    6960
ctgaagccag gagctgcctg gacagtgtac gttggcattg ttacaatgct ctctccaatg    7020
ttgcaccact ggatcaaagt cgaatatggc aacctgtctc tgtctggaat agcccagtca    7080
gcctcagtcc tttctttcat ggacaagggg ataccattca tgaagatgaa tatctcggtc    7140
```

-continued

```
ataatgctgc tggtcagtgg ctggaattca ataacagtga tgcctctgct ctgtggcata    7200
gggtgcgcca tgctccactg gtctctcatt ttacctggaa tcaaagcgca gcagtcaaag    7260
cttgcacaga gaagggtgtt ccatggcgtt gccaagaacc ctgtggttga tgggaatcca    7320
acagttgaca ttgaggaagc tcctgaaatg cctgcccttt atgagaagaa actggctcta    7380
tatctccttc ttgctctcag cctagcttct gttgccatgt gcagaacgcc cttttcattg    7440
gctgaaggca ttgtcctagc atcagctgcc ctagggccgc tcatagaggg aaacaccagc    7500
cttctttgga atggacccat ggctgtctcc atgacaggag tcatgagggg gaatcactat    7560
gcttttgtgg gagtcatgta caatctatgg aagatgaaaa ctggacgccg ggggagcgcg    7620
aatgaaaaaa ctttgggtga agtctggaag agggaactga atctgttgga caagcgacag    7680
tttgagttgt ataaaaggac cgacattgtg gaggtggatc gtgatacggc acgcaggcat    7740
ttggccgaag ggaaggtgga caccggggtg gcggtctcca ggggaccgc aaagttaagg     7800 tggttccatg agcgtggcta tgtcaagctg gaaggtaggg tgattgacct ggggtgtggc    7860
cgcggaggct ggtgttacta cgctgctgcg caaaaggaag tgagtggggt caaaggattt    7920
actcttggaa gagacggcca tgagaaaccc atgaatgtgc aaagtctggg atggaacatc    7980
atcaccttca aggacaaaac tgatatccac cgcctagaac cagtgaaatg tgacacccct    8040
ttgtgtgaca ttggagagtc atcatcgtca tcggtcacag aggggaaag gaccgtgaga     8100 gttcttgata ctgtagaaaa atggctggct tgtgggggttg acaacttctg tgtgaaggtg   8160
ttagctccat acatgccaga tgttctcgag aaactggaat tgctccaaag gaggtttggc    8220
ggaacagtga tcaggaaccc tctctccagg aattccactc atgaaatgta ctacgtgtct    8280
ggagcccgca gcaatgtcac atttactgtg aaccaaacat cccgcctcct gatgaggaga    8340
atgaggcgtc caactggaaa agtgacccctg gaggctgacg tcatcctccc aattgggaca   8400
cgcagtgttg agacagacaa gggacccctg gacaaagagg ccatagaaga aagggttgag    8460
aggataaaat ctgagtacat gacctcttgg ttttatgaca tgacaaccc ctacaggacc     8520 tggcactact gtggctccta tgtcacaaaa acctcaggaa gtgcggcgag catggtaaat    8580
ggtgttatta aaattctgac atatccatgg gacaggatag aggaggtcac aagaatggca    8640
atgactgaca caacccctttt tggacagcaa agagtgttta agaaaaagt tgacaccaga    8700 gcaaaggatc caccagcggg aactaggaag atcatgaaag ttgtcaacag gtggctgttc    8760
cgccacctgg ccagagaaaa gaaccccaga ctgtgcacaa aggaagaatt tattgcaaaa    8820
gtccgaagtc atgcagccat tggagcttac ctggaagaac aagaacagtg gaagactgcc    8880
aatgaggctg tccaagaccc aaagttctgg gaactggtgg atgaagaaag gaagctgcac    8940
caacaaggca ggtgtcggac ttgtgtgtac aacatgatgg ggaaaagaga agaagctgctg   9000 tcagagtttg gaaagcaaa gggaagccgt gccatatggt atatgtggct gggagcgcgg    9060
tatcttgagt ttgaggccct gggattcctg aatgaggacc attgggcttc cagggaaaac    9120
tcaggaggag gagtggaagg cattggctta caatacctag gatatgtgat cagagacctg    9180
gctgcaatgg atggtggtgg attctacgcg gatgacaccg ctggatggga cacgcgcatc    9240
acagaggcag accttgatga tgaacaggag atcttgaact acatgagccc acatcacaaa    9300
aaactggcac aagcagtaat ggaaatgaca tacaagaaca agtggtgaa agtgttgaga     9360 ccagccccag gagggaaagc ctacatggat gtcataagtc gacgagacca gagaggatcc    9420
gggcaggtag tgacttatgc tctgaacacc atcaccaact tgaaagtcca attgatcaga    9480
atggcagaag cagagatggt gatacatcac caacatgttc aagattgtga tgaatcagtt    9540
```

```
ctgaccaggc tggaggcatg gctcactgag cacggatgta acagactgaa gaggatggcg   9600
gtgagtggag acgactgtgt ggtccggccc atcgatgaca ggttcggcct ggccctgtcc   9660
catctcaacg ccatgtccaa ggttagaaag acatatctg  aatggcagcc atcaaaaggg   9720
tggaatgatt gggagaatgt gcccttctgt tcccaccact tccatgaact acagctgaag   9780
gatggcagga ggattgtggt gccttgccga aacaggacg  agctcattgg gagaggaagg   9840
gtgtctccag aaacggctg  gatgatcaag gaaacagctt gcctcagcaa agcctatgcc   9900
aacatgtggt cactgatgta ttttcacaaa agggacatga ggctactgtc attggctgtt   9960
tcctcagctg ttcccacctc atgggttcca caaggacgca acatggtc  gattcatggg   10020 aaaggggagt ggatgaccac ggaagacatg cttgaggtgt ggaacagagt atggataacc  10080
aacaacccac acatgcagga caagacaatg gtgaaaaaat ggagagatgt cccttatcta  10140
accaagagac aagacaagct gtgcggatca ctgattggaa tgaccaatag ggccacctgg  10200
gcctcccaca tccatttggt catccatcgt atccgaacgc tgattggaca ggagaaatac  10260
actgactacc taacagtcat ggacaggtat tctgtggatg ctgacctgca actgggtgag  10320
cttatctgaa acaccatcta acaggaataa ccgggataca aaccacgggt ggagaaccgg  10380
actccccaca acctgaaacc gggatataaa ccacggctgg agaaccggac tccgcactta  10440
aaatgaaaca gaaccggga  taaaaactac ggatggagaa ccggactcca cacattgaga  10500
cagaagaagt tgtcagccca gaaccccaca cgagttttgc cactgctaag ctgtgaggca  10560
gtgcaggctg ggacagccga cctccaggtt gcgaaaaacc tggtttctgg gacctcccac  10620
cccagagtaa aagaacgga  gcctccgcta ccaccctccc acgtggtggt agaaagacgg  10680
ggtctagagg ttagaggaga ccctccaggg aacaaatagt gggaccatat tgacgccagg  10740
gaaagaccgg agtggttctc tgcttttcct ccagaggtct gtgagcacag tttgctcaag  10800
aataagcaga c                                                       10811
```

<210> SEQ ID NO 12
<211> LENGTH: 10785
<212> TYPE: DNA
<213> ORGANISM: Flaviviridae Flavivirus Yellow Fever Virus

<400> SEQUENCE: 12

```
tcgagttgct aggcaataaa cacatttgga ttaattttaa tcgttcgttg agcgattagc     60
agagaactga ccagaacatg tctggtcgta aagctcaggg aaaaaccctg ggcgtcaata    120
tggtacgacg aggagttcgc tccttgtcaa acaaaataaa acaaaaaaca aacaaattg     180 gaaacagacc tggaccttca agaggtgttc aaggatttat ctttttcttt ttgttcaaca    240
ttttgactgg aaaaaagatc acagcccacc taaagaggtt gtggaaaatg ctggacccaa    300
gacaaggctt ggctgttcta aggaaagtca agagagtggg ggccagtttg atgagaggat    360
tgtcctcaag gaaacgccgt tcccatgatg ttctgactgt gcaattccta atttgggaa     420 tgctgttgat gacgggtgga gtgacccttg gtcggaaaaa cagatggttg ctcctaaatg    480
tgacatctga ggacctcggg aaaacattct ctgtgggcac aggcaactgc acaacaaaca    540
ttttggaagc caagtactgg tgcccagact caatggaata caactgtccc aatctcagtc    600
caagagagga gccagatgac attgattgct ggtgctatgg ggtggaaaac gttagagtcg    660
catatggtaa gtgtgactca gcaggcaggt ctaggaggtc aagaagggcc attgacttgc    720
ctacgcatga aaaccatggt ttgaagaccc ggcaagaaaa atggatgact ggaagaatgg    780
gtgaaaggca actccaaaag attgagagat ggttcgtgag gaacccttt  tttgcagtga    840
```

```
cggctctgac cattgcctac cttgtgggaa gcaacatgac gcaacgagtc gtgattgccc      900
tactggtctt ggctgttggt ccggcctact cagctcactg cattggaatt actgacaggg      960
atttcattga gggggtgcat ggaggaactt gggtttcagc taccctggag caagacaagt     1020
gtgtcactgt tatggcccct gacaagcctt cattggacat ctcactagag acagtagcca     1080
ttgatagacc tgctgaggtg aggaaagtgt gttacaatgc agttctcact catgtgaaga     1140
ttaatgacaa gtgcccagc actggagagg cccacctagc tgaagagaac gaagggaca       1200 atgcgtgcaa gcgcacttat tctgatagag ctggggcaa tggctgtggc ctatttggga      1260
aagggagcat tgtggcatgc gccaaattca cttgtgccaa atccatgagt ttgtttgagg     1320
ttgatcagac caaaattcag tatgtcatca gagcacaatt gcatgtaggg gccaagcagg     1380
aaaattggac taccgacatt aagactctca gtttgatgc cctgtcaggc tcccaggaag      1440
tcgagttcat tgggtatgga aaagctacac tggaatgcca ggtgcaaact gcggtggact     1500
ttggtaacag ttacatcgct gagatggaaa cagagagctg gatagtggac agacagtggg     1560
cccaggactt gaccctgcca tggcagagtg gaagtggcgg ggtgtggaga gagatgcatc     1620
atcttgtcga atttgaacct ccgcatgccg ccactatcag agtactggcc ctgggaaacc     1680
aggaaggctc cttgaaaaca gctcttactg gcgcaatgag ggttacaaag gacacaaatg     1740
acaacaacct ttacaaacta catggtggac atgtttcttg cagagtgaaa ttgtcagctt     1800
tgacactcaa ggggacatcc tacaaaatat gcactgacaa aatgtttttt gtcaaaaacc     1860
caactgacac tggccatggc actgttgtga tgcaggtgaa agtgtcaaaa ggagccccct     1920
gcaggattcc agtgatagta gctgatgatc ttacagcggc aatcaataaa gcatttggg      1980 ttacagttaa ccccatcgcc tcaaccaatg atgatgaagt gctgattgag gtgaacccac     2040
cttttggaga cagctacatt atcgttggga gaggagattc acgtctcact taccagtggc     2100
acaaagaggg aagctcaata ggaaagttgt tcactcagac catgaaaggc gtggaacgcc     2160
tggccgtcat gggagacacc gcctgggatt tcagctccgc tggagggttc ttcacttcgg     2220
ttgggaaagg aattcatacg gtgtttggct ctgcctttca ggggctattt ggcggcttga     2280
actggataac aaaggtcatc atgggggcgg tacttatatg ggttggcatc aacacaagaa     2340
acatgacaat gtccatgagc atgatcttgg taggagtgat catgatgttt ttgtctctag     2400
gagttggggc ggatcaagga tgcgccatca actttggcaa gagagagctc aagtgcggag     2460
atggtatctt catatttaga gactctgatg actggctgaa caagtactca tactatccag     2520
aagatcctgt gaagcttgca tcaatagtga agcctctttt tgaagaaggg aagtgtggcc     2580
taaattcagt tgactccctt gagcatgaga tgtggagaag cagggcagat gagatcaatg     2640
ccatttttga ggaaaacgag gtggacattt ctgttgtcgt gcaggatcca aagaatgttt     2700
accagagagg aactcatcca tttttccagaa ttcgggatgg tctgcagtat ggttggaaga     2760 cttgggtaa gaaccttgtg ttctccccag ggaggaagaa tggaagcttc atcatagatg      2820
gaaagtccag gaaagaatgc ccgttttcaa accgggtctg gaattctttc cagatagagg     2880
agtttgggac gggagtgttc accacacgcg tgtacatgga cgcagtcttt gaatacacca     2940
tagactgcga tggatctatc ttgggtgcag cggtgaacgg aaaaaagagt gcccatggct     3000
ctccaacatt ttggatggga agtcatgaag taaatggac atggatgatc cacaccttgg       3060
aggcattaga ttacaaggag tgtgagtggc cactgacaca tacgattgga acatcagttg     3120
aagagagtga aatgttcatg ccgagatcaa tcggaggccc agttagctct cacaatcata     3180
tccctggata caaggttcag acgaacggac cttggatgca ggtaccacta gaagtgaaga     3240
```

```
gagaagcttg cccagggact agcgtgatca ttgatggcaa ctgtgatgga cggggaaaat   3300
caaccagatc caccacggat agcgggaaag ttattcctga atggtgttgc cgctcctgca   3360
caatgccgcc tgtgagcttc catggtagtg atgggtgttg gtatcccatg gaaattaggc   3420
caaggaaaac gcatgaaagc catctggtgc gctcctgggt tacagctgga gaaatacatg   3480
ctgtcccttt tggtttggtg agcatgatga tagcaatgga agtggtccta aggaaaagac   3540
agggaccaaa gcaaatgttg gttggaggag tagtgctctt gggagcaatg ctggtcgggc   3600
aagtaactct ccttgatttg ctgaaactca cagtggctgt gggattgcat ttccatgaga   3660
tgaacaatgg aggagacgcc atgtatatgg cgttgattgc tgccttttca atcagaccag   3720
ggctgctcat cggctttggg ctcaggaccc tatggagccc tcgggaacgc cttgtgctga   3780
ccctaggagc agccatggtg gagattgcct tgggtggcgt gatgggcggc ctgtggaagt   3840
atctaaatgc agtttctctc tgcatcctga caataaatgc tgttgcttct aggaaagcat   3900
caaataccat cttgcccctc atggctctgt tgacacctgt cactatggct gaggtgagac   3960
ttgccgcaat gttctttttgt gccgtggtta tcatagggt ccttcaccag aatttcaagg   4020
acacctccat gcagaagact atacctctgg tggccctcac actcacatct tacctgggct   4080
tgacacaacc ttttttgggc ctgtgtgcat ttctggcaac ccgcatattt gggcgaagga   4140
gtatcccagt gaatgaggca ctcgcagcag ctggtctagt gggagtgctg caggactgg   4200
cttttcagga gatggagaac ttccttggtc cgattgcagt tggaggactc ctgatgatgc   4260
tggttagcgt ggctgggagg gtggatgggc tagagctcaa gaagcttggt gaagtttcat   4320
gggaagagga ggcggagatc agcgggagtt ccgcccgcta tgatgtggca ctcagtgaac   4380
aaggggagtt caagctgctt tctgaagaga aagtgccatg ggaccaggtt gtgatgacct   4440
cgctggcctt ggttggggct gccctccatc catttgctct tctgctggtc cttgctgggt   4500
ggctgtttca tgtcagggga ctaggagaa gtggggatgt cttgtgggat attcccactc   4560
ctaagatcat cgaggaatgt gaacatctgg aggatgggat ttatggcata ttccagtcaa   4620
ccttcttggg ggcctcccag cgaggagtgg gagtggcaca gggagggtg ttccacacaa   4680
tgtggcatgt cacaagagga gctttccttg tcaggaatgg caagaagttg attccatctt   4740
gggcttcagt aaaggaagac cttgtcgcct atggtggctc atggaagttg gaaggcagat   4800
gggatggaga ggaagaggtc cagttgatcg cggctgttcc aggaaagaac gtggtcaacg   4860
tccagacaaa accgagcttg ttcaaagtga ggaatgggg agaaatcggg gctgtcgctc   4920
ttgactatcc gagtggcact tcaggatctc ctattgttaa caggaacgga gaggtgattg   4980
ggctgtacgg caatgcatc cttgtcggtg acaactcctt cgtgtccgcc atatcccaga   5040
ctgaggtgaa ggaagaagga aaggaggagc tccaagagat cccgacaatg ctaaagaaag   5100
gaatgacaac tgtccttgat tttcatcctg gagctgggaa gacaagacgt ttcctcccac   5160
agatcttggc cgagtgcgca cggagacgct tgcgcactct tgtgttggcc cccaccaggg   5220
ttgttctttc tgaaatgaag gaggcttttc acggcctgga cgtgaaattc cacacacagg   5280
cttttttccgc tcacggcagc gggagagaag tcattgatgc tatgtgccat gccaccctaa   5340
cttacaggat gttggaacca actagggttg ttaactggga agtgatcatt atggatgaag   5400
cccatttttt ggatccagct agcatagccg ctagaggttg ggcagcgcac agagctaggg   5460
caaatgaaag tgcaacaatc ttgatgacag ccacaccgcc tgggactagt gatgaatttc   5520
cacattcaaa tggtgaaata gaagatgttc aaacggacat acccagtgag ccctggaaca   5580
cagggcatga ctggatcctg gctgacaaaa ggcccacggc atggttcctt ccatccatca   5640
```

```
gagctgcaaa tgtcatggct gcctctttgc gtaaggctgg aaagagtgtg gtggtcctga    5700
acaggaaaac ctttgagaga gaatacccca cgataaagca gaagaaacct gactttatat    5760
tggccactga catagctgaa atgggagcca acctttgcgt ggagcgagtg ctggattgca    5820
ggacggcttt taagcctgtg cttgtggatg aagggaggaa ggtggcaata aaagggccac    5880
ttcgtatctc cgcatcctct gctgctcaaa ggagggggcg cattgggaga atcccaaca    5940 gagatggaga ctcatactac tattctgagc ctacaagtga aaataatgcc caccacgtct    6000
gctggttgga ggcctcaatg ctcttggaca acatggaggt gaggggtgga atggtcgccc    6060
cactctatgg cgttgaagga actaaaacac cagtttcccc tggtgaaatg agactgaggg    6120
atgaccagag gaaagtcttc agagaactag tgaggaattg tgacctgccc gtttggcttt    6180
cgtggcaagt ggccaaggct ggtttgaaga cgaatgatcg taagtggtgt tttgaaggcc    6240
ctgaggaaca tgagatcttg aatgacagcg gtgaaacagt gaagtgcagg gctcctggag    6300
gagcaaagaa gcctctgcgc ccaaggtggt gtgatgaaag ggtgtcatct gaccagagtg    6360
cgctgtctga atttattaag tttgctgaag gtaggagggg agctgctgaa gtgctagttg    6420
tgctgagtga actccctgat ttcctggcta aaaaggtgg agaggcaatg gataccatca     6480
gtgtgtttct ccactctgag gaaggctcta gggcttaccg caatgcacta tcaatgatgc    6540
ctgaggcaat gacaatagtc atgctgttta tactggctgg actactgaca tcgggaatgg    6600
tcatcttttt catgtctccc aaaggcatca gtagaatgtc tatggcgatg ggcacaatgg    6660
ccggctgtgg atatctcatg ttccttggag gcgtcaaacc cactcacatc tcctatatca    6720
tgctcatatt ctttgtcctg atggtggttg tgatccccga gccagggcaa caaaggtcca    6780
tccaagacaa ccaagtggca tacctcatta ttggcatcct gacgctggtt tcagcggtgg    6840
cagccaacga gctaggcatg ctggagaaaa ccaaagagga cctctttggg aagaagaact    6900
taattccatc tagtgcttca ccctggagtt ggccggatct tgacctgaag ccaggagctg    6960
cctggacagt gtacgttggc attgttacaa tgctctctcc aatgttgcac cactggatca    7020
aagtcgaata tggcaacctg tctctgtctg aatagcccca gtcagcctca gtcctttctt    7080
tcatggacaa ggggatacca ttcatgaaga tgaatatctc ggtcataatg ctgctggtca    7140
gtggctggaa ttcaataaca gtgatgcctc tgctctgtgg catggggtgc gccatgctcc    7200
actggtctct cattttacct ggaatcaaag cgcagcagtc aaagcttgca cagagaaggg    7260
tgttccatgg cgttgccaag aaccctgtgg ttgatgggaa tccaacagtt gacattgagg    7320
aagctcctga aatgcctgcc ctttatgaga agaaactggc tctatatctc cttcttgctc    7380
tcagcctagc ttctgttgcc atgtgcagaa cgcccttttc attggctgaa ggcattgtcc    7440
tagcatcagc tgccctaggg ccgctcatag agggaaacac cagccttctt tggaatggac    7500
ccatggctgt ctccatgaca ggagtcatga ggggaatca ctatgctttt gtgggagtca     7560
tgtacaatct atggaagatg aaaactggac gccgggggag cgcgaatgga aaaactttgg    7620
gtgaagtctg gaagagggaa ctgaatctgt ggacaagcg acagtttgag ttgtataaaa     7680
ggaccgacat tgtggaggtg gatcgtgata cggcacgcag gcatttggcc gaagggaagg    7740
tggacaccgg ggtggcggtc tccagggga ccgcaaagtt aaggtggttc catgagcgtg      7800
gctatgtcaa gctggaaggt agggtgattg acctggggt tggccgcgga ggctggtgtt     7860
actacgctgc tgcgcaaaag gaagtgagtg gggtcaaagg atttactctt ggaagagacg    7920
gccatgagaa acccatgaat gtgcaaagtc tgggatggaa catcatcacc ttcaaggaca    7980
aaactgatat ccaccgccta gaaccagtga atgtgacac ccttttgtgt gacattggag      8040
```

```
agtcatcatc gtcatcggtc acagaggggg aaaggaccgt gagagttctt gatactgtag    8100
aaaaatggct ggcttgtggg gttgacaact tctgtgtgaa ggtgttagct ccatacatgc    8160
cagatgttct cgagaaactg gaattgctcc aaaggaggtt tggcggaaca gtgatcagga    8220
accctctctc caggaattcc actcatgaaa tgtactacgt gtctggagcc cgcagcaatg    8280
tcacatttac tgtgaaccaa acatcccgcc tcctgatgag gagaatgagg cgtccaactg    8340
gaaaagtgac cctggaggct gacgtcatcc tcccaattgg gacacgcagt gttgagacag    8400
acaagggacc cctggacaaa gaggccatag aagaaagggt tgagaggata aaatctgagt    8460
acatgacctc ttggttttat gacaatgaca accccctacag gacctggcac tactgtggct    8520
cctatgtcac aaaaacctca ggaagtgcgg cgagcatggt aaatggtgtt attaaaattc    8580
tgacatatcc atgggacagg atagaggagg tcacaagaat ggcaatgact gacacaaccc    8640
cttttggaca gcaaagagtg tttaaagaaa aagttgacac cagagcaaag gatccaccag    8700
cgggaactag gaagatcatg aaagttgtca acaggtggct gttccgccac ctggccagag    8760
aaaagaaccc cagactgtgc acaaaggaag aatttattgc aaaagtccga agtcatgcag    8820
ccattggagc ttacctggaa gaacaagaac agtggaagac tgccaatgag gctgtccaag    8880
acccaaagtt ctgggaactg gtggatgaag aaaggaagct gcaccaacaa ggcaggtgtc    8940
ggacttgtgt gtacaacatg atggggaaaa gagagaagaa gctgtcagag tttgggaaag    9000
caaagggaag ccgtgccata tggtatatgt ggctgggagc gcggtatctt gagtttgagg    9060
ccctgggatt cctgaatgag gaccattggg cttccaggga aaactcagga ggaggagtgg    9120
aaggcattgg cttacaatac ctaggatatg tgatcagaga cctggctgca atggatggtg    9180
gtggattcta cgcggatgac accgctgat gggacacgcg catcacagag gcagaccttg    9240
atgatgaaca ggagatcttg aactacatga gcccacatca caaaaactg gcacaagcag    9300 tgatggaaat gacatacaag aacaaagtgg tgaaagtgtt gagaccagcc ccaggaggga    9360
aagcctacat ggatgtcata agtcgacgag accagagagg atccgggcag gtagtgactt    9420
atgctctgaa caccatcacc aacttgaaag tccaattgat cagaatggca gaagcagaga    9480
tggtgataca tcaccaacat gttcaagatt gtgatgaatc agttctgacc aggctggagg    9540
catggctcac tgagcacgga gtgtaacagac tgaagaggat ggcggtgagt ggagacgact    9600
gtgtggtccg gcccatcgat gacaggtttg gcctggccct gtcccatctc aacgccatgt    9660
ccaaggttag aaaggacata tctgaatggc agccatcaaa agggtggaat gattgggaga    9720
atgtgcccct ctgttccac cacttccatg aactacagct gaaggatggc aggaggattg    9780
tggtgccttg ccgagaacag gacgagctca ttgggagagg aagggtgtct ccaggaaacg    9840
gctggatgat caaggaaaca gcttgcctca gcaaagccta tgccaacatg tggtcactga    9900
tgtattttca caaagggac atgaggctac tgtcattggc tgtttcctca gctgttccca    9960
cctcatgggt tccacaagga cgcacaacat ggtcgattca tgggaagggg gagtggatga   10020
ccacggaaga catgcttgag gtgtggaaca gagtatggat aaccaacaac ccacacatgc   10080
aggacaagac aatggtgaaa aaatggagag atgtcccta tctaaccaag agacaagaca   10140
agctgtgcgg atcactgatt ggaatgacca atagggccac ctgggcctcc cacatccatt   10200
tggtcatcca tcgtatccga acgctgattg acaggagaa atacactgac tacctaacag   10260
tcatggacag gtattctgtg gatgctgacc tgcaactggg tgagcttatc tgaaacacca   10320
tctaacagga ataaccggga tacaaaccac gggtggagaa ccggactccc cacaacctga   10380
aaccgggata taaccacgg ctggagaacc ggactccgca cttaaaatga aacagaaacc   10440
```

```
gggataaaaa ctacggatgg agaaccggac tccacacatt gagacagaag aagttgtcag    10500
cccagaaccc cacacgagtt ttgccactgc taagctgtga ggcagtgcag gctgggacag    10560
ccgacctcca ggttgcgaaa aacctggttt ctgggacctc ccaccccaga gtaaaaagaa    10620
cggagcctcc gctaccaccc tcccacgtgg tggtagaaag acggggtcta gaggttagag    10680
gagaccctcc agggaacaaa tagtgggacc atattgacgc cagggaaaga ccggagtggt    10740
tctctgcttt tcctccagag gtctgtgagc acagtttgct caaga                   10785

<210> SEQ ID NO 13
<211> LENGTH: 3411
<212> TYPE: PRT
<213> ORGANISM: Flaviviridae Flavivirus Yellow Fever Virus

<400> SEQUENCE: 13

Met Ser Gly Arg Lys Ala Gln Gly Lys Thr Leu Gly Val Asn Met Val
 1               5                  10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320
```

```
Pro Asp Lys Pro Ser Leu Asp Ile Ser Leu Glu Thr Val Ala Ile Asp
            325                 330                 335

Arg Pro Ala Glu Val Arg Lys Val Cys Tyr Asn Ala Val Leu Thr His
            340                 345                 350

Val Lys Ile Asn Asp Lys Cys Pro Ser Thr Gly Glu Ala His Leu Ala
            355                 360                 365

Glu Glu Asn Glu Gly Asp Asn Ala Cys Lys Arg Thr Tyr Ser Asp Arg
370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
            405                 410                 415

Gln Thr Lys Ile Gln Tyr Val Ile Arg Ala Gln Leu His Val Gly Ala
            420                 425                 430

Lys Gln Glu Asn Trp Thr Thr Asp Ile Lys Thr Leu Lys Phe Asp Ala
            435                 440                 445

Leu Ser Gly Ser Gln Glu Val Glu Phe Ile Gly Tyr Gly Lys Ala Thr
450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
            485                 490                 495

Asp Leu Thr Leu Pro Trp Gln Ser Gly Ser Gly Gly Val Trp Arg Glu
            500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
            530                 535                 540

Gly Ala Met Arg Val Thr Lys Asp Thr Asn Asp Asn Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
            580                 585                 590

Lys Asn Pro Thr Asp Thr Gly His Gly Thr Val Val Met Gln Val Lys
            595                 600                 605

Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
            645                 650                 655

Gly Asp Ser Tyr Ile Ile Val Gly Arg Gly Asp Ser Arg Leu Thr Tyr
            660                 665                 670

Gln Trp His Lys Glu Gly Ser Ser Ile Gly Lys Leu Phe Thr Gln Thr
            675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
            725                 730                 735

Ile Thr Lys Val Ile Met Gly Ala Val Leu Ile Trp Val Gly Ile Asn
```

```
                        740                 745                 750
Thr Arg Asn Met Thr Met Ser Met Ser Met Ile Leu Val Gly Val Ile
                755                 760                 765
Met Met Phe Leu Ser Leu Gly Val Gly Ala Asp Gln Gly Cys Ala Ile
                770                 775                 780
Asn Phe Gly Lys Arg Glu Leu Lys Cys Gly Asp Gly Ile Phe Ile Phe
785                 790                 795                 800
Arg Asp Ser Asp Asp Trp Leu Asn Lys Tyr Ser Tyr Tyr Pro Glu Asp
                805                 810                 815
Pro Val Lys Leu Ala Ser Ile Val Lys Ala Ser Phe Glu Glu Gly Lys
                820                 825                 830
Cys Gly Leu Asn Ser Val Asp Ser Leu Glu His Glu Met Trp Arg Ser
                835                 840                 845
Arg Ala Asp Glu Ile Asn Ala Ile Phe Glu Glu Asn Glu Val Asp Ile
                850                 855                 860
Ser Val Val Val Gln Asp Pro Lys Asn Val Tyr Gln Arg Gly Thr His
865                 870                 875                 880
Pro Phe Ser Arg Ile Arg Asp Gly Leu Gln Tyr Gly Trp Lys Thr Trp
                885                 890                 895
Gly Lys Asn Leu Val Phe Ser Pro Gly Arg Lys Asn Gly Ser Phe Ile
                900                 905                 910
Ile Asp Gly Lys Ser Arg Lys Glu Cys Pro Phe Ser Asn Arg Val Trp
                915                 920                 925
Asn Ser Phe Gln Ile Glu Glu Phe Gly Thr Gly Val Phe Thr Thr Arg
                930                 935                 940
Val Tyr Met Asp Ala Val Phe Glu Tyr Thr Ile Asp Cys Asp Gly Ser
945                 950                 955                 960
Ile Leu Gly Ala Ala Val Asn Gly Lys Lys Ser Ala His Gly Ser Pro
                965                 970                 975
Thr Phe Trp Met Gly Ser His Glu Val Asn Gly Thr Trp Met Ile His
                980                 985                 990
Thr Leu Glu Ala Leu Asp Tyr Lys Glu Cys Glu Trp Pro Leu Thr His
                995                 1000                1005
Thr Ile Gly Thr Ser Val Glu Glu Ser Glu Met Phe Met Pro Arg Ser
                1010                1015                1020
Ile Gly Gly Pro Val Ser Ser His Asn His Ile Pro Gly Tyr Lys Val
1025                1030                1035                1040
Gln Thr Asn Gly Pro Trp Met Gln Val Pro Leu Glu Val Lys Arg Glu
                1045                1050                1055
Ala Cys Pro Gly Thr Ser Val Ile Ile Asp Gly Asn Cys Asp Gly Arg
                1060                1065                1070
Gly Lys Ser Thr Arg Ser Thr Thr Asp Ser Gly Lys Val Ile Pro Glu
                1075                1080                1085
Trp Cys Cys Arg Ser Cys Thr Met Pro Pro Val Ser Phe His Gly Ser
                1090                1095                1100
Asp Gly Cys Trp Tyr Pro Met Glu Ile Arg Pro Arg Lys Thr His Glu
1105                1110                1115                1120
Ser His Leu Val Arg Ser Trp Val Thr Ala Gly Glu Ile His Ala Val
                1125                1130                1135
Pro Phe Gly Leu Val Ser Met Met Ile Ala Met Glu Val Val Leu Arg
                1140                1145                1150
Lys Arg Gln Gly Pro Lys Gln Met Leu Val Gly Val Val Leu Leu
                1155                1160                1165
```

-continued

Gly Ala Met Leu Val Gly Gln Val Thr Leu Leu Asp Leu Leu Lys Leu
        1170                1175                1180

Thr Val Ala Val Gly Leu His Phe His Glu Met Asn Asn Gly Gly Asp
1185                1190                1195                1200

Ala Met Tyr Met Ala Leu Ile Ala Ala Phe Ser Ile Arg Pro Gly Leu
                1205                1210                1215

Leu Ile Gly Phe Gly Leu Arg Thr Leu Trp Ser Pro Arg Glu Arg Leu
            1220                1225                1230

Val Leu Thr Leu Gly Ala Ala Met Val Glu Ile Ala Leu Gly Gly Val
        1235                1240                1245

Met Gly Gly Leu Trp Lys Tyr Leu Asn Ala Val Ser Leu Cys Ile Leu
    1250                1255                1260

Thr Ile Asn Ala Val Ala Ser Arg Lys Ala Ser Asn Thr Ile Leu Pro
1265                1270                1275                1280

Leu Met Ala Leu Leu Thr Pro Val Thr Met Ala Glu Val Arg Leu Ala
                1285                1290                1295

Ala Met Phe Phe Cys Ala Val Val Ile Ile Gly Val Leu His Gln Asn
                1300                1305                1310

Phe Lys Asp Thr Ser Met Gln Lys Thr Ile Pro Leu Val Ala Leu Thr
            1315                1320                1325

Leu Thr Ser Tyr Leu Gly Leu Thr Gln Pro Phe Leu Gly Leu Cys Ala
        1330                1335                1340

Phe Leu Ala Thr Arg Ile Phe Gly Arg Arg Ser Ile Pro Val Asn Glu
1345                1350                1355                1360

Ala Leu Ala Ala Ala Gly Leu Val Gly Val Leu Ala Gly Leu Ala Phe
                1365                1370                1375

Gln Glu Met Glu Asn Phe Leu Gly Pro Ile Ala Val Gly Gly Leu Leu
            1380                1385                1390

Met Met Leu Val Ser Val Ala Gly Arg Val Asp Gly Leu Glu Leu Lys
        1395                1400                1405

Lys Leu Gly Glu Val Ser Trp Glu Glu Ala Glu Ile Ser Gly Ser
    1410                1415                1420

Ser Ala Arg Tyr Asp Val Ala Leu Ser Glu Gln Gly Glu Phe Lys Leu
1425                1430                1435                1440

Leu Ser Glu Glu Lys Val Pro Trp Asp Gln Val Val Met Thr Ser Leu
                1445                1450                1455

Ala Leu Val Gly Ala Ala Leu His Pro Phe Ala Leu Leu Leu Val Leu
                1460                1465                1470

Ala Gly Trp Leu Phe His Val Arg Gly Ala Arg Arg Ser Gly Asp Val
            1475                1480                1485

Leu Trp Asp Ile Pro Thr Pro Lys Ile Ile Glu Glu Cys Glu His Leu
    1490                1495                1500

Glu Asp Gly Ile Tyr Gly Ile Phe Gln Ser Thr Phe Leu Gly Ala Ser
1505                1510                1515                1520

Gln Arg Gly Val Gly Val Ala Gln Gly Gly Val Phe His Thr Met Trp
                1525                1530                1535

His Val Thr Arg Gly Ala Phe Leu Val Arg Asn Gly Lys Lys Leu Ile
            1540                1545                1550

Pro Ser Trp Ala Ser Val Lys Glu Asp Leu Val Ala Tyr Gly Gly Ser
        1555                1560                1565

Trp Lys Leu Glu Gly Arg Trp Asp Gly Glu Glu Val Gln Leu Ile
    1570                1575                1580

Ala Ala Val Pro Gly Lys Asn Val Val Asn Val Gln Thr Lys Pro Ser
1585                1590                1595                1600

```
Leu Phe Lys Val Arg Asn Gly Gly Glu Ile Gly Ala Val Ala Leu Asp
            1605                1610                1615

Tyr Pro Ser Gly Thr Ser Gly Ser Pro Ile Val Asn Arg Asn Gly Glu
            1620                1625                1630

Val Ile Gly Leu Tyr Gly Asn Gly Ile Leu Val Gly Asp Asn Ser Phe
            1635                1640                1645

Val Ser Ala Ile Ser Gln Thr Glu Val Lys Glu Gly Lys Glu Glu
            1650                1655                1660

Leu Gln Glu Ile Pro Thr Met Leu Lys Lys Gly Met Thr Thr Val Leu
1665                1670                1675                1680

Asp Phe His Pro Gly Ala Gly Lys Thr Arg Arg Phe Leu Pro Gln Ile
                1685                1690                1695

Leu Ala Glu Cys Ala Arg Arg Arg Leu Arg Thr Leu Val Leu Ala Pro
                1700                1705                1710

Thr Arg Val Val Leu Ser Glu Met Lys Glu Ala Phe His Gly Leu Asp
                1715                1720                1725

Val Lys Phe His Thr Gln Ala Phe Ser Ala His Gly Ser Gly Arg Glu
                1730                1735                1740

Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
                1765                1770                1775

Phe Leu Asp Pro Ala Ser Ile Ala Ala Arg Gly Trp Ala Ala His Arg
                1780                1785                1790

Ala Arg Ala Asn Glu Ser Ala Thr Ile Leu Met Thr Ala Thr Pro Pro
                1795                1800                1805

Gly Thr Ser Asp Glu Phe Pro His Ser Asn Gly Glu Ile Glu Asp Val
                1810                1815                1820

Gln Thr Asp Ile Pro Ser Glu Pro Trp Asn Thr Gly His Asp Trp Ile
1825                1830                1835                1840

Leu Ala Asp Lys Arg Pro Thr Ala Trp Phe Leu Pro Ser Ile Arg Ala
                1845                1850                1855

Ala Asn Val Met Ala Ala Ser Leu Arg Lys Ala Gly Lys Ser Val Val
                1860                1865                1870

Val Leu Asn Arg Lys Thr Phe Glu Arg Glu Tyr Pro Thr Ile Lys Gln
                1875                1880                1885

Lys Lys Pro Asp Phe Ile Leu Ala Thr Asp Ile Ala Glu Met Gly Ala
1890                1895                1900

Asn Leu Cys Val Glu Arg Val Leu Asp Cys Arg Thr Ala Phe Lys Pro
1905                1910                1915                1920

Val Leu Val Asp Glu Gly Arg Lys Val Ala Ile Lys Gly Pro Leu Arg
                1925                1930                1935

Ile Ser Ala Ser Ser Ala Ala Gln Arg Arg Gly Arg Ile Gly Arg Asn
                1940                1945                1950

Pro Asn Arg Asp Gly Asp Ser Tyr Tyr Tyr Ser Glu Pro Thr Ser Glu
                1955                1960                1965

Asn Asn Ala His His Val Cys Trp Leu Glu Ala Ser Met Leu Leu Asp
            1970                1975                1980

Asn Met Glu Val Arg Gly Gly Met Val Ala Pro Leu Tyr Gly Val Glu
1985                1990                1995                2000

Gly Thr Lys Thr Pro Val Ser Pro Gly Glu Met Arg Leu Arg Asp Asp
                2005                2010                2015

Gln Arg Lys Val Phe Arg Glu Leu Val Arg Asn Cys Asp Leu Pro Val
```

-continued

```
                   2020                2025                2030
Trp Leu Ser Trp Gln Val Ala Lys Ala Gly Leu Lys Thr Asn Asp Arg
            2035                2040                2045
Lys Trp Cys Phe Glu Gly Pro Glu His Glu Ile Leu Asn Asp Ser
    2050                2055                2060
Gly Glu Thr Val Lys Cys Arg Ala Pro Gly Gly Ala Lys Lys Pro Leu
2065                2070                2075                2080
Arg Pro Arg Trp Cys Asp Glu Arg Val Ser Ser Asp Gln Ser Ala Leu
            2085                2090                2095
Ser Glu Phe Ile Lys Phe Ala Glu Gly Arg Arg Gly Ala Ala Glu Val
                2100                2105                2110
Leu Val Val Leu Ser Glu Leu Pro Asp Phe Leu Ala Lys Lys Gly Gly
            2115                2120                2125
Glu Ala Met Asp Thr Ile Ser Val Phe Leu His Ser Glu Glu Gly Ser
            2130                2135                2140
Arg Ala Tyr Arg Asn Ala Leu Ser Met Met Pro Glu Ala Met Thr Ile
2145                2150                2155                2160
Val Met Leu Phe Ile Leu Ala Gly Leu Leu Thr Ser Gly Met Val Ile
            2165                2170                2175
Phe Phe Met Ser Pro Lys Gly Ile Ser Arg Met Ser Met Ala Met Gly
            2180                2185                2190
Thr Met Ala Gly Cys Gly Tyr Leu Met Phe Leu Gly Gly Val Lys Pro
            2195                2200                2205
Thr His Ile Ser Tyr Ile Met Leu Ile Phe Phe Val Leu Met Val Val
            2210                2215                2220
Val Ile Pro Glu Pro Gly Gln Gln Arg Ser Ile Gln Asp Asn Gln Val
2225                2230                2235                2240
Ala Tyr Leu Ile Ile Gly Ile Leu Thr Leu Val Ser Ala Val Ala Ala
            2245                2250                2255
Asn Glu Leu Gly Met Leu Glu Lys Thr Lys Glu Asp Leu Phe Gly Lys
            2260                2265                2270
Lys Asn Leu Ile Pro Ser Ser Ala Ser Pro Trp Ser Trp Pro Asp Leu
            2275                2280                2285
Asp Leu Lys Pro Gly Ala Ala Trp Thr Val Tyr Val Gly Ile Val Thr
            2290                2295                2300
Met Leu Ser Pro Met Leu His His Trp Ile Lys Val Glu Tyr Gly Asn
2305                2310                2315                2320
Leu Ser Leu Ser Gly Ile Ala Gln Ser Ala Ser Val Leu Ser Phe Met
            2325                2330                2335
Asp Lys Gly Ile Pro Phe Met Lys Met Asn Ile Ser Val Ile Met Leu
            2340                2345                2350
Leu Val Ser Gly Trp Asn Ser Ile Thr Val Met Pro Leu Leu Cys Gly
            2355                2360                2365
Ile Gly Cys Ala Met Leu His Trp Ser Leu Ile Leu Pro Gly Ile Lys
            2370                2375                2380
Ala Gln Gln Ser Lys Leu Ala Gln Arg Val Phe His Gly Val Ala
2385                2390                2395                2400
Lys Asn Pro Val Val Asp Gly Asn Pro Thr Val Asp Ile Glu Glu Ala
            2405                2410                2415
Pro Glu Met Pro Ala Leu Tyr Glu Lys Lys Leu Ala Leu Tyr Leu Leu
            2420                2425                2430
Leu Ala Leu Ser Leu Ala Ser Val Ala Met Cys Arg Thr Pro Phe Ser
            2435                2440                2445
```

```
Leu Ala Glu Gly Ile Val Leu Ala Ser Ala Ala Leu Gly Pro Leu Ile
    2450                2455                2460
Glu Gly Asn Thr Ser Leu Leu Trp Asn Gly Pro Met Ala Val Ser Met
2465                2470                2475                2480
Thr Gly Val Met Arg Gly Asn His Tyr Ala Phe Val Gly Val Met Tyr
                2485                2490                2495
Asn Leu Trp Lys Met Lys Thr Gly Arg Arg Gly Ser Ala Asn Gly Lys
            2500                2505                2510
Thr Leu Gly Glu Val Trp Lys Arg Glu Leu Asn Leu Leu Asp Lys Arg
        2515                2520                2525
Gln Phe Glu Leu Tyr Lys Arg Thr Asp Ile Val Glu Val Asp Arg Asp
    2530                2535                2540
Thr Ala Arg Arg His Leu Ala Glu Gly Lys Val Asp Thr Gly Val Ala
2545                2550                2555                2560
Val Ser Arg Gly Thr Ala Lys Leu Arg Trp Phe His Glu Arg Gly Tyr
                2565                2570                2575
Val Lys Leu Glu Gly Arg Val Ile Asp Leu Gly Cys Gly Arg Gly Gly
            2580                2585                2590
Trp Cys Tyr Tyr Ala Ala Ala Gln Lys Glu Val Ser Gly Val Lys Gly
        2595                2600                2605
Phe Thr Leu Gly Arg Asp Gly His Glu Lys Pro Met Asn Val Gln Ser
    2610                2615                2620
Leu Gly Trp Asn Ile Ile Thr Phe Lys Asp Lys Thr Asp Ile His Arg
2625                2630                2635                2640
Leu Glu Pro Val Lys Cys Asp Thr Leu Leu Cys Asp Ile Gly Glu Ser
                2645                2650                2655
Ser Ser Ser Ser Val Thr Glu Gly Glu Arg Thr Val Arg Val Leu Asp
            2660                2665                2670
Thr Val Glu Lys Trp Leu Ala Cys Gly Val Asp Asn Phe Cys Val Lys
        2675                2680                2685
Val Leu Ala Pro Tyr Met Pro Asp Val Leu Glu Lys Leu Glu Leu Leu
    2690                2695                2700
Gln Arg Arg Phe Gly Gly Thr Val Ile Arg Asn Pro Leu Ser Arg Asn
2705                2710                2715                2720
Ser Thr His Glu Met Tyr Tyr Val Ser Gly Ala Arg Ser Asn Val Thr
                2725                2730                2735
Phe Thr Val Asn Gln Thr Ser Arg Leu Leu Met Arg Arg Met Arg Arg
            2740                2745                2750
Pro Thr Gly Lys Val Thr Leu Glu Ala Asp Val Ile Leu Pro Ile Gly
        2755                2760                2765
Thr Arg Ser Val Glu Thr Asp Lys Gly Pro Leu Asp Lys Glu Ala Ile
    2770                2775                2780
Glu Glu Arg Val Glu Arg Ile Lys Ser Glu Tyr Met Thr Ser Trp Phe
2785                2790                2795                2800
Tyr Asp Asn Asp Asn Pro Tyr Arg Thr Trp His Tyr Cys Gly Ser Tyr
                2805                2810                2815
Val Thr Lys Thr Ser Gly Ser Ala Ala Ser Met Val Asn Gly Val Ile
            2820                2825                2830
Lys Ile Leu Thr Tyr Pro Trp Asp Arg Ile Glu Glu Val Thr Arg Met
        2835                2840                2845
Ala Met Thr Asp Thr Thr Pro Phe Gly Gln Gln Arg Val Phe Lys Glu
    2850                2855                2860
Lys Val Asp Thr Arg Ala Lys Asp Pro Pro Ala Gly Thr Arg Lys Ile
2865                2870                2875                2880
```

```
Met Lys Val Val Asn Arg Trp Leu Phe Arg His Leu Ala Arg Glu Lys
            2885                2890                2895

Asn Pro Arg Leu Cys Thr Lys Glu Glu Phe Ile Ala Lys Val Arg Ser
            2900                2905                2910

His Ala Ala Ile Gly Ala Tyr Leu Glu Glu Gln Glu Gln Trp Lys Thr
            2915                2920                2925

Ala Asn Glu Ala Val Gln Asp Pro Lys Phe Trp Glu Leu Val Asp Glu
            2930                2935                2940

Glu Arg Lys Leu His Gln Gln Gly Arg Cys Arg Thr Cys Val Tyr Asn
2945                2950                2955                2960

Met Met Gly Lys Arg Glu Lys Lys Leu Ser Glu Phe Gly Lys Ala Lys
            2965                2970                2975

Gly Ser Arg Ala Ile Trp Tyr Met Trp Leu Gly Ala Arg Tyr Leu Glu
            2980                2985                2990

Phe Glu Ala Leu Gly Phe Leu Asn Glu Asp His Trp Ala Ser Arg Glu
            2995                3000                3005

Asn Ser Gly Gly Gly Val Glu Gly Ile Gly Leu Gln Tyr Leu Gly Tyr
            3010                3015                3020

Val Ile Arg Asp Leu Ala Ala Met Asp Gly Gly Phe Tyr Ala Asp
3025                3030                3035                3040

Asp Thr Ala Gly Trp Asp Thr Arg Ile Thr Glu Ala Asp Leu Asp Asp
            3045                3050                3055

Glu Gln Glu Ile Leu Asn Tyr Met Ser Pro His His Lys Lys Leu Ala
            3060                3065                3070

Gln Ala Val Met Glu Met Thr Tyr Lys Asn Lys Val Val Lys Val Leu
            3075                3080                3085

Arg Pro Ala Pro Gly Gly Lys Ala Tyr Met Asp Val Ile Ser Arg Arg
            3090                3095                3100

Asp Gln Arg Gly Ser Gly Gln Val Val Thr Tyr Ala Leu Asn Thr Ile
3105                3110                3115                3120

Thr Asn Leu Lys Val Gln Leu Ile Arg Met Ala Glu Ala Glu Met Val
            3125                3130                3135

Ile His His Gln His Val Gln Asp Cys Asp Glu Ser Val Leu Thr Arg
            3140                3145                3150

Leu Glu Ala Trp Leu Thr Glu His Gly Cys Asn Arg Leu Lys Arg Met
            3155                3160                3165

Ala Val Ser Gly Asp Asp Cys Val Val Arg Pro Ile Asp Asp Arg Phe
            3170                3175                3180

Gly Leu Ala Leu Ser His Leu Asn Ala Met Ser Lys Val Arg Lys Asp
3185                3190                3195                3200

Ile Ser Glu Trp Gln Pro Ser Lys Gly Trp Asn Asp Trp Glu Asn Val
            3205                3210                3215

Pro Phe Cys Ser His His Phe His Glu Leu Gln Leu Lys Asp Gly Arg
            3220                3225                3230

Arg Ile Val Val Pro Cys Arg Glu Gln Asp Glu Leu Ile Gly Arg Gly
            3235                3240                3245

Arg Val Ser Pro Gly Asn Gly Trp Met Ile Lys Glu Thr Ala Cys Leu
            3250                3255                3260

Ser Lys Ala Tyr Ala Asn Met Trp Ser Leu Met Tyr Phe His Lys Arg
3265                3270                3275                3280

Asp Met Arg Leu Leu Ser Leu Ala Val Ser Ser Ala Val Pro Thr Ser
            3285                3290                3295

Trp Val Pro Gln Gly Arg Thr Thr Trp Ser Ile His Gly Lys Gly Glu
```

```
                     3300              3305              3310
Trp Met Thr Thr Glu Asp Met Leu Glu Val Trp Asn Arg Val Trp Ile
            3315              3320              3325

Thr Asn Asn Pro His Met Gln Asp Lys Thr Met Val Lys Lys Trp Arg
            3330              3335              3340

Asp Val Pro Tyr Leu Thr Lys Arg Gln Asp Lys Leu Cys Gly Ser Leu
3345              3350              3355              3360

Ile Gly Met Thr Asn Arg Ala Thr Trp Ala Ser His Ile His Leu Val
            3365              3370              3375

Ile His Arg Ile Arg Thr Leu Ile Gly Gln Glu Lys Tyr Thr Asp Tyr
            3380              3385              3390

Leu Thr Val Met Asp Arg Tyr Ser Val Asp Ala Asp Leu Gln Leu Gly
            3395              3400              3405

Glu Leu Ile
    3410

<210> SEQ ID NO 14
<211> LENGTH: 3411
<212> TYPE: PRT
<213> ORGANISM: Flaviviridae Flavivirus Yellow Fever Virus

<400> SEQUENCE: 14

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
```

```
                260             265             270
Ile Ala Leu Leu Val Leu Ala Val Gly Pro Ala Tyr Ser Ala His Cys
            275             280             285
Ile Gly Ile Thr Asp Arg Asp Phe Ile Glu Gly Val His Gly Gly Thr
            290             295             300
Trp Val Ser Ala Thr Leu Glu Gln Asp Lys Cys Val Thr Val Met Ala
305             310             315             320
Pro Asp Lys Pro Ser Leu Asp Ile Ser Leu Glu Thr Val Ala Ile Asp
            325             330             335
Arg Pro Ala Glu Val Arg Lys Val Cys Tyr Asn Ala Val Leu Thr His
            340             345             350
Val Lys Ile Asn Asp Lys Cys Pro Ser Thr Gly Glu Ala His Leu Ala
            355             360             365
Glu Glu Asn Glu Gly Asp Asn Ala Cys Lys Arg Thr Tyr Ser Asp Arg
            370             375             380
Gly Trp Gly Asn Gly Cys Gly Leu Phe Gly Lys Gly Ser Ile Val Ala
385             390             395             400
Cys Ala Lys Phe Thr Cys Ala Lys Ser Met Ser Leu Phe Glu Val Asp
            405             410             415
Gln Thr Lys Ile Gln Tyr Val Ile Arg Ala Gln Leu His Val Gly Ala
            420             425             430
Lys Gln Glu Asn Trp Thr Thr Asp Ile Lys Thr Leu Lys Phe Asp Ala
            435             440             445
Leu Ser Gly Ser Gln Glu Val Glu Phe Ile Gly Tyr Gly Lys Ala Thr
450             455             460
Leu Glu Cys Gln Val Gln Thr Ala Val Asp Phe Gly Asn Ser Tyr Ile
465             470             475             480
Ala Glu Met Glu Thr Glu Ser Trp Ile Val Asp Arg Gln Trp Ala Gln
            485             490             495
Asp Leu Thr Leu Pro Trp Gln Ser Gly Ser Gly Val Trp Arg Glu
            500             505             510
Met His His Leu Val Glu Phe Glu Pro Pro His Ala Ala Thr Ile Arg
            515             520             525
Val Leu Ala Leu Gly Asn Gln Glu Gly Ser Leu Lys Thr Ala Leu Thr
            530             535             540
Gly Ala Met Arg Val Thr Lys Asp Thr Asn Asp Asn Leu Tyr Lys
545             550             555             560
Leu His Gly Gly His Val Ser Cys Arg Val Lys Leu Ser Ala Leu Thr
            565             570             575
Leu Lys Gly Thr Ser Tyr Lys Ile Cys Thr Asp Lys Met Phe Phe Val
            580             585             590
Lys Asn Pro Thr Asp Thr Gly His Gly Thr Val Val Met Gln Val Lys
            595             600             605
Val Ser Lys Gly Ala Pro Cys Arg Ile Pro Val Ile Val Ala Asp Asp
            610             615             620
Leu Thr Ala Ala Ile Asn Lys Gly Ile Leu Val Thr Val Asn Pro Ile
625             630             635             640
Ala Ser Thr Asn Asp Asp Glu Val Leu Ile Glu Val Asn Pro Pro Phe
            645             650             655
Gly Asp Ser Tyr Ile Ile Val Gly Arg Gly Asp Ser Arg Leu Thr Tyr
            660             665             670
Gln Trp His Lys Glu Gly Ser Ser Ile Gly Lys Leu Phe Thr Gln Thr
            675             680             685
```

-continued

```
Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Pro Glu Asp
                805                 810                 815

Pro Val Lys Leu Ala Ser Ile Val Lys Ala Ser Phe Glu Glu Gly Lys
                820                 825                 830

Cys Gly Leu Asn Ser Val Asp Ser Leu Glu His Glu Met Trp Arg Ser
                835                 840                 845

Arg Ala Asp Glu Ile Asn Ala Ile Phe Glu Glu Asn Glu Val Asp Ile
850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
                900                 905                 910

Ile Asp Gly Lys Ser Arg Lys Glu Cys Pro Phe Ser Asn Arg Val Trp
                915                 920                 925

Asn Ser Phe Gln Ile Glu Glu Phe Gly Thr Gly Val Phe Thr Thr Arg
930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
                965                 970                 975

Thr Phe Trp Met Gly Ser His Glu Val Asn Gly Thr Trp Met Ile His
                980                 985                 990

Thr Leu Glu Ala Leu Asp Tyr Lys Glu Cys Glu Trp Pro Leu Thr His
                995                 1000                1005

Thr Ile Gly Thr Ser Val Glu Glu Ser Glu Met Phe Met Pro Arg Ser
                1010                1015                1020

Ile Gly Gly Pro Val Ser Ser His Asn His Ile Pro Gly Tyr Lys Val
1025                1030                1035                1040

Gln Thr Asn Gly Pro Trp Met Gln Val Pro Leu Glu Val Lys Arg Glu
                1045                1050                1055

Ala Cys Pro Gly Thr Ser Val Ile Ile Asp Gly Asn Cys Asp Gly Arg
                1060                1065                1070

Gly Lys Ser Thr Arg Ser Thr Thr Asp Ser Gly Lys Val Ile Pro Glu
                1075                1080                1085

Trp Cys Cys Arg Ser Cys Thr Met Pro Pro Val Ser Phe His Gly Ser
                1090                1095                1100

Asp Gly Cys Trp Tyr Pro Met Glu Ile Arg Pro Arg Lys Thr His Glu
1105                1110                1115                1120
```

```
Ser His Leu Val Arg Ser Trp Val Thr Ala Gly Glu Ile His Ala Val
            1125                1130                1135

Pro Phe Gly Leu Val Ser Met Met Ile Ala Met Glu Val Val Leu Arg
            1140                1145                1150

Lys Arg Gln Gly Pro Lys Gln Met Leu Val Gly Gly Val Val Leu Leu
            1155                1160                1165

Gly Ala Met Leu Val Gly Gln Val Thr Leu Leu Asp Leu Leu Lys Leu
            1170                1175                1180

Thr Val Ala Val Gly Leu His Phe His Glu Met Asn Asn Gly Gly Asp
1185                1190                1195                1200

Ala Met Tyr Met Ala Leu Ile Ala Ala Phe Ser Ile Arg Pro Gly Leu
            1205                1210                1215

Leu Ile Gly Phe Gly Leu Arg Thr Leu Trp Ser Pro Arg Glu Arg Leu
            1220                1225                1230

Val Leu Thr Leu Gly Ala Ala Met Val Glu Ile Ala Leu Gly Gly Val
            1235                1240                1245

Met Gly Gly Leu Trp Lys Tyr Leu Asn Ala Val Ser Leu Cys Ile Leu
            1250                1255                1260

Thr Ile Asn Ala Val Ala Ser Arg Lys Ala Ser Asn Thr Ile Leu Pro
1265                1270                1275                1280

Leu Met Ala Leu Leu Thr Pro Val Thr Met Ala Glu Val Arg Leu Ala
            1285                1290                1295

Ala Met Phe Phe Cys Ala Val Val Ile Ile Gly Val Leu His Gln Asn
            1300                1305                1310

Phe Lys Asp Thr Ser Met Gln Lys Thr Ile Pro Leu Val Ala Leu Thr
            1315                1320                1325

Leu Thr Ser Tyr Leu Gly Leu Thr Gln Pro Phe Leu Gly Leu Cys Ala
            1330                1335                1340

Phe Leu Ala Thr Arg Ile Phe Gly Arg Arg Ser Ile Pro Val Asn Glu
1345                1350                1355                1360

Ala Leu Ala Ala Ala Gly Leu Val Gly Val Leu Ala Gly Leu Ala Phe
            1365                1370                1375

Gln Glu Met Glu Asn Phe Leu Gly Pro Ile Ala Val Gly Gly Leu Leu
            1380                1385                1390

Met Met Leu Val Ser Val Ala Gly Arg Val Asp Gly Leu Glu Leu Lys
            1395                1400                1405

Lys Leu Gly Glu Val Ser Trp Glu Glu Glu Ala Glu Ile Ser Gly Ser
            1410                1415                1420

Ser Ala Arg Tyr Asp Val Ala Leu Ser Glu Gln Gly Glu Phe Lys Leu
1425                1430                1435                1440

Leu Ser Glu Glu Lys Val Pro Trp Asp Gln Val Val Met Thr Ser Leu
            1445                1450                1455

Ala Leu Val Gly Ala Ala Leu His Pro Phe Ala Leu Leu Leu Val Leu
            1460                1465                1470

Ala Gly Trp Leu Phe His Val Arg Gly Ala Arg Arg Ser Gly Asp Val
            1475                1480                1485

Leu Trp Asp Ile Pro Thr Pro Lys Ile Ile Glu Glu Cys Glu His Leu
            1490                1495                1500

Glu Asp Gly Ile Tyr Gly Ile Phe Gln Ser Thr Phe Leu Gly Ala Ser
1505                1510                1515                1520

Gln Arg Gly Val Gly Val Ala Gln Gly Gly Val Phe His Thr Met Trp
            1525                1530                1535

His Val Thr Arg Gly Ala Phe Leu Val Arg Asn Gly Lys Lys Leu Ile
```

-continued

```
                1540                1545                1550

Pro Ser Trp Ala Ser Val Lys Glu Asp Leu Val Ala Tyr Gly Gly Ser
        1555                1560                1565

Trp Lys Leu Glu Gly Arg Trp Asp Gly Glu Glu Val Gln Leu Ile
    1570                1575                1580

Ala Ala Val Pro Gly Lys Asn Val Asn Val Gln Thr Lys Pro Ser
1585                1590                1595                1600

Leu Phe Lys Val Arg Asn Gly Gly Glu Ile Gly Ala Val Ala Leu Asp
        1605                1610                1615

Tyr Pro Ser Gly Thr Ser Gly Ser Pro Ile Val Asn Arg Asn Gly Glu
        1620                1625                1630

Val Ile Gly Leu Tyr Gly Asn Gly Ile Leu Val Gly Asp Asn Ser Phe
        1635                1640                1645

Val Ser Ala Ile Ser Gln Thr Glu Val Lys Glu Glu Gly Lys Glu Glu
        1650                1655                1660

Leu Gln Glu Ile Pro Thr Met Leu Lys Lys Gly Met Thr Thr Val Leu
1665                1670                1675                1680

Asp Phe His Pro Gly Ala Gly Lys Thr Arg Arg Phe Leu Pro Gln Ile
        1685                1690                1695

Leu Ala Glu Cys Ala Arg Arg Arg Leu Arg Thr Leu Val Leu Ala Pro
        1700                1705                1710

Thr Arg Val Val Leu Ser Glu Met Lys Glu Ala Phe His Gly Leu Asp
        1715                1720                1725

Val Lys Phe His Thr Gln Ala Phe Ser Ala His Gly Ser Gly Arg Glu
        1730                1735                1740

Val Ile Asp Ala Met Cys His Ala Thr Leu Thr Tyr Arg Met Leu Glu
1745                1750                1755                1760

Pro Thr Arg Val Val Asn Trp Glu Val Ile Ile Met Asp Glu Ala His
        1765                1770                1775

Phe Leu Asp Pro Ala Ser Ile Ala Ala Arg Gly Trp Ala Ala His Arg
        1780                1785                1790

Ala Arg Ala Asn Glu Ser Ala Thr Ile Leu Met Thr Ala Thr Pro Pro
        1795                1800                1805

Gly Thr Ser Asp Glu Phe Pro His Ser Asn Gly Glu Ile Glu Asp Val
        1810                1815                1820

Gln Thr Asp Ile Pro Ser Glu Pro Trp Asn Thr Gly His Asp Trp Ile
1825                1830                1835                1840

Leu Ala Asp Lys Arg Pro Thr Ala Trp Phe Leu Pro Ser Ile Arg Ala
        1845                1850                1855

Ala Asn Val Met Ala Ala Ser Leu Arg Lys Ala Gly Lys Ser Val Val
        1860                1865                1870

Val Leu Asn Arg Lys Thr Phe Glu Arg Glu Tyr Pro Thr Ile Lys Gln
        1875                1880                1885

Lys Lys Pro Asp Phe Ile Leu Ala Thr Asp Ile Ala Glu Met Gly Ala
        1890                1895                1900

Asn Leu Cys Val Glu Arg Val Leu Asp Cys Arg Thr Ala Phe Lys Pro
1905                1910                1915                1920

Val Leu Val Asp Glu Gly Arg Lys Val Ala Ile Lys Gly Pro Leu Arg
        1925                1930                1935

Ile Ser Ala Ser Ser Ala Ala Gln Arg Arg Gly Arg Ile Gly Arg Asn
        1940                1945                1950

Pro Asn Arg Asp Gly Asp Ser Tyr Tyr Tyr Ser Glu Pro Thr Ser Glu
        1955                1960                1965
```

```
Asn Asn Ala His His Val Cys Trp Leu Glu Ala Ser Met Leu Leu Asp
        1970                1975                1980
Asn Met Glu Val Arg Gly Gly Met Val Ala Pro Leu Tyr Gly Val Glu
1985                1990                1995                2000
Gly Thr Lys Thr Pro Val Ser Pro Gly Glu Met Arg Leu Arg Asp Asp
            2005                2010                2015
Gln Arg Lys Val Phe Arg Glu Leu Val Arg Asn Cys Asp Leu Pro Val
        2020                2025                2030
Trp Leu Ser Trp Gln Val Ala Lys Ala Gly Leu Lys Thr Asn Asp Arg
        2035                2040                2045
Lys Trp Cys Phe Glu Gly Pro Glu Glu His Glu Ile Leu Asn Asp Ser
        2050                2055                2060
Gly Glu Thr Val Lys Cys Arg Ala Pro Gly Gly Ala Lys Lys Pro Leu
2065                2070                2075                2080
Arg Pro Arg Trp Cys Asp Glu Arg Val Ser Ser Asp Gln Ser Ala Leu
            2085                2090                2095
Ser Glu Phe Ile Lys Phe Ala Glu Gly Arg Arg Gly Ala Ala Glu Val
        2100                2105                2110
Leu Val Val Leu Ser Glu Leu Pro Asp Phe Leu Ala Lys Lys Gly Gly
            2115                2120                2125
Glu Ala Met Asp Thr Ile Ser Val Phe Leu His Ser Glu Glu Gly Ser
        2130                2135                2140
Arg Ala Tyr Arg Asn Ala Leu Ser Met Met Pro Glu Ala Met Thr Ile
2145                2150                2155                2160
Val Met Leu Phe Ile Leu Ala Gly Leu Leu Thr Ser Gly Met Val Ile
            2165                2170                2175
Phe Phe Met Ser Pro Lys Gly Ile Ser Arg Met Ser Met Ala Met Gly
            2180                2185                2190
Thr Met Ala Gly Cys Gly Tyr Leu Met Phe Leu Gly Gly Val Lys Pro
            2195                2200                2205
Thr His Ile Ser Tyr Ile Met Leu Ile Phe Phe Val Leu Met Val Val
        2210                2215                2220
Val Ile Pro Glu Pro Gly Gln Gln Arg Ser Ile Gln Asp Asn Gln Val
2225                2230                2235                2240
Ala Tyr Leu Ile Ile Gly Ile Leu Thr Leu Val Ser Ala Val Ala Ala
            2245                2250                2255
Asn Glu Leu Gly Met Leu Glu Lys Thr Lys Glu Asp Leu Phe Gly Lys
            2260                2265                2270
Lys Asn Leu Ile Pro Ser Ser Ala Ser Pro Trp Ser Trp Pro Asp Leu
        2275                2280                2285
Asp Leu Lys Pro Gly Ala Ala Trp Thr Val Tyr Val Gly Ile Val Thr
        2290                2295                2300
Met Leu Ser Pro Met Leu His His Trp Ile Lys Val Glu Tyr Gly Asn
2305                2310                2315                2320
Leu Ser Leu Ser Gly Ile Ala Gln Ser Ala Ser Val Leu Ser Phe Met
            2325                2330                2335
Asp Lys Gly Ile Pro Phe Met Lys Met Asn Ile Ser Val Ile Met Leu
        2340                2345                2350
Leu Val Ser Gly Trp Asn Ser Ile Thr Val Met Pro Leu Leu Cys Gly
            2355                2360                2365
Ile Gly Cys Ala Met Leu His Trp Ser Leu Ile Leu Pro Gly Ile Lys
        2370                2375                2380
Ala Gln Gln Ser Lys Leu Ala Gln Arg Arg Val Phe His Gly Val Ala
2385                2390                2395                2400
```

```
Lys Asn Pro Val Val Asp Gly Asn Pro Thr Val Asp Ile Glu Glu Ala
                2405                2410                2415

Pro Glu Met Pro Ala Leu Tyr Glu Lys Lys Leu Ala Leu Tyr Leu Leu
                2420                2425                2430

Leu Ala Leu Ser Leu Ala Ser Val Ala Met Cys Arg Thr Pro Phe Ser
                2435                2440                2445

Leu Ala Glu Gly Ile Val Leu Ala Ser Ala Leu Gly Pro Leu Ile
                2450                2455                2460

Glu Gly Asn Thr Ser Leu Leu Trp Asn Gly Pro Met Ala Val Ser Met
2465                2470                2475                2480

Thr Gly Val Met Arg Gly Asn His Tyr Ala Phe Val Gly Val Met Tyr
                2485                2490                2495

Asn Leu Trp Lys Met Lys Thr Gly Arg Arg Gly Ser Ala Asn Gly Lys
                2500                2505                2510

Thr Leu Gly Glu Val Trp Lys Arg Glu Leu Asn Leu Leu Asp Lys Arg
                2515                2520                2525

Gln Phe Glu Leu Tyr Lys Arg Thr Asp Ile Val Glu Val Asp Arg Asp
                2530                2535                2540

Thr Ala Arg Arg His Leu Ala Glu Gly Lys Val Asp Thr Gly Val Ala
2545                2550                2555                2560

Val Ser Arg Gly Thr Ala Lys Leu Arg Trp Phe His Glu Arg Gly Tyr
                2565                2570                2575

Val Lys Leu Glu Gly Arg Val Ile Asp Leu Gly Cys Gly Arg Gly Gly
                2580                2585                2590

Trp Cys Tyr Tyr Ala Ala Ala Gln Lys Glu Val Ser Gly Val Lys Gly
                2595                2600                2605

Phe Thr Leu Gly Arg Asp Gly His Glu Lys Pro Met Asn Val Gln Ser
                2610                2615                2620

Leu Gly Trp Asn Ile Ile Thr Phe Lys Asp Lys Thr Asp Ile His Arg
2625                2630                2635                2640

Leu Glu Pro Val Lys Cys Asp Thr Leu Leu Cys Asp Ile Gly Glu Ser
                2645                2650                2655

Ser Ser Ser Ser Val Thr Glu Gly Glu Arg Thr Val Arg Val Leu Asp
                2660                2665                2670

Thr Val Glu Lys Trp Leu Ala Cys Gly Val Asp Asn Phe Cys Val Lys
                2675                2680                2685

Val Leu Ala Pro Tyr Met Pro Asp Val Leu Glu Lys Leu Glu Leu Leu
                2690                2695                2700

Gln Arg Arg Phe Gly Gly Thr Val Ile Arg Asn Pro Leu Ser Arg Asn
2705                2710                2715                2720

Ser Thr His Glu Met Tyr Tyr Val Ser Gly Ala Arg Ser Asn Val Thr
                2725                2730                2735

Phe Thr Val Asn Gln Thr Ser Arg Leu Leu Met Arg Arg Met Arg Arg
                2740                2745                2750

Pro Thr Gly Lys Val Thr Leu Glu Ala Asp Val Ile Leu Pro Ile Gly
                2755                2760                2765

Thr Arg Ser Val Glu Thr Asp Lys Gly Pro Leu Asp Lys Glu Ala Ile
                2770                2775                2780

Glu Glu Arg Val Glu Arg Ile Lys Ser Glu Tyr Met Thr Ser Trp Phe
2785                2790                2795                2800

Tyr Asp Asn Asp Asn Pro Tyr Arg Thr Trp His Tyr Cys Gly Ser Tyr
                2805                2810                2815

Val Thr Lys Thr Ser Gly Ser Ala Ala Ser Met Val Asn Gly Val Ile
```

-continued

```
            2820                2825                2830
Lys Ile Leu Thr Tyr Pro Trp Asp Arg Ile Glu Glu Val Thr Arg Met
            2835                2840                2845

Ala Met Thr Asp Thr Thr Pro Phe Gly Gln Gln Arg Val Phe Lys Glu
            2850                2855                2860

Lys Val Asp Thr Arg Ala Lys Asp Pro Pro Ala Gly Thr Arg Lys Ile
2865                2870                2875                2880

Met Lys Val Val Asn Arg Trp Leu Phe Arg His Leu Ala Arg Glu Lys
            2885                2890                2895

Asn Pro Arg Leu Cys Thr Lys Glu Glu Phe Ile Ala Lys Val Arg Ser
            2900                2905                2910

His Ala Ala Ile Gly Ala Tyr Leu Glu Glu Gln Glu Gln Trp Lys Thr
            2915                2920                2925

Ala Asn Glu Ala Val Gln Asp Pro Lys Phe Trp Glu Leu Val Asp Glu
            2930                2935                2940

Glu Arg Lys Leu His Gln Gln Gly Arg Cys Arg Thr Cys Val Tyr Asn
2945                2950                2955                2960

Met Met Gly Lys Arg Glu Lys Lys Leu Ser Glu Phe Gly Lys Ala Lys
            2965                2970                2975

Gly Ser Arg Ala Ile Trp Tyr Met Trp Leu Gly Ala Arg Tyr Leu Glu
            2980                2985                2990

Phe Glu Ala Leu Gly Phe Leu Asn Glu Asp His Trp Ala Ser Arg Glu
            2995                3000                3005

Asn Ser Gly Gly Gly Val Glu Gly Ile Gly Leu Gln Tyr Leu Gly Tyr
            3010                3015                3020

Val Ile Arg Asp Leu Ala Ala Met Asp Gly Gly Gly Phe Tyr Ala Asp
3025                3030                3035                3040

Asp Thr Ala Gly Trp Asp Thr Arg Ile Thr Glu Ala Asp Leu Asp Asp
            3045                3050                3055

Glu Gln Glu Ile Leu Asn Tyr Met Ser Pro His His Lys Lys Leu Ala
            3060                3065                3070

Gln Ala Val Met Glu Met Thr Tyr Lys Asn Lys Val Val Lys Val Leu
            3075                3080                3085

Arg Pro Ala Pro Gly Gly Lys Ala Tyr Met Asp Val Ile Ser Arg Arg
            3090                3095                3100

Asp Gln Arg Gly Ser Gly Gln Val Val Thr Tyr Ala Leu Asn Thr Ile
3105                3110                3115                3120

Thr Asn Leu Lys Val Gln Leu Ile Arg Met Ala Glu Ala Glu Met Val
            3125                3130                3135

Ile His His Gln His Val Gln Asp Cys Asp Glu Ser Val Leu Thr Arg
            3140                3145                3150

Leu Glu Ala Trp Leu Thr Glu His Gly Cys Asn Arg Leu Lys Arg Met
            3155                3160                3165

Ala Val Ser Gly Asp Asp Cys Val Val Arg Pro Ile Asp Asp Arg Phe
            3170                3175                3180

Gly Leu Ala Leu Ser His Leu Asn Ala Met Ser Lys Val Arg Lys Asp
3185                3190                3195                3200

Ile Ser Glu Trp Gln Pro Ser Lys Gly Trp Asn Asp Trp Glu Asn Val
            3205                3210                3215

Pro Phe Cys Ser His His Phe His Glu Leu Gln Leu Lys Asp Gly Arg
            3220                3225                3230

Arg Ile Val Val Pro Cys Arg Glu Gln Asp Glu Leu Ile Gly Arg Gly
            3235                3240                3245
```

-continued

```
Arg Val Ser Pro Gly Asn Gly Trp Met Ile Lys Glu Thr Ala Cys Leu
     3250                3255                3260

Ser Lys Ala Tyr Ala Asn Met Trp Ser Leu Met Tyr Phe His Lys Arg
3265                3270                3275                3280

Asp Met Arg Leu Leu Ser Leu Ala Val Ser Ser Ala Val Pro Thr Ser
            3285                3290                3295

Trp Val Pro Gln Gly Arg Thr Thr Trp Ser Ile His Gly Lys Gly Glu
            3300                3305                3310

Trp Met Thr Thr Glu Asp Met Leu Glu Val Trp Asn Arg Val Trp Ile
        3315                3320                3325

Thr Asn Asn Pro His Met Gln Asp Lys Thr Met Val Lys Lys Trp Arg
    3330                3335                3340

Asp Val Pro Tyr Leu Thr Lys Arg Gln Asp Lys Leu Cys Gly Ser Leu
3345                3350                3355                3360

Ile Gly Met Thr Asn Arg Ala Thr Trp Ala Ser His Ile His Leu Val
            3365                3370                3375

Ile His Arg Ile Arg Thr Leu Ile Gly Gln Glu Lys Tyr Thr Asp Tyr
            3380                3385                3390

Leu Thr Val Met Asp Arg Tyr Ser Val Asp Ala Asp Leu Gln Leu Gly
            3395                3400                3405

Glu Leu Ile
    3410

<210> SEQ ID NO 15
<211> LENGTH: 10862
<212> TYPE: DNA
<213> ORGANISM: Flaviviridae Flavivirus Yellow Fever Virus

<400> SEQUENCE: 15
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa acaaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggcctgttct    360 aaggaaagtc aagagagtgg tggccagttt gatgagagga ttgtcctcaa ggaaacgccg     420
ttcccatgat gttctgactg tgcaattcct aatttttggga atgctgttga tgacgggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg    780
tttgaagacc cggcaagaaa aatgatgac tggaagaatg ggtgaaaggc aactccaaaa     840
gattgagaga tggttcgtga ggaaccccctt ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg agggggtgca    1020
tggaggaact tgggtttcag ctaccctgga gcaagacaag tgtgtcactg ttatggcccc    1080
tgacaagcct tcattggaca tctcactaga gacagtagcc attgatagac ctgctgaggt    1140
gaggaaagtg tgttacaatg cagttctcac tcatgtgaag attaatgaca gtgccccag    1200
```

```
cactggagag gcccacctag ctgaagagaa cgaaggggac aatgcgtgca agcgcactta   1260
ttctgataga ggctggggca atggctgtgg cctatttggg aaagggagca ttgtggcatg   1320
cgccaaattc acttgtgcca aatccatgag tttgtttgag gttgatcaga ccaaaattca   1380
gtatgtcatc agagcacaat tgcatgtagg ggccaagcag gaaaattgga ctaccgacat   1440
taagactctc aagtttgatg ccctgtcagg ctcccaggaa gtcgagttca ttgggtatgg   1500
aaaagctaca ctggaatgcc aggtgcaaac tgcggtggac tttggtaaca gttacatcgc   1560
tgagatggaa acagagagct ggatagtgga cagacagtgg gcccaggact tgaccctgcc   1620
atggcagagt ggaagtggcg gggtgtggag agagatgcat catcttgtcg aatttgaacc   1680
tccgcatgcc gccactatca gagtactggc cctgggaaac caggaaggct ccttgaaaac   1740
agctcttact ggcgcaatga gggttacaaa ggacacaaat gacaacaacc tttacaaact   1800
acatggtgga catgtttctt gcagagtgaa attgtcagct ttgacactca aggggacatc   1860
ctacaaaata tgcactgaca aaatgttttt tgtcaagaac ccaactgaca ctggccatgg   1920
cactgttgtg atgcaggtga aagtgtcaaa aggagccccc tgcaggattc cagtgatagt   1980
agctgatgat cttacagcgg caatcaataa aggcattttg gttacagtta accccatcgc   2040
ctcaaccaat gatgatgaag tgctgattga ggtgaaccca ccttttggag acagctacat   2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc agggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aactttggca agagagagct caagtgcgga gatggtatct tcatatttag   2520
agactctgat gactggctga acaagtactc atactatcca gaagatcctg tgaagcttgc   2580
atcaatagta aaagcctctt ttgaagaagg gaagtgtggc ctaaattcag ttgactccct   2640
tgagcatgag atgtggagaa gcagggcaga tgagatcaat gccattttg aggaaaacga   2700 ggtggacatt tctgttgtcg tgcaggatcc aaagaatgtt taccagagag gaactcatcc   2760
attttccaga attcgggatg gtctgcagta tggttggaag acttggggta agaaccttgt   2820
gttctcccca gggaggaaga atggaagctt catcatagat ggaaagtcca ggaaagaatg   2880
cccgttttca aaccgggtct ggaattcttt ccagatagag gagtttggga cgggagtgtt   2940
caccacacgc gtgtacatgg acgcagtctt tgaatacacc atagactgcg atggatctat   3000
cttgggtgca gcggtgaacg gaaaaaagag tgcccatggc tctccaacat tttggatggg   3060
aagtcatgaa gtaaatggga catggatgat ccacaccttg gaggcattag attacaagga   3120
gtgtgagtgg ccactgacac atacgattgg aacatcagtt gaagagagtg aaatgttcat   3180
gccgagatca atcggaggcc cagttagctc tcacaatcat atccctggat acaaggttca   3240
gacgaacgga ccttggatgc aggtaccact agaagtgaag agagaagctt gcccagggac   3300
tagcgtgatc attgatggca actgtgatgg acgggaaaaa tcaaccagat ccaccacgga   3360
tagcgggaaa gttattcctg aatggtgttg ccgctcctgc acaatgccgc ctgtgagctt   3420
ccatggtagt gatgggtgtt ggtatcccat ggaaattagg ccaaggaaaa cgcatgaaag   3480
ccatctggtc cgctcctggg ttacagctgg agaaatacat gctgtccctt ttggtttggt   3540
gagcatgatg atagcaatgg aagtggtcct aaggaaaaga cagggaccaa agcaaatgtt   3600
```

```
ggttggagga gtagtgctct tgggagcaat gctggtcggg caagtaactc tccttgattt   3660
gctgaaactc acagtggctg tgggattgca tttccatgag atgaacaatg gaggagacgc   3720
catgtatatg gcgttgattg ctgccttttc aatcagacca gggctgctca tcggctttgg   3780
gctcaggacc ctatggagcc ctcgggaacg ccttgtgctg accctaggag cagccatggt   3840
ggagattgcc ttgggtggcg tgatgggcgg cctgtggaag tatctaaatg cagtttctct   3900
ctgcatcctg acaataaatg ctgttgcttc taggaaagca tcaaatacca tcttgcccct   3960
catggctctg ttgacacctg tcactatggc tgaggtgaga cttgccgcaa tgttcttttg   4020
tgccgtggtt atcatagggg tccttcacca gaatttcaag gacacctcca tgcagaagac   4080
tatacctctg gtggccctca cactcacatc ttacctgggc ttgacacaac ctttttgggg   4140
cctgtgtgca tttctggcaa cccgcatatt tgggcgaagg agtatcccag tgaatgaggc   4200
actcgcagca gctggtctag tgggagtgct ggcaggactg gcttttcagg agatggagaa   4260
cttccttggt ccgattgcag ttggaggact cctgatgatg ctggttagcg tggctggag    4320 ggtggatggg ctagagctca agaagcttgg tgaagtttca tgggaagagg aggcggagat   4380 cagcggggagt tccgcccgct atgatgtggc actcagtgaa caaggggagt tcaagctgct   4440
ttctgaagag aaagtgccat gggaccaggt tgtgatgacc tcgctggcct tggttggggc   4500
tgccctccat ccatttgctc ttctgctggt ccttgctggg tggctgtttc atgtcagggg   4560
agctaggaga agtggggatg tcttgtggga tattcccact cctaagatca tcgaggaatg   4620
tgaacatctg gaggatggga tttatggcat attccagtca accttcttgg gggcctccca   4680
gcgaggagtg ggagtggcac agggaggggt gttccacaca atgtggcatg tcacaagagg   4740
agctttcctt gtcaggaatg gcaagaagtt gattccatct tgggcttcag taaaggaaga   4800
ccttgtcgcc tatggtggct catggaagtt ggaaggcaga tgggatggag aggaagaggt   4860
ccagttgatc gcggctgttc caggaaagaa cgtggtcaac gtccagacaa aaccgagctt   4920
gttcaaagtg aggaatgggg gagaaatcgg ggctgtcgct cttgactatc cgagtggcac   4980
ttcaggatct cctattgtta acaggaacgg agaggtgatt gggctgtacg gcaatggcat   5040
ccttgtcggt gacaactcct tcgtgtccgc catatcccag actgaggtga aggaagaagg   5100
aaaggaggag ctccaagaga tcccgacaat gctaaagaaa ggaatgacaa ctgtccttga   5160
ttttcatcct ggagctggga agacaagacg tttcctccca cagatcttgg ccgagtgcgc   5220
acggagacgc ttgcgcactc ttgtgttggc ccccaccagg gttgttcttt ctgaaatgaa   5280
ggaggctttt cacggcctgg acgtgaaatt ccacacacag gcttttccg ctcacggcag    5340 cgggagagaa gtcattgatg ctatgtgcca tgccacccta acttacagga tgttggaacc   5400
aactagggtt gttaactggg aagtgatcat tatggatgaa gcccattttt tggatccagc   5460
tagcatagcc gctagaggtt gggcagcgca cagagctagg gcaaatgaaa gtgcaacaat   5520
cttgatgaca gccacaccgc ctgggactag tgatgaattt ccacattcaa atggtgaaat   5580
agaagatgtt caaacggaca tacccagtga gccctggaac acagggcatg actggatcct   5640
ggctgacaaa aggcccacgg catggttcct tccatccatc agagctgcaa atgtcatggc   5700
tgcctctttg cgtaaggctg gaaagagtgt ggtggtcctg aacagaaaaa cctttgagag   5760
agaatacccc acgataaagc agaagaaacc tgactttata ttggccactg acatagctga   5820
```

```
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggaggggggc gcattgggag aaatcccaac agagatggag actcatacta   6000
ctattctgag cctacaagtg aaaataatgc ccaccacgtc tgctggttgg aggcctcaat   6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtgtg ttttgaaggc cctgaggaac atgagatctt     6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgtttc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg gatatctcat    6720
gttccttgga ggcgtcaaac ccactcacat ctcctatatc atgctcatat tctttgtcct    6780
gatggtggtt gtgatccccg agccagggca acaaggtcc atccaagaca accaagtggc     6840
atacctcatt attggcatcc tgacgctggt ttcagcggtg gcagccaacg agctaggcat    6900
gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca agggggtacc   7140
attcatgaag atgaatatct cggtcataat gctgctggtc agtggctgga attcaataac   7200
agtgatgcct ctgctctgtg cataggggtg cgccatgctc cactggtctc tcattttacc    7260
tggaatcaaa gcgcagcagt caaagcttgc acagagaagg gtgttccatg gcgttgccaa    7320
gaaccctgtg ttgatgggaa atccaacagt tgacattgag gaagctcctg aaatgcctgc    7380
cctttatgag aagaaactgg ctctatatct ccttcttgct ctcagcctag cttctgttgc    7440
catgtgcaga acgccttttt cattggctga aggcattgtc ctagcatcag ctgccctagg   7500
gccgctcata gagggaaaca ccagccttct ttggaatgga cccatggctg tctccatgac   7560
aggagtcatg aggggggaatc actatgcttt tgtgggagtc atgtacaatc tatggaagat   7620
gaaaactgga cgccggggga gcgcgaatgg aaaaaactttg ggtgaagtct ggaagaggga    7680
actgaatctg ttggacaagc gacagtttga gttgtataaa aggaccgaca ttgtggaggt    7740
ggatcgtgat acggcacgca gcatttggc cgaagggaag gtgacaccg gggtggcggt     7800
ctccaggggg accgcaaagt taaggtggtt ccatgagcgt ggctatgtca agctggaagg    7860
tagggtgatt gacctgggt gtggccgcgg aggctggtgt tactacgctg ctgcgcaaaa    7920
ggaagtgagt ggggtcaaag gatttactct tggaagagac ggccatgaga acccatgaa     7980
tgtgcaaagt ctgggatgga acatcatcac cttcaaggac aaaactgata tccaccgcct    8040
agaaccagtg aaatgtgaca ccctttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc tcgagaaact    8220
```

```
ggaattgctc caaaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
tgacgtcatc ctcccaattg ggacacgcag tgttgagaca gacaagggac ccctggacaa    8460
agaggccata gaagaaaggg ttgagaggat aaaatctgag tacatgacct cttggtttta    8520
tgacaatgac aaccccctaca ggacctggca ctactgtggc tcctatgtca caaaacctc    8580
aggaagtgcg gcgagcatgg taaatggtgt tattaaaatt ctgacatatc catgggacag    8640
gatagaggag gtcacaagaa tggcaatgac tgacacaacc ccttttggac agcaaagagt    8700
gtttaaagaa aaagttgaca ccagagcaaa ggatccacca gcgggaacta ggaagatcat    8760
gaaagttgtc aacaggtggc tgttccgcca cctggccaga gaaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt ctgggaact    8940
ggtggatgaa gaaaggaagc tgcaccaaca aggcaggtgt cggacttgtg tgtacaacat    9000
gatggggaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg cttacaata    9180
cctaggatat gtgatcagag acctggctgc aatggatggt ggtggattct acgcggatga    9240
caccgctgga tgggacacgc gcatcacaga ggcagacctt gatgatgaac aggagatctt    9300
gaactacatg agcccacatc acaaaaaact ggcacaagca gtgatggaaa tgacatacaa    9360
gaacaaagtg gtgaaagtgt tgagaccagc cccaggaggg aaagcctaca tggatgtcat    9420
aagtcgacga gaccagagag gatccgggca ggtagtgact tatgctctga acaccatcac    9480
caacttgaaa gtccaattga tcagaatggc agaagcagag atggtgatac atcaccaaca    9540
tgttcaagat tgtgatgaat cagttctgac caggctggag gcatggctca ctgagcacgg    9600
atgtaacaga ctgaagagga tggcggtgag tggagacgac tgtgtggtcc ggcccatcga    9660
tgacaggttc ggcctggccc tgtcccatct caacgccatg tccaaggtta gaagggacat    9720
atctgaatgg cagccatcaa aagggtggaa tgattgggag aatgtgccct tctgttccca    9780
ccacttccat gaactacagc tgaaggatgg caggaggatt gtggtgcctt gccgagaaca    9840
ggacgagctc attgggagag aagggtgtc tccaggaaac ggctggatga tcaaggaaac    9900
agcttgcctc agcaaagcct atgccaacat gtggtcactg atgtattttc acaaagggaa    9960
catgaggcta ctgtcattgg ctgtttcctc agctgttccc acctcatggg ttccacaagg   10020
acgcacaaca tggtcgattc atgggaaagg ggagtggatg accacggaag acatgcttga   10080
ggtgtggaac agagtatgga taaccaacaa cccacacatg caggacaaga caatggtgaa   10140
aaaatggaga gatgtccctt atctaaccaa gagacaagac aagctgtgcg gatcactgat   10200
tggaatgacc aatagggcca cctgggcctc ccacatccat ttggtcatcc atcgtatccg   10260
aacgctgatt ggacaggaga aatacactga ctacctaaca gtcatggaca ggtattctgt   10320
ggatgctgac ctgcaactgg gtgagcttat ctgaaacacc atctaacagg aataaccggg   10380
atacaaacca cggtgggaga accggactcc ccacaacctg aaaccgggat ataaaccacg   10440
gctggagaac cggactccgc acttaaatg aaacagaaac cgggataaaa actacggatg   10500
gagaaccgga ctccacacat tgagacagaa gaagttgtca gcccagaacc ccacacgagt   10560
tttgccactg ctaagctgtg aggcagtgca ggctgggaca gccgacctcc aggttgcgaa   10620
```

-continued

```
aaacctggtt tctgggacct cccacccag  agtaaaaaga acggagcctc cgctaccacc   10680
ctcccacgtg gtggtagaaa gacggggtct agaggttaga ggagaccctc cagggaacaa   10740
atagtgggac catattgacg ccagggaaag accggagtgg ttctctgctt ttcctccaga   10800
ggtctgtgag cacagtttgc tcaagaataa gcagaccttt ggatgacaaa cacaaaacca   10860
ct                                                                 10862
```

HIGH YIELD YELLOW FEVER VIRUS STRAIN WITH INCREASED PROPAGATION IN CELLS

RELATED APPLICATION

This application is a continuation-in-part of copending International Application No. PCT/US2010/043010, filed on Jul. 23, 2010, which claims the benefit of priority to U.S. Provisional Application No. 61/230,483, filed on Jul. 31, 2009. The entire teachings of the above applications are incorporated herein by reference.

BACKGROUND OF THE INVENTION

The Yellow Fever virus is endemic, that is, continuously present with low levels of infection in some tropical areas of Africa and the Americas, where it regularly amplifies into epidemics. Other parts of the world, including coastal regions of South America, the Caribbean islands, and Central and North America, are infested with the mosquito vector capable of transmitting the virus and are therefore considered at risk for yellow fever epidemics (World Health Organization Fact Sheet No. 100, revised December, 2001).

For example, in Africa alone, thirty-three countries with a combined population of 508 million, are at risk (Id.). Each year, the World Health Organization (WHO) estimates there are 200,000 cases of yellow fever, with 30,000 deaths (Id.). Travel to these tropical regions also is believed to result in a small number of imported cases in countries generally free of yellow fever. Although yellow fever cases have not been reported in Asia, "this region is at risk because the appropriate primates and mosquitoes are present" (Id.).

The Yellow Fever (YF) virus is in the genus *Flavivirus*, in the family Flaviviridae. In the so-called "jungle" or "sylvan cycle", the YF virus is enzootic, maintained and transmitted by canopy breeding mosquitoes to monkeys in the rainforests. The "urban cycle" begins when humans become infected by entering the rainforests and are bitten by YF-infected mosquitoes. The "urban cycle" continues with peridomestic transmission from humans to mosquitoes and thence to other humans, and can result in yellow fever epidemics in villages and cities. Illness ranges in severity from a self-limited febrile illness to severe hepatitis and fatal hemorrhagic disease.

Unvaccinated humans, including both native people and travelers to YF endemic areas are at significant risk of YF infection when occupational and other activities bring them in contact with infected mosquitoes in the sylvan cycle or the urban cycle.

Patients with yellow fever may be viremic, i.e., have virus in their blood, for 3 to 6 days during the early phase of illness. This phase may be followed by a short period of symptom remission.

The toxic phase develops as the fever returns, with clinical symptoms including, for example, high fever and nausea, hemorrhagic symptoms, including hematemesis (black vomit), epistaxis (nose bleed), gum bleeding, and petechial and purpuric hemorrhages (bruising). Deepening jaundice and proteinuria frequently occur in severe cases.

In the late stages of disease, patients can develop hypotension, shock, metabolic acidosis, acute tubular necrosis, myocardial dysfunction, and cardiac arrhythmia. Confusion, seizures, and coma can also occur, as well as complications such as secondary bacterial infections and kidney failure.

There is no specific treatment for yellow fever. Steps to prevent yellow fever include use of insect repellent, protective clothing, and vaccination with the available, but risky attenuated vaccine.

Live, attenuated vaccines produced from the 17D substrain, are available, but adverse events associated with the attenuated vaccine can lead to a severe infection with the live 17D virus, and serious and fatal adverse neurotropic and viscerotropic events, the latter resembling the severe infection by the wild-type YF virus. Thus there is a need for a safer, inactivated, non-replicating vaccine that will elicit a neutralizing antibody response while eliminating the potential for neurotropic and viscerotropic adverse events.

Thus, there is an on-going need for an effective, inactivated, "killed" or non-replicating vaccine in order to avoid the potential for neurotropic and viscerotropic adverse events associated with the currently available attenuated YF 17D vaccine. Further, there is a need for an improved vaccine produced in Vero cells without animal-derived proteins, a vaccine that can be safely used for persons for whom the live vaccine is contraindicated or for whom warnings appear on the label. Such individuals include immuno-suppressed persons, persons with thymic disease, egg-allergic, young infants, and the elderly.

A problem with any potential inactivated virus is that it may need to be delivered at a higher titer than the existing live attenuated vaccines, because the latter can expand antigenic mass during cycles of replication in the host whereas an inactivated vaccine contains a fixed dose of antigen. Therefore, in order to develop a sufficiently potent inactivated vaccine, it is desirable to modify the YF virus in order to produce a high yield of virus in the conditioned medium (also called supernatant fluid) of a cell culture. It is highly desirable to use the attenuated 17D vaccine strain for vaccine manufacturing, since the 17D strain can be manipulated at a lower level of biocontainment than the wild-type virulent YF virus. However, the attenuated 17D vaccine strain yields in cell culture are inherently lower than yields of wild-type virus. For these reasons, modifications of the 17D vaccine strain to achieve higher yields in cell culture used for vaccine production would be useful.

BRIEF SUMMARY OF THE INVENTION

The invention provides a vaccine comprising a strain or strains of Yellow Fever virus which have been adapted to propagate in Vero cells to higher yields than an unadapted virus. "Unadapted virus" is defined to mean that Yellow Fever virus vaccine known as 17D. Sequence analysis of examples of such strains demonstrates that an adapted virus possessing a mutation in the envelope (E) protein resulting in a lysine to arginine substitution in amino acid residue 160 has improved properties. The invention also provides for vaccines comprising a Yellow Fever virus containing one or more mutations in the E protein, that result in increased propagation in Vero cells and in higher yields when using serum free culture medium than the unadapted virus.

Additional examples of adapted Yellow Fever virus strains which propagate in Vero cells to higher yields than unadapted virus have been identified. These include modified Yellow Fever virus strains wherein the nucleic acid molecules of said modified Yellow Fever virus strains comprise at least one amino acid mutation selected from: an amino acid mutation in the NS1 protein, an amino acid mutation in the NS2A protein, and an amino acid mutation in the NS4B protein, optionally wherein said at least one amino acid mutation is in further combination with an amino acid mutation in the envelope protein. Preferred embodiments include 1) a strain having three mutations: a) a lysine to arginine substitution in amino acid residue 160 (lys$_{160}$arg) in the E protein, b) a threonine to isoleucine substitution in amino acid residue 317 (thr$_{317}$ile) in the non-structural protein 1 (NS1), and c) a phenylalanine to leucine substitution in amino acid residue 170 (phe$_{170}$leu) in the non-structural protein 2A (NS2A); and 2) a strain with a mutation in the non-structural protein 4B (NS4B), resulting in an isoleucine to methionine substitution at amino acid residue 113 (ile$_{113}$met).

The invention provides for vaccines comprising a Yellow Fever virus containing one or more mutations selected from: a mutation in the NS1 protein optionally combined with a mutation in the E protein; a mutation in the NS2A protein optionally combined with a mutation in the E protein; and a mutation in the NS4B protein optionally combined with a mutation in the E protein that result in increased propagation in Vero cells and in higher yields than the unadapted virus.

The Yellow Fever virus is the prototype species in the genus *Flavivirus*, in the family Flaviviridae. Structural and functional studies of the E protein of tick-borne encephalitis (TBE) virus, a fast-growing, virulent member of the *flavivirus* genus, indicate that Domains I and II in the E protein of TBE participate in an acidic pH-dependent conformational change that facilitates *flavivirus* membrane fusion with the host and subsequent infectivity. The junction of Domains I and II function as a 'molecular hinge' resulting in a major rearrangement of these domains from of the normal dimeric structure of the E protein at acid pH into a homotrimeric state. [Rey F A et al. The envelope glycoprotein from tick-borne encephalitis virus at 2 Åresolution. *Nature* 375: 291-298 (1995); Heinz F X et al. Structural changes and functional control of the tick-borne encephalitis virus glycoprotein E by the heterodimeric association with protein prM. *Virology* 198: 109-117 (1994); Mandl C W et al. Antigenic structure of the *flavivirus* envelope protein E at the molecular level, using tick-borne encephalitis virus as a model. *Journal of Virology* 63(2): 564-571 (1989); Harrison S C. Viral membrane fusion. *Nature structural and molecular biology* 15(7): 690-698 (2008); Stiasny K et al. Molecular mechanisms of *flavivirus* membrane fusion. *Amino acids* DOI 10.1007/s00726-009-0370-4, published on line 1 Nov. 2009.]

Lys 160 in the E protein of Yellow Fever virus is located in the molecular hinge region between Domains I and II. Mutations in this region could alter the acid-dependent conformational change in region Domain I of the E protein required for fusion and virus internalization into the cell cytoplasm. Without being bound by theory, higher yields seen with the lysine to arginine change at amino acid 160 in Domain I of the E protein of the adapted Yellow Fever virus strain may be due to an increased affinity for protons that arginine provides as compared with lysine, that results in enhanced membrane fusion with the host and more efficient infectivity. In regard to the invention, it is important to note that the side chains of lysine and arginine have pKa values of 10.53 and 12.48, respectively, indicating a one hundred fold greater affinity for protons in arginine than in lysine. The increased affinity for protons that the side chain of arginine shows relative to lysine's side chain may enhance the rate and efficiency of E protein conformational change at the molecular hinge, membrane fusion, and *flavivirus* infectivity, resulting in higher yields of virus in the adapted virus strain.

Other members within the genus *Flavivirus* include West Nile, dengue, and Japanese encephalitis viruses. The non-structural proteins found in West Nile Virus are known to be directly or indirectly involved in viral RNA synthesis. Amino acid substitutions in the non-structural proteins of these viruses have been shown to affect the yields of mutant viruses grown in Vero cells. For example, a proline to leucine substitution at amino acid 250 in the NS1 protein of the *flavivirus* Kunjin, a West Nile Virus subtype, grows at 100-fold lower titers than wild-type virus. Similarly, mutation of the C-terminal sites in the NS2A protein of yellow fever virus was shown to be lethal for virus replication. Brinton Mass. The molecular biology of west nile virus: a new invader of the western hemisphere. *Annual Review of Microbiology* 56: 371-402 (2002).

In a first aspect, the invention provides a modified Yellow Fever virus strain that results in increased propagation in Vero cells and a higher yield in the conditioned medium of a cell culture relative to the unadapted virus comprising at least one mutation relative to the unadapted virus selected from: a mutation in the E protein, a mutation in the NS1 protein, a mutation in the NS2A protein, and a mutation in the NS4B protein, optionally wherein said at least one mutation in the NS1 protein, the NS2A protein, or the NS4B protein is in further combination with a mutation of the E protein.

Replacement of basic amino acids that are located within 20 amino acids, or within 10 Angstroms, of lysine 160 in the E protein of the Yellow Fever virus (including lysine 160 itself), with amino acids having higher side chain pKa values than the replaced basic amino acids, can result in strains of Yellow Fever virus that produce higher yields of virus than an unadapted Yellow Fever virus. The invention thus provides for Yellow Fever viruses, and vaccines containing them, comprising a modified nucleic acid molecule encoding an E protein, the virus being capable of propagating in Vero cells to higher yields than the unadapted virus. Preferred embodiments include viruses comprising a modified E protein with an increased pKa within 20 amino acids, or within 10 Angstroms, of lysine 160 in the E protein.

In a third aspect, the invention provides a nucleic acid molecule comprising a sequence encoding a modified envelope protein of the Yellow Fever virus, wherein said nucleic acid molecule comprises a nucleotide mutation in the codon for the amino acid at position 160 of the envelope protein. In an embodiment of this aspect, the invention provides a nucleic acid molecule comprising a sequence encoding at least one modified nucleic acid relative to the nucleic acid of the unadapted virus, wherein said at least one modified nucleic acid is selected from: a modified nucleic acid of the NS1 protein, a modified nucleic acid of the NS2A protein and a modified nucleic acid of the NSB4 protein, optionally wherein said at least one modified nucleic acid is in further combination with a modified nucleic acid of the envelope protein of the Yellow Fever virus, wherein said optional modified nucleic acid of the envelope protein comprises a nucleotide mutation in the codon for the amino acid at position 160 of the envelope protein. In a further embodiment of this aspect, the nucleotide mutation in the codon for the amino acid at position 160 of the envelope protein results in a change from AAG to AGG, AGA, CGC, CGA, CGG or CGU. Additionally, the invention provides for vectors, constructs, modified Yellow Fever virus strains, and cells comprising or containing such a nucleic acid molecule or a protein encoded thereby.

In a fourth aspect, the invention provides a modified Yellow Fever virus strain, wherein the nucleic acid molecule of said strain comprises a sequence encoding an envelope protein of the Yellow Fever virus, wherein said envelope protein comprises an amino acid mutation at position 160 of the envelope protein. In an embodiment of this aspect, the invention provides a modified Yellow Fever virus strain, wherein the nucleic acid molecule of said strain comprises a sequence encoding an envelope protein of the Yellow Fever virus, wherein said envelope protein optionally comprises an amino acid mutation at position 160 of the envelope protein.

In a fifth aspect, the invention provides a nucleic acid molecule comprising a sequence encoding an envelope protein of the Yellow Fever virus, wherein said envelope protein comprises an amino acid mutation at position 160 of the envelope protein. In an embodiment of this aspect, the invention optionally provides a nucleic acid molecule comprising a sequence encoding an envelope protein of the Yellow Fever virus, wherein said envelope protein comprises an amino acid mutation at position 160 of the envelope protein. Additionally, the invention provides for vectors, constructs, modified Yellow Fever virus strains, and cells comprising or containing such nucleic acid molecules or proteins encoded thereby. The nucleic acid molecules preferably comprise a sequence encoding a modified envelope protein of the Yellow Fever virus, wherein said nucleic acid molecule encodes the protein sequence in SEQ ID NO. 4, 6, or 7.

In a sixth aspect, the invention provides a method for enhancing the propagation of Yellow Fever virus in cells. In an embodiment of this aspect, the method comprises mutating a nucleic acid molecule comprising a sequence encoding the envelope protein of the Yellow Fever virus, wherein the mutation comprises a nucleotide mutation in the codon for the amino acid at position 160 of the envelope protein. In another embodiment of this aspect, the method optionally comprises mutating a nucleic acid molecule comprising a sequence encoding the envelope protein of the Yellow Fever virus, wherein the mutation comprises a nucleotide mutation in the codon for the amino acid at position 160 of the envelope protein. In a further embodiment, the method comprises mutating a nucleic acid molecule comprising a sequence encoding the envelope protein of the Yellow Fever virus, wherein said mutation comprises an amino acid mutation at position 160 of the envelope protein. In a final embodiment, the method optionally comprises mutating a nucleic acid molecule comprising a sequence encoding the envelope protein of the Yellow Fever virus, wherein said mutation comprises an amino acid mutation at position 160 of the envelope protein. The word "mutating" is intended to mean selecting for a mutation, or introducing a mutation. The relevant mutant viruses can be obtained by a method of selection and evolutionary pressure during passages in a specific host cell line (such as Vero cells) or by site-directed mutagenesis using infectious clone technology well known in the art. However, the former method is preferred because it identifies mutated viruses by virtue of the desired phenotypic characteristic (increased yields in Vero cell cultures).

In a seventh aspect, the invention provides a modified Yellow Fever virus strain, wherein the nucleic acid molecule of said strain comprises a nucleotide mutation in the codon for amino acids flanking the E160 codon selected from position 134, 137, 144, 148, 157, 160, 175, or 177 of the envelope protein of Yellow Fever virus. In an embodiment of this aspect, the invention provides a modified Yellow Fever virus strain, wherein the nucleic acid molecule of said strain optionally comprises a nucleotide mutation in the codon for amino acids flanking the E160 codon selected from position 134, 137, 144, 148, 157, 160, 175, or 177 of the envelope protein of Yellow Fever virus. In another embodiment of this aspect, the mutated codon within 20 amino acids flanking the E160 mutation results in an amino acid mutation in the envelope protein at that position, wherein the pKa value of the side chain of the mutated amino acid is higher than the pKa value of the side chain of the original amino acid at that position.

In an eighth aspect, the invention provides for Yellow Fever viruses, and vaccines containing them, comprising a modified nucleic acid molecule encoding an NS1 protein, the virus being capable of propagating in Vero cells to higher yields than the unadapted virus. Preferred embodiments include viruses comprising a modified NS1 protein and a modified E protein. A more preferred embodiment includes viruses comprising a modified NS1 protein and a modified E protein with an increased pKa within 20 amino acids, or within 10 Angstroms, of lysine 160 in the E protein.

In a ninth aspect, the invention provides for Yellow Fever viruses, and vaccines containing them, comprising a modified nucleic acid molecule encoding an NS2A protein, the virus being capable of propagating in Vero cells to higher yields than the unadapted virus. Preferred embodiments include viruses comprising a modified NS2A protein and a modified E protein. A more preferred embodiment includes viruses comprising a modified NS2A protein and a modified E protein with an increased pKa within 20 amino acids, or within 10 Angstroms, of lysine 160 in the E protein.

In a tenth aspect, the invention provides for Yellow Fever viruses, and vaccines containing them, comprising a modified nucleic acid molecule encoding an NS1 protein and an NS2A protein, the virus being capable of propagating in Vero cells to higher yields than the unadapted virus. Preferred embodiments include viruses comprising a modified NS1 protein, a modified NS2 protein, and a modified E protein. A more preferred embodiment includes viruses comprising a modified NS1 protein, a modified NS2 protein, and a modified E protein with an increased pKa within 20 amino acids, or within 10 Angstroms, of lysine 160 in the E protein.

In an eleventh aspect, the invention provides for Yellow Fever viruses, and vaccines containing them, comprising a modified nucleic acid molecule encoding an NS4B protein, the virus being capable of propagating in Vero cells to higher yields than the unadapted virus.

In a twelfth aspect, the invention provides a nucleic acid molecule comprising a sequence encoding a modified non-structural protein 1 of the Yellow Fever virus, wherein said nucleic acid molecule comprises a nucleotide mutation in the codon for the amino acid at position 317 of the non-structural protein 1. In an embodiment of this aspect, the nucleotide mutation in the codon for the amino acid at position 317 of the non-structural protein 1 results in a change from ACA to AUA. Additionally, the invention provides for vectors, constructs, modified Yellow Fever virus strains, and cells comprising or containing such a nucleic acid molecule or a protein encoded thereby.

In a thirteenth aspect, the invention provides a nucleic acid molecule comprising a sequence encoding a modified non-structural protein 2A of the Yellow Fever virus, wherein said nucleic acid molecule comprises a nucleotide mutation in the codon for the amino acid at position 170 of the non-structural protein 2A. In an embodiment of this aspect, the nucleotide mutation in the codon for the amino acid at position 170 of the non-structural protein 2A results in a change from UUU to CUU. Additionally, the invention provides for vectors, constructs, modified Yellow Fever virus strains, and cells comprising or containing such a nucleic acid molecule or a protein encoded thereby.

In a fourteenth aspect, the invention provides a nucleic acid molecule comprising a sequence encoding a modified non-structural protein 4B of the Yellow Fever virus, wherein said nucleic acid molecule comprises a nucleotide mutation in the codon for the amino acid at position 113 of the non-structural protein 4B. In an embodiment of this aspect, the nucleotide mutation in the codon for the amino acid at position 113 of the non-structural protein 4B results in a change from AUA to AUG. Additionally, the invention provides for vectors, constructs, modified Yellow Fever virus strains, and cells comprising or containing such a nucleic acid molecule or a protein encoded thereby.

In a fifteenth aspect, the invention provides a modified Yellow Fever virus strain, wherein the nucleic acid molecule of said strain comprises a sequence encoding proteins of the Yellow Fever virus, wherein said proteins comprise an amino acid mutation at position 160 of the envelope protein, at position 317 of the NS1 protein, at position 170 of the NS2A protein, or at position 113 of the NS4B protein.

In a sixteenth aspect, the invention provides a nucleic acid molecule comprising a sequence encoding an envelope protein, an NS1 non-structural protein, an NS2A non-structural protein, or an NS4B non-structural protein of the Yellow Fever virus, wherein said proteins comprise an amino acid mutation at position 160 of the envelope protein, at position 317 of the NS1 protein, at position 170 of the NS2A protein, or at position 113 of the NS4B protein. Additionally, the invention provides for vectors, constructs, modified Yellow Fever virus strains, and cells comprising or containing such a nucleic acid molecule or proteins encoded thereby. The nucleic acid molecules preferably comprise a sequence encoding a modified protein of the Yellow Fever virus, wherein said nucleic acid molecule encodes the protein sequence in SEQ ID NO: 7 and SEQ ID NO: 8.

In a seventeenth aspect, the invention provides a method for enhancing the propagation of Yellow Fever virus in cells. In an embodiment of this aspect, the method comprises mutating a nucleic acid molecule comprising a sequence encoding the envelope protein, the NS1 non-structural protein, the NS2A non-structural protein, or the NS4B non-structural protein of the Yellow Fever virus, wherein said mutations comprise an amino acid mutation at position 160 of the envelope protein, at position 317 of the NS1 protein, at position 170 of the NS2A protein, or at position 113 of the NS4B protein. The word "mutating" is intended to mean selecting for a mutation, or introducing a mutation.

In an eighteenth aspect, the invention provides a modified Yellow Fever virus strain, wherein the nucleic acid molecule of said strain comprises a nucleotide mutation in the codon for amino acids 317 of the NS1 protein, 170 of the NS2A protein, or 113 of the NS4B protein, and wherein the nucleic acid molecule also comprises a nucleotide mutation in the codon for amino acids flanking the E160 codon selected from position 134, 137, 144, 148, 157, 160, 175, or 177 of the envelope protein of Yellow Fever virus. In an embodiment of this aspect, the mutated codon within 20 amino acids flanking the E160 mutation results in an amino acid mutation in the envelope protein at that position, wherein the pKa value of the side chain of the mutated amino acid is higher than the pKa value of the side chain of the original amino acid at that position.

The invention also provides methods of making and using the nucleic acid molecules, modified E proteins, modified NS1 proteins, modified NS2A proteins, modified NS4B proteins, modified Yellow Fever viruses, vectors, constructs and cells containing the same.

BRIEF DESCRIPTION OF THE DRAWINGS

Figure 3B:
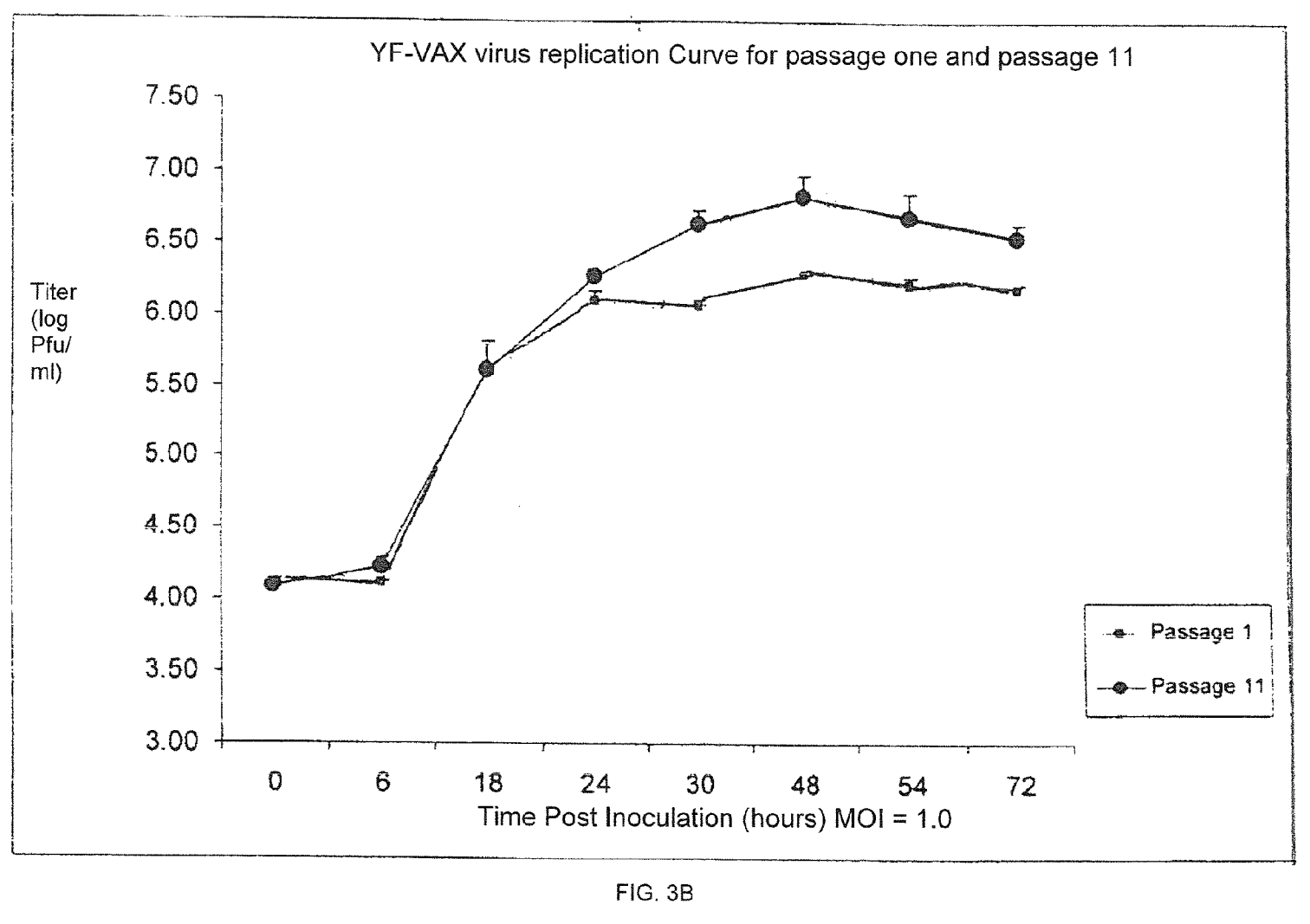

FIG. 3B is a graphical representation of the virus replication for passage one (P1) and passage 11 (P11) of the initial experiment, in which P11 virus differs from P1 by a single mutation at E160 (lys→arg)

FIG. 4A-L depicts the consensus alignment of the P1 and P11 nucleic acid sequences. The starting nucleic acid sequence, P1, is identified herein as SEQ ID NO: 1. A comparison of the P1 passage and the P11 passage revealed a genetic mutation at nucleotide residue #211 of SEQ ID NO: 1, and a second mutation at nucleotide residue #1452 of SEQ ID NO: 1. Thus, "P1 consensus" corresponds to SEQ ID NO.1; "P11 consensus" corresponds to SEQ ID NO. 2 having the codon mutation at envelope protein amino acid position 160.

FIG. 5A-J depicts the amino acid sequence of P1 and P11, with the Series B-P1 and Series B3-P11 amino acid sequences from the repeat passaging study. The amino acid sequence for P1 is identified herein as SEQ ID NO: 3. A comparison of the amino acid sequence for P1 and that of P11 (SEQ ID NO. 4) revealed a mutation at amino acid residue 160 of the envelope protein (E160) (amino acid 445 of the P1 amino acid sequence in FIG. 5B). Series B-P1 and Series B3-P11 present partial amino acid sequences from the repeat passaging study. The amino acid sequence for B-P1 is identified herein as SEQ ID NO: 5. A comparison of the amino acid sequence for B-P1 and that of B3-P11 (SEQ ID NO. 6) revealed a mutation at amino acid residue 160 of the envelope protein (E160) in B3-P11 (amino acid 445 of the P1 amino acid sequence).

Figure 8D:
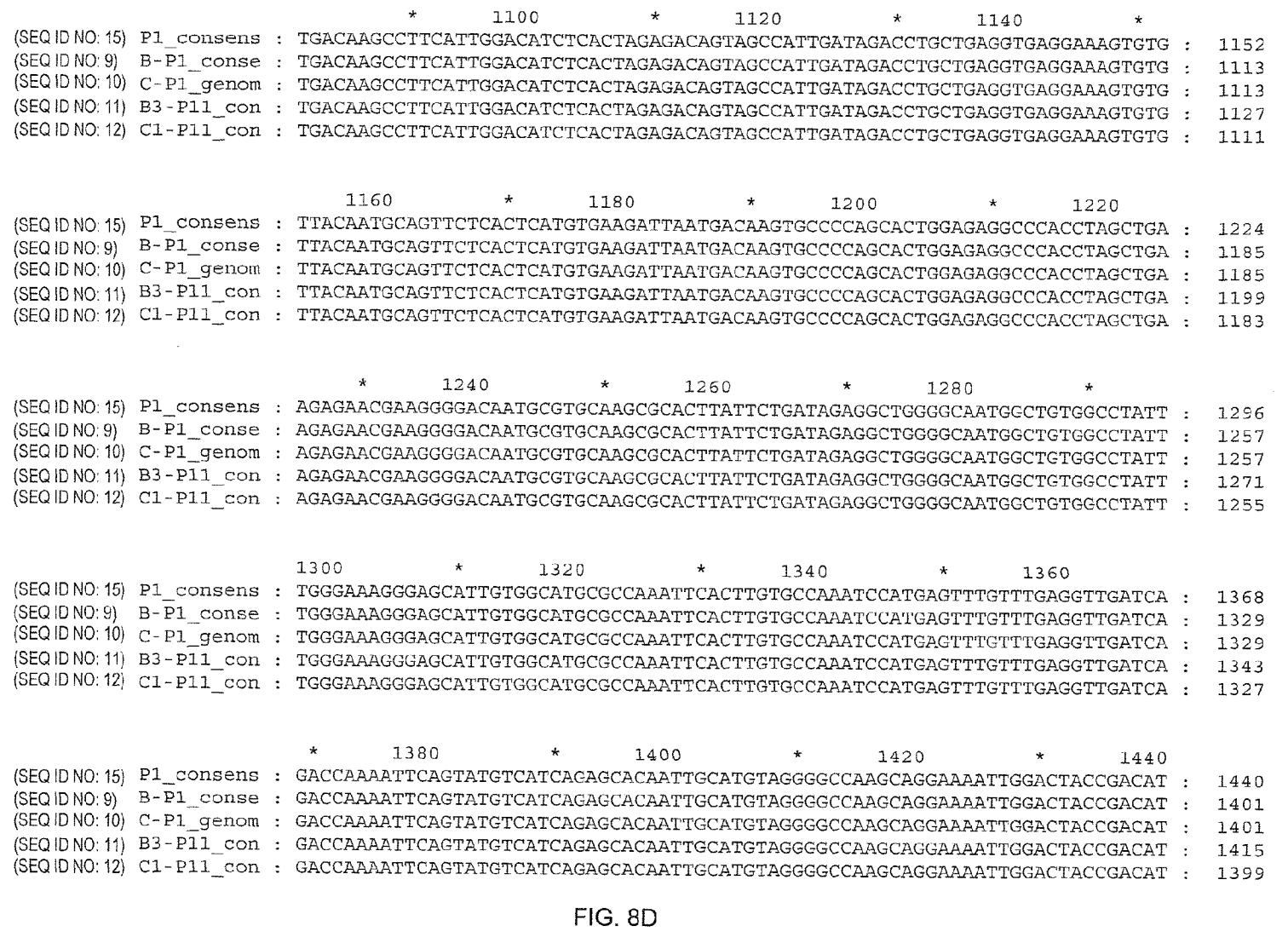
Figure 8G:
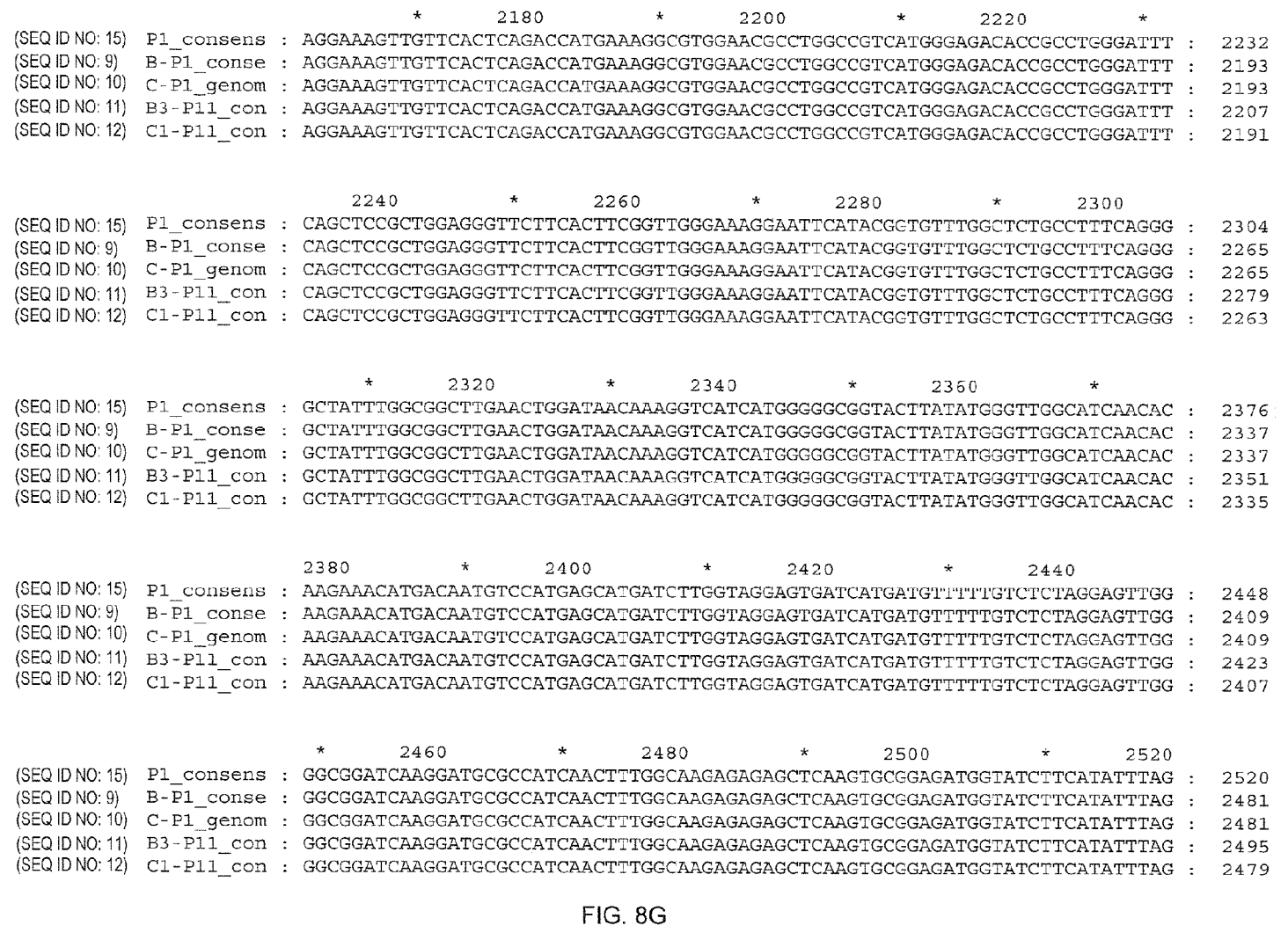
Figure 8N:
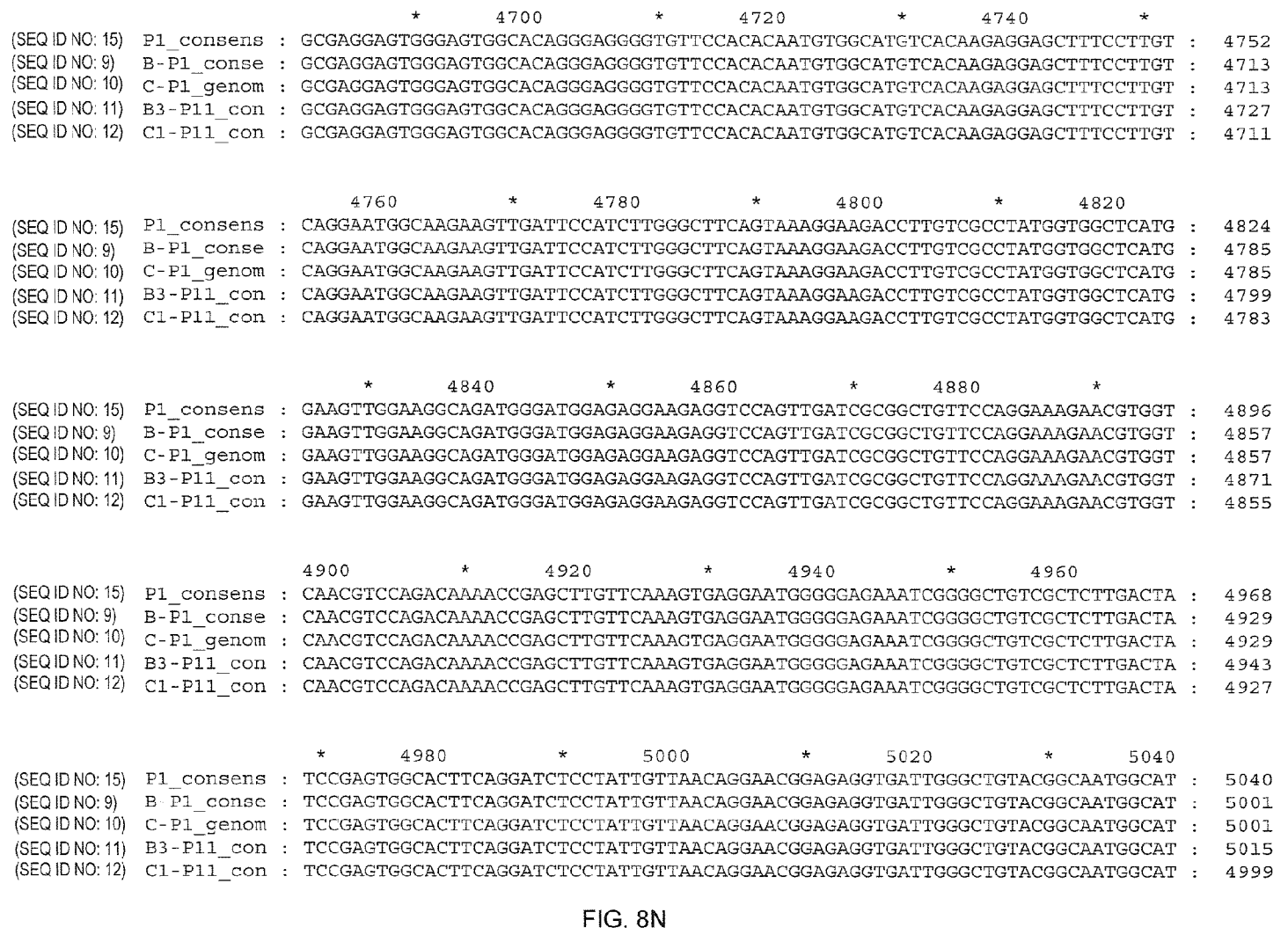
Figure 8U:
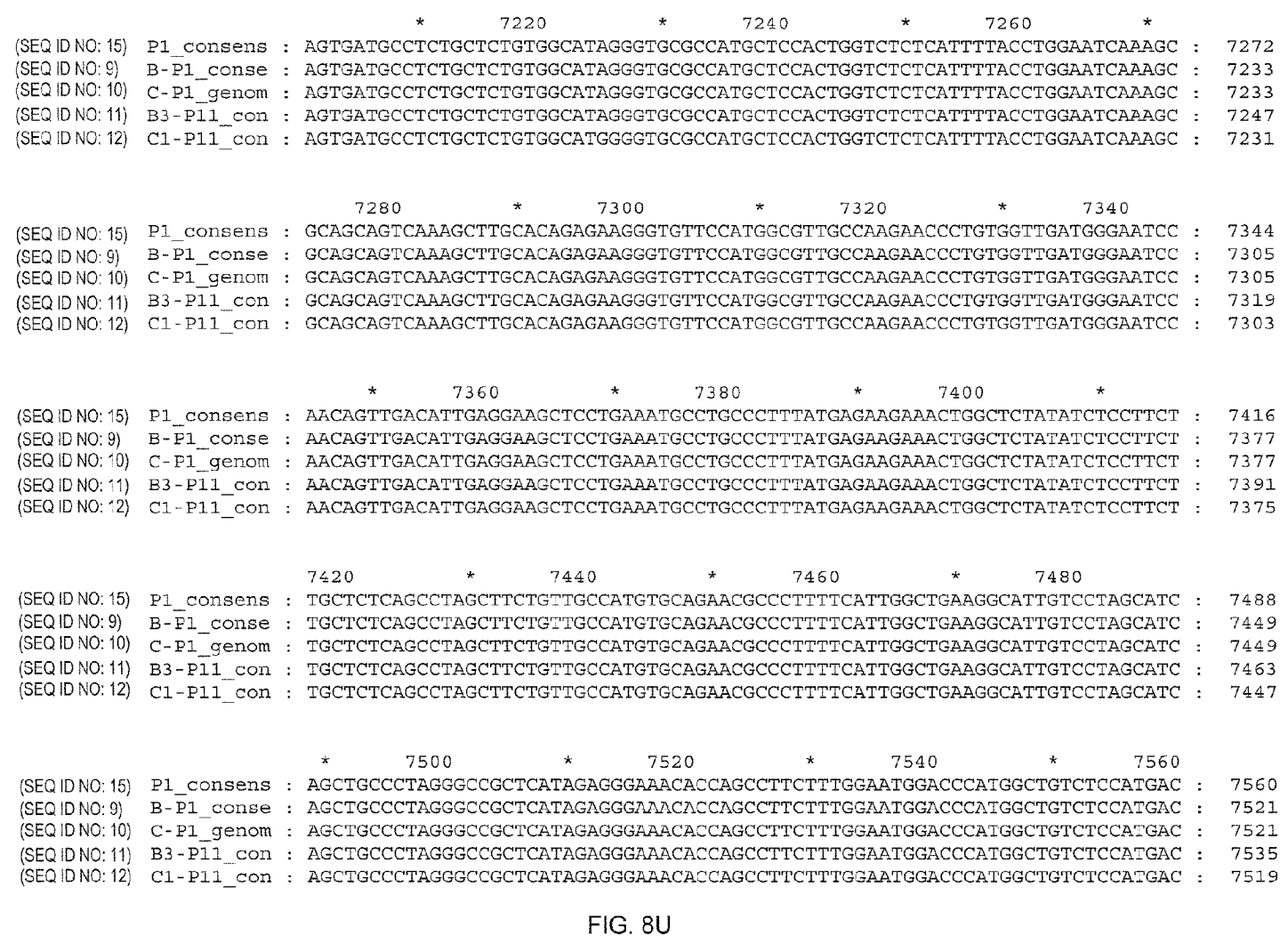
Figure 8Y:
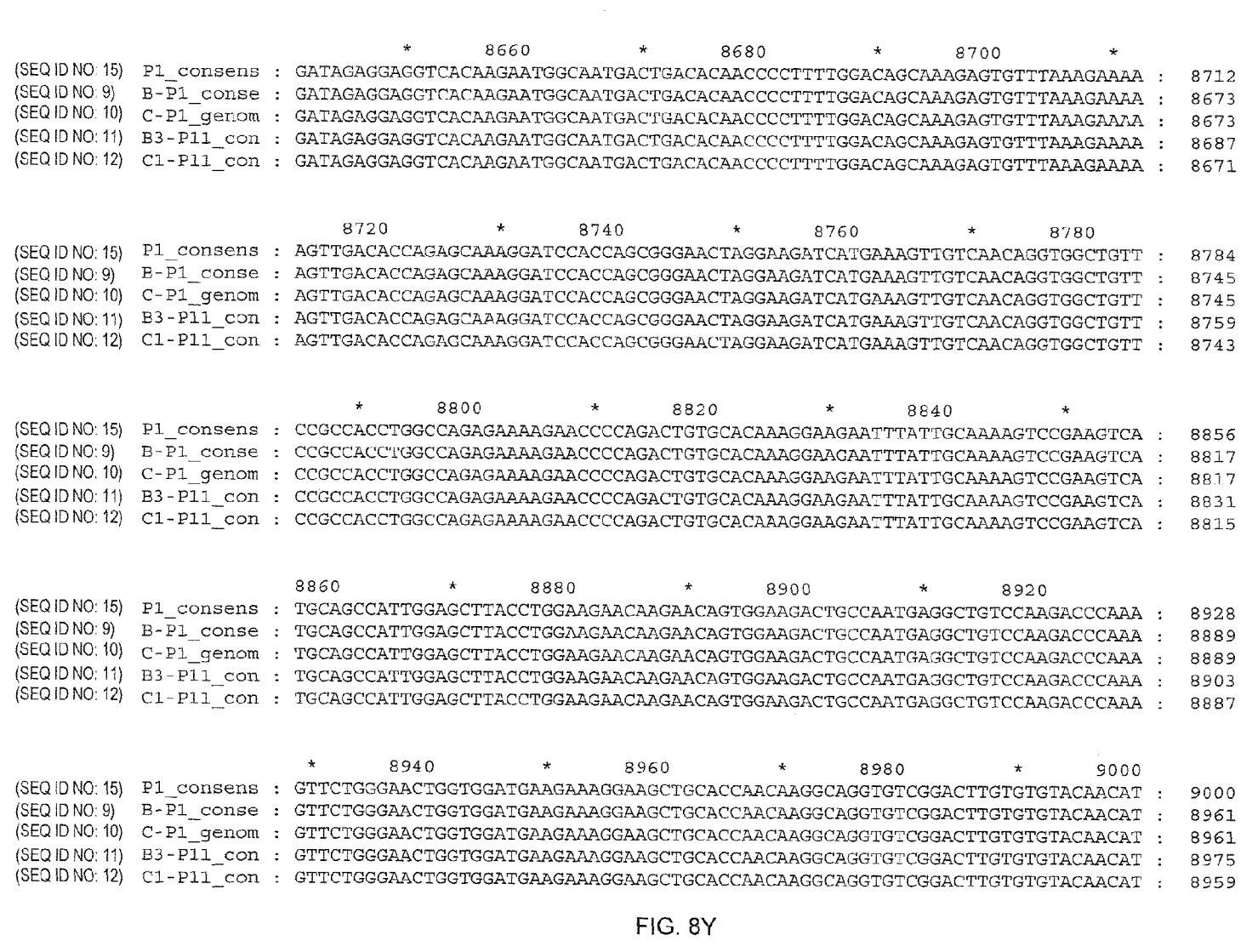

FIG. 8A-EE depicts the consensus alignment of the P1, B-P1, C-P1, B3-P11 and C1-P11 nucleic acid sequences. The nucleic acid sequence, P1, is identified herein as SEQ ID NO: 15. The nucleic acid sequence, B-P1, is identified herein as SEQ ID NO: 9. The nucleic acid sequence, B3-P11, is identified herein as SEQ ID NO: 11. The nucleic acid sequence, C-P1, is identified herein as SEQ ID NO: 10. The nucleic acid sequence, C1-P11, is identified herein as SEQ ID NO: 12. A comparison of the B-P1 passage and the B3-P11 passage revealed a genetic mutation in B3-P11 at nucleotide residue #1452 of SEQ ID NO: 15, a second mutation in B3-P11 at nucleotide residue #3402 of SEQ ID NO: 15, and a third mutation in B3-P11 at nucleotide residue #4016 of SEQ ID NO: 15. A comparison of the C-P1 passage and the C1-P11 passage revealed a genetic mutation in C1-P11 at nucleotide residue #7225 of SEQ ID NO: 15. SEQ ID NO: 11 corresponds to B3-P11, and has the codon mutations at envelope protein amino acid position 160, non-structural protein 1 amino acid position 317, and non-structural protein 2A amino acid position 170. SEQ ID NO.12 corresponds to C1-P11, and has the codon mutation at non-structural protein 4B amino acid position 113.

FIG. 9A-F depicts the amino acid sequence of B-P1 and B3-P11 from the repeat passaging study. The amino acid sequence for B-P1 is identified herein as SEQ ID NO: 13. A comparison of the amino acid sequence for B-P1 and that of B3-P11 (SEQ ID NO: 7) revealed a mutation at amino acid residue 160 of the envelope protein (E160) (amino acid 445 in FIG. 9A), a mutation at amino acid residue 317 of the non-structural protein 1 (NS1-317) (amino acid 1095 in FIG. 9B), and a mutation at amino acid residue 170 of the non-structural protein 2A (NS2A-170) (amino acid 1300 in FIG. 9C). Series B-P1 and Series B3-P11 present complete amino acid sequences from the repeat passaging study.

FIG. 10A-F depicts the amino acid sequence of C-P1 and C1-P11 from the repeat passaging study. The amino acid sequence for C-P1 is identified herein as SEQ ID NO: 14. A comparison of the amino acid sequence for C-P1 and that of C1-P11 (SEQ ID NO: 8) revealed a mutation at amino acid residue 113 of the non-structural protein 4B (NS4B-113) (amino acid 2369 in FIG. 10E). Series C-P1 and Series C1-P11 present complete amino acid sequences from the repeat passaging study.

DETAILED DESCRIPTION OF THE PREFERRED EMBODIMENTS

Figure 1:
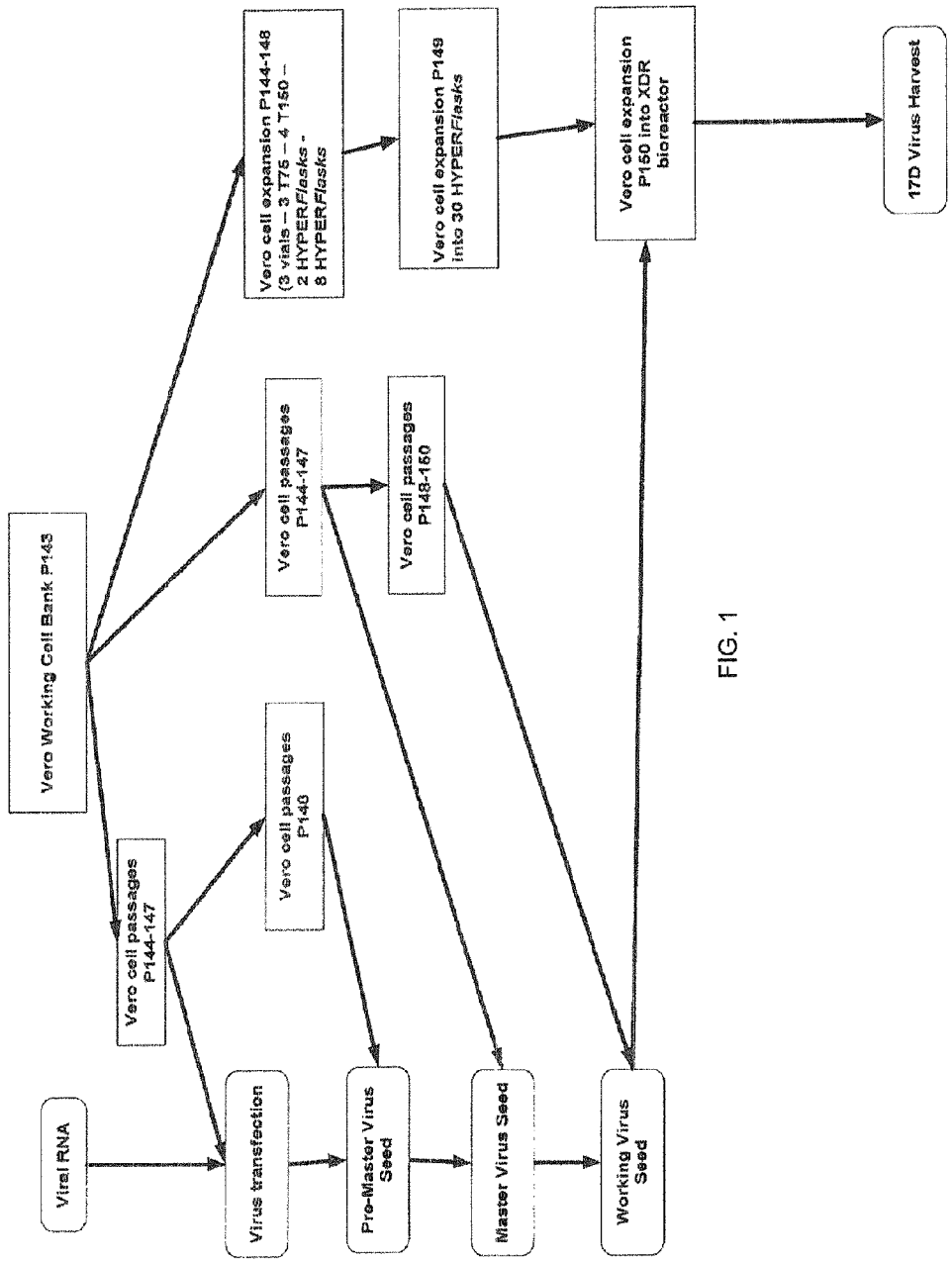
FIG. 1 is a schematic representation of the passage history of Vero cells during the manufacture of the disclosed yellow fever vaccine.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Overview of Approach and Benefits

The invention relates to compositions and methods for use in preventing Yellow Fever virus infection. Disclosed herein is a method of producing an inactivated Yellow Fever virus candidate, the method comprising the serial passage of the YF 17D virus (i.e., an "unadapted virus") in certified African green monkey kidney cells (VERO) to increase the titer to yield a sufficient antigenic mass to induce a protective immune response and/or modify the nucleotide sequence of the viral genome. This method has been repeated and shown to be reproducible.

One embodiment of the invention is a modified Yellow Fever (YF) virus that will grow to high titers in Vero cells. Another embodiment of the invention is a vaccine comprising a whole virion, chemically inactivated Yellow Fever (YF) virus prepared from serum-free conditioned medium from Vero cells infected with 17D virus. In one embodiment of the invention, the virus has been purified from host cell DNA and proteins by depth filtration, ultrafiltration, diafiltration, and chromatographic separation. The method is described in U.S. Application Ser. No. 61/228,026 filed on Jul. 23, 2009, and its corresponding International Application No. PCT/US2010/043013 filed on Jul. 23, 2010, which are each incorporated herein by reference. The purified virus may be inactivated by using a method that ensures preservation of critical, neutralizing epitopes. For example, the virus can be inactivated using formalin, heat, UV, gamma irradiation or beta-propiolactone. A purified, inactivated virus may be formulated with an adjuvant, such as adsorbed to aluminum hydroxide adjuvant, and stored as a liquid at temperatures of from about 2 degrees Celsius (2° C.) to about 8 degrees Celsius (8° C.).

A vaccine containing the purified, inactivated virus is believed to be safer than the currently available attenuated, live YF virus vaccine because the disclosed inactivated YF virus vaccine is non-replicating. The inventors of the present subject matter have now developed a safer, inactivated, non-replicating YF vaccine that will elicit a neutralizing antibody response while eliminating the potential for neurotropic and viscerotropic adverse events. In addition, the improved vaccine can be manufactured by modern methods in Vero cells without animal derived proteins, and therefore it can be used safely in persons (including egg-allergic persons) for whom the live vaccine (produced in hens' eggs) is contraindicated or for whom warnings appear in the label. Such warnings would include, for example warnings to immunosuppressed persons, persons with thymic disease, egg-allergic persons, infants <9 months, and the elderly.

Adaptation of Yellow Fever Virus for Robust Production in Vero Cells:

The Vero cells used in the virus development phase were obtained from the World Health Organization (W.H.O.) seed lot, WHO Vero 10-87 Cell Bank at Passage 134. The WHO Vero 10-87 Cell Bank was originally made by the Institut Merieux using the ATCC Vero cell line CCL81 at Passage 129. The cells were thawed into OptiPRO™ SFM (serum-free medium) supplemented with 5% fetal bovine serum which was removed 24 hours later and replaced with OptiPRO™ SFM medium without fetal bovine serum. The serum, certified as being of USA origin, was gamma irradiated and had been tested for adventitious agents by the manufacturer; additional testing for sterility, mycoplasma, and adventitious viruses was performed on this material by WuXi AppTec. All subsequent passages of Vero cells to make the cell banks, virus seeds, and vaccine were made in OptiPRO™SFM without serum. No other animal derived materials or products were used in producing the cell banks or the final vaccine according to an embodiment of the invention.

Preparation of Vero Cell Banks:

Master and Working Cell banks were prepared according to cGMP and were tested and characterized according to FDA Points to Consider. The Vero cells had an established provenance and were free from regulatory concerns about Bovine spongiform encephalitis (BSE). Serum-free growth medium was employed in propagating cells.

Passage History of Vero Cells During Manufacture of Seed Viruses and Vaccine Lots:

The passage history of Vero cells during the manufacture of the disclosed yellow fever vaccine is shown schematically in FIG. 1. The WHO cells were received at Passage 134, the Master Cell Bank (MCB) and Working Cell bank (MWCB) were banked at Passages 139 and 143 respectively. The cells were further expanded a maximum of 11 passages to Passage 154 during cell expansion in stationary cultures prior to seeding of the bioreactor used for virus production. The estimated number of population doublings in the bioreactor is calculated to be 1 to 3.

Figure 2:
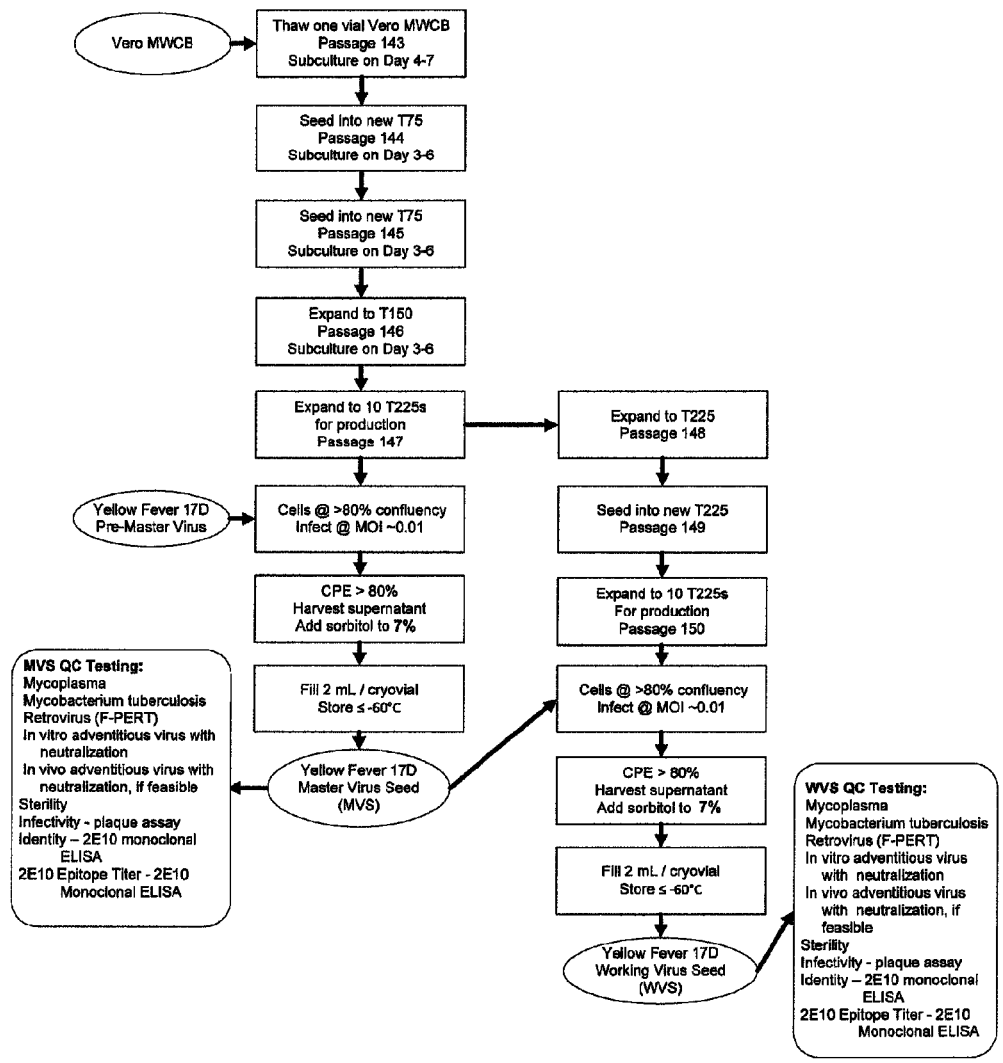
FIG. 2 is a schematic representation of the preparation of the virus seeds.

Preparation of Master and Working Virus Seeds:

FIG. 2 is a schematic representation of the preparation of Virus seeds according to an embodiment of the invention. An important safety factor for the disclosed vaccine is the use of the attenuated YF 17D vaccine for manufacture. The attenuated virus used as a starting material was a commercial vaccine, YF-VAX® (Sanofi Pasteur, Swiftwater Pa.) which had undergone various tests for adventitious agents. The original YF-VAX® material used to inoculate Vero cells was derived from embryonated hens' eggs, and contained hydrolyzed porcine gelatin as a stabilizer. However, the likelihood of carry-over of an adventitious agent from eggs was mitigated by use of RNA transfection to produce the Pre-Master Virus Seed.

The cells were propagated in OptiPro-SFM medium (Invitrogen, Grand Island, N.Y.). To develop the modified Yellow Fever (YF) virus that will grow to high titers in Vero cells, initially the YF-17D virus at a 0.01 multiplicity of infection (MOI) was used to infect a T-25 flask with a confluent layer of Vero cells. The cell culture was incubated at 37° C. and 5 percent $CO_2$.

Figure 3A:
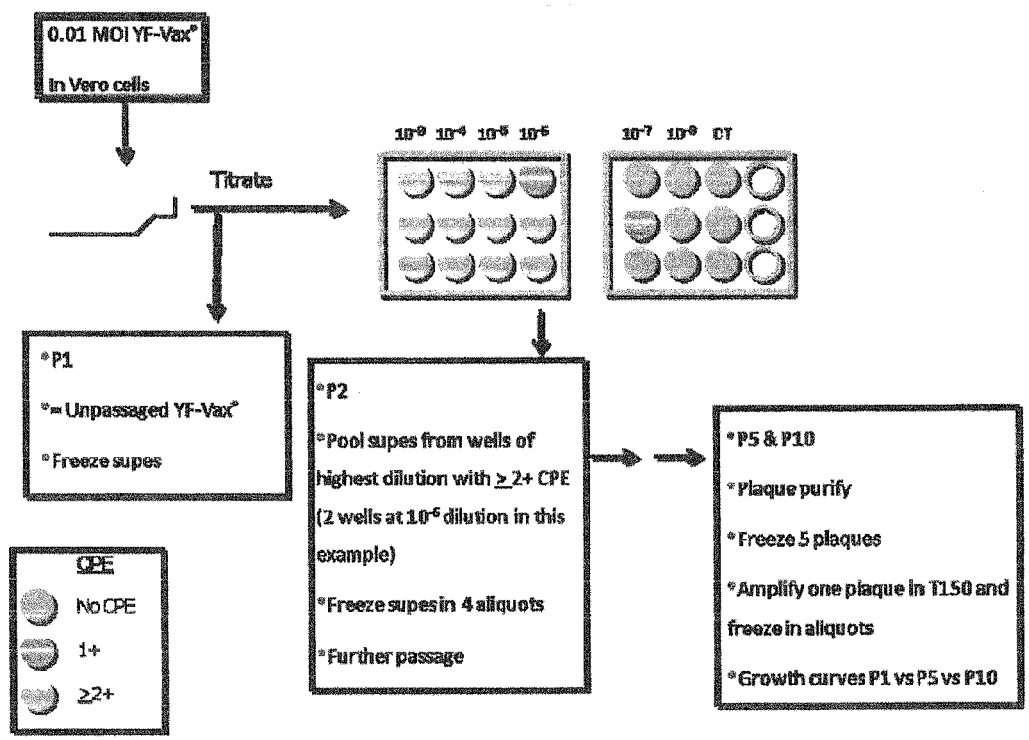
FIG. 3A is a schematic of the process used for 10 serial passages (P1 through P10) to modify the nucleotide sequence of the viral genome virus to develop a seed virus with enhanced growth in Vero cells for preparation of an inactivated Yellow Fever virus candidate.

Once cytopathic effect (CPE) was observed in about 2+(50%) of the cells, aliquots of the culture were prepared, labeled as passage one (P1) and stored at −80° C. for use as the inoculum to continue the serial passages. A schematic of the procedure used to make P1 through P10 is shown in FIG. 3A.

An aliquot of the Passage 1 (P1) virus was diluted $10^{-1}$ through $10^{-8}$ and each dilution was inoculated onto confluent monolayers of three (3) Vero cell cultures propagated in sterile 12 well plates from which growth medium had been removed.

$Log_{10}$ dilutions were prepared by transferring 0.2 ml of virus to 1.8 ml of phosphate buffered saline (PBS) to equal a $10^{-1}$ dilution. The virus plus PBS was mixed and then a new pipette was used to transfer 0.2 ml to 1.8 ml of PBS=$10^{-2}$, and then repeated through $10^{-8}$ dilution. Twelve well confluent monolayers of Vero cell culture were labeled and $log_{10}$ dilutions of the P1 material (negative control, $10^{-1}$ (3 wells), $10^{-2}$ (3 wells), $10^{-3}$ (3 wells), $10^{-4}$ (3 wells), $10^{-5}$ (3 wells), $10^{-6}$ (3 wells), $10^{-7}$ (3 wells) and $10^{-8}$ (3 wells) were prepared and inoculated onto medium-free cultures using a new pipette for each dilution of inoculum. The negative control cultures were inoculated with a similar volume of PBS. After inoculating the cultures they were incubated at 37° C. for 1 hour with intermittent rocking and then 1.0 ml of maintenance medium was added per culture. Cells were observed each day for cytopathic effect (CPE) and recorded as 1+(25% of the cell monolayer effected), 2+(50% of the cell monolayer effected), 3+(75% of the cell monolayer effected) and 100% (all of the cell monolayer effected). Estimates of CPE were based on a comparison with the control cells. The plaque assay was also performed on the same dilutions of inoculum to verify that the CPE represented viral infectivity.

Once CPE (2+) developed in these cultures, five 0.5 ml aliquots of the medium were harvested from the cultures that received the highest dilution or next to the highest dilution of inoculum. The five aliquots were prepared and stored as passage 2 (P2) at −80° C. The strategy was to select the virus population that replicated at or near the highest $log_{10}$ dilution based on the appearance of CPE in the cells. As such, the virus population selected would be the population that was best adapted to replicate in the cells with possible genetic changes that will allow for an increase in viral titer.

Subsequently, $log_{10}$ dilutions were prepare of an aliquot of the P2 virus and used to infect cultures of Vero cell propagated in 12-well plates as described for passage one YF virus. Similar methods were employed to complete 10 serial passages of the virus.

P10 and P11:

At each serial passage, each of the aliquots used as the inoculum was also tested to determine the infectivity titers by plaque assay in Vero cells. At passage 10, five single, well isolated plaques, each representing progeny from a single infectious virus particle, were selected at the highest dilution that yielded plaques. Each plaque was suspended in 0.3 ml of medium containing Human Serum Albumin (HSA) to protect the virus infectivity during freezing and stored at −80° C.

The series of passages (P1 to P10) of the YF 17D virus in Vero static cultures at dilutions of $10^{-1}$ to $10^{-8}$ were performed at the University of Texas Medical Branch (Galveston, Tex.). The strategy was to select the virus population that replicated at or near the highest log10 dilution based on the microscopic appearance of CPE in the Vero cells. The virus population that showed cytopathic effects at the highest dilution, the P10 harvest, was selected as the optimized, "high-yield" virus. The high yield virus population that showed CPE at the highest dilution was sequenced.

The High Yield Virus:

The "high yield" virus was adapted for increased replication in Vero cells by 10 serial virus passages at terminal dilution in Vero cells. At Virus Passage 10, a single plaque forming unit was picked and passed in fluid culture to produce a mini-seed stock at Virus Passage 11. The graph in FIG. 3B shows comparative growth curves of P1 and P11 viruses, that had been inoculated at high MOI; the data indicate that the P11 virus has a higher peak titer than the P1 virus. This virus (P11) showed a 3-7 fold increased replication capacity in Vero cells compared to the YF 17D at Virus Passage 1. The Virus Passage 11 virus stock was used for RNA extraction and the RNA used to produce cGMP grade virus seeds.

RNA Sequence of the Vero Adapted 17D Virus (P11)

The full genomic consensus sequences of the viruses at P1 and P11 from the original YF-VAX® were determined. Two genetic mutations or nucleotide differences were found, as shown in Table 1 below. One nucleotide difference lies in the capsid (C) gene and one in the envelope (E) gene. The term "capsid" as used herein, refers to the shell of protein that surrounds and protects the nucleic acid of a virus. The change in the C gene was silent (no amino acid change), whereas the E gene mutation resulted in an amino acid (Lys→Arg) mutation.

TABLE 1

RNA sequence and mutations in the YF 17D virus adaptedto Vero cells

| NT residue # | Nucleotide Change | | Amino Acid Change | | Location | Codon | |
|---|---|---|---|---|---|---|---|
| | P1 | P11 | P1 | P11 | | P1 | P11 |
| 211 | A | G | Threonine | Threonine | C31 | ACA | ACG |
| 1452 | A | G | Lysine | Arginine | E160 | AAG | AGG |

Figure 5B:
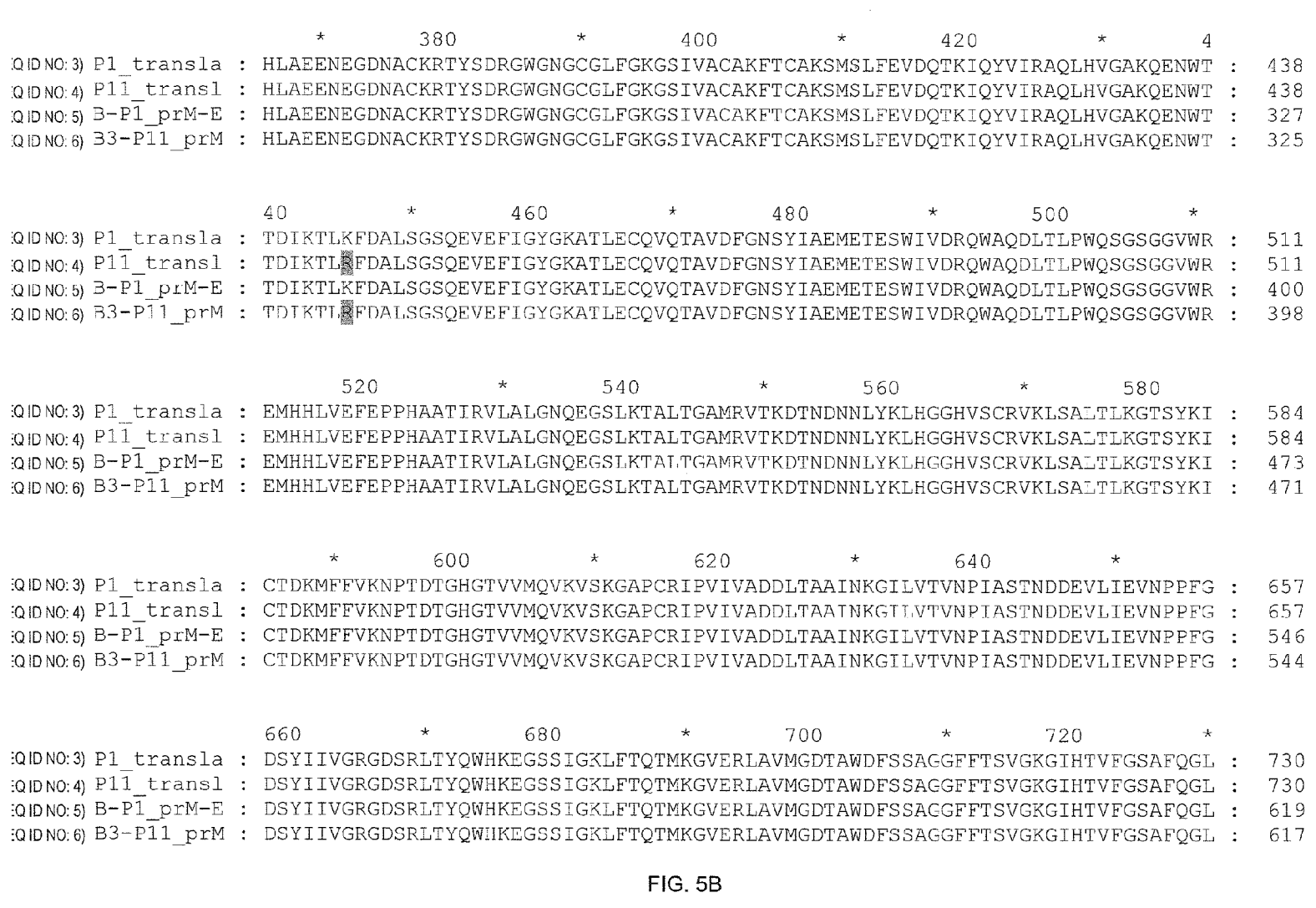

The first mutation was an A to G conversion at nucleotide residue #211, according to SEQ ID NO: 1, which resulted in a change in the codon for the amino acid at position 31 of the capsid protein (C31) from ACA to ACG. This mutation, however, did not change the amino acid residue at this position. The second mutation was an A to G conversion at nucleotide residue #1452, according to SEQ ID NO: 1, which resulted in a change in the codon for the amino acid at position 160 of the envelope protein (E160) from AAG to AGG. This mutation resulted in a Lysine to Arginine substitution at this position. A consensus alignment of the nucleic acid and amino acid sequences for P1 and P11 are depicted in FIGS. 4 and 5.

Plaque Purification of P10 Harvest:

As described above, virus from P10 was purified by plaque formation. The virus isolated from one plaque was inoculated into a T 150 flask. The conditioned medium from this flask was harvested when 50 percent of the cells exhibited CPE. This material was aliquoted in one mL aliquots and designated P11. The P11 virus was then used as the source of RNA for transfection of Vero cells. The P11 titer of plaque forming units was determined to be $8.5 \times 10^7$ plaque forming units (PFU). The RNA isolated from the P 11 virus was used to transfect cells to produce a Pre-Master Seed. The Pre-Master Seed virus was passaged in additional cultures of Vero cells to produce a Master and Working Virus Seed stock.

Manufacture of Master Virus Seed:

The Master Virus Seed (MVS) was produced in Vero cells under serum-free conditions using a single vial of the Pre-Master Seed as the virus inoculum, as represented schematically in FIG. 2. Cells from the Manufacturer's Working Cell Bank (MWCB) of Vero cells at Passage 143 were expanded to eleven (11) 225 cm³ T-flasks. Once the cells became confluent, one flask was trypsinized and used to determine cell number and also to seed additional flasks used to produce the Working Virus Seed. The OptiPRO™ SFM medium was removed from the remaining 10 T-flasks and the cells were inoculated with Pre-Master Seed virus at a multiplicity of infection (MOI) ~0.01 PFU/cell. The virus was allowed to adsorb for 60 (±5) minutes at 37°±2° C., after which pre-warmed OptiPRO™ SFM medium was added to the flasks. The infected culture was then incubated at 37°±2° C. with ~5% $CO_2$.

After 3 days, when CPE was observed in ≥80% of the cell population, the virus propagation process was terminated by harvesting the cell culture fluid. The virus-containing culture fluid was pooled from all flasks, centrifuged to remove cell debris, and mixed with sterile 70% sorbitol to a final sorbitol concentration of 7%. This mixture was filled into 4 mL cryovials at 2 mL per vial and frozen at ≤−60° C. The frozen virus stock constitutes the YF 17D MVS.

As shown in FIG. 2, the highest Vero cell passage level used for production of the MVS was 147.

Manufacture of Working Virus Seed:

The Working Virus Seed (WVS) was produced as shown in FIG. 2, from a single vial of the MVS under cGMP conditions. Starting with cells in the 11th T225 flask used to determine the cell density in the production of MVS, four T225 flasks were seeded at a cell density $1 \times 10^6$ viable cells per flasks, Passage 147. The cells were passaged into 4 new T225 flasks to allow time for the production of the Master Seed Stock. Cells at Passage 148 were then seeded into eleven T225 flasks for the production of the WVS.

When the cells were greater than 80% confluent, the cell density in one flask was determined. This cell density was used to estimate the cell density in the remaining ten flasks and the cells in the 10 flasks were infected with virus from the MVS at a MOI of 0.01 PFU/cell. To perform the infection, the medium was removed from the flasks and then diluted virus was added in phosphate buffered saline. After one hour fresh medium was added to each flask and the cells were returned to the incubator. The cells were observed microscopically for CPE. When CPE was greater than 80% the virus was harvested. The medium from the 10 flasks was centrifuged to remove cellular debris and the clarified supernatant was pooled into one vessel. Sorbitol (final concentration 7%) was added to the virus-containing supernatant as a cryo-preservative. The pooled virus was aliquoted into 4 mL cryovials, two mL per vial. The filled vials were stored at ≤−60° C. Once frozen, one vial from the end of the bank was tested in a plaque assay in Vero cells to determine the virus titer.

Increase in Titer Achieved in P11 Compared to P1:

The original YF virus and P11 harvest of YF virus were titrated by plaque assay in Vero cells to determine the infectivity titers expressed as plaque forming units (PFU) (Table 1). The original YF-VAX 17D vaccine contained $10^{3.7}$ $\log_{10}$ per ml in Vero cells. The peak titer for passage one was 6.68 $\log_{10}$ per ml and remained at about the same titer through P6 and then increased significantly to 7.67 $\log_{10}$ by P10. Thus, in this experiment, there was a 1.0 $\log_{10}$ (10-fold) increase in the titer of the passage 10 (7.67 $\log_{10}$) over the titer (6.68 $\log_{10}$) of the P1 virus (see Table 2).

Virus growth curves were also performed concurrently on the P1 and P11 viruses. Growth curves was performed by infecting duplicate 75 cm² flasks of Vero cells at high MOI of 1.0 and a second growth curve was performed using a low MOI of 0.001. At high MOI it is expected that all cells are infected at initiation of the culture, while at low MOI, virus released by a small number of cells initially infected would infect the remaining cells of the culture; thus, virus in a low-MOI growth curve would be expected to be somewhat delayed compared to a high-MOI culture. At times 0, 6, 18, 24, 30, 48, 54 and 72 hr post inoculation, conditioned medium (2 mL) was removed from the cultures, stabilized with 2% HSA and frozen (duplicate one ml samples) at −80° C. $\log_{10}$ dilutions of each sample were tested in Vero cells to determine the infectivity titer and the growth curves were plotted over time.

TABLE 2

Peak infectivity titer for each sequential passage of YF virus

| Passages of YF-VAX in Vero cells | Highest Dilutions yielding plaques | Average # of plaques | Peak infectivity titer (PFU/ml) | Conversion of plaque forming units to equal the infectivity titer in $\log_{10}$ PFU per ml |
|---|---|---|---|---|
| 0 | $10^{-3}$ | 1 | $5 \times 10^3$ | 3.7 |
| 1 | $10^{-5}$ | 9.67 | $4.83 \times 10^6$ | 6.68 |
| 2 | $10^{-5}$ | 12.67 | $6.33 \times 10^6$ | 6.80 |
| 3 | $10^{-4}$ | 21.67 | $1.08 \times 10^6$ | 6.03 |
| 4 | $10^{-5}$ | 12.67 | $6.33 \times 10^6$ | 6.80 |
| 6 | $10^{-6}$ | 1.00 | $5.00 \times 10^6$ | 6.70 |
| 8 | $10^{-6}$ | 3.00 | $1.50 \times 10^7$ | 7.18 |
| 9 | $10^{-6}$ | 5.67 | $2.83 \times 10^7$ | 7.45 |
| 10 | $10^{-6}$ | 9.33 | $4.67 \times 10^7$ | 7.67 |

The growth curve results using an MOI of 1.0 indicated that the P1 YF virus increased from a titer of 4.09 $\log_{10}$ at 0 hours; or at the time of inoculation to a maximum titer of 6.28 $\log_{10}$ at 48 hours post inoculation (PI) and the titers showed a slight decrease of 6.21 and 6.18 $\log_{10}$ at 60 and 72 hours PI, respectively. The results for passage 11 (P11) showed an increase in titers over the passage one virus (P1). At the time of inoculation, the titer was 4.15 $\log_{10}$ and reached a maximum titer of 6.83 $\log_{10}$ at 48 hours P.I. and had decreased to a titer of 6.54 $\log_{10}$ at 72 hours P.I (see Table 3). The peak virus titer at approximately 48 hours for the P11 virus was 0.55 $\log_{10}$ or 3.5 times higher than for the P1 virus.

TABLE 3

Growth curve of Yellow Fever 17D
Passage 1 and Passage 11 virus at high MOI (1.0)

| | Time points (hr) | | | | | | |
|---|---|---|---|---|---|---|---|
| | 0 | 6 | 18 | 24 | 30 | 48 | 54 | 72 |
| Passage 1 | 4.15 | 4.11 | 5.63 | 6.09 | 6.05 | 6.28 | 6.21 | 6.18 |
| Passage 11 | 4.09 | 4.22 | 5.60 | 6.27 | 6.63 | 6.83 | 6.68 | 6.54 |
| P1 STDEV | 0.11 | 0.02 | 0.17 | 0.08 | 0.05 | 0.03 | 0.05 | 0.04 |
| P11 STDEV | 0.04 | 0.08 | 0.21 | 0.02 | 0.10 | 0.14 | 0.18 | 0.10 |

As compared to the growth curve using high MOI, the pattern of the growth curve using an MOI of 0.001 showed a lag in replication but maximum titers were higher. At the time of inoculation, the titers were 1.7 and 0.57 $\log_{10}$ for the passage 1 and 11, respectively. There was a linear increase in titers and by 72 hours PI, maximum titers of 7.35 and 8.17 $\log_{10}$ had been attained by P1 and P11, respectively. The peak virus titer at approximately 72 hours for the P11 virus was 0.82 $\log_{10}$ or 6.6 times higher than for the P1 virus. These results indicated that the serial passage of YF-VAX produced a substantial increase in titer and that this approach appears to be promising for developing an inactivated YF vaccine (see Table 4).

TABLE 4

Growth curve of Yellow Fever 17D
Passage 1 and Passage 11 virus at low MOI (0.001)

| | Time points (hr) | | | | | | | |
|---|---|---|---|---|---|---|---|---|
| | 0 | 6 | 18 | 24 | 30 | 48 | 54 | 72 |
| Passage 1 | 1.70 | 2.00 | 2.57 | 4.14 | 4.72 | 6.44 | 7.19 | 7.35 |
| Passage 11 | 0.57 | 0.67 | 3.01 | 4.44 | 5.18 | 7.04 | 7.38 | 8.17 |
| P1 STDEV | 0.00 | 0.30 | 0.19 | 0.07 | 0.06 | 0.04 | 0.02 | 0.03 |
| P11 STDEV | 0.98 | 1.15 | 0.14 | 0.05 | 0.05 | 0.02 | 0.10 | 0.10 |

These results indicated that the serial passage of the YF virus produced a substantial increase in titer. Next, as described above, the sequence analysis of P1 and P11 was performed, the comparative results of which show that the serial passages may have resulted in two genetic mutations in the YF virus, one of which resulted in an amino acid change.

The disclosed modified YF virus produced by the serial passage of the attenuated YF 17D virus vaccine in certified African green monkey kidney cells (Vero) showed enhanced productivity in cells. The methods of the invention involve vaccination of subjects with the modified, inactivated YF virus to produce immunity to Yellow Fever.

Vaccine Production in Bioreactors:

Bioreactors containing approximately 5 g/L of Cytodex 1 microcarriers were seeded with approximately $5 \times 10^5$ Vero-cells/mL in OptiPRO™ SFM medium. The cells were allowed to propagate for 3 to 4 days until cells attached to the microcarriers achieved a density of $\geq 7 \times 10^5$ nuclei per mL. For virus inoculation, the agitation and parameter controls are turned off and the microcarriers and cells are allowed to settle. Approximately 75% of the medium volume was removed through a 90 µm sieve tube which is designed to retain microcarriers in the reactor. WVS virus is introduced at a MOI of ~0.01 PFU/cell. Low agitation was applied at this low volume for about 1 hour to allow virus to adsorb to and infect cells. Fresh medium was added to the full volume before agitation and parameter controls are returned to their original settings. On day 3 or 4 post infection, 75% of the conditioned medium was removed, and the reactor was re-fed with fresh medium. The culture was allowed to proceed for 2 or 3 more days and on Day 5, 6, or 7 post infection the conditioned medium was harvested. To ensure biosafety, harvest samples were taken from the bioreactor immediately before microcarrier removal and tested for sterility, mycoplasma, retroviruses and adventitious viruses (in vitro assay).

The reactor mixing was stopped to allow for settling of the microcarriers. The culture is transferred from the bioreactor through a 90 µm sieve tube into a bioprocess bag. The 90 µm sieve reduces the amount of microcarriers and large particulates from transferring into the harvest. This was the Virus Harvest. The Virus Harvest was sampled and tested for infectivity, potency, identity, endotoxin, sterility, residual Vero cell DNA, and residual Vero cell proteins.

Virus Purification and Inactivation:

The culture conditioned medium was harvested, clarified in two steps, digested with BENZONASE®, purified by ultrafiltration and diafiltration and then sterile filtered to generate the Live Virus Bulk. The Live Virus Bulk was then inactivated by treatment with β-propiolactone (BPL) which permeates the virus envelope and disrupts the viral RNA by alkylating purine residues, rendering the virus inactive. The inactivated virus is further purified by cellufine sulfate column chromatography and diluted to the desired viral concentration to form the Bulk Vaccine Drug Substance.

Repeat of YFV 17D Passaging Study:

Experiments were performed to repeat the passage of YF virus from unpassaged virus stock through P11 using similar techniques as in the original passage series.

Preparation of the Virus Stocks:

Vero cells were maintained under serum-free conditions throughout the study, using OptiPRO SFM.

The initial source of the YFV 17D virus was from a single vial of YF-VAX® (Sanofi Pasteur, Swiftwater Pa.). The vial was originally reconstituted and dispensed into aliquots. One of these aliquots was used for the repeat experiments. The repeat serial passaging was performed in duplicate such that there were two runs of the study, performed in parallel, referred to here as series B and C.

At each passage of the virus, the virus sample was diluted in serial 10-fold dilutions, and the diluted virus was used to inoculate Vero cells seeded in 12 well plates. The serial dilutions performed at each passage were inoculated in duplicate such that one set of plates was used for the preparing the next passage of virus, inoculating 4 wells per dilution, and the other set of plates was used to determine the titer of the passaged virus, inoculating 2 wells per dilution.

For the serial passages of the virus, the dilution selected for passaging the virus was the last dilution where generalized cytopathic effect (CPE) was observed, three to four days after infection. The media from the four wells was pooled for the next passage. The titer of the virus was determined by plaque assay using an immunostain to visualize and count the plaques. The immunostain method allowed for determining the titer after 3 days of infection.

For the initial passage of the virus, 0.3 ml of the YF-VAX aliquot was diluted into 3 mL final, using OptiPRO SFM, for a $10^{-1}$ dilution. The diluted virus was divided equally into three aliquots. From each of these aliquots, serial 10-fold dilutions were made to $10^{-5}$, making two dilution series (B and C). This is referred to here as the P0→P1 passage. From the plaque assay inoculated using the dilution series, of the P0 virus was determined, and for the plates inoculated for passage, the P1 virus was generated. Each round of the passaging is summarized in the Table 5.

TABLE 5

Serial Passages of YFV 17D (Results same for series B and C)

| Passage | Dilutions plated | Dilution harvested for next passage |
|---|---|---|
| P0 (initial vial) | N/A | N/A |
| P0 → P1 | $10^{-1}$ to $10^{-5}$ | $10^{-3}$ |
| P1 → P2 | $10^{-2}$ to $10^{-7}$ | $10^{-5}$ |
| P2 → P3 | $10^{-3}$ to $10^{-8}$ | $10^{-5}$ |
| P3 → P4 | $10^{-3}$ to $10^{-9}$ | $10^{-5}$ |
| P4 → P5 | $10^{-3}$ to $10^{-9}$ | $10^{-5}$ |
| P5 → P6 | $10^{-3}$ to $10^{-9}$ | $10^{-4}$ |
| P6 → P7 | $10^{-3}$ to $10^{-9}$ | $10^{-5}$ |
| P7 → P8 | $10^{-3}$ to $10^{-7}$ | $10^{-4}$ |
| P8 → P9 | $10^{-3}$ to $10^{-7}$ | $10^{-5}$ |
| P9 → P10 | $10^{-3}$ to $10^{-7}$ | $10^{-5}$ |

The passaging was repeated for 10 serial passages of the virus. Once the virus was harvested from the last passage, the titers were generated for the P10 virus from each series. The P10 viruses were then diluted for inoculating cells such that only one plaque per well would develop after inoculation. Well-isolated plaques could then be picked from the wells. From the B series, six well-isolated plaques were picked, and from C, two were picked. The picked plaques were used to inoculate T25 flasks to generate the P11 virus stocks for growth curve studies.

Growth Curve Analysis:

For the growth curve studies, the P1 stock virus from each series was compared to the P11 stocks for each series. Since the volume of the P1 stocks would have been limiting for this, an aliquot of P1 virus from each series was diluted three-fold, then aliquots made from the diluted virus to generate P1 stocks for the growth curve. For the P11 stocks, three stocks from the B series were analyzed, and the two from the C series. Prior to the growth curve studies, aliquots of the virus stocks were assayed to confirm the level of infectivity.

Figure 3C:
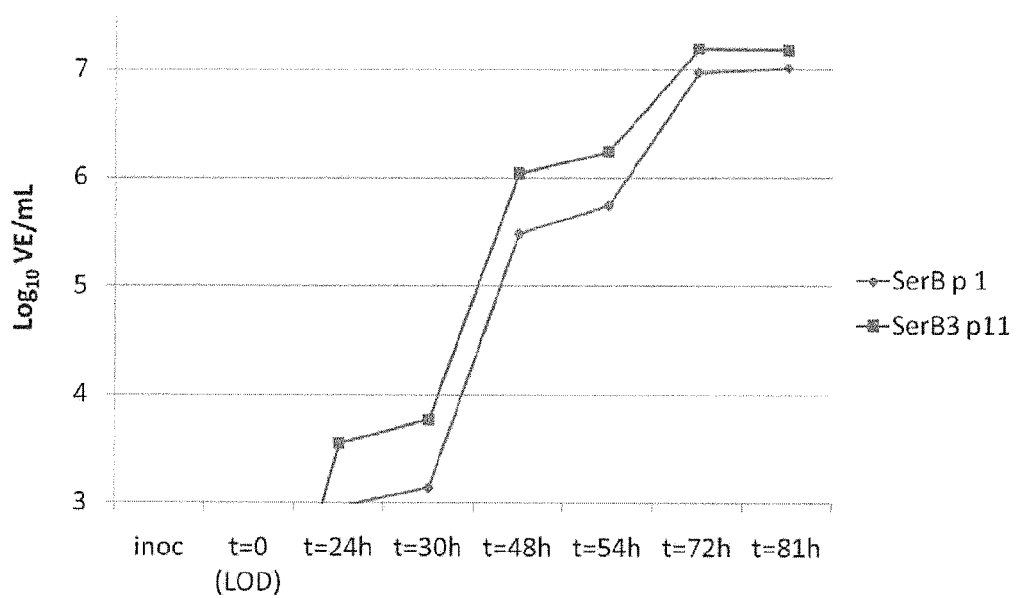
FIG. 3C is a graphical representation of a repeat passaging study of passage one (Bp1, Cp1) and passage 11 (B-p11, C-p11) virus performed in a series of experiments: Series B and C.
Figure 3C:
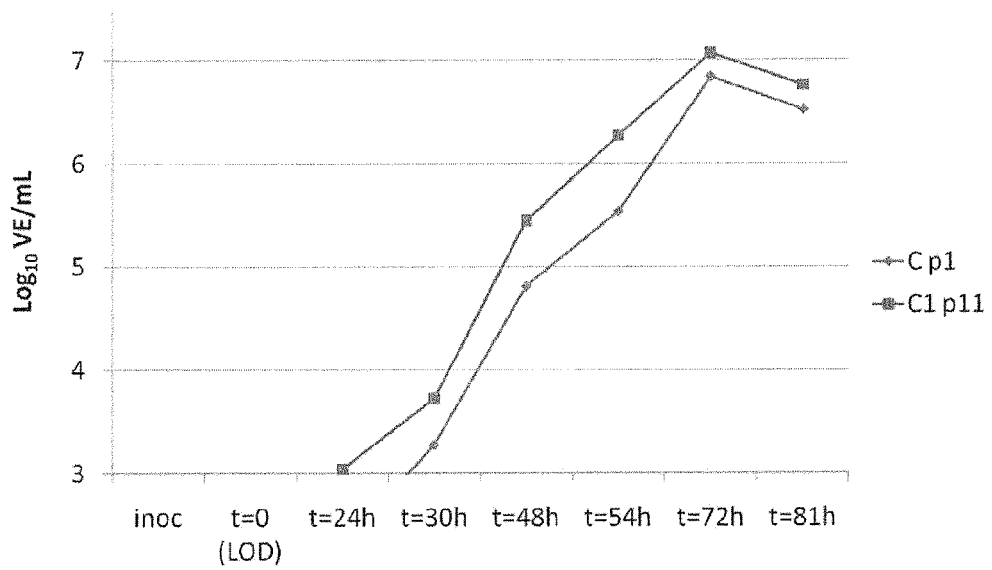

The growth curve analysis was performed by infecting Vero cells in T25 flasks, at low MOI of 0.001 PFU/cell. The study was conducted under serum free conditions using OptiPRO SFM as the culture medium. After diluting the virus stocks to achieve the target 0.001 MOI, a sample was reserved to confirm the titer of the inoculum. The virus inocula were allowed to adsorb to the cells for approximately one hour. After adsorption, the monolayers were washed three times then the cultures were fed with 8 ml of medium. At each time point, 1 mL was removed from each culture, and 1 mL fresh media was added back. The reserved one mL of medium was clarified by centrifugation and stored at −80° C. in the presence of sorbitol, until ready to assay. The time points for which samples were taken were 0, 24, 30, 48, 54, 72, and 81 hours after infection. A plaque assay was performed on all samples. The results of the study are detailed in FIG. 3C.

For both the B and C series, there was one P11 virus stock that was shown to replicate to higher titers than the P1 virus stock from the series. The P1 stocks for both B and C, and the B3-P11 stock and the C1-P11 stock were selected for sequence analysis. The sequence analysis illustrates that the B3 stock enjoys the same Lys→Arg mutation at E160 as was observed in the original passage series, as well as a Threonine (Thr)→Isoleucine (Ile) mutation at amino acid position 317 in non-structural protein 1 (NS1-317), and a Phenylalanine (Phe)→Leucine (Leu) mutation at amino acid position 170 in non-structural protein 2A (NS2A-170). While, the C1 stock did not carry the same mutation in the E gene, further study of the C1 stock genome is ongoing, and has revealed a mutation at amino acid position 113 in non-structural protein NS4B (NS4B-113).

Table 6 summarizes the nucleotide and amino acid changes found in the modified Yellow Fever viruses obtained from the original and repeat passage studies.

TABLE 6

Nucleotide and amino acid changes in the consensus sequence between passage 1 (P1) and P11 in three separate passage series of yellow fever 17D vaccine (YF-VAX ®) in Vero cells.

| Protein | Original passage series | | Repeat Series B | | Repeat Series C | |
|---|---|---|---|---|---|---|
| | Nucleotide | Amino acid | Nucleotide | Amino acid | Nucleotide | Amino acid |
| 5'NCR | | | | | | |
| prM | | | | | | |
| E | 211 A→G | | 211 A→G | | | |
| | 1452 A→G | 160 K→R | 1452 A→G | 160 K→R | | |
| | | | 1507 T→C | | | |
| | | | | | 1897 G→A | |
| NS1 | | | 3402 C→T | 317 T→I | | |
| NS2a | | | 4016 T→C | 170 F→L | | |
| NS2b | | | | | | |
| NS3 | | | | | | |
| NS4a | | | | | | |
| NS4b | | | | | 7225 A→G | 113 I→M |
| NS5 | | | | | | |
| 3'NCR | | | 9343 G→A | | | |
| | | | | | 9670 C→T | |

The position of the altered nucleotide or amino acid in the designated viral protein (or non-coding region, NCR) is shown.
Some nucleotide changes were silent (did not result in corresponding amino acid mutations).

Non-Limiting Aspects of the Invention:

A Yellow Fever viral strain was produced to develop a safer, inactivated, non-replicating vaccine that will elicit a neutralizing antibody response while eliminating the potential for neurotropic and viscerotropic adverse events for the prevention of human disease. Additional Yellow Fever virus strains are produced to develop safer, inactivated, non-replicating vaccines that will elicit a neutralizing antibody response while eliminating the potential for neurotropic and viscerotropic adverse events for the prevention of human disease. These embodiments of the invention are set forth above in the Summary.

The invention provides a modified Yellow Fever virus strain, wherein the nucleic acid molecule of said strain comprises an amino acid mutation at one or more positions flanking the 160 mutation, for example residues 134, 137, 144, 148, 157, 160, 175, 177 of the envelope protein. In an embodiment of this aspect, the invention provides a modified Yellow Fever virus strain, wherein the nucleic acid molecule of said strain comprises at least one amino acid mutation selected from: an amino acid mutation in the NS1 protein, an amino acid mutation in the NS2A protein, an amino acid mutation in the NS4B protein, optionally wherein said at least one amino acid mutation is in further combination with an amino acid mutation at one or more positions 134, 137, 144, 148, 157, 160, 175, 177 of the envelope protein. In a further embodiment of this aspect, the amino acid mutation(s) at position 157 is lysine to arginine; at position 148 is lysine to arginine; at position 144 is histidine to arginine, tyrosine or lysine; at position 137 is tyrosine to arginine or lysine, at position 175 is tyrosine to arginine or lysine; and/or at position 177 is lysine to arginine.

The invention also provides a modified Yellow Fever virus strain, wherein the nucleic acid molecule of said strain comprises an amino acid mutation at one or more positions flanking the 160 mutation, for example residues 134, 137, 144, 148, 157, 160, 175, 177 of the envelope protein, in combination with mutations at one or more positions 317 of NS1, 170 of NS2A, 113 of NS4B. In an embodiment of this aspect, the amino acid mutation(s) in the envelope protein at position 157 is lysine to arginine; at position 148 is lysine to arginine; at position 144 is histidine to arginine, tyrosine or lysine; at position 137 is tyrosine to arginine or lysine; at position 175 is tyrosine to arginine or lysine; and/or at position 177 is lysine to arginine; and the amino acid mutation in NS1 at position 317 is threonine to isoleucine, in NS2A at position 170 is phenylalanine to leucine, in NS4B at position 113 is isoleucine to methionine.

In embodiments according to certain aspects of the invention, the cells are selected from Vero cells. Other cells suitable for propagation of the Yellow Fever virus may utilized, including but not limited to, primary chick embryo, primary duck embryo, primary dog kidney, primary rabbit kidney, WI-38, MRC-5, or fetal rhesus lung.

In some embodiments of these aspects, the nucleotide mutation in the codon for the amino acid at position 160 of the envelope protein results in a change from AAG to AGG, AGA, CGC, CGA, CGG or CGU. In other embodiments of these aspects, the amino acid mutation at position 160 is lysine to arginine.

In still other embodiments of these aspects, the nucleotide mutation in the codon for the amino acid at position 317 of NS1 results in a change from ACA to AUA, the nucleotide mutation in the codon for the amino acid at position 170 of NS2A results in a change from UUU to CUU, the nucleotide mutation in the codon for the amino acid at position 113 of NS4B results in a change from AUA to AUG. In other embodiments of these aspects, the amino acid mutation at position 317 of NS1 is threonine to isoleucine, at position 170 of NS2A is phenylalanine to leucine, at position 113 of NS4B is isoleucine to methionine.

In the methods according to the various aspects of the invention, the Yellow Fever virus or vaccines of the invention can be administered in amounts and by using methods that can readily be determined by persons of ordinary skill in this art. The chemically inactivated viral vaccines can be administered and formulated, for example, as a sterile aqueous solution containing between $10^2$ and $10^8$, e.g., or between $10^6$ and $10^7$, inactivated equivalents of infectious units (e.g., plaque-forming units (PFU) or tissue culture infectious doses) in a dose volume of from about 0.1 to about 1.0 ml, or about 0.5 ml. to be administered by, for example, subcutaneous, intramuscular, epidermal, or intradermal routes. In addition, in an appropriate formulation, a mucosal route, such as the intranasal oral route, can be selected. Selection of an appropriate amount of virus to administer can be determined by those of skill in this art, and this amount can vary due to numerous factors, e.g., the size and general health of the subject to whom the virus is to be administered. The subject can be vaccinated a single time or, if necessary, follow-up immunization can take place.

As is noted above, the vaccines can be administered as primary prophylactic agents to a subject that is at risk of Yellow Fever virus infection. Also, although not required, adjuvants can be used to enhance the immunogenicity of the Yellow Fever virus vaccines. Selection of appropriate adjuvants can readily be carried out by those of skill in this art.

Also as is noted above, the live virus can be inactivated by treatment with β-propiolactone (BPL), rendering the virus inactive. Other suitable methods of virus inactivation include, but are not limited to, formalin, ultraviolet radiation, ethylenimine, acetylethylenimine, and binary ethylenimine.

Exemplification

The examples below are intended to further illustrate certain preferred embodiments of the invention, and are not intended to limit the scope of the invention.

Antibody Responses in Mice:

The neutralizing antibody responses in female, outbred BALB/c and CD-1 mice after immunization with inactivated yellow fever vaccine compared to live virus was assessed. Yellow fever (YF) virus was inactivated with beta propiolactone (BPL), formulated with alum adjuvant and injected by the intramuscular route as two or three doses, each separated by 14 days. Two dose levels of virus were tested in BALB/c mice, the high dose level only was tested in CD1 mice. Sera taken at 14 days after the last immunization were tested for neutralizing antibody activity.

Preimmunization Procedures:

Female BALB/c and CD-1 strain mice (6 weeks of age) were acclimated in designated isolators in a restricted virus animal facility. Serum sample were collected Study Day 28 or 42 upon sacrifice. Mice were housed at 5 mice per cage and each animal was uniquely identified on the cage cards, and by ear notch. Mice were acclimated for a week prior to the initiation of any treatments. Mice received sterilized food and water and were housed in sterilized polycarbonate cages with sterilized bedding with a 12-hour light cycle (on at 6 am and off at 6 pm). General health was evaluated by technical staff daily and by a veterinarian weekly and as needed for health issues. Body weights were collected on Day 0 prior to immunization and on Day 28 and 42.

Immunization Procedure:

Body weight was determined on Day 0 prior to immunization. Immunization was given by either the i.m. (alum formulations) or s.c. (live virus or inactivated vaccine with Freund's adjuvant) route. Injections were given with mice under light anesthesia with suboptimal dose of ketamine/xylazine mixture. For s.c. route with live virus, a volume of 100 μl of vaccine in a 1 ml syringe fitted with a 27 gauge needle is injected between the skin and underlying layers of tissue in the scapular region on the backs of mice. For i.m. administration, a volume of 100 μl of vaccine in a 0.5 ml insulin syringe is injected into the muscle bundles of 2 rear upper legs of mice (50 μl/leg).

Sacrifice:

Mice were sacrificed 28 or 42 days after the first vaccination. Body weight was determined on all mice on Study Day 28 and prior to sacrifice. Blood was collected for neutralizing antibody testing. Blood (0.7-1.0 ml) was removed by cardiac puncture from mice anesthetized with light ketamine/xylazine treatment before they are humanely terminated by ketamine/xylazine overdose.

Experimental Design:

Alum-formulated vaccine prepared the day prior to immunization as a suspension and the vaccine was well mixed prior to filling each syringe. Alum-formulated preparations were administered by the i.m. route, a volume of 100 μl of vaccine in a 0.5 ml insulin syringe was injected into the muscle bundles of 2 rear upper legs of mice (50 μl/leg).

Live Yellow Fever (YF) vaccine was reconstituted with 0.6 ml of saline to a virus concentration of approximately 1.1× $10^5$ pfu/ml. A dose of 1×$10^4$ PFU (i.e. $\frac{1}{10}^{th}$ the human dose) was delivered in a volume of 100 μl of sterile saline administered on day 0 s.c.

Freund's adjuvanted vaccine was formulated the day of vaccination by placing 2 ml of antigen solution into a glass syringe, and 2 ml of the adjuvant into another glass syringe. The syringes were connected through the luer fitting to the 3-way valve. The plunger from the antigen solution was carefully depressed first, pushing the antigen into the oil of the adjuvant. The plungers were alternately pushed, to mix the adjuvant and the antigen solution into an emulsion (approximately 8 to 10 minutes). A 0.5 ml volume was delivered s.c. between the skin and underlying layers of tissue in the scapular region on the backs of mice (Formulation with Freund's adjuvant).

Live Yellow Fever (YF Vax™) vaccine was reconstituted with 0.6 ml of supplied saline to a virus concentration of approximately $1.1 \times 10^5$ PFU/ml.

The inactivated whole virion vaccine adsorbed to 0.2% aluminum hydroxide ("alum") adjuvant was prepared no more than 2 weeks prior to day of dosing.

Preliminary Mouse Studies

Groups of 5 mice each were dosed with as outlined in Table 7. Serum samples were collected by cardiac puncture 14 or 28 days post last vaccination.

were higher than BALB/c mice immunized with 3 doses of inactivated virus delivered with Freund's adjuvant (Group 6, titers 16-128). CD1 mice immunized with 2 doses of alum bound inactivated virus at the $10^8$ EU/dose level achieved higher titers (Group 9; titers 512-1024) than did similarly immunized BALB/c mice (Group 3; titers of 32-64). Only 1 in 5 mice receiving live YF Vax® (Group 8) mounted a neutralizing antibody response that was above the baseline levels in the mice receiving alum only (Groups 11).

Figure 7:
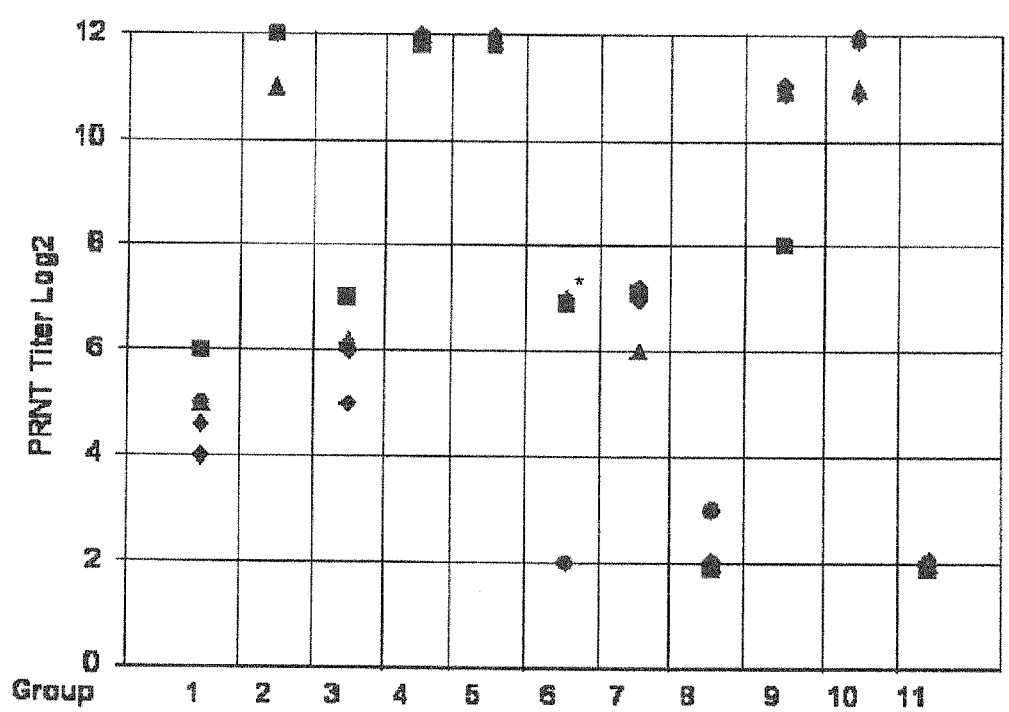
FIG. 7 is a graphical representation of PRNT50 antibody titers for the preliminary mouse study (M-9003-002).

In FIG. 7, each symbol represents an individual mouse. Treatment groups are shown in Tables 7 and 8. For Group 6 (*) the highest dilution of serum tested was 1:128. For Group 9 (**) the highest dilution of serum tested was 1:2048.

This study demonstrates that robust neutralizing antibody titers can be achieved in mice immunized with 2 or more inoculations of the disclosed inactivated YF virus delivered with alum. Outbred CD1 mice had higher antibody responses than an inbred strain (BALB/c). Alum was a superior adjuvant to Freund's, but this result could also be related to the route of immunization (SC for Freund's vs. IM for alum). Additional

TABLE 7

| Group | # Mice | Strain | Vaccine (Volume = 0.1 ml) | Route | Vaccination schedule | Neut. Ab |
|---|---|---|---|---|---|---|
| 1 | 5 | BALB/c | $10^8$ BPL-inactivated in 0.2% alum | IM | Day 0, 14 | Day 28 |
| 2 | 5 | BALB/c | $10^8$ BPL-inactivated in 0.2% alum | IM | Day 0, 14, 28 | Day 42 |
| 3 | 5 | BALB/c | $10^7$ BPL-inactivated in 0.2% alum | IM | Day 0, 14 | Day 28 |
| 4 | 5 | BALB/c | $10^7$ BPL-inactivated in 0.2% alum | IM | Day 0, 14, 28 | Day 42 |
| 5 | 5 | BALB/c | $10^8$ BPL-inactivated in Freund's complete/incomplete | SC | Day 0, 14, 28 | Day 42 |
| 6 | 5 | BALB/c | $10^7$ BPL-inactivated Freund's complete/incomplete | SC | Day 0, 14, 28 | Day 42 |
| 7 | 5 | BALB/c | $10^8$ BPL-inactivated no adjuvant | IM | Day 0, 14, 28 | Day 42 |
| 8 | 5 | BALB/c | Live YF Vax ® | SC | Day 0 | Day 28 |
| 9 | 5 | CD1 | $10^8$ BPL-inactivated in 0.2% alum | IM | Day 0, 14 | Day 28 |
| 10 | 5 | CD1 | $10^8$ BPL-inactivated in 0.2% alum | IM | Day 0, 14, 28 | Day 42 |
| 11 | 5 | BALB/c | 0.2% alum | IM | Day 0, 14, 28 | Day 42 |

Plaque reduction neutralization activity in mouse sera

Plaque reduction neutralization test was performed using a dilution of 17D virus which, in the absence of neutralization, produces 10-40 plaque forming units per well in 12 well plates. An equal volume of serially diluted mouse serum was incubated with virus for 16-20 h at 4° C. and then the inoculated into duplicate wells of Vero cells in 12 well plates. After virus absorption for 60 minutes at 37° C., the wells are overlaid with medium containing 0.75% methylcellulose, incubated for 4 days at 37° C., fixed and stained with crystal violet and plaques counted using a stereomicroscope over light box. The 50% plaque reduction titer represents the final mouse serum dilution resulting in less than 50% of the average plaque counts when no serum is added.

Figure 6:
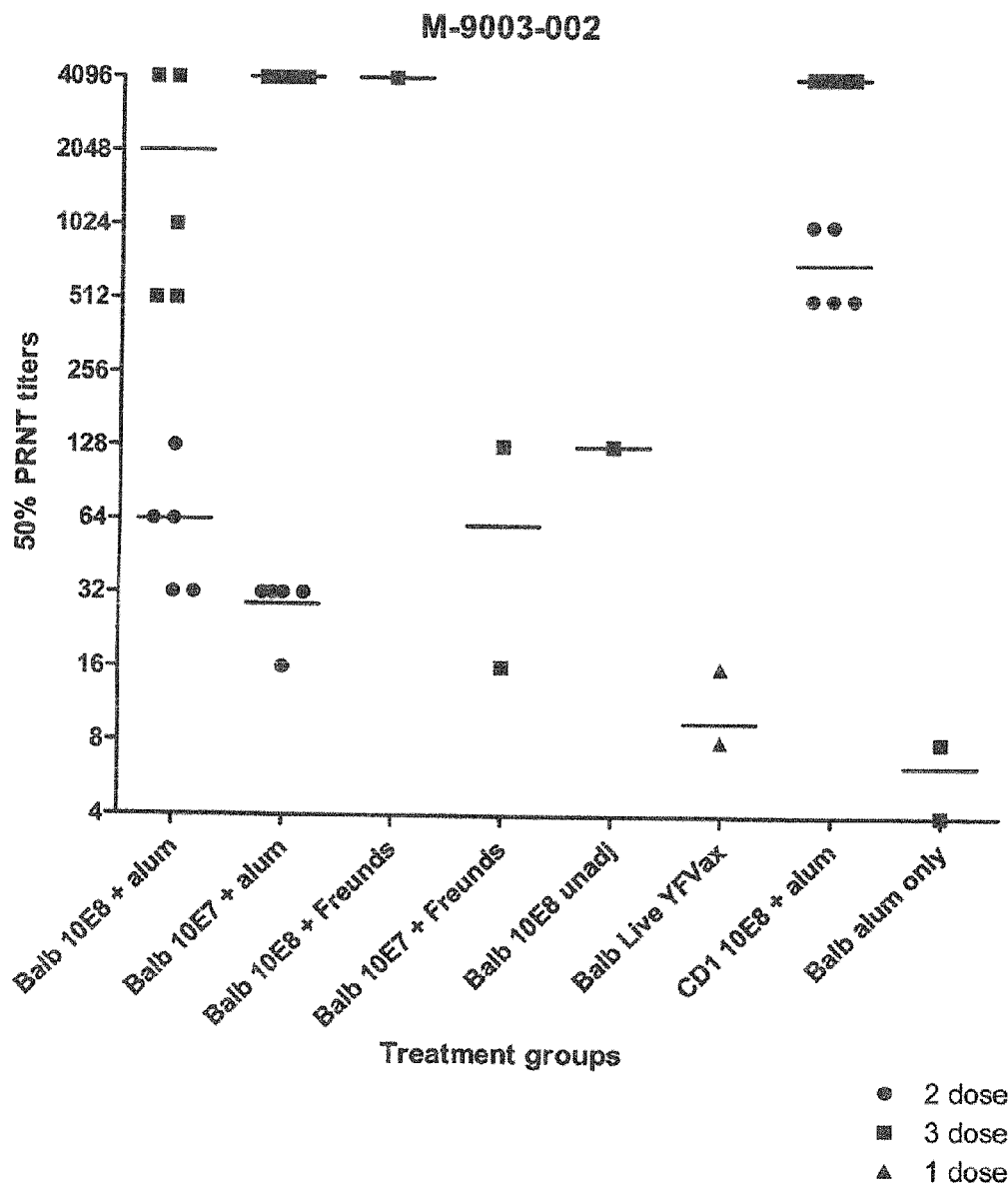
FIG. 6 depicts the comparative 50% plaque reduction neutralization test (PRNT50) titers between treatment groups of BALB/c and CD-1 strain mice in a preliminary mouse study (M-9003-002) of the efficacy of inactivated Yellow Fever vaccine.

The plaque reduction neutralization test (PRNT) responses and titers are shown in Table 8 and FIGS. 6 and 7. The PRNT test is currently the generally accepted standard for antibodies against Yellow Fever virus. All mice, regardless of strain, receiving 2 or 3 doses of inactivated vaccine given either without adjuvant (Group 7), with alum (Groups 1, 2, 3, 4, 9, 10, 11), or with Freund's adjuvant (Groups 5, 6) developed neutralizing antibody responses. Titers of greater than 4096 were found in 5 of 5 BALB/c mice immunized with 3 doses of alum bound inactivated virus at the $10^7$ EU/dose. These titers studies will be performed to determine if immunogenicity can be achieved with a single dose of vaccine.

TABLE 8

Mice with plaque reduction neutralization activity

| | | | Schedule | | % Positive |
|---|---|---|---|---|---|
| Group | Strain of mice | Vaccine | Vaccination | Sacrifice | (+/total) |
| 1 | BALB/c | $10^8$ BPL-inactivated in 0.2% alum | Day 0, 14 | Day 28 | 100% (5/5) |
| 2 | BALB/c | $10^8$ BPL-inactivated in 0.2% alum | Day 0, 14, 28 | Day 42 | 100% (5/5) |
| 3 | BALB/c | $10^7$ BPL-inactivated in 0.2% alum | Day 0, 14 | Day 28 | 100% (5/5) |
| 4 | BALB/c | $10^7$ BPL-inactivated in 0.2% alum | Day 0, 14, 28 | Day 42 | 100% (5/5) |
| 5 | BALB/c | $10^8$ BPL-inactivated in Freund's complete/incomplete | Day 0, 14, 28 | Day 42 | 100% (5/5) |
| 6 | BALB/c | $10^7$ BPL-inactivated in Freund's complete/incomplete | Day 0, 14, 28 | Day 42 | 100% (5/5) |

TABLE 8-continued

Mice with plaque reduction neutralization activity

| Group | Strain of mice | Vaccine | Schedule Vaccination | Sacrifice | % Positive (+/total) |
|---|---|---|---|---|---|
| 7 | BALB/c | 10$^8$ BPL-inactivated no adjuvant | Day 0, 14, 28 | Day 42 | 100% (5/5) |
| 8 | BALB/c | Live YF Vax ® | Day 0 | Day 28 | 20% (1/5) |
| 9 | CD1 | 10$^8$ BPL-inactivated in 0.2% alum | Day 0, 14 | Day 28 | 100% (5/5) |
| 10 | CD1 | 10$^8$ BPL-inactivated in 0.2% alum | Day 0, 14, 28 | Day 42 | 100% (5/5) |
| 11 | BALB/c | 0.2% alum | Day 0, 14, 28 | Day 42 | 0% (0/5) |

Equivalents

While this invention has been particularly shown and described with references to preferred embodiments thereof, it will be understood by those skilled in the art that various changes in form and details may be made therein without departing from the scope of the invention encompassed by the appended claims. Additionally, the references, patents and patent publications cited herein are incorporated by reference in their entirety.

What is claimed is:

1. A modified Yellow Fever virus strain that results in increased propagation in cells and a higher yield in the conditioned medium of a cell culture relative to Yellow Fever virus, wherein said modified Yellow fever virus strain comprises a nucleic acid molecule encoding an envelope protein wherein the nucleic acid molecule comprises a mutation in the codon for the amino acid at position 160, wherein the nucleic acid mutation in the codon for the amino acid at position 160 results in a change from AAG to AGG, AGA, CGC, CGA, CGG or CGU.

2. The modified Yellow Fever virus strain of claim 1, comprising a nucleic acid molecule encoding an envelope protein wherein the nucleic acid molecule comprises a mutated codon within 10 Angstroms or twenty amino acids from amino acid 160 and results in a pKa value of the side chain of the mutated amino acid at that position is higher than the pKa value of the side chain of the original amino acid at that position.

3. The modified Yellow Fever virus strain of claim 1, comprising a nucleic acid molecule comprising a sequence of nucleotides encoding a modified envelope protein of the Yellow Fever virus, wherein said nucleic acid molecule encodes the protein sequence in SEQ ID NO. 4.

4. The modified Yellow Fever virus strain of claim 3, comprising a nucleic acid molecule encoding an envelope protein wherein the nucleic acid molecule comprises a mutated codon in the molecular hinge region between Domain I and II and results in a pKa value of the side chain of the mutated amino acid at that position is higher than the pKa value of the side chain of the original amino acid at that position.

5. A vaccine comprising the modified Yellow Fever virus strain of claim 1, wherein the modified Yellow Fever virus strain is inactivated.

6. The vaccine of claim 5, further comprising an adjuvant.

7. The vaccine of claim 6, wherein the adjuvant is an aluminum salt.

8. The vaccine of claim 7, wherein the aluminum salt is aluminum hydroxide.

9. An inactivated modified Yellow Fever virus wherein the modified Yellow Fever virus of claim 1 is inactivated with Beta-propiolactone.

10. A method for inducing an immune response to Yellow Fever virus in a subject, the method comprising administering the vaccine of claim 5.

11. The method of claim 10, wherein the subject is at risk of developing, but does not have, Yellow Fever virus infection.

* * * * *